United States Patent
Barbet et al.

(10) Patent No.: US 12,186,381 B2
(45) Date of Patent: *Jan. 7, 2025

(54) VIRB10 FOR VACCINATION AGAINST GRAM NEGATIVE BACTERIA

(71) Applicant: UNIVERSITY OF FLORIDA RESEARCH FOUNDATION, INCORPORATED, Gainesville, FL (US)

(72) Inventors: Anthony F. Barbet, Essex (GB); Francy L. Crosby, Ocala, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 113 days.

This patent is subject to a terminal disclaimer.

(21) Appl. No.: 17/142,792

(22) Filed: Jan. 6, 2021

(65) Prior Publication Data
US 2021/0205430 A1 Jul. 8, 2021

Related U.S. Application Data

(63) Continuation of application No. 15/580,740, filed as application No. PCT/US2016/037728 on Jun. 16, 2016, now Pat. No. 10,918,707.

(60) Provisional application No. 62/180,245, filed on Jun. 16, 2015.

(51) Int. Cl.
*A61K 39/02* (2006.01)
*A61P 31/04* (2006.01)

(52) U.S. Cl.
CPC .......... *A61K 39/0233* (2013.01); *A61P 31/04* (2018.01)

(58) Field of Classification Search
CPC ...... A61K 39/0233; A61K 39/02; A81P 31/04
See application file for complete search history.

(56) References Cited

U.S. PATENT DOCUMENTS

| | | |
|---|---|---|
| 6,972,194 B1 | 12/2005 | Zybin et al. |
| 10,918,707 B2 | 2/2021 | Barbet et al. |
| 2009/0280137 A1 | 11/2009 | Samoylova et al. |

(Continued)

OTHER PUBLICATIONS

Lopez et al., ("Immunogenicity of A. marginale type IV secretion system proteins in a protective outer-membrane vaccine." Infect. Immun. 75, 2333, 2007) (Year: 2007).*

(Continued)

*Primary Examiner* — Jana A Hines
(74) *Attorney, Agent, or Firm* — Timothy H. Van Dyke; Wolter Van Dyke Davis, PLLC

(57) ABSTRACT

The invention pertains to the use of VirB10 to immunize a host against an infection by a bacterium having T4SS. The invention provides a vaccine comprising VirB10, a fragment of VirB10, a polynucleotide encoding VirB10 or a polynucleotide encoding a fragment of VirB10 and a pharmaceutically acceptable carrier and/or adjuvant. The invention also provides a method of immunizing a host against an infection caused by a bacterium having T4SS, the method comprising administering to the host a vaccine of the invention. The vaccines and the methods of the invention can be used to immunize against infections caused by bacteria having T4SS in dogs, rabbits, cats, pigs, cattle, sheep, goats, deer, horses, rodents and humans.

7 Claims, 7 Drawing Sheets
Specification includes a Sequence Listing.

(56) References Cited

U.S. PATENT DOCUMENTS

| | | | |
|---|---|---|---|
| 2010/0143411 A1* | 6/2010 | Brown | A61P 31/04 424/234.1 |
| 2011/0053189 A1* | 3/2011 | Hoey | G01N 33/6854 536/23.7 |
| 2011/0143377 A1 | 6/2011 | Hoey et al. | |
| 2018/0296657 A1 | 10/2018 | Barbet et al. | |
| 2021/0205430 A1 | 7/2021 | Barbet et al. | |

OTHER PUBLICATIONS

Written Opinion in International Application No. PCT/US2016/037728, Oct. 21, 2016, pp. 1-6.

Araujo, F.R. et al., "IgG and IgG2 antibodies from cattle naturally infected with Anaplasma marginale recognize the recombinant vaccine canidate antigens VirB9, VirB10, and elongation factor-Tu", Memorias do Instituto OswaldorCruz, 2008, vol. 103, No. 2, pp. 186-190.

Castelão, A. B. C et al. "Caracterização da imunogenicidade das proteinas recombinantes Virb9, Virb 10 e fator termo instavel de Elongacao de Peptideos de Anaplasma marginale em camundongos" Braz. J. Vet. Res. Anim. Sci., 2012, pp. 377-385, vol. 49, No. 5.

Coelho, Adriana Leticia Mendez, et al., "Immune response of calves immunized with cocktail of DNA vaccine encoding complexed outer membrane proteins from Anaplasma marginale," Semina: Ciencias Argrarias, Londrima, 2013, vol. 34, No. 6, suplemento 2, pp. 3877-3888.

Crosby, Francy L. et al., "VirB10 vaccination for protection against Anaplasma phagocytophilum," BMC Microbiology, 2018, vol. 18, No. 217, 12 pages.

Lopez, Job E. et al., "Immunogenicity of Anaplasma marginale Type IV Secretion System Proteins in the Protective Outer Membrane Vaccine," Infection and Immunity, May 2007, pp. 2333-2342.

Morse, Kaitlyn et al., "Association and Evidence for Linked Recognition of Type IV Sectrection System Proteins VirB9-1, VirB9-2, and VirB10 in Anaplasma marginale," Infection and Immunity, vol. 80, No. 1, Jan. 2012, pp. 215-227.

Brito et al. (2013), Vaccine adjuvant formulations: A pharmaceutical perspective, Seminars in Immunology, 25:130-145.

Avanti (2012), Innovative strategies for stabilization of therapeutic peptides in aqueous formulations (Doctoral Dissertation), project D6-202 of the Dutch Top Institute Pharma.

Li et al. (2014), Peptide Vaccine: Progress and Challenges, Vaccines, 2:515-536.

Woodland et al. (2004), Jump-starting the immune system: prime-boosting comes of age, TRENDS in Immunology, 25(2):98-104.

Goodwin et al. (2009), Peptides as therapeutics with enhanced bioactivity, Current Medicinal Chemistry, 19:4451-4461.

Yang et al. (2009), An introduction to epitope prediction methods and software, Reviews in Medical Virology, 19: 77-96.

Gentilucci et al. (2010), Chemical modifications designed to improve peptide stability: Incorporation of non-natural amino acids, pseudo-peptide bonds, and cyclization, Current Pharmaceutical Design, 16:3185-3203.

* cited by examiner

Recombinant VirB9-1

Recombinant VirB9-2

Recombinant VirB10

Figure 7

VIRB10 FOR VACCINATION AGAINST GRAM NEGATIVE BACTERIA

STATEMENT OF FEDERAL FUNDING

This invention was made with government support under U54AI1057156 awarded by National Institutes of Health. The government has certain rights in the invention.

BACKGROUND OF THE INVENTION

Type 4 secretion system (T4SS) is used by many gram negative bacteria, including certain pathogenic bacteria, to secrete effector proteins and DNA across cell membranes. The bacteria belonging to the genus *Rickettsia* and *Anaplasma* provide examples of the pathogenic bacteria having T4SS. Rickettsial diseases are present worldwide and pose the threat of use in a biological weapon. Vaccines currently available against diseases mediated by the bacteria having T4SS are inadequate.

BRIEF SUMMARY OF THE INVENTION

T4SS is typically formed from a macromolecular complex of about 12 proteins. One of the proteins of T4SS is VirB10. The invention provides for the use of VirB10 to immunize against an infection by a bacterium having T4SS. Accordingly, the invention provides a vaccine comprising VirB10, a fragment of VirB10, a polynucleotide encoding VirB10 or a polynucleotide encoding a fragment of VirB10 and a pharmaceutically acceptable carrier and/or an adjuvant.

The invention also provides a method of immunizing a host against an infection caused by a bacterium having T4SS, the method comprising administering to the host a vaccine comprising or consisting of VirB10, a fragment of VirB10, a polynucleotide encoding VirB10 or a polynucleotide encoding a fragment of VirB10 and a pharmaceutically acceptable carrier and/or an adjuvant. The vaccines and the methods of the invention can be used to prevent infections caused by bacteria having T4SS in various hosts, for example, dogs, rabbits, cats, pigs, cattle, sheep, goats, deer, horses, rodents and humans.

BRIEF DESCRIPTION OF THE DRAWINGS

FIG. 7. CLUSTAL format alignment of VirB10s from multiple organisms by MAFFT (v7.220) (Amarginale_Virb, SEQ ID NO: 123; Aphagocytophilu, SEQ ID NO: 124; Echaffeenis_Vi, SEQ ID NO: 125; Eruminantium_Vi, SEQ ID NO: 126; Rtyphi_Virb10_C, SEQ ID NO: 127; Rprowazekii_Vir; SEQ ID NO: 128; Rconorii_VirB10; SEQ ID NO: 129; Rrickettsii_Vir, SEQ ID NO: 130; Otsutsugamushi_, SEQ ID NO: 131; and Ecoli_VirB10_3J, SEQ ID NO: 132).

BRIEF DESCRIPTION OF THE SEQUENCES

Figure 1A:
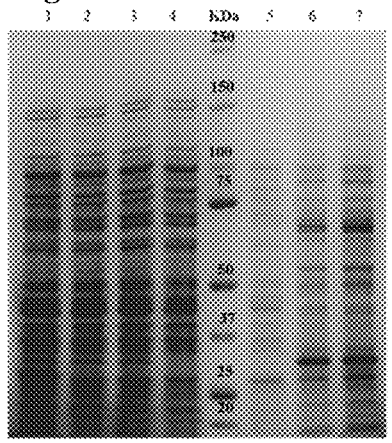
FIGS. 1A-1F. SDS-PAGE and Western Blot analysis of the recombinant proteins VirB9-1, VirB9-2 and VirB10. SDS-PAGE analysis of recombinant VirB9-1 (A), VirB9-2 (C), and VirB10 (E). Lanes represent the different fractions analyzed during the purification procedure, 1=Total crude protein, 2=Supernatant fraction obtained after high speed centrifugation, 3=Filtered supernatant, 4=Nickel Column filtrate, 5=Washed fraction, 6=Eluted protein, 7=Concentrated protein. Western Blot analysis using the monoclonal anti-His$_6$-tag antibody reacting with the recombinant protein (red arrows) VirB9-1 (33.5 KDa) (B), VirB9-2 (31.6 KDa) (D) and VirB10 (52.2 KDa) (F) in different fractions.
Figure 1B:
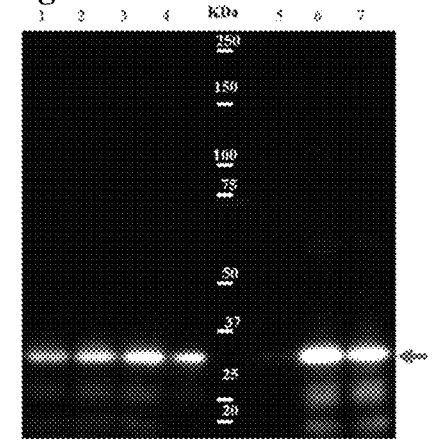
Figure 1C:
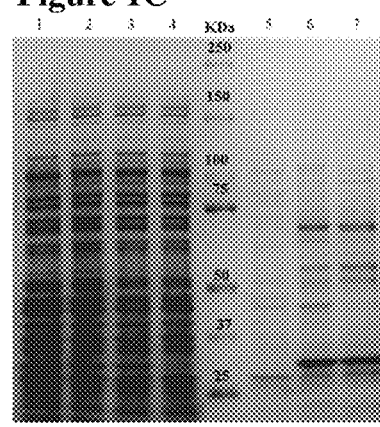
Figure 1D:
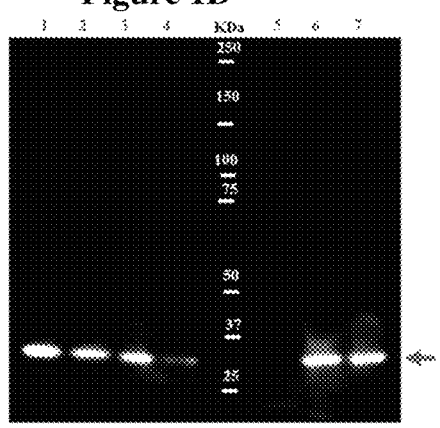
Figure 1E:
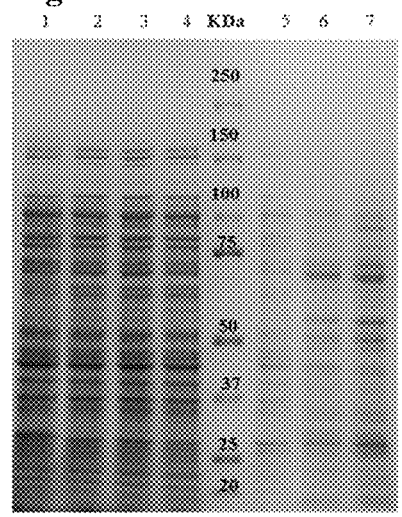
Figure 1F:
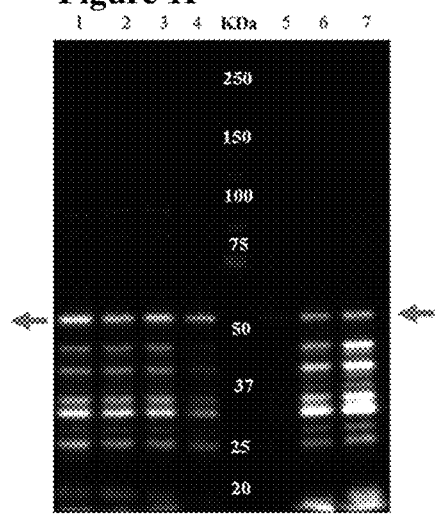

SEQ ID NO: 1: Sequence of VirB10 from *A. phagocytophilum* strain HZ.

SEQ ID NO: 2: Sequence of VirB9-1 protein from *A. phagocytophilum* strain HZ.

SEQ ID NO: 3: Sequence of VirB9-2 protein from *A. phagocytophilum* strain HZ.

SEQ ID NO: 4: Forward primer for amplification of DNA encoding Vir9B-1 protein.

SEQ ID NO: 5: Reverse primer for amplification of DNA encoding Vir9B-1 protein.

SEQ ID NO: 6: Forward primer for amplification of DNA encoding Vir9B-2 protein.

SEQ ID NO: 7: Reverse primer for amplification of DNA encoding Vir9B-2 protein.

SEQ ID NO: 8: Forward primer for amplification of DNA encoding VirB10.

SEQ ID NO: 9: Reverse primer for amplification of DNA encoding VirB10.

SEQ ID NO: 10: Forward primer for amplification of msp5 gene from *A. phagocytophilum* strain HZ for qPCR.

SEQ ID NO: 11: Reverse primer for amplification of msp5 gene from *A. phagocytophilum* strain HZ for qPCR.

SEQ ID NO: 12: Sequence of the qPCR probe for msp5 gene from *A. phagocytophilum* strain HZ.

SEQ ID NOs: 13 to 27: Sequences of antigenic peptides of VirB10.

SEQ ID NOs: 28-113: VirB10 sequences obtained from UniProt (web site: uniprot.org/uniprot).

SEQ ID NOs: 114-122: Sequences of PCR primers used to amplify VirB9-1, VirB9-2 and VirB10 and Taqman qPCR primers and probes used to quantify *A. phagocytophilum* load.

SEQ ID NOs: 123-132: Sequences of VirB10s from multiple organisms.

The Sequence Listing for this application is labeled "Seq-List.txt" which was created on Jun. 10, 2016 and is 343 KB. The entire content of the sequence listing are incorporated herein by reference in its entirety.

DETAILED DISCLOSURE OF THE INVENTION

Human granulocytic anaplasmosis (HGA) is a tick-borne disease caused by the etiologic agent *A. phagocytophilum*, a bacterium containing T4SS. HGA was designated as a nationally notifiable disease in the United States in 1998. HGA is described as a zoonosis since the pathogen infects humans as well as animals including dogs, cattle, sheep, deer, horses and rodents. Vaccines against HGA are not currently available and the currently available vaccines against other bacteria containing T4SS are not adequate. Thus, the subject application provides a component of T4SS as a vaccine against diseases caused by bacteria having T4SS, for example, *A. phagocytophilum* and methods of immunizing a host against an infection by a bacterium having T4SS. In some embodiments, outer membranes and fragments thereof that are obtained from bacteria having T4SS and which contain VirB10 are excluded as vaccine components in the methods of immunizing a host against infection by a bacterium having T4SS or as components of a vaccine.

In one embodiment, the invention provides a protein present in T4SS, for example, VirB10 or a fragment of VirB10, to immunize against an infection by a bacterium having T4SS, for example, *A. phagocytophilum*. In another embodiment, the invention provides a polynucleotide encoding VirB10 or a polynucleotide encoding a fragment of VirB10 to immunize against an infection by a bacterium having T4SS, for example, *A. phagocytophilum*. In particular embodiments, the VirB10 polypeptide comprises SEQ ID NO: 1.

Typically, T4SS is present in gram negative bacteria, such as *Rickettsia* spp., *Ehrlichia* spp., *Helicobacter* spp., *Legionella* spp., *Bartonella* spp., *Brucella* spp., and *Anaplasma* spp.

Non-limiting examples of the bacterial species containing endogenous T4SS include: *Rickettsia typhi, Rickettsia prowazekii, Rickettsia rickettsia, Rickettsia conorii, Ehrlichia chaffeensis, Helicobacter pylori, Legionella pneumophila, Bartonella species, Anaplasma marginale, Anaplasma phagocytophilum, Ehrlichia ruminantium, Brucella* species and *Ehrlichia canis*. Additional examples of bacterial species having T4SS and in which the invention can be practiced are well known to a person of ordinary skill in the art and such embodiments are within the purview of the invention. The subject invention can also provide protection against bacterial species that lack an endogenous T4SS system and which have been genetically manipulated to express T4SS.

In one embodiment, VirB10 of *Anaplasma phagocytophilum* or a fragment of VirB10 can be used to immunize a host against *A. phagocytophilum* infection. VirB10 in bacteria other than *A. phagocytophilum* can be identified based on sequence homology and such VirB10 or their fragments can be used in a vaccine to immunize against the infection by bacteria having T4SS. The following list provides non-limiting examples of UniProt entries for VirB10 proteins (each of which is hereby incorporated by reference in its entirety) in various bacteria having T4SS: A0A011QMA5 (SEQ ID NO: 28), A0A011TLZ5 (SEQ ID NO: 29), A0A021WBD5 (SEQ ID NO: 30), A0A021XC05 (SEQ ID NO: 31), A0A059FPP8 (SEQ ID NO: 32), A0A061Q3H1 (SEQ ID NO: 33), A0A063X2U5 (SEQ ID NO: 34), A0A068HFV0 (SEQ ID NO: 35), A0A069HMU4 (SEQ ID NO: 36), A0A070A750 (SEQ ID NO: 37), A0A071M5U1 (SEQ ID NO: 38), A0A0731Y47 (SEQ ID NO: 39), A0A074MLS9 (SEQ ID NO: 40), A0A074TCY6 (SEQ ID NO: 41), A0A076G4V3 (SEQ ID NO: 42), A0A085AA72 (SEQ ID NO: 43), A0A085IIV0 (SEQ ID NO: 44), A0A090MT70 (SEQ ID NO: 45), A0A095CKP1 (SEQ ID NO: 46), A0A099QA58 (SEQ ID NO: 47), A0A0A0XLH7 (SEQ ID NO: 48), A0A0A1FHZ1 (SEQ ID NO: 49), A0A0A1IXK7 (SEQ ID NO: 50), A0A0A1PDK4 (SEQ ID NO: 51), A0A0A6W9W5 (SEQ ID NO: 52), A0A0B2BVJ6 (SEQ ID NO: 53), A0A0B2C1C1 (SEQ ID NO: 54), A0A0B5E2C6 (SEQ ID NO: 55), A0A0B7J1D9 (SEQ ID NO: 56), A0A0B7MV56 (SEQ ID NO: 57), A0A0C1ELG7 (SEQ ID NO: 58), A0A0C1MQK6 (SEQ ID NO: 59), A0A0D6GL13 (SEQ ID NO: 60), A0A0D6PK86 (SEQ ID NO: 61), A0A0D6QEJ3 (SEQ ID NO: 62), A1YBN8 (SEQ ID NO: 63), A3U3E8 (SEQ ID NO: 64), A3UHL6 (SEQ ID NO: 65), A3VIX9 (SEQ ID NO: 66), A3XDX0 (SEQ ID NO: 67), A5CFI6 (SEQ ID NO: 68), A7FCK5 (SEQ ID NO: 69), B2FJH5 (SEQ ID NO: 70), B4RHY3 (SEQ ID NO: 71), B6JK51 (SEQ ID NO: 72), B9JE62 (SEQ ID NO: 73), C3KFT1 (SEQ ID NO: 74), C6V5M2 (SEQ ID NO: 75), D3NTS2 (SEQ ID NO: 76), D5T6H3 (SEQ ID NO: 77), E0SJI8 (SEQ ID NO: 78), E5Y6Z7 (SEQ ID NO: 79), F0J7S0 (SEQ ID NO: 80), F4GMM5 (SEQ ID NO: 81), F7XVQ3 (SEQ ID NO: 82), H2ERZ5 (SEQ ID NO: 83), H9AY00 (SEQ ID NO: 84), I0EPK5 (SEQ ID NO: 85), I4MQG7 (SEQ ID NO: 86), I7F101 (SEQ ID NO: 87), J0B7G3 (SEQ ID NO: 88), JIIY73 (SEQ ID NO: 89), J8TK55 (SEQ ID NO: 90), K9PIS4 (SEQ ID NO: 91), L7SYL6 (SEQ ID NO: 92), NIMENI (SEQ ID NO: 93), Q0FXR1 (SEQ ID NO: 94), QILN34 (SEQ ID NO: 95), Q2K2E3 (SEQ ID NO: 96), Q2YJ81 (SEQ ID NO: 97), Q52SK2 (SEQ ID NO: 98), Q5EPB9 (SEQ ID NO: 99), Q69BE6 (SEQ ID NO: 100), Q8 RPM1 (SEQ ID NO: 101), Q9A5M5 (SEQ ID NO: 102), Q9AGG7 (SEQ ID NO: 103), S2WS02 (SEQ ID NO: 104), S5YJB5 (SEQ ID NO: 105), S9QA92 (SEQ ID NO: 106), T0HQB6 (SEQ ID NO: 107), T0QH67 (SEQ ID NO: 108), T1XMT8 (SEQ ID NO: 109), U1H6S8 (SEQ ID NO: 110), V8QMP0 (SEQ ID NO: 111), X6JZV3 (SEQ ID NO: 112) and X7EE79 (SEQ ID NO: 113). A person of ordinary skill in the art can identify VirB10 in additional bacteria having T4SS and such embodiments are within the purview of the invention.

Accordingly, an embodiment of the invention provides a vaccine comprising an immunologically effective amount of VirB10 or a fragment of VirB10 and a pharmaceutically acceptable carrier and/or an adjuvant. Another embodiment of the invention provides a vaccine comprising an immunologically effective amount of a polynucleotide encoding VirB10 or a polynucleotide encoding a fragment of VirB10 and a pharmaceutically acceptable carrier and/or an adjuvant. For the purposes of this invention the term "immunologically effective amount" refers to the amount of VirB10 or a fragment of the VirB10 which elicits immune response in a host so that the host is protected from future infection caused by the bacterium in which VirB10 is present naturally (endogenously) or a bacterium genetically modified to express VirB10.

The term "endogenous" (and grammatical variations thereof) or the phrase "the bacterium in which VirB10 is present naturally" indicates that a particular VirB10 is a part of the T4SS present in the bacterium as the bacterium exists in nature, i.e., in the wild type bacterium.

In one embodiment VirB10, a fragment of VirB10, a polynucleotide encoding VirB10 or a polynucleotide encoding a fragment of VirB10 is labeled. The label can be designed for in vivo visualization of the protein, peptide or polynucleotide, for targeting the protein, peptide or polynucleotide to a specific tissue, organ or cell of the host, to increase the in vivo stability of the protein, peptide or polynucleotide or to increase immunogenicity of the protein or peptide.

Non-limiting examples of a label designed to visualize VirB10, a fragment of VirB10, a polynucleotide encoding VirB10 or a polynucleotide encoding a fragment of VirB10 include a fluorescent label, an enzyme label and a chromophore label. Additional examples of labels designed to visualize VirB10, a fragment of VirB10, a polynucleotide encoding VirB10 or a polynucleotide encoding a fragment of VirB10 are well known to a person of ordinary skill in the art and such embodiments are within the purview of the invention.

A label designed to target VirB10, a fragment of VirB10, a polynucleotide encoding VirB10 or a polynucleotide encoding a fragment of VirB10 to a tissue, organ or cell includes antibodies or fragments of antibodies or other biomolecules which specifically bind to one or more surface biomolecules present on the target tissue, organ or cell. The label can be designed to target, for example, Fc receptors, C-type lectins, complement receptors, major histocompatibility proteins, or other receptors present on the surface of dendritic cells or antigen presenting cells. Additional examples of suitable target biomolecules and corresponding binding biomolecules are well known to a person of ordinary skill in the art and such embodiments are within the purview of the invention.

A label designed to increase the in vivo stability or immunogenicity of VirB10 or a fragment of VirB10 includes tripalmitoyl-S-glyceryl cysteine, polylysine core, carbohydrate, N-pyroglutamate, amide group on the C terminus, acetyl group, glycosyl group, lipid group, unnatural amino acids, peptidomimetics, peptide carriers and polyethylene glycol (PEG). Non-limiting examples of labels that increase the in vivo stability or immunogenicity of VirB10 or a fragment of VirB10 are discussed in Goodwin et al. The contents of Goodwin et al. are herein incorporated by reference in their entirety. Additional examples of labels which can increase the in vivo stability or immunogenicity of VirB10 or a fragment of VirB10 are well known to a person of ordinary skill in the art and such embodiments are within the purview of the invention.

In one embodiment, VirB10 or a fragment of VirB10 is modified to increase its in vivo stability. Non-limiting examples of modifications which increase the in vivo stability of VirB10 or a fragment of VirB10 include incorporation of non-natural amino acids, pseudo-peptide bonds and cyclization. Additional examples of modifications that increase the in vivo stability of VirB10 or a fragment of VirB10 are also described in Goodwin et al. and Gentilucci et al. The contents Goodwin et al. and Gentilucci et al. are herein incorporated by reference in their entirety. Additional examples of modifications which can increase the in vivo stability of VirB10 or a fragment of VirB10 are well known to a person of ordinary skill in the art and such embodiments are within the purview of the invention.

An embodiment of the invention provides a vaccine comprising a fragment of VirB10 or a polynucleotide encoding a fragment of VirB10 and a pharmaceutically acceptable carrier and/or an adjuvant, wherein the fragment elicits an immune response in a host and the host is immune to a future infection caused by the bacterium in which the particular VirB10 is present naturally. The fragment of VirB10 used in the vaccines of the invention can comprise about 5 to about 50, about 10 to about 40, about 15 to about 30, about 20, about 10 or about 5 amino acids.

In one embodiment, the fragment of VirB10 is selected from the fragments provided in Table 1. In another embodiment, the VirB10 fragment or VirB10 polypeptide can be fused to a heterologous sequence, such as a carrier protein (e.g., bovine serum albumin, keyhole limpet hemocyanin, ovalbumin or other carrier protein used to stimulate an immune response to peptides).

TABLE 1

Examples of fragments of VirB10 protein used in the vaccines of the invention.

| SEQ ID NO | Start Position in SEQ ID NO: 1 | Sequence | End Position in SEQ ID NO: 1 |
| --- | --- | --- | --- |
| 13 | 16 | DNVNVVGVAKSKKLFVIIVVLIATGLMYYFF | 46 |
| 14 | 85 | APRILTPPPRLPELPPLVMPTVPDIPVVTKLLKP | 118 |
| 15 | 147 | EISLPLPYK | 155 |
| 16 | 214 | QSPSVRA | 220 |
| 17 | 227 | RYIILQG | 233 |
| 18 | 235 | MIDAVLET | 242 |
| 19 | 247 | DISGVLRAVVSRDVYASSGDAVVIPKG | 273 |
| 20 | 275 | RLIGSYFF | 282 |
| 21 | 289 | VRVDVNWSRVILPHGVDIQIA | 309 |

TABLE 1-continued

Examples of fragments of VirB10 protein used in the vaccines of the invention.

| SEQ ID NO | Start Position in SEQ ID NO: 1 | Sequence | End Position in SEQ ID NO: 1 |
|---|---|---|---|
| 22 | 321 | ISGVVDN | 327 |
| 23 | 329 | VGSILTSTIFLAGISLGTAYVTEQIPS | 355 |
| 24 | 357 | RTETVKVET | 365 |
| 25 | 376 | TSSSLSTKIVSD | 387 |
| 26 | 407 | TPTVYVDQ | 414 |
| 27 | 416 | TVMKVFVNQDVVFP | 429 |

The vaccine of the invention can be formulated using adjuvants, emulsifiers, pharmaceutically-acceptable carriers or other ingredients routinely provided in a vaccine. Optimum formulations can be readily designed by one of ordinary skill in the art and can include formulations for immediate release and/or for sustained release, and for induction of systemic immunity and/or induction of localized mucosal immunity (e.g., the formulation can be designed for intranasal, intravaginal or intrarectal administration).

Guidelines for designing optimal vaccines can be found in Brito et al., Avanti and Li et al. The contents of Brito et al. are herein incorporated by reference in their entirety, particularly, page 132, Table 1; page 133 under immune potentiator adjuvants; page 133-136 under aluminum salt adjuvants; page 136-139 under emulsions; 139-140 under liposomes as adjuvants; page 140-141 under PLG particulate delivery systems; and page 141 under alternate particulate systems. The contents of Avanti et al. are also herein incorporated by reference in their entirety, particularly Chapters 1, 2 and 7. Further, the contents of Li et al. are herein incorporated by reference in their entirety, particularly pages 521-527 under Particulate Peptide Vaccine Delivery Methods.

The vaccine disclosed herein can be formed with a pharmaceutically acceptable carrier such as a phosphate buffered saline, a bicarbonate solution, or an adjuvant to produce a pharmaceutical composition. The carrier must be "acceptable" in the sense that it is compatible with the active ingredient of the composition, and preferably capable of stabilizing the active ingredient and not deleterious to the subject to be treated. The carrier is selected on the basis of the mode and route of administration and standard pharmaceutical practice. Suitable pharmaceutical carriers and diluents, as well as pharmaceutical necessities for their use, are described in Remington's Pharmaceutical Sciences.

In one embodiment, the antigen is mixed with an adjuvant to form a composition useful for immune modulation. This composition may be prepared as injectable, as liquid solutions or as emulsions. See U.S. Pat. Nos. 4,601,903; 4,599,231; 4,599,230; and 4,596,792. An "adjuvant" refers to a substance added to an immunogenic composition, such as a vaccine, that, while not having any specific antigenic effect in itself, can stimulate the immune system and increase the immune response to the immunogenic composition. Examples of adjuvants include, but are not limited to, alum, alum-precipitate, Freund's complete adjuvant, Freund's incomplete adjuvant, monophosphoryl-lipid A/trehalose dicorynomycolate adjuvant and water in oil emulsions.

A further embodiment of the invention provides a method of immunizing a host against an infection by a bacterium having T4SS, the method comprising administering to the host a vaccine comprising a pharmaceutically effective amount of VirB10, a fragment of VirB10, a polynucleotide encoding VirB10 or a polynucleotide encoding the fragment of VirB10 and a pharmaceutically acceptable carrier and/or an adjuvant.

The method of the invention can be used to immunize a host, for example, a mammal, against an infection by a bacterium having the T4SS. Non-limiting examples of mammals in which the methods of the invention can be practiced include dogs, cats, pigs, cattle, rabbits, sheep, goats, deer, horses, rodents and humans. Additional examples of hosts in which the methods of the invention can be practiced are well known to a person of ordinary skill in the art and such embodiments are within the purview of the invention.

In one embodiment, the invention provides a method of immunizing a host against an infection by a bacterium containing T4SS, wherein the method comprises administering to the host a vaccine comprising VirB10, a fragment of VirB10, a polynucleotide encoding VirB10 or a polynucleotide encoding the fragment of VirB10 and a pharmaceutically acceptable carrier and/or an adjuvant, and wherein the bacterium is a member of *Rickettsia* spp., *Ehrlichia* spp., *Helicobacter* spp., *Legionella* spp., *Bartonella* spp., *Brucella* spp., and/or *Anaplasma* spp. In certain embodiments, the bacterium is *Rickettsia prowazekii, Rickettsia rickettsia, Rickettsia conorii, Ehrlichia chaffeensis, Helicobacter pylori, Legionella pneumophila,* a *Bartonella* species, a *Brucella* species (e.g., *Brucella abortus*), *Anaplasma marginale, Anaplasma phagocytophilum, Ehrlichia ruminantium* or *Ehrlichia canis*.

The vaccine of the invention can be administered by any convenient route including subcutaneous, intradermal, intranasal, oral, intramuscular, intraperitoneal, or other parenteral or enteral route. A person of ordinary skill in the art can identify a particular route of administration suitable for a particular host and a given bacterium and such embodiments are within the purview of the invention.

VirB10, a fragment of VirB10, a polynucleotide encoding VirB10 or a polynucleotide encoding a fragment of VirB10 can be administered as a single dose or multiple doses. Optimum immunization schedules can be readily determined by the ordinarily skilled artisan and can vary with parameters, for example, age, weight and species of the host, the type of vaccine composition and the bacterium against which immunization is desired and such embodiments are within the purview of the invention.

An embodiment of the invention provides a method of immunizing a host against an infection by a bacterium having T4SS, wherein the immunization is performed according to prime boost immunization. For the purpose of this invention, the phrase "prime boost immunization" indicates that the VirB10, a fragment of VirB10, a polynucleotide encoding VirB10 or a polynucleotide encoding a fragment of VirB10 is administered in a plurality of doses. As such, the immune system of a host encounters multiple exposures to VirB10, a fragment of VirB10, a polynucleotide encoding VirB10 or a polynucleotide encoding a fragment of VirB10, which results in a stronger immune response compared to single administration of the vaccine. Certain examples of prime boost immunizations are discussed in Woodland et al., the contents of which are herein incorporated by reference in their entirety.

In one embodiment, the prime boost immunization comprises administering a pharmaceutically effective amount of a polynucleotide encoding VirB10 or a polynucleotide encoding a fragment of VirB10 followed by administering a pharmaceutically effective amount of VirB10 or a fragment of VirB10. In another embodiment, the prime boost immunization comprises administering a pharmaceutically effective amount of VirB10 or a fragment of VirB10 followed by administering a polynucleotide encoding VirB10 or a polynucleotide encoding a fragment of VirB10.

In certain embodiments, the interval between the administration of the polynucleotide and the protein or a fragment of the protein is about 1 week to about 4 weeks, about 2 weeks to 3 weeks, 2 to 4 weeks, or about 2 weeks. In another embodiment of the invention, the vaccine is administered in the form of a "cocktail" that contains at least two polynucleotides or at least two peptides. The cocktail can also contain a mixture of a polynucleotide and a peptide.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Preparation of Soluble Recombinant VirB9-1, VirB9-2 and VirB10s

The open reading frames of *A. phagocytophilum* virB9-1, virB9-2 and virB10 genes were amplified by PCR (Table 2) and the purified products cloned into a DNA vaccine vector and the pET101/D-TOPO directional expression system. Recombinant constructs were purified and sequences were confirmed by PCR and DNA sequencing. The pET101 constructs were re-transformed into *E. coli* BL21 Star (DE3) cells and induced to express with 0.5 mM IPTG and growth in M9 minimal media supplemented with 50 μg/ml carbenicillin and 1% glucose. Expression of recombinant VirB9-1, Vir9-2 and VirB10 was verified by SDS-PAGE followed by Western blot analyses using His-tagged monoclonal antibody (FIG. 1). 500 ml of IPTG-induced cultures were processed and soluble fractions containing the recombinant $His_6$-tagged fusion proteins were purified using low-density Nickel agarose bead columns. Eluted protein was concentrated using Centricon Plus-70 centrifugal filter units, and concentration determined using a Qubit protein assay kit. The recombinant proteins were run on a SDS-PAGE gel to confirm purity.

For preparation of the DNA vaccine, the VirB9-1, VirB9-2, and VirB10 were separately amplified by PCR and cloned into the vector pcDNA3.1/CT-GFP-TOPO (Invitrogen). This vector provides the CMV (cytomegalovirus) promoter 5' to the inserted gene for constitutive expression in mammalian cells and the GFP (Green Fluorescent Protein) gene 3' to the inserted gene. The validity of the constructs was checked prior to use in immunizations by sequencing the gene insert and junction regions and by transfecting RF6A endothelial cells with isolated plasmid DNA to verify GFP expression by fluorescence. For preparation of immunizing plasmid DNA, bacteria were grown in LB/Ampicillin 100 μg/ml. The ZR Plasmid Gigaprep kit (Zymo Research) was used to isolate endotoxin-free plasmid DNA from the bacterial pellets. The yields of DNA obtained were: TOPO-GFP (control, no inserted gene): 6 liters of culture gave ~6.5 mg; VirB 9-1 plasmid: 6 liters of culture gave ~29 mg; VirB 9-2 plasmid: 6 liters of culture gave ~19 mg; and VirB10 plasmid: 4 liters of culture gave ~23 mg.

The culture and purification conditions described above were optimized to produce adequate yields of soluble recombinant VirB9-1, VirB9-2 and VirB10. For protein expression the temperature was reduced to 4° C. to avoid protein aggregation and reduction of heat shock proteases that could promote inclusion body formation, cellular toxicity and high levels of protein degradation. Additionally, modification of nutrient media was employed to avoid excess bacterial growth and depletion of substrates and cofactors. This resulted in the isolation of soluble recombinant VirB9-1, VirB9-2 and VirB10s (FIG. 1) suitable for use in the immunization experiments.

TABLE 2

PCR primers used to amplify VirB9-1, VirB9-2 and VirB10 and Taqman qPCR primers and probes used to quantify *A. phagocytophilum* load.

|  |  | Target | Size |
|---|---|---|---|
|  | PCR |  |  |
| AB1703 | CACCATGAGCACAAATATTGGCGTACCAG (SEQ ID NO: 114) | virB9-1 | 769 bp |
| AB1704 | ACTAAGAGCCTGATTCACAACTTCTACACTCCTGC (SEQ ID NO: 115) |  |  |

TABLE 2-continued

PCR primers used to amplify VirB9-1, VirB9-2 and VirB10 and Taqman qPCR primers and probes used to quantify A. phagocytophilum load.

|  |  | Target | Size |
|---|---|---|---|
| AB1705 | CACCATGGCTGATGATCACATTAAGACCTTGAAC (SEQ ID NO: 116) | virB9-2 | 736 bp |
| AB1706 | TTTCCGGCGTCTTTCAGCACCCTTC (SEQ ID NO: 117) |  |  |
| AB1707 | CACCATGGCTGACGAAATAAGGGGTTCTAG (SEQ ID NO: 118) | virB10 | 1306 bp |
| AB1708 | CCTCACCGCATCACGAGGAAATACTACG (SEQ ID NO: 119) |  |  |
| qPCR |  |  |  |
| AB1334 | AGATGCTGACTGGGGATGAG (SEQ ID NO: 120) | msp5 | 125 bp |
| AB1335 | TCGGCATCAACCAAGTACAA (SEQ ID NO: 121) |  |  |
| *AB1336 | CGTAGGTGAGTCTGATAGTGAAGG (SEQ ID NO: 122) |  |  |

*Oligonucleotide labeled with Hexachloro-fluorescein (HEX) at the 5' end and Tetramethylrhodamine TAMRA at the 3' end Example 2—*A. phagocytophilum* Infection Kinetics in Different Mouse Strains Three different mouse strains (C57BL/6, C3H/HeN, and Balb/C) were tested to evaluate *A. phagocytophilum* infection kinetics and to select an appropriate mouse strain for *A. phagocytophilum* infection for immunization and challenge experiments. Two C57BL/6, two C3H/HeN and two Balb/C mice were inoculated with isolated organisms from $5.22 \times 10^5$ infected HL-60 cells (>90% infection). DNA extracted from blood collected every other day over 24 days was used to determine the *A. phagocytophilum* load by measuring the increase in the number of genome equivalents (GE) using qPCR with primers and probes that target the single copy gene msp5 (Table 2). Ten-fold serial dilutions of the NY18E2/pCR-TOPO plasmid carrying the msp5 gene were used for standard curve preparation, and the msp5 gene copy numbers were calculated based on the standard curve.

Figure 2:
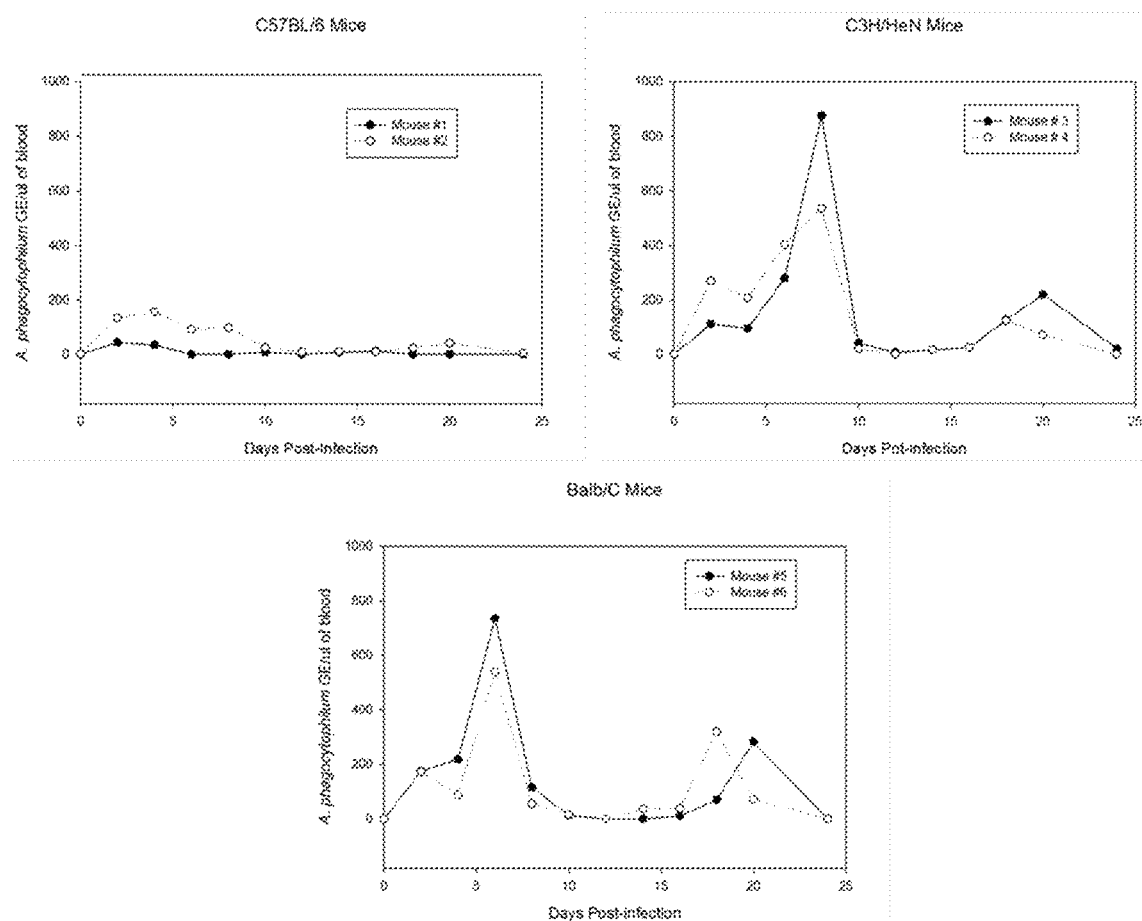
FIG. 2. *A. phagocytophilum* burden in mouse blood (different strains infected with HZ). *A. phagocytophilum* growth kinetics in blood were measured by determining GE/µl based on the single copy gene msp5. GE/µl calculations were normalized based on the volume of blood collected per animal at each time point.

Results showed that C3H/HeN and Balb/C mice are susceptible to *A. phagocytophilum* (human HZ strain) infection as shown by an increase of GE in blood at 8 days post-infection for C3H/HeN mice (average of 705 GE/µl of blood) and between 6 and 8 days post-infection in Balb/C mice (average of 636 GE/µl of blood) (FIG. 2). In contrast, in C57BL/6 mice, only mouse #2 presented a minor increase of up to 150 GE/µl of blood at day 6 post-infection indicating that this strain better controlled *A. phagocytophilum* infection. During the course of infection, a relapse peak of infection was detected after 16 days post-infection in both C3H/HeN and Balb/C strains suggesting a possible chronic infection. C3H/HeN strain was selected to determine mouse response to immunization with DNA vaccine followed by a recombinant protein vaccine encoding VirB9-1, VirB9-2 and VirB10 because the results presented here support previous work which indicate that C3H/HeN is a good model for *A. phagocytophilum* infection.

Immunization and Challenge of C3H/HeN 5 groups of 10 mice were vaccinated in a prime boost fashion with plasmid DNA immunization followed by recombinant proteins as described in Table 3.

TABLE 3

C3H/HeN mice immunization schedule.

| Group | Immunogen | Dosage | Amount |  |
|---|---|---|---|---|
| I | virB9-1 plasmid | 2 | 100 µg | 2 week intervals |
|  | rVirB9-1 protein | 2 | 100 µg | 2 week intervals |
| II | virB9-2 plasmid | 2 | 100 µg | 2 week intervals |
|  | rVirB9-2 protein | 2 | 100 µg | 2 week intervals |
| III | virB10 plasmid | 2 | 100 µg | 2 week intervals |
|  | rVirB102 protein | 2 | 100 µg | 2 week intervals |
|  | virB9-1 plasmid, virB9-2 plasmid, virB10 plasmid | 2 | 100 µg/ plasmid | 2 week intervals |
| IV | rVirB9-1, rVirB9-2, rVirB10 | 2 | 100 µg/ protein | 2 week intervals |
|  | Empty TOPO-GFP | 2 | 100 µg | 2 week intervals |
| V | Ovalbumin | 2 | 100 µg | 2 week intervals |

Figure 3A:
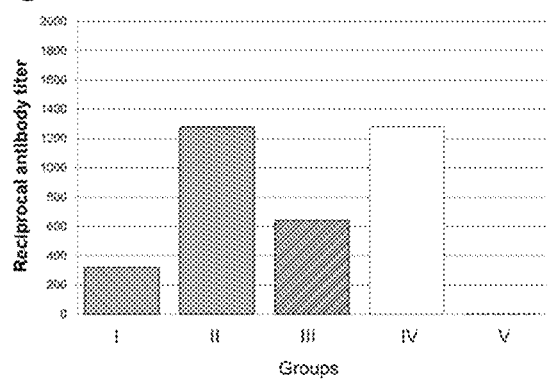
FIGS. 3A-3B. *A. phagocytophilum* antibody responses in immunized C3H/HeN mice. A) *A. phagocytophilum* specific antibody responses in immunized mice were measured by IFA and titers expressed as the reciprocal of the highest dilution at which specific fluorescence was detected (B). Binding of antibodies specific to *A. phagocytophilum* was seen as defined red fluorescent inclusions (morulae) in infected HL-60 cells; in contrast similar fluorescent inclusions were not visualized using antibodies from negative control group V. Picture taken at 1:160 dilution of all antisera.
Figure 3B:
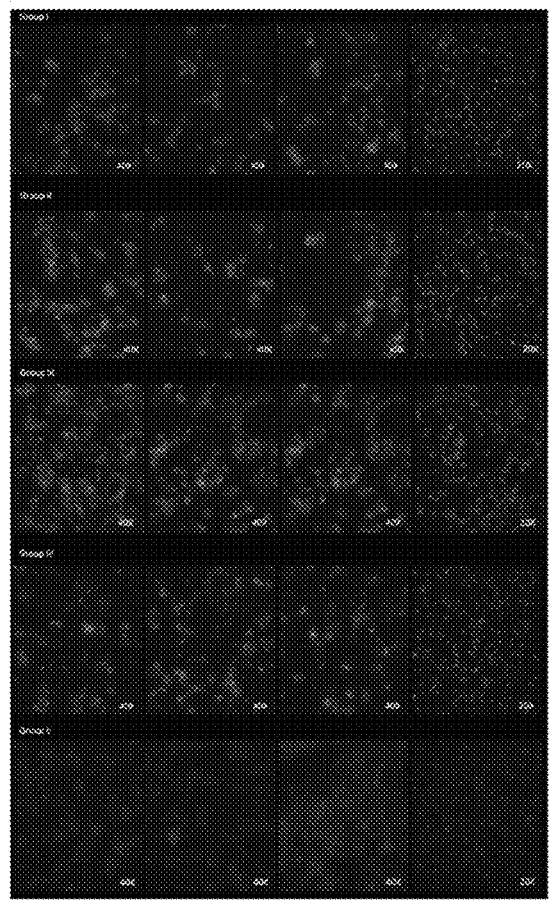

Two weeks after the last immunization, three mice were randomly selected for serum collection and for isolation of spleen and lymph nodes from each group. Preliminary serological work was performed using immunofluorescence assay (IFA) to determine how the immunized mice reacted to whole *A. phagocytophilum* organisms and to measure antibody titers. Antigen slides were prepared from *A. phagocytophilum*/HZ infected HL-60 cells. Sera from the three mice in each group were combined and serially diluted starting from 1:80 up to 1:81920. Ten microliters of serum was applied to each well with duplicates for each dilution and incubated for 1 hour at room temperature in a humidified chamber. After incubation the serum was removed and the slides washed five times for 5 minutes. Ten microliters of Alexa fluor 568-Goat anti-mouse IgG antibody at a dilution of 1:1600 was applied to each well and incubated for 1 hour at room temperature. The slides then were washed as described above and mounted with ProLong Gold antifade reagent with DAPI (4',6-diamidino-2-phenylindole) (FIG. 3). IFA analysis showed that higher titers of antibodies against *A. phagocytophilum* were detected in the serum of vaccinated animals (Groups I through IV), compared to negative control mice (Group V) vaccinated with Empty TOPO-GFP/Ovalbumin (FIG. 3).

Figure 4:
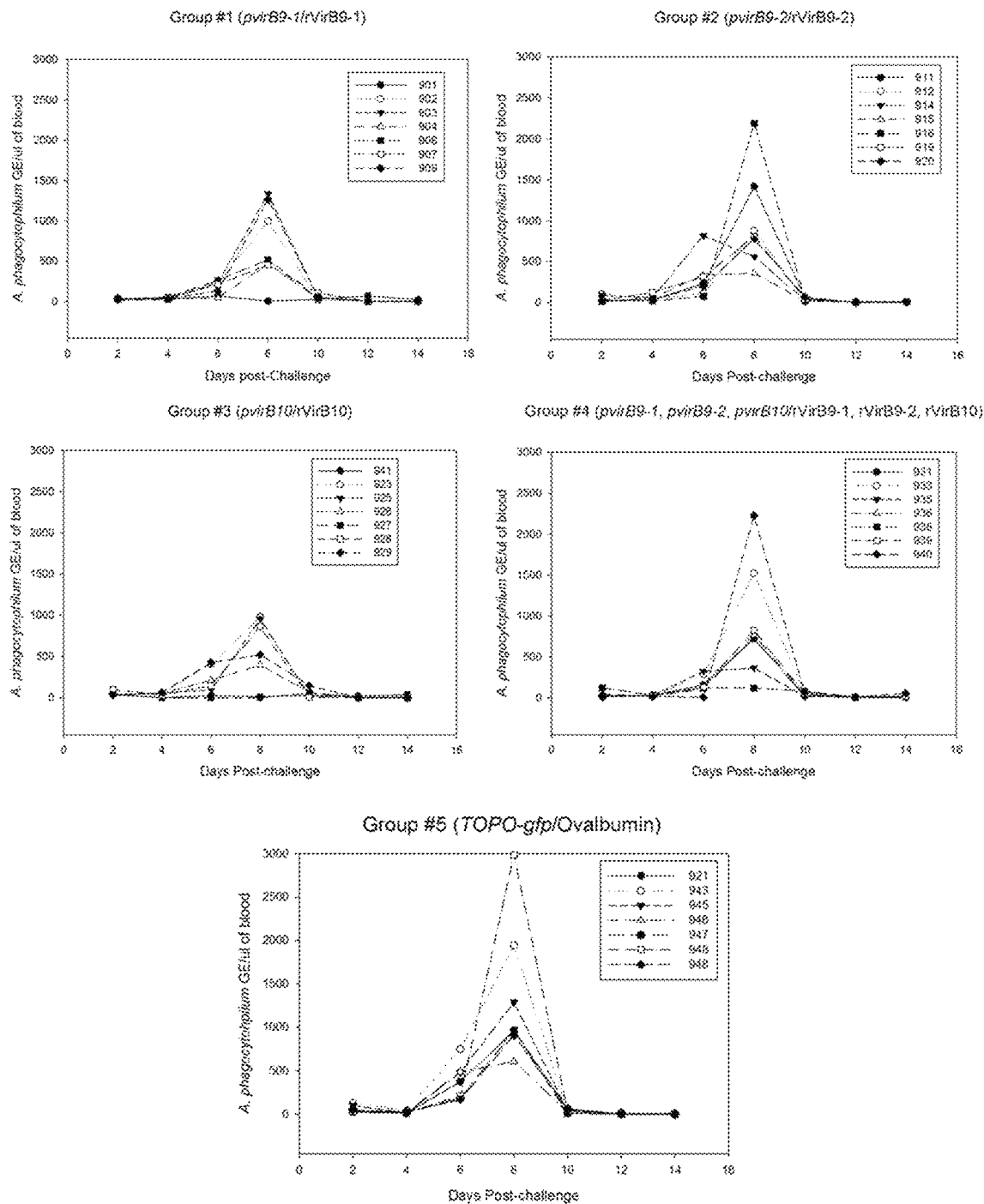
FIG. 4. *A. phagocytophilum* burden in immunized/challenged C3H/HeN mice blood. *A. phagocytophilum* growth kinetics in blood were measured by determining GE/µl based on the single copy gene msp5. GE/µl calculations were normalized based on the volume of blood collected per animal at each time point.
Figure 5:
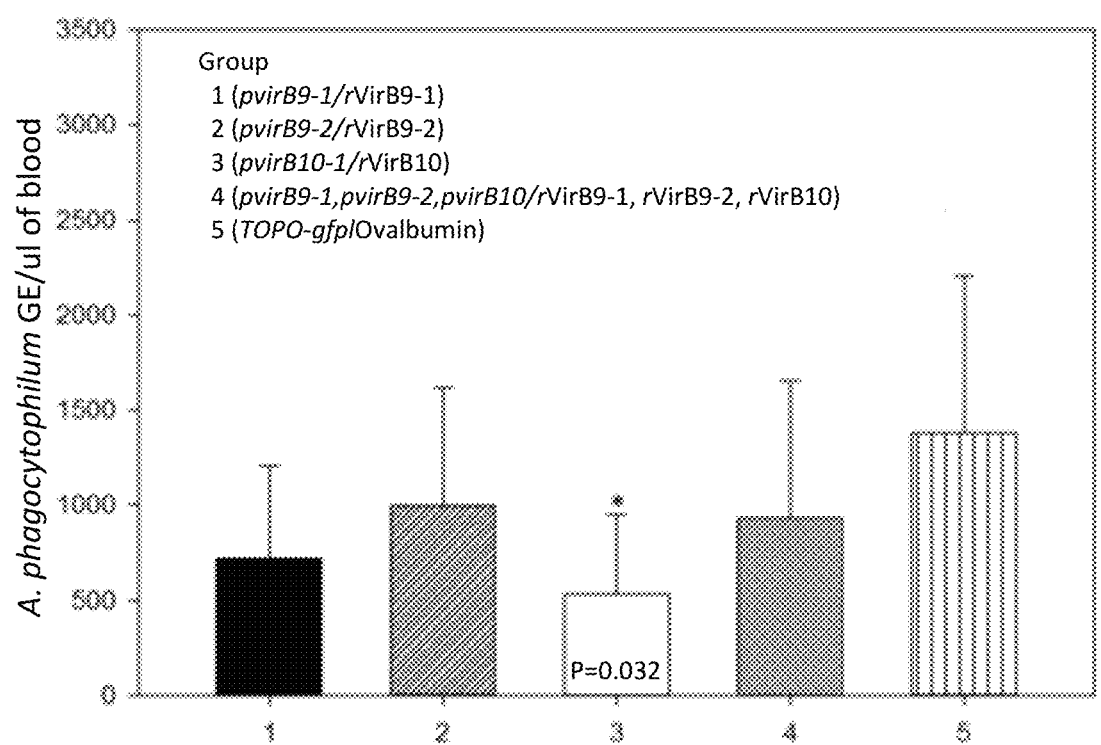
FIG. 5. Protection against *A. phagocytophilum* induced by immunization. *A. phagocytophilum* GE means plus standard deviations (error bars) at the peak of infection. 7 mice from each group were used for this analysis. The values that are significantly different from the values for the control group are indicated by asterisks *, $p<0.05$.
Figure 6:
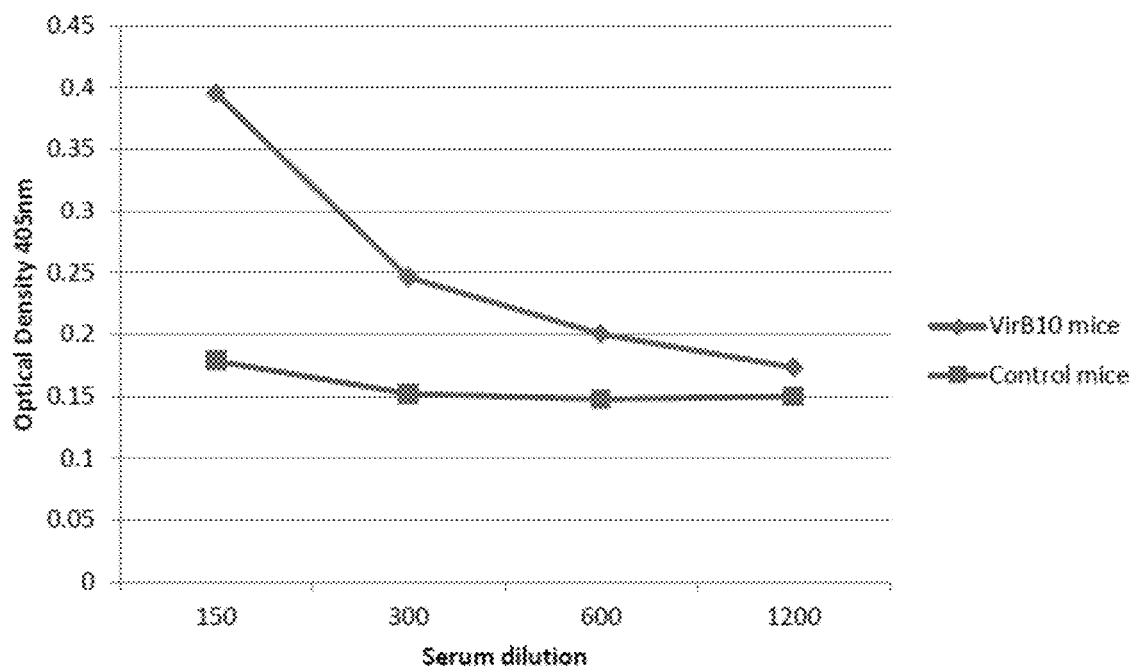
FIG. 6. 3 mice from the groups immunized with either VirB10 or ovalbumin control were sacrificed prior to challenge. Their antibody response was assayed by ELISA using intact *A. phagocytophilum* organisms attached to the ELISA plate. The values represent the average of duplicate readings from the three mice in either the VirB10 or control group. The data show the response of VirB10-immunized mice to whole organisms on the plate and suggest epitopes of VirB10 are surface-exposed and available to bind antibodies.

Protection against *A. phagocytophilum* induced by virB9/VirB9, virB9-2/VirB9-2, and virB10/VirB10 was evaluated. 35 immunized mice (7 mice/group) were challenged with one dose of isolated organisms from $5.63 \times 10^5$ HL-60 infected cells (>90% infected) and the bacterial burden in the blood of each mouse was measured by real time qPCR targeting the single copy gene msp5 to determine the number of *A. phagocytophilum* GE as described above. On day 8, the bacterial load in the blood ranged from 451 GE/µl up to 1267 GE/µl in the mice in Group I, from 358 GE/µl up to 2188 GE/µl in Group II, from 396 GE/µl up to 980 GE/µl in Group III, from 118 GE/µl up to 2225 GE/µl in Group IV and from 607 GE/µl up to 2988 GE/µl in negative control Group V (FIG. 4). However real time qPCR did not detect any *A. phagocytophilum* GE in one mouse from Group I, or in two mice from Group III. Although the bacterial load in Groups I, II and IV was lower than in Group V, these differences were not significant. In contrast, there was a significant difference between the bacterial load in Group III when compared with Group V ($p=0.032$).

These results indicate that immunized mice (pre-challenge) with VirB9, VirB9-2, VirB10 and the mixture of VirB9-1, VirB9-2 and VirB10 developed antibodies that reacted with *A. phagocytophilum*. However real-time qPCR of DNA extracted from the blood of the challenged mice showed that the bacterial load was significantly lower only in Group III when compared to the negative control mice in Group V. Such an result was not expected in view of the antibody titers observed in the Group II and Group IV mice and in view of the Group IV animals that were immunized (primed and boosted) with a mixture of VirB9-1, VirB9-2 and VirB10 (see Table 3 and FIG. 3).

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

REFERENCES

1. Brito et al. (2013), Vaccine adjuvant formulations: A pharmaceutical perspective, *Seminars in Immunology*, 25:130-145.
2. Avanti (2012), Innovative strategies for stabilization of therapeutic peptides in aqueous formulations (Doctoral Dissertation), project D6-202 of the Dutch Top Institute Pharma.
3. Li et al. (2014), Peptide Vaccine: Progress and Challenges, *Vaccines*, 2:515-536.
4. Woodland et al. (2004), Jump-starting the immune system: prime-boosting comes of age, *TRENDS in Immunology*, 25 (2): 98-104.
5. Goodwin et al. (2009), Peptides as therapeutics with enhanced bioactivity, *Current Medicinal Chemistry*, 19:4451-4461.
6. Yang et al. (2009), An introduction to epitope prediction methods and software, *Reviews in Medical Virology*, 19:77-96.
7. Gentilucci et al. (2010), Chemical modifications designed to improve peptide stability: Incorporation of non-natural amino acids, pseudo-peptide bonds, and cyclization, *Current Pharmaceutical Design*, 16:3185-3203.

---

What is claimed is:

1. A method of immunizing a host against an infection by a bacterium having Type 4 secretory system (T4SS), the method comprising administering an effective amount to the host an immunogenic composition comprising an immunologically effective amount of a T4SS protein, optionally conjugated to a carrier protein, and a pharmaceutically acceptable carrier and/or an adjuvant; wherein the T4SS protein consists of VirB10 or a fragment of VirB10 of *Anaplasma phagocytophilum*, and wherein the bacterium is an *Ehrlichia* spp, and further wherein said method of immunizing confers protection against an *Ehrlichia* spp.

2. The method of claim 1, wherein the *Ehrlichia* spp is *Ehrlichia chafeensis*.

3. The method of claim 1, wherein the carrier protein is keyhole limpet hemocyanin, ovalbumin or bovine serum albumin.

4. The method of claim 1, wherein VirB10 or the fragment of VirB10 is cyclized or comprises SEQ ID NO: 1.

5. The method of claim 1, wherein the fragment of VirB10 comprises about 5 to about 50 amino acids.

6. The method of claim 1, wherein the fragment of VirB10 is selected from SEQ ID NO: 13 to 27.

7. The method of claim 6, wherein the fragment of VirB10 is selected from SEQ ID NO: 23 and 25.

* * * * *

SEQUENCE LISTING

```
<160> NUMBER OF SEQ ID NOS: 132

<210> SEQ ID NO 1
<211> LENGTH: 434
<212> TYPE: PRT
<213> ORGANISM: Anaplasma phagocytophilum

<400> SEQUENCE: 1

Met Ala Asp Glu Ile Arg Gly Ser Ser Ser Gly Glu Asn Ile Glu Asp
1               5                   10                  15

Asn Val Asn Val Val Gly Val Ala Lys Ser Lys Lys Leu Phe Val Ile
            20                  25                  30

Ile Val Val Leu Ile Ala Thr Gly Leu Met Tyr Tyr Phe Phe Phe Phe
        35                  40                  45

Asn Lys Glu Ser Ser Asp Asn Glu Glu Asp Thr Gln Ile Pro Arg Val
    50                  55                  60

Ile Glu Glu Lys Glu Val Glu Lys Leu Arg Lys Asp Ala Gly Arg Pro
65                  70                  75                  80

Ala Gln Glu Thr Ala Pro Arg Ile Leu Thr Pro Pro Pro Arg Leu Pro
                85                  90                  95

Glu Leu Pro Pro Leu Val Met Pro Thr Val Pro Asp Ile Pro Val Val
            100                 105                 110

Thr Lys Leu Leu Lys Pro Pro Val Glu Glu Glu Phe Val Glu Glu Tyr
        115                 120                 125

Asn Val Gln Glu Val Pro Ser Pro Met Gly Asn Ile Ala Pro Pro Glu
    130                 135                 140
```

```
Arg Glu Glu Ile Ser Leu Pro Leu Pro Tyr Lys Thr Ile Thr Thr Glu
145                 150                 155                 160

Gln Pro Ser Phe Leu Gly Tyr Asp Lys Glu Lys Arg Gly Ala Pro Met
                165                 170                 175

Ile Ala Phe Gly Gly Gly Gly Glu Ala Ala Gly Ser Glu Ser Gly
            180                 185                 190

Asp Gly Ser Val Gly Gly Lys Glu Asp Ala Arg Phe Thr Ala Trp Gln
195                 200                 205

Gly Leu Glu Gly Thr Gln Ser Pro Ser Val Arg Ala Thr Arg Val Gly
    210                 215                 220

Asp Thr Arg Tyr Ile Ile Leu Gln Gly His Met Ile Asp Ala Val Leu
225                 230                 235                 240

Glu Thr Ala Ile Asn Ser Asp Ile Ser Gly Val Leu Arg Ala Val Val
                245                 250                 255

Ser Arg Asp Val Tyr Ala Ser Ser Gly Asp Ala Val Val Ile Pro Lys
                260                 265                 270

Gly Ser Arg Leu Ile Gly Ser Tyr Phe Phe Asp Ser Ala Gly Asn Asn
            275                 280                 285

Val Arg Val Asp Val Asn Trp Ser Arg Val Ile Leu Pro His Gly Val
290                 295                 300

Asp Ile Gln Ile Ala Ser Ser Gly Thr Asp Glu Leu Gly Arg Asn Gly
305                 310                 315                 320

Ile Ser Gly Val Val Asp Asn Lys Val Gly Ser Ile Leu Thr Ser Thr
                325                 330                 335

Ile Phe Leu Ala Gly Ile Ser Leu Gly Thr Ala Tyr Val Thr Glu Gln
            340                 345                 350

Ile Pro Ser Leu Arg Thr Glu Thr Val Lys Val Glu Thr Pro Ala Asp
            355                 360                 365

Gly Lys Asp Gly Lys Lys Thr Thr Ser Ser Ser Leu Ser Thr Lys Ile
    370                 375                 380

Val Ser Asp Ala Ile Lys Asp Phe Ser Asp Ser Met Lys Glu Ile Val
385                 390                 395                 400

Asn Lys Tyr Ser Asn Arg Thr Pro Thr Val Tyr Val Asp Gln Gly Thr
                405                 410                 415

Val Met Lys Val Phe Val Asn Gln Asp Val Val Phe Pro Arg Asp Ala
            420                 425                 430

Val Arg

<210> SEQ ID NO 2
<211> LENGTH: 281
<212> TYPE: PRT
<213> ORGANISM: Anaplasma phagocytophilum

<400> SEQUENCE: 2

Met Met Asn Phe Tyr Lys Asn Phe Tyr Val Ala Leu Val Thr Ala Phe
1               5                   10                  15

Ala Leu Phe Ser Met Ser Lys Ala Cys Phe Ala Ser Thr Asn Ile Gly
                20                  25                  30

Val Pro Val Ser Val Asp Ser Arg Ile Lys Thr Phe Val Tyr Ser Gln
            35                  40                  45

Asn Glu Val Phe Pro Val Val Phe Asn Tyr Gly Tyr His Ser Tyr Ile
        50                  55                  60

Glu Phe Ser Gln Gly Glu Thr Val Arg Val Met Ala Leu Gly Asp Asn
65                  70                  75                  80
```

```
Ala Asn Trp Lys Ile Arg Pro Val Asp Asn Lys Leu Tyr Val Met Pro
            85                  90                  95

Leu Glu Lys Glu Gly His Thr Asn Met Leu Ile Glu Thr Ser Lys Gly
        100                 105                 110

Arg Ser Tyr Ala Phe Asp Leu Ile Ser Thr Ala Ile Pro Leu Ser Gly
        115                 120                 125

Gly Ala Ala Ser Ser Ile Asn Lys Leu Gly Lys Thr Asn Ser Ala Leu
        130                 135                 140

Ala Asp Leu Ala Tyr Val Val Arg Phe Tyr Tyr Pro Gln Ser Asp Arg
145                 150                 155                 160

Asn Phe Asp Ile Met Gly Gln Lys Leu Glu Ile Ser Pro Pro Ser Leu
                165                 170                 175

Ala Ser Ser Leu Asp Ala Asp Asp Val Glu Ile Glu Pro Asn Ala Thr
                180                 185                 190

Arg Thr Asn Tyr Met Phe Thr Gly Gly Ser Ala His Val Ser Leu Ala
                195                 200                 205

Pro Thr Gln Ala Phe Asp Asp Gly Tyr Leu Thr Tyr Phe Gln Phe Gly
        210                 215                 220

Lys Asn Asn Lys Glu Ile Pro Lys Ile Tyr Val Val Lys Lys Asp Gly
225                 230                 235                 240

Lys Lys Val Pro Cys Lys Met Leu Leu Leu Arg Asp Tyr Val Ile Val
                245                 250                 255

Glu Gly Val His Glu Leu Phe Tyr Leu Asp Phe Gly Asp Gly Arg Ser
                260                 265                 270

Val Glu Val Val Asn Gln Ala Leu Ser
        275                 280

<210> SEQ ID NO 3
<211> LENGTH: 271
<212> TYPE: PRT
<213> ORGANISM: Anaplasma phagocytophilum

<400> SEQUENCE: 3

Met Arg Ser Ala Leu Leu Ile Phe Val Val Leu Leu Tyr Ser Ser
1               5                   10                  15

Ala Gly Leu Ser Lys Gln Glu Pro Arg Ser Ile Ala Ala Asp Asp His
            20                  25                  30

Ile Lys Thr Leu Asn Tyr Asn Pro Gln Ser Ile His Lys Tyr Thr Gly
        35                  40                  45

Phe Tyr Gly Tyr Gln Ser Ser Ile Leu Phe Glu Ala Gly Glu Thr Ile
    50                  55                  60

Ser Thr Val Ser Met Gly Asp Ser Thr Gly Trp Gln Leu Val Pro Gln
65                  70                  75                  80

Gly Asn Arg Leu Phe Ile Lys Pro Val Ala Asp Asn Ala Asp Thr Asn
                85                  90                  95

Val Thr Ile Leu Thr Asn Arg Arg Val Tyr Tyr Phe Glu Leu His Ala
                100                 105                 110

Glu Glu Ala Ser Gly Leu Asp Asp Pro Arg Leu Ala Tyr Glu Val Arg
        115                 120                 125

Leu Val Tyr Pro Ser Leu Glu Gly Ser Ile Gly Gly Asn Val Ser Ala
        130                 135                 140

Val Gly Gly Asp Val Leu Phe Pro Ser Tyr Gln Thr Asp Val Pro Asp
145                 150                 155                 160

Leu Arg Asn Pro Asp Val Ala Arg Lys Gly Leu Asn Phe Asn Tyr Thr
                165                 170                 175
```

-continued

```
Val Ser His Thr Pro Gly Ser Glu Asp Ile Val Pro Leu Arg Val Phe
            180                 185                 190

Asp Asp Gly Lys Phe Thr Tyr Met Gln Phe Ser Gly Val Asn Gly Asp
        195                 200                 205

Leu Pro Ser Val Phe Asn Val Asp Ala Gln Gly Tyr Glu Ser Leu Ile
    210                 215                 220

Asn Phe Arg Met Val Gly Asp Tyr Val Val Ile Glu Arg Thr Ser Arg
225                 230                 235                 240

Ala Phe Thr Leu Arg Tyr Gly Ser Ser Thr Ala Cys Ile Phe Asn Glu
                245                 250                 255

Lys Arg Ala Phe Pro Val Val Lys Gly Ala Glu Arg Arg Lys
            260                 265                 270

<210> SEQ ID NO 4
<211> LENGTH: 29
<212> TYPE: DNA
<213> ORGANISM: Artificial sequence
<220> FEATURE:
<223> OTHER INFORMATION: Forward primer for amplification of DNA
      encoding Vir9B-1 protein

<400> SEQUENCE: 4
caccatgagc acaaatattg gcgtaccag                                    29

<210> SEQ ID NO 5
<211> LENGTH: 35
<212> TYPE: DNA
<213> ORGANISM: Artificial sequence
<220> FEATURE:
<223> OTHER INFORMATION: Reverse primer for amplification of DNA
      encoding Vir9B-1 protein

<400> SEQUENCE: 5
actaagagcc tgattcacaa cttctacact cctgc                             35

<210> SEQ ID NO 6
<211> LENGTH: 34
<212> TYPE: DNA
<213> ORGANISM: Artificial sequence
<220> FEATURE:
<223> OTHER INFORMATION: Forward primer for amplification of DNA
      encoding Vir9B-2 protein

<400> SEQUENCE: 6
caccatggct gatgatcaca ttaagaccct tgaac                             34

<210> SEQ ID NO 7
<211> LENGTH: 25
<212> TYPE: DNA
<213> ORGANISM: Artificial sequence
<220> FEATURE:
<223> OTHER INFORMATION: Reverse primer for amplification of DNA
      encoding Vir9B-2 protein

<400> SEQUENCE: 7
tttccggcgt ctttcagcac ccttc                                        25

<210> SEQ ID NO 8
<211> LENGTH: 30
<212> TYPE: DNA
<213> ORGANISM: Artificial sequence
<220> FEATURE:
<223> OTHER INFORMATION: Forward primer for amplification of DNA
      encoding VirB10
```

-continued

<400> SEQUENCE: 8
caccatggct gacgaaataa ggggttctag 30

<210> SEQ ID NO 9
<211> LENGTH: 28
<212> TYPE: DNA
<213> ORGANISM: Artificial sequence
<220> FEATURE:
<223> OTHER INFORMATION: Reverse primer for amplification of DNA encoding VirB10

<400> SEQUENCE: 9
cctcaccgca tcacgaggaa atactacg 28

<210> SEQ ID NO 10
<211> LENGTH: 20
<212> TYPE: DNA
<213> ORGANISM: Artificial sequence
<220> FEATURE:
<223> OTHER INFORMATION: Forward primer for amplification of msp5 gene from A. phagocytophilum strain HZ for qPCR

<400> SEQUENCE: 10
agatgctgac tggggatgag 20

<210> SEQ ID NO 11
<211> LENGTH: 20
<212> TYPE: DNA
<213> ORGANISM: Artificial sequence
<220> FEATURE:
<223> OTHER INFORMATION: Reverse primer for amplification of msp5 gene from A. phagocytophilum strain HZ for qPCR

<400> SEQUENCE: 11
tcggcatcaa ccaagtacaa 20

<210> SEQ ID NO 12
<211> LENGTH: 24
<212> TYPE: DNA
<213> ORGANISM: Artificial sequence
<220> FEATURE:
<223> OTHER INFORMATION: Sequence of the qPCR probe for msp5 gene from A. phagocytophilum strain HZ

<400> SEQUENCE: 12
cgtaggtgag tctgatagtg aagg 24

<210> SEQ ID NO 13
<211> LENGTH: 31
<212> TYPE: PRT
<213> ORGANISM: Artificial sequence
<220> FEATURE:
<223> OTHER INFORMATION: fragments of VirB10 protein from A. phagocytophilum strain HZ

<400> SEQUENCE: 13

```
Asp Asn Val Asn Val Val Gly Val Ala Lys Ser Lys Lys Leu Phe Val
1               5                   10                  15

Ile Ile Val Val Leu Ile Ala Thr Gly Leu Met Tyr Tyr Phe Phe
            20                  25                  30
```

<210> SEQ ID NO 14
<211> LENGTH: 34
<212> TYPE: PRT
<213> ORGANISM: Artificial sequence -continued
<220> FEATURE:
<223> OTHER INFORMATION: fragments of VirB10 protein from A.
      phagocytophilum strain HZ

<400> SEQUENCE: 14

Ala Pro Arg Ile Leu Thr Pro Pro Pro Arg Leu Pro Glu Leu Pro Pro
1               5                   10                  15

Leu Val Met Pro Thr Val Pro Asp Ile Pro Val Val Thr Lys Leu Leu
            20                  25                  30

Lys Pro

<210> SEQ ID NO 15
<211> LENGTH: 9
<212> TYPE: PRT
<213> ORGANISM: Artificial sequence
<220> FEATURE:
<223> OTHER INFORMATION: fragments of VirB10 protein from A.
      phagocytophilum strain HZ

<400> SEQUENCE: 15

Glu Ile Ser Leu Pro Leu Pro Tyr Lys
1               5

<210> SEQ ID NO 16
<211> LENGTH: 7
<212> TYPE: PRT
<213> ORGANISM: Artificial sequence
<220> FEATURE:
<223> OTHER INFORMATION: fragments of VirB10 protein from A.
      phagocytophilum strain HZ

<400> SEQUENCE: 16

Gln Ser Pro Ser Val Arg Ala
1               5

<210> SEQ ID NO 17
<211> LENGTH: 7
<212> TYPE: PRT
<213> ORGANISM: Artificial sequence
<220> FEATURE:
<223> OTHER INFORMATION: fragments of VirB10 protein from A.
      phagocytophilum strain HZ

<400> SEQUENCE: 17

Arg Tyr Ile Ile Leu Gln Gly
1               5

<210> SEQ ID NO 18
<211> LENGTH: 8
<212> TYPE: PRT
<213> ORGANISM: Artificial sequence
<220> FEATURE:
<223> OTHER INFORMATION: fragments of VirB10 protein from A.
      phagocytophilum strain HZ

<400> SEQUENCE: 18

Met Ile Asp Ala Val Leu Glu Thr
1               5

<210> SEQ ID NO 19
<211> LENGTH: 27
<212> TYPE: PRT
<213> ORGANISM: Artificial sequence
<220> FEATURE:
<223> OTHER INFORMATION: fragments of VirB10 protein from A.
      phagocytophilum strain HZ

```
<400> SEQUENCE: 19

Asp Ile Ser Gly Val Leu Arg Ala Val Ser Arg Asp Val Tyr Ala
1               5                   10                  15

Ser Ser Gly Asp Ala Val Val Ile Pro Lys Gly
            20                  25

<210> SEQ ID NO 20
<211> LENGTH: 8
<212> TYPE: PRT
<213> ORGANISM: Artificial sequence
<220> FEATURE:
<223> OTHER INFORMATION: fragments of VirB10 protein from A.
      phagocytophilum strain HZ

<400> SEQUENCE: 20

Arg Leu Ile Gly Ser Tyr Phe Phe
1               5

<210> SEQ ID NO 21
<211> LENGTH: 21
<212> TYPE: PRT
<213> ORGANISM: Artificial sequence
<220> FEATURE:
<223> OTHER INFORMATION: fragments of VirB10 protein from A.
      phagocytophilum strain HZ

<400> SEQUENCE: 21

Val Arg Val Asp Val Asn Trp Ser Arg Val Ile Leu Pro His Gly Val
1               5                   10                  15

Asp Ile G

```
<400> SEQUENCE: 24

Arg Thr Glu Thr Val Lys Val Glu Thr
1               5

<210> SEQ ID NO 25
<211> LENGTH: 12
<212> TYPE: PRT
<213> ORGANISM: Artificial sequence
<220> FEATURE:
<223> OTHER INFORMATION: fragments of VirB10 protein from A.
      phagocytophilum strain HZ

<400> SEQUENCE: 25

Thr Ser Ser Ser Leu Ser Thr Lys Ile Val Ser Asp
1               5                   10

<210> SEQ ID NO 26
<211> LENGTH: 8
<212> TYPE: PRT
<213> ORGANISM: Artificial sequence
<220> FEATURE:
<223> OTHER INFORMATION: fragments of VirB10 protein from A.
      phagocytophilum strain HZ

<400> SEQUENCE: 26

Thr Pro Thr Val Tyr Val Asp Gln
1               5

<210> SEQ ID NO 27
<211> LENGTH: 14
<212> TYPE: PRT
<213> ORGANISM: Artificial sequence
<220> FEATURE:
<223> OTHER INFORMATION: fragments of VirB10 protein from A.
      phagocytophilum strain HZ

<400> SEQUENCE: 27

Thr Val Met Lys Val Phe Val Asn Gln Asp Val Val Phe Pro
1               5                   10

<210> SEQ ID NO 28
<211> LENGTH: 428
<212> TYPE: PRT
<213> ORGANISM: Candidatus Accumulibacter sp. BA-93

<400> SEQUENCE: 28

Met Ser Gln Asp Asp Thr Pro Asp Leu Ala Thr Pro Gln Ala Gly Lys
1               5                   10                  15

Val Ala Pro Glu Ala Val Ala Leu Arg Ala Gln Pro Arg Pro Val Thr
            20                  25                  30

Arg Leu Asn Arg Arg Thr Leu Ala Ile Leu Val Gly Gly Leu Ser Val
        35                  40                  45

Ala Val Leu Gly Ala Thr Ile Trp Ser Leu Gln Pro Gln Arg Arg Ser
    50                  55                  60

Ala Ser Glu Gln Thr Glu Leu Tyr Asn Val Asp Arg Val Ser Lys Ser
65                  70                  75                  80

Glu Gly Leu Asp Ala Leu Pro Thr Asp Tyr Ser Lys Leu Pro Pro Ala
                85                  90                  95

Leu Pro Pro Asp Val Pro Glu Leu Gly Pro Pro Leu Pro Gly Asp Leu
            100                 105                 110

Gly Pro Ala Ile Val Ala Ser Gln Gln Pro Val Thr Pro Gly Tyr Ser
        115                 120                 125
```

Pro Pro Gly His Asp Pro Glu Asp Ala Leu Arg Lys Glu Ala Asp Ala
            130                 135                 140

Ala Ala Ala Ser Ser Val Phe Phe Arg Ser Gly Gly Gln Gly Gln Ala
145                 150                 155                 160

Ala Ala Thr Val Ala Gln Ala Ala Pro Gly Ala Pro Gly Val Ala Asn
                165                 170                 175

Thr Leu Ala Ala Phe Asp Pro Leu Ala Ala Gly Pro Ala Ser Thr Ala
            180                 185                 190

Ala Gln Pro Ala Asp Pro Thr Thr Val Gln Asn Arg Gln Asp Gln Lys
            195                 200                 205

Glu Ala Phe Leu Lys Ala Gly Ser Thr Glu Thr Arg Asn Ser Gly Asn
210                 215                 220

Leu Ala Leu Pro Ala Ser Pro Tyr Gln Val Ile Ala Gly Thr Val Ile
225                 230                 235                 240

Ala Gly Ala Leu Val Thr Gly Ile Lys Ser Asp Leu Pro Gly Asp Val
                245                 250                 255

Ile Gly Thr Val Thr Glu Pro Val Tyr Asp Thr Ala Thr Gly Lys Phe
            260                 265                 270

Leu Leu Ile Pro Gln Gly Ser Arg Ile Leu Gly Arg Tyr Asn Ser Gln
            275                 280                 285

Val Ser Tyr Gly Gln Ser Arg Val Gln Val Val Trp Asn Arg Ile Ile
290                 295                 300

Leu Pro Asp Thr Ser Ser Leu Thr Leu Asp Asn Leu Val Gly Thr Asp
305                 310                 315                 320

Pro Ala Gly Tyr Ala Gly Leu Glu Asp Asp Val Asp Trp His Trp Asn
                325                 330                 335

Arg Ile Phe Ala Gly Ala Val Leu Thr Thr Leu Leu Gly Val Gly Ala
            340                 345                 350

Glu Leu Ala Ala Pro Glu Asn Arg Gln Asp Gly Asn Arg Ile Val Ile
            355                 360                 365

Ala Gly Arg Asp Ser Ala Gln Asp Ser Ile Asn Gln Val Gly Gln Glu
370                 375                 380

Ile Thr Arg Arg Asn Val Asn Ile Gln Pro Thr Leu Thr Glu Arg Pro
385                 390                 395                 400

Gly Leu Pro Val Arg Ile Ile Val Asn Arg Asp Leu Val Leu Arg Pro
                405                 410                 415

Tyr Gln Pro Leu Phe Phe Asn Arg Gly Ala Ser Gln
            420                 425

<210> SEQ ID NO 29
<211> LENGTH: 784
<212> TYPE: PRT
<213> ORGANISM: Ochrobactrum anthropic

<400> SEQUENCE: 29

Met Ala Asp Glu Glu Glu Ala Arg Ile Pro Gly Glu Arg Thr Glu Thr
1               5                   10                  15

Ile Thr Asp Gln Arg Ile Asp Ser Asn Pro Ala Val Lys Arg Gly Ala
            20                  25                  30

Ile Ala Leu Ala Val Val Ala Phe Ile Ala Phe Ala Ile Trp Ser Thr
        35                  40                  45

Ser Gly Lys Asp Asn Lys Asp Gln Arg Thr Tyr Pro Glu Arg Val Ile
    50                  55                  60

Ile Arg Gln Thr Asn Ala Phe Glu Pro Ala Lys Glu Lys Val Glu Pro
65                  70                  75                  80

```
Val Ala Pro Val Pro Ala Pro Lys Thr Val Leu Pro Ile Pro Thr Leu
                85                  90                  95

Glu Pro Val Pro Glu Ile Glu Asp Lys Leu Leu Asp Ser Ala Arg Arg
            100                 105                 110

Ala Pro Val Leu Ala Tyr Ser Arg Glu Gln Gly Lys Ser Pro Val Arg
            115                 120                 125

Gln Ser Gly Asp Asn Pro Ala Gln Ser Ile Asp Gly Asn Phe Leu Pro
130                 135                 140

Leu Asp Ser Asn Ala Met Ser Gln Gly Gln Val Ser Asn Asp Glu Gln
145                 150                 155                 160

Arg Phe Asp Ser Leu Leu Arg Pro Thr Leu Leu Glu Gly Ala Arg Ala
                165                 170                 175

Gly Thr Leu Gly Asn Arg Asn Phe Ile Val Ala Met Gly Asn Ser Ile
                180                 185                 190

Pro Cys Val Leu Glu Thr Ala Leu Ala Ser Asp Gln Pro Gly Phe Thr
            195                 200                 205

Ser Cys Val Ile Asp Arg Asp Val Leu Ser Asp Asn Gly Arg Val Val
            210                 215                 220

Leu Met Lys Lys Gly Thr Gln Val Val Gly Glu Tyr Arg Gly Gly Leu
225                 230                 235                 240

Gln Arg Gly Gln Lys Arg Leu Leu Val Leu Trp Asn Arg Ala Lys Thr
                245                 250                 255

Pro Glu Gly Val Ile Ile Thr Leu Ala Ser Pro Ala Thr Asp Ala Leu
                260                 265                 270

Gly Arg Ser Gly Phe Asp Gly His Val Asp Arg His Trp Trp Glu Arg
                275                 280                 285

Phe Gly Ser Ala Leu Leu Leu Ser Ile Val Gly Asp Thr Thr Ser Tyr
290                 295                 300

Ala Ser Ser Arg Leu Gln Asn Ser Gly Val Glu Ala Gln Asp Thr Met
305                 310                 315                 320

Ser Ala Gly Gln Gln Ala Ala Ile Ala Val Glu Lys Ser Ile Asp
                325                 330                 335

Ile Pro Pro Thr Leu Asn Lys His Gln Gly Glu Val Val Ser Ile Phe
            340                 345                 350

Val Ala Arg Asp Leu Asp Phe Ser Asp Val Tyr Arg Leu Arg Val Thr
            355                 360                 365

Glu Pro Lys Asn Arg Ile Phe Asp Arg Ala Ile Leu Gly Asp Phe Lys
            370                 375                 380

Pro Glu Ser Lys Val Val Thr Lys Met Ala Asp Glu Glu Ala Arg
385                 390                 395                 400

Ile Pro Gly Glu Arg Thr Glu Thr Ile Thr Asp Gln Arg Ile Asp Ser
                405                 410                 415

Asn Pro Ala Val Lys Arg Gly Ala Ile Ala Leu Ala Val Val Ala Phe
            420                 425                 430

Ile Ala Phe Ala Ile Trp Ser Thr Ser Gly Lys Asp Asn Lys Asp Gln
            435                 440                 445

Arg Thr Tyr Pro Glu Arg Val Ile Ile Arg Gln Thr Asn Ala Phe Glu
450                 455                 460

Pro Ala Lys Glu Lys Val Glu Pro Val Ala Pro Val Pro Ala Pro Lys
465                 470                 475                 480

Thr Val Leu Pro Ile Pro Thr Leu Glu Pro Val Pro Glu Ile Glu Asp
                485                 490                 495
```

Lys Leu Leu Asp Ser Ala Arg Arg Ala Pro Val Leu Ala Tyr Ser Arg
            500                 505                 510

Glu Gln Gly Lys Ser Pro Val Arg Gln Ser Gly Asp Asn Pro Ala Gln
            515                 520                 525

Ser Ile Asp Gly Asn Phe Leu Pro Leu Asp Ser Asn Ala Met Ser Gln
            530                 535                 540

Gly Gln Val Ser Asn Asp Glu Gln Arg Phe Asp Ser Leu Leu Arg Pro
545                 550                 555                 560

Thr Leu Leu Glu Gly Ala Arg Ala Gly Thr Leu Gly Asn Arg Asn Phe
            565                 570                 575

Ile Val Ala Met Gly Asn Ser Ile Pro Cys Val Leu Glu Thr Ala Leu
            580                 585                 590

Ala Ser Asp Gln Pro Gly Phe Thr Ser Cys Val Ile Asp Arg Asp Val
            595                 600                 605

Leu Ser Asp Asn Gly Arg Val Val Leu Met Lys Lys Gly Thr Gln Val
            610                 615                 620

Val Gly Glu Tyr Arg Gly Gly Leu Gln Arg Gly Gln Lys Arg Leu Leu
625                 630                 635                 640

Val Leu Trp Asn Arg Ala Lys Thr Pro Glu Gly Val Ile Ile Thr Leu
            645                 650                 655

Ala Ser Pro Ala Thr Asp Ala Leu Gly Arg Ser Gly Phe Asp Gly His
            660                 665                 670

Val Asp Arg His Trp Trp Glu Arg Phe Gly Ser Ala Leu Leu Leu Ser
            675                 680                 685

Ile Val Gly Asp Thr Thr Ser Tyr Ala Ser Ser Arg Leu Gln Asn Ser
            690                 695                 700

Gly Val Glu Ala Gln Asp Thr Met Ser Ala Gly Gln Gln Ala Ala Ala
705                 710                 715                 720

Ile Ala Val Glu Lys Ser Ile Asp Ile Pro Pro Thr Leu Asn Lys His
            725                 730                 735

Gln Gly Glu Val Val Ser Ile Phe Val Ala Arg Asp Leu Asp Phe Ser
            740                 745                 750

Asp Val Tyr Arg Leu Arg Val Thr Glu Pro Lys Asn Arg Ile Phe Asp
            755                 760                 765

Arg Ala Ile Leu Gly Asp Phe Lys Pro Glu Ser Lys Val Val Thr Lys
            770                 775                 780

<210> SEQ ID NO 30
<211> LENGTH: 411
<212> TYPE: PRT
<213> ORGANISM: Lysobacter capsici AZ78

<400> SEQUENCE: 30

Met Ser Gln Asn Leu Pro Pro Asn Gln Pro Gly Asn Pro Asp Glu Ser
1               5                   10                  15

Gly Gly Thr Ala Glu Asn Asn Ser Ser Tyr Gly Tyr Ala Gly Ala Asn
            20                  25                  30

Pro Tyr Tyr Gly Gln Gln Ala Thr Gly Pro Ala Pro Asp Leu Asp Ala
            35                  40                  45

Asn Ala Pro Thr Leu Lys Ser Ser Asp Val Gln Arg Leu Asn Arg Lys
            50                  55                  60

Ala Leu Leu Phe Leu Gly Gly Ile Val Leu Leu Ile Val Ala Ala
65                  70                  75                  80

Leu Trp Met Phe Asn Ala Ala Thr Ser Gly Asp Asp Lys Lys Pro Lys
            85                  90                  95

Val Glu Glu Glu Val Val Asn Ile Pro Asp Leu Pro Lys Thr Val Ala
                100                 105                 110

Asp Pro Pro Leu Pro Val Asp Pro Leu Ala Gly Met Pro Pro Leu
            115                 120                 125

Pro Val Val Asp Gln Ala Pro Pro Met Pro Met Pro Pro Gln Glu
    130                 135                 140

Asp Met Glu Pro Val Lys Arg Gly Pro Ser Leu Leu Glu Arg Arg Ile
145                 150                 155                 160

Ser Gly Glu Gly Gly Gly Asp Gly Gly Gly Gly Gly Asn
            165                 170                 175

Leu Pro Pro Gly Val Met Ser Pro Glu Ala Tyr Ala Gln Ala Met Met
            180                 185                 190

Ala Ala Asn Gly Gln Gly Pro Ala Arg Pro Gln Gln Glu Gln Glu Lys
            195                 200                 205

Ala Thr Ser Ala Gln Pro Ile Tyr Asn Pro Asp Thr Leu Leu Val Arg
    210                 215                 220

Gly Thr Tyr Ile Arg Cys Val Met Glu Thr Arg Ile Val Thr Asp Leu
225                 230                 235                 240

Pro Gly Phe Thr Ser Cys Val Val Thr Glu Pro Thr Tyr Ser Ile Asn
            245                 250                 255

Gly Arg Arg Leu Leu Leu Pro Lys Gly Ser Lys Val Ser Gly Arg Tyr
            260                 265                 270

Gln Ser Asp Asn Ile Asn Gly Pro Arg Val Ser Val Ile Trp Asp Arg
    275                 280                 285

Ile Thr Thr Pro Asn Gly Ile Asp Val Asn Met Ala Ser Pro Gly Ile
    290                 295                 300

Asp Asn Leu Gly Gly Ala Gly His Pro Gly Asp Tyr Asn Ala His Trp
305                 310                 315                 320

Gly Ser Arg Ile Ala Ser Ala Leu Leu Ile Ser Leu Ile Ser Asp Ala
            325                 330                 335

Phe Lys Tyr Ala Ala Ala Lys Asn Gly Pro Glu Ser Ser Thr Val Thr
            340                 345                 350

Asn Ser Gly Asn Val Val Gln Gln Pro Tyr Glu Ser Asn Thr Ala Glu
            355                 360                 365

Ala Met Glu Arg Leu Ala Asn Gln Ala Leu Asp Lys Ser Ile Asn Arg
    370                 375                 380

Pro Pro Thr Val Thr Ile Asn Gln Gly Thr Val Val Asn Ile Tyr Val
385                 390                 395                 400

Ala Lys Asp Val Asp Phe Ser Ser Val Leu Arg
            405                 410

<210> SEQ ID NO 31
<211> LENGTH: 472
<212> TYPE: PRT
<213> ORGANISM: Shinella sp. DD12

<400> SEQUENCE: 31

Met Ser Lys Ile Asp Phe Asp Asn Leu Asp Gly Gln Ser Ser Val Ala
1               5                   10                  15

Ser Asp Arg Asn Gly Arg Leu Gly Lys Leu Ala Leu Pro Leu Leu Leu
            20                  25                  30

Val Ala Gly Val Gly Val Leu Ala Tyr Val Asn Trp Pro Ala Gly Pro
        35                  40                  45

Gln Asn Pro Thr Val Thr Asp Gly Asn Gly Glu Thr Phe Glu Thr Ser

```
            50                  55                  60
Asn Ser Ser Ile Arg Asn Phe Pro Asp Glu Pro Val Lys Gln Ala Ala
 65                  70                  75                  80

Asp Pro Asn Leu Val Gln Ile Pro Val Glu Glu Lys Asn Pro Val Asp
                     85                  90                  95

Pro Ala Thr Val Asp Val Lys Val Asn Glu Gly Asp Asp Leu Glu Lys
                100                 105                 110

Leu Arg Glu Ile Glu Glu Ala Arg Arg Ala Glu Glu Glu Arg Leu
            115                 120                 125

Arg Met Glu Glu Ala Arg Arg Ala Glu Glu Glu Ala Arg Leu Ala
        130                 135                 140

Glu Leu Glu Ala Lys Arg Arg Glu Glu Glu Lys Ala Arg Trp Glu
145                 150                 155                 160

Arg Leu Arg Ser Glu Gln Ile Val Leu Asp Gly Ser Arg Glu Thr
                165                 170                 175

Leu Ser Gly Asp Gln Ala Val Ser Ile Ala Asp Asp Gly Gln Leu Val
                180                 185                 190

Ala Val Pro Gly Ala Glu Ser Asp Ala Asn Lys Ala Phe Leu Ala Gln
                195                 200                 205

Ser Glu Lys Gln Thr Ala Gly Ile Val Lys Ala Thr Arg Phe Asp Arg
                210                 215                 220

Thr Asp Ala Leu Val Ala Gln Gly Thr Met Ile Arg Gly Phe Leu Glu
225                 230                 235                 240

Thr Ala Ile Asn Thr Asp Leu Pro Gly Met Val Arg Ala Val Val Arg
                245                 250                 255

Glu Asp Val Arg Ser Leu Asp Gly Gly Arg Ile Leu Ile Pro Lys Gly
                260                 265                 270

Ser Arg Leu Ile Gly Glu Tyr Lys Ser Gly Leu Val Arg Gly Gln Lys
                275                 280                 285

Arg Ile Phe Ile Val Trp Ser Arg Val Ile Arg Ser Asp Gly Val Ser
                290                 295                 300

Val Glu Ile Ala Ser Pro Gly Ala Asp Arg Leu Gly Arg Ala Gly Leu
305                 310                 315                 320

Thr Gly Glu Ile Asp Thr His Phe Trp Glu Arg Phe Gly Ser Ala Ile
                325                 330                 335

Met Leu Ser Val Ile Gly Gly Ala Ala Glu Tyr Val Ser Ser Leu Gly
                340                 345                 350

Asn Thr Ala Ser Glu Ser Ala Arg Ser Ile Ser Thr Val Asp Pro Ile
                355                 360                 365

Thr Gly Ala Val Thr Thr Ile Thr Thr Glu Pro Ser Arg Thr Ala Thr
                370                 375                 380

Glu Ala Arg Ser Ile Ala Glu Lys Ser Ala Ile Leu Gln Asp
385                 390                 395                 400

Ile Ala Asn Glu Ala Phe Lys Glu Ser Ser Lys Ile Pro Pro Thr Ile
                405                 410                 415

Tyr Val Ala Gln Gly Glu Ser Ile Ile Val Phe Leu Arg Arg Asp Leu
                420                 425                 430

Asp Phe Ser Thr Phe Tyr Ala Asp Pro Val Arg Gln Glu Met Met Arg
                435                 440                 445

Leu Lys Arg Gly Gly Gln Ile Arg Arg Asn Val Asp Pro Thr Pro Tyr
                450                 455                 460

Tyr Pro Val Ala Pro Val Tyr Lys
465                 470
```

<210> SEQ ID NO 32
<211> LENGTH: 414
<212> TYPE: PRT
<213> ORGANISM: Hyphomonas hirschiana VP5

<400> SEQUENCE: 32

```
Met Thr Gln Pro Pro Leu Lys Glu Thr Ala Arg Gln Leu Glu Ile
1               5                   10                  15

Arg Ser Lys Pro Lys Pro Ala Thr Arg Ile Asn Arg Lys Leu Leu
            20                  25                  30

Ala Gly Ala Gly Leu Gly Ala Leu Gly Leu Phe Ala Ala Thr Phe
            35                  40                  45

Ala Leu Ala Pro Pro Arg Pro Pro Glu Pro Ala Pro Gln Asp Glu Leu
50                  55                  60

Leu Val Ala Gly Lys Arg Lys Pro Asp Gly Phe Ser Ala Leu Pro Ala
65                  70                  75                  80

Asp Tyr Thr Ala Leu Gly Asp Val Pro Val Leu Gly Thr Pro Val Ser
                    85                  90                  95

Gly Asp Leu Gly Ala Thr Ile Arg Ala Ala Glu Glu Ala Tyr Gly Ile
                    100                 105                 110

Glu Pro Asp Phe Gln Thr Glu Tyr Arg Thr Asp Phe Arg Pro Arg Pro
                    115                 120                 125

Glu Glu Glu Ala Ala Arg Thr Ala Arg Leu Glu Ala Ala Leu Ala
            130                 135                 140

Glu Glu Ala Ala Arg Ala Pro Leu Leu Phe Arg Leu Gly Asn Ala Ala
145                 150                 155                 160

Ala Pro Gly Pro Ala Pro Ala Arg Pro Thr Asp Ala Ser Phe Asp Leu
                    165                 170                 175

Ser Ser Glu Leu Leu Ala Leu Ala Arg Pro Ser Pro Asn Ala Gly Ala
                    180                 185                 190

Ser Pro Pro Pro Asp Pro Asn Leu Gln Ala Arg Lys Ala Ala Phe Ala
            195                 200                 205

Ser Asp Arg Ala Gly Gly Pro Ile Tyr Asn Pro Asp Arg Val Gln Asp
210                 215                 220

Pro Leu Ser Pro Tyr Gln Leu Met Ala Gly Ser Leu Ile Pro Ala Ser
225                 230                 235                 240

Leu Ile Thr Gly Ile Asn Ser Asp Leu Pro Gly Ala Val Ile Ala Gln
                    245                 250                 255

Val Thr Gln Asn Val Tyr Asp Thr Val Arg Gly Gln His Arg Leu Ile
            260                 265                 270

Pro Gln Gly Ser Arg Leu Ile Gly Arg Tyr Gln Ser Glu Val Ser Phe
            275                 280                 285

Gly Gln Asp Arg Ala Leu Val Val Trp Asp Arg Ile Leu Met Pro Asp
            290                 295                 300

Gly Ser Ser Ile Thr Ile Ser Glu Pro Gly Ser Asp Thr Ala Gly Tyr
305                 310                 315                 320

Ala Gly Leu Lys Asp Arg Thr Asp His His Trp Asp Arg Val Phe Ala
                    325                 330                 335

Ala Ala Gly Leu Ala Thr Met Leu Gly Ile Gly Ala Glu Leu Gly Pro
            340                 345                 350

Ser Glu Asp Gly Asp Ile Glu Arg Ala Ile Arg Arg Gly Thr Thr Asp
            355                 360                 365

Thr Ile Asn Glu Ala Gly Gln Arg Ala Val Asp Arg Ser Leu Gly Val
```

```
            370                 375                 380
Gln Pro Ser Ile Thr Ile Arg Pro Gly Trp Pro Val Arg Val Leu Val
385                 390                 395                 400

Thr Lys Asp Leu Val Leu Arg Pro Tyr Pro Glu Thr Ala Pro
                405                 410
```

<210> SEQ ID NO 33
<211> LENGTH: 397
<212> TYPE: PRT
<213> ORGANISM: Vibrio sp. JCM 19052

<400> SEQUENCE: 33

```
Met Ser Asp Asp Asn Thr Ile Pro Ser Ala Tyr Glu Asn Ala Asn Leu
1               5                   10                  15

Asp Arg Gly Glu Leu Thr Val Ser Gly Arg Lys Lys Asn Lys Ala
            20                  25                  30

Val Ile Val Ile Ala Leu Val Ile Leu Ala Leu Val Val Ala Val
            35                  40                  45

Gly Val Leu Phe Ala Ile Asn Gln Phe Arg Glu Ala Glu Val Glu Thr
50                  55                  60

Lys Pro Leu Gln Pro Glu Ser Thr Ala Glu Val Val Gly Val Glu Lys
65                  70                  75                  80

Gly Thr Val Gly Asn Asp Ser Ala Trp Phe Glu Lys Ala Lys Arg Asp
                85                  90                  95

His Glu Lys Asp Lys Ala Gln Gln Glu Arg Ala Ala Gln Trp Lys Arg
                100                 105                 110

Glu Gln Glu Leu Lys Gln Ala Lys Ala Gln Ala Thr His Gln Gln Pro
            115                 120                 125

Val Thr Val Pro Lys Thr Gly Val Pro Glu Pro Asn Val Ala Lys Gln
            130                 135                 140

Pro Ser Thr Thr Ser Lys Arg Asp Lys Asn Ala Pro Pro Thr Pro Gln
145                 150                 155                 160

Glu Arg Arg Leu Met Gly Ser Leu Met Val Asn Val Glu Ser Gly Asn
                165                 170                 175

Ala Ala Asn Gly Gln Ser Thr Ser Glu Pro Ala Ser Tyr Asp Asn Ser
            180                 185                 190

Tyr Asp Ala Pro Thr Phe Ala Met Gly Gln Ala Ser Lys Arg Lys Gln
            195                 200                 205

Glu Gly Leu Asp Phe Leu Leu Lys His Gly Ser Ile Ile Pro Cys Ala
            210                 215                 220

Leu Tyr Ser Gln Val Ile Ser Asp Tyr Gln Gly Ile Val Met Cys Arg
225                 230                 235                 240

Val Thr Gln Asp Val Tyr Ser Ala Asn Gly Lys Ala Leu Leu Val Glu
                245                 250                 255

Arg Gly Ser Leu Leu Thr Gly Ser Gln Asn Val Gln Leu Glu Ala Gly
            260                 265                 270

Lys Asn Arg Val Phe Thr Thr Trp Ala Asp Ile Glu Thr Pro Asn Gly
            275                 280                 285

Ile Ala Ile Arg Ile Asp Ser Leu Gly Ala Gly Arg Leu Gly Ala Ser
            290                 295                 300

Gly Asn Glu Ala Trp Val Asp Asn His Phe Lys Glu Arg Phe Gly Gly
305                 310                 315                 320

Ala Ile Leu Leu Ser Phe Leu Asp Asp Ala Phe Gly Ala Leu Ala Glu
                325                 330                 335
```

```
Lys Ala Ala Ser Ser Asp Gly Asp Ile Thr Phe Asp Ser Ser Thr Glu
                340                 345                 350

Asn Ala Ser Asn Met Ala Glu Lys Ala Leu Glu Ser Ser Ile Asn Ile
            355                 360                 365

Ser Pro Thr Gly Tyr Thr Gln Ile Gly Gln Arg Ile Asn Ile Val
        370                 375                 380

Ala Arg Asp Ile Asp Met Ser Ser Val Tyr Thr Phe Glu
385                 390                 395

<210> SEQ ID NO 34
<211> LENGTH: 411
<212> TYPE: PRT
<213> ORGANISM: Acetobacter aceti 1023

<400> SEQUENCE: 34

Met Ala Phe Lys Phe Lys Gln Ile Phe Ser Ser Ala Gly Glu Gly Gly
1               5                   10                  15

Asn Arg Arg Leu Phe Met Ile Gly Gly Val Val Gly Thr Leu Val Ile
            20                  25                  30

Gly Val Leu Ala Leu Ser Ser Ile His His Arg Glu Met Pro Gln Ser
        35                  40                  45

Asn Ala Gly Val Thr Gln Ala Val Asn Pro Leu Pro Gly Gly Leu Asn
    50                  55                  60

Ala Thr Pro Lys Gln Glu Glu Leu Arg Lys Gln Asp Leu Glu Glu Gly
65                  70                  75                  80

Ala Thr Thr Ala Gln Asn Thr Gly Gln Ser Phe Thr Pro Asp Leu Ala
                85                  90                  95

Pro Gly Lys Ser Ala Asn Pro Glu Pro Val His Glu Val Gly Glu
            100                 105                 110

Val Gly Gln Asp Glu Asp Pro Ser Met Ala Lys Arg Leu Pro Ser Pro
        115                 120                 125

Pro Ser Pro Gln Val Ala Glu Ile Pro Ala Gln Pro Leu Val Gln Thr
    130                 135                 140

Ser Pro Ala Tyr Ala Val Ala Pro Val Asp Gly Gln Gly Gly Asn Pro
145                 150                 155                 160

Lys Asn Lys Leu Tyr Ala Asp Ala Ile Ala Asp Leu Arg Lys Thr Leu
                165                 170                 175

Ser Pro His Met Pro Val Thr Ser Val Met Tyr Thr Gln Asp Glu Leu
            180                 185                 190

Thr Pro Lys Asp Glu Pro Ser Ala Ser Ser Lys Ala Asn Thr Ser Lys
        195                 200                 205

Ser Pro Glu Asn Ser Leu Ser Gln Ala Ala Ser Asn Ser Thr Ser Thr
    210                 215                 220

Gln Asn Lys Val Leu Ile Pro Ala Gly Arg Gly Ile Tyr Ala His Thr
225                 230                 235                 240

Val Thr Ala Thr Asn Ser Asp Leu Asn Gly Asp Val Ile Leu Glu Ala
                245                 250                 255

Asp Ser Gly Pro Ile Ala Gly Asp Arg Met Ile Ala Ser Val Ser Arg
            260                 265                 270

Ala Gly Gly His Met Asn Arg Leu Val Leu Ala Val Arg Ser Val Met
        275                 280                 285

His Lys Gly Gln Thr Leu Ser Val Thr Gly Met Val Val Ala Pro Arg
    290                 295                 300

Thr Met Glu Ala Ala Val Ala Ser Ser Val Asp Gln Leu Tyr Val Glu
305                 310                 315                 320
```

```
Arg Phe Leu Leu Pro Gly Ala Ala Phe Val Gln Gly Leu Gly Ser
            325                 330                 335

Ala Leu Glu Thr Thr Ser Asn Thr Val Gly Ser Ile Gly Gly Leu Gly
            340                 345                 350

Asn Val Asn Tyr Val Glu Arg Leu Asn Phe Pro Gln Gln Leu Gly Val
            355                 360                 365

Ala Ala Gly Gln Ala Ala Ser Gln Ile Asn Ser Ala Leu Met Gln Gln
            370                 375                 380

Met Pro Thr Gln Pro Arg Val Asn Leu Ala Ala Asn Val Ser Val Gly
385                 390                 395                 400

Val Val Phe Thr Ala Asn Val Thr Ala Lys Gln
            405                 410
```

<210> SEQ ID NO 35
<211> LENGTH: 417
<212> TYPE: PRT
<213> ORGANISM: Klebsiella oxytoca KONIH1

<400> SEQUENCE: 35

```
Met Asn Asp Glu His Pro His Pro Glu Pro Asp Glu Ser Arg Pro Ser
1               5                   10                  15

Pro Ala Gln Thr Asp Asp Ile Ala Ala Leu Glu Arg Glu Thr Arg
            20                  25                  30

Ala Arg Arg Glu Ala Glu Leu Leu Thr Ala Gln Asp Glu Glu Asn
            35                  40                  45

Asp Pro Val Gln Pro Ala Ile Asn Lys Leu Lys Lys Arg Arg Gly
50                  55                  60

Arg Ala Thr Ala Phe Leu Ala Leu Ala Ala Val Ala Leu Ile Ala Leu
65                  70                  75                  80

Ala Trp Ala Gly Asn Trp Val Tyr Arg Asn Leu Leu Trp Gln Pro Gly
                85                  90                  95

Glu Glu Lys Arg Gln Asp Ala Ala Pro Gln Pro Asn Arg Ser Asp Tyr
            100                 105                 110

Arg Gln Arg Thr Asp Leu Gly Thr His Asp Thr Gly Pro Ala Ala Pro
            115                 120                 125

Glu Pro Ser Asp Asn Ser Pro Arg Ser Thr Thr Val Thr Gly Pro Glu
            130                 135                 140

Thr Pro Pro Glu Leu Asp Lys Ala Arg Phe Leu Val Arg Arg Asp Ser
145                 150                 155                 160

Ser Ala Ala Ala Arg Asn Pro Val Arg Thr Arg Gln Gln Glu Met
            165                 170                 175

Thr Gln Val Ser Ser Ala Gly Gln Ser Ser Gly Thr Pro Ser Pro Gly
            180                 185                 190

Thr Gly Gln Gln Pro Asp Thr Thr Pro Ser Gln Pro Glu His Ser Pro
            195                 200                 205

Ser Val Val Arg Arg Ile Pro Tyr Asn Pro Asp Leu Tyr Val Pro Glu
            210                 215                 220

Asn Thr Ala Ile Pro Cys Ser Leu Asp Tyr Arg Phe Val Ser Asp Arg
225                 230                 235                 240

Ala Gly Lys Ile Arg Cys Thr Val Ala Ser Asp Ile Trp Ser Ala Ser
                245                 250                 255

Gly Asn Thr Arg Leu Ile Glu Lys Gly Thr Thr Ala Thr Gly Val Tyr
            260                 265                 270

Gln Thr Gly Ala Glu Thr Gly Met Thr His Gly Gln Gly Arg Ala Phe
```

```
                    275                 280                 285
Leu Ile Ile Thr Lys Leu Arg Thr Arg Gln Pro Pro Tyr Leu Asp Ile
    290                 295                 300

Pro Leu Val Asp Thr Arg Ala Ala Gly Glu Leu Gly Glu Ala Gly Val
305                 310                 315                 320

Asp Gly Trp Ile Asp Ser His Phe Ser Glu Arg Phe Gly Gly Ala Leu
                325                 330                 335

Leu Val Gly Met Ile Pro Asp Val Ala Ala Trp Ala Ser Asp Ser Ala
            340                 345                 350

Gly Gln Lys Asp Arg Asn Thr Asp Tyr Thr Glu Asn Ser Arg Gln Ala
        355                 360                 365

Met Ala Asp Met Ala Arg Thr Thr Leu Glu Asn Ser Ile Asn Ile Pro
    370                 375                 380

Pro Thr Val His Lys Asn Gln Gly Glu Ile Ile Asn Leu Ile Thr Gly
385                 390                 395                 400

Gln Asp Ile Asp Phe Ser Gly Ile Tyr Thr Leu Arg Met Lys Asn Asp
                405                 410                 415

Arg

<210> SEQ ID NO 36
<211> LENGTH: 390
<212> TYPE: PRT
<213> ORGANISM: Ensifer adhaerens (Sinorhizobium morelense)

<400> SEQUENCE: 36

Met Leu Glu Glu Asp Glu Asn Arg Ile Pro Gly Glu Arg Gly Glu Thr
1               5                   10                  15

Val Pro Gly Gly Arg Val Asp Asn Asn Pro Val Leu Lys Arg Gly Ala
                20                  25                  30

Val Ala Leu Ala Val Val Thr Phe Val Ala Phe Ala Leu Trp Ser Met
            35                  40                  45

Ser Gly Glu His Thr Pro Thr Asp Thr Thr Arg Pro Glu Arg Val Val
        50                  55                  60

Ile Arg Gln Thr Ala Asn Phe Glu Pro Val Lys Glu Lys Met Glu Pro
65                  70                  75                  80

Val Gln Ala Val Pro Glu Val Lys Leu Pro Thr Pro Leu Ala Ala Glu
                85                  90                  95

Glu Val Glu Asp Glu Asp Pro Leu Leu Asp Ser Ala Arg Arg Ala Pro
                100                 105                 110

Val Ile Ala Phe Ser Gly Gly Gln Lys Asn Thr Thr Ser His Arg Glu
            115                 120                 125

Ile Ala Asp Pro Glu Val Ser Ala Asp Ser His Phe Val Pro Leu Asp
        130                 135                 140

Gly Ser Arg Val Gly Gln Asn Ser Ala Asn Ala Asp Glu Gln Arg Phe
145                 150                 155                 160

Asn Gly Leu Leu Arg Pro Thr Arg Leu Glu Gly Ser Arg Ala Gly Thr
                165                 170                 175

Leu Gly Asn Arg Asn Phe Val Val Ala Met Gly Ser Ser Ile Pro Cys
            180                 185                 190

Val Leu Glu Thr Ala Met Ala Ser Asp Gln Pro Gly Phe Thr Ser Cys
        195                 200                 205

Val Ile Asp Arg Asp Ile Leu Ser Asp Asn Gly Arg Val Val Leu Met
    210                 215                 220

Glu Lys Gly Thr Gln Val Val Gly Glu Tyr Arg Gly Gly Leu Gln Arg
```

```
225                 230                 235                 240
Gly Gln Lys Arg Leu Phe Val Leu Trp Asn Arg Ala Lys Thr Pro Asn
                245                 250                 255
Gly Val Ile Val Thr Leu Ala Ser Pro Ala Thr Asp Ala Leu Gly Arg
                260                 265                 270
Ala Gly Val Asn Gly Tyr Val Asp Thr His Trp Trp Glu Arg Phe Gly
                275                 280                 285
Ser Ala Leu Leu Leu Ser Ile Val Gly Asp Ala Thr Ser Tyr Ala Asn
                290                 295                 300
Ser Arg Leu Arg Asn Ser Asp Val Asp Thr Glu Asn Thr Thr Asn Ala
305                 310                 315                 320
Gly Gln Gln Ala Ala Ala Ile Ala Val Glu Gln Ser Ile Asn Ile Pro
                325                 330                 335
Pro Thr Leu Asn Lys Asn Gln Gly Glu Leu Val Ser Ile Phe Val Ala
                340                 345                 350
Arg Asp Leu Asp Phe Ser Gly Val Tyr Gly Leu Arg Val Ile Gly Pro
                355                 360                 365
Lys Asn Lys Ile Leu Asp Arg Ala Val Leu Gly Asp Val Arg Pro Arg
                370                 375                 380
Ser Thr Arg Val Thr Lys
385                 390

<210> SEQ ID NO 37
<211> LENGTH: 412
<212> TYPE: PRT
<213> ORGANISM: Komagataeibacter rhaeticus AF1

<400> SEQUENCE: 37

Met Lys Pro Arg Phe Asn Gln Leu Phe Ser Asp Ala Ser Arg Gly Gly
1               5                   10                  15
Asn Arg Arg Leu Leu Ala Ile Leu Gly Ser Ile Gly Thr Val Leu Gly
                20                  25                  30
Val Thr Leu Leu Ile Ser Thr Ile His Arg Lys Glu Leu Pro Arg Ser
                35                  40                  45
Asp Pro Gly Arg Pro Pro Ala Ala Asn Pro Leu Pro Gly Gly Leu Asn
                50                  55                  60
Ser Asn Pro Arg Gln Gln Glu Leu Arg Glu Asp Gln Ile Arg Asp Glu
65              70                  75                  80
Ala Gly Arg Ala Gln Thr Ala Gly Gln Ser Tyr Ser Pro Asp Ile Ala
                85                  90                  95
Pro Gly Thr Pro Thr His Pro Asp Asp Lys Pro Pro Pro Pro Pro Val
                100                 105                 110
Ala Gln Glu Val Gly Ala Asp Val Asn Pro Ala Met Ala Lys Ala Ala
                115                 120                 125
Ala Ala Pro Ala Pro His Ala Pro Glu Val Val Pro Ser Val Pro Val
                130                 135                 140
Val Pro Val Gln Thr Asp Ala Ala Phe Arg Ala Ala Met Pro Arg Asp
145                 150                 155                 160
Pro Gln Leu Gln Lys Asp Ala Ile Thr Ala Tyr Arg His Ala Ile Met
                165                 170                 175
Asp Leu Ala Gly Arg Leu Asp Gly Arg Phe Pro Val Thr Asn Val Leu
                180                 185                 190
Tyr Glu Lys Thr Glu Thr Gly Arg Glu Gln Thr Lys Lys Pro Ala Val
                195                 200                 205
```

```
Ser Ser Ser Ile Thr Ser Ala Ala Thr Ala Asn Ser Gln Thr Ala Leu
    210                 215                 220

Ser Arg Val Leu Val Pro Ala Gly Arg Gly Ile Tyr Ala His Thr Val
225                 230                 235                 240

Ser Ala Thr Asn Ser Asp Leu Gly Gly Glu Ile Ile Leu Glu Ala Asp
                245                 250                 255

Ser Gly Pro Leu Ala Gly Asp Arg Met Lys Ala Ser Val Arg Arg Ala
            260                 265                 270

Gly Gly His Leu Asn Arg Leu Val Val Arg Ala Asp Gln Val Phe His
        275                 280                 285

Lys Asn Asp Pro Thr Pro Ile Gln Val Glu Gly Met Val Val Ala Pro
    290                 295                 300

Asp Thr Met Glu Ala Ala Val Ala Ser Ser Val Asp Gln Leu Tyr Val
305                 310                 315                 320

Glu Arg Phe Val Leu Pro Ala Ala Ala Ala Phe Val Gln Gly Leu Gly
                325                 330                 335

Gln Ala Ile Glu Met Thr Ser Asn Thr Thr Gly Ser Ile Gly Ala Leu
            340                 345                 350

Gly Asn Val Asn Tyr Val Gln Ser Leu Asn Phe Pro Gln Gln Leu Gly
        355                 360                 365

Val Ala Ala Gly Ala Ala Ala Ser Gln Val Asn Ser Ala Leu Met Gln
    370                 375                 380

Gln Met Pro Thr Gln Pro Arg Val Asn Leu Ala Ala Gln Val Ser Val
385                 390                 395                 400

Gly Val Ile Phe Met Ser Asp Val Val Met Lys Lys
                405                 410

<210> SEQ ID NO 38
<211> LENGTH: 408
<212> TYPE: PRT
<213> ORGANISM: Burkholderia cenocepacia

<400> SEQUENCE: 38

Met Asn Asp Asp Thr Pro Arg Asn Val Ile Gly Pro Asp Asp Gly Leu
1               5                   10                  15

Asp Arg Gln His Glu Asp Gly Gln Asn Ala Gly Ala Ser Asn Val Ser
            20                  25                  30

Ala Asp Arg Gly Met Pro Ala Leu Gly Gln Tyr Arg Gly Ala Arg Pro
        35                  40                  45

Arg Ala Trp Trp Leu Thr Pro Val Met Ile Val Leu Ile Val Gly Gly
    50                  55                  60

Gly Ala Val Trp Thr Val His Gly Phe Leu Ala Arg His Asp Ala Glu
65                  70                  75                  80

Ala Lys Ala Arg Arg Asp Ser Met Ala Gly Thr Ser Ser Gln Gly Arg
                85                  90                  95

Met Phe Asn Asp Leu Pro Ala Ser Ser Val Gly Ser Ala Ala Ser Ala
            100                 105                 110

Thr Val Pro Ala Ser Ala Val Ala Val Arg Pro Ala Ser Ser Ala Gly
        115                 120                 125

Val Val Thr Pro Ala Arg Ile Ala His Ala Ala Thr Pro Arg Ser Tyr
    130                 135                 140

Tyr Asp Ala Pro Leu Leu Ala Thr Gly Gly Gly Gln Glu Leu Ala Gly
145                 150                 155                 160

Val Ala Pro Gly Val Pro Gly Ser Gly Ser Ala Pro Phe Pro Leu Thr
                165                 170                 175
```

```
Ala Gly Ile Asn Gly Gly Ala Gly Ala Ser Ala Arg Asp Pro Gly Gln
            180                 185                 190

Met Gly Ser Gly Leu Thr Gln Ala Leu Met Pro Thr Val Thr Pro Arg
        195                 200                 205

Val Gln Ala Ser Thr Leu Gly Asn Arg Ser Leu Val Leu Ala Gln Gly
    210                 215                 220

Ala Lys Ile Asp Cys Ala Gly Asp Thr Ala Phe Asp Ser Thr Glu Ala
225                 230                 235                 240

Gly Val Ser Thr Cys Thr Ala Thr Lys Asn Val Tyr Ser Asp Asp Gly
                245                 250                 255

His Val Val Leu Ile Glu Arg Gly Ser Gln Ile Asn Ser Gln Tyr Arg
            260                 265                 270

Ala Asn Met Ser Val Gly Gln Lys Arg Val Phe Val Leu Ser Ala Arg
        275                 280                 285

Ile Lys Thr Pro Asn Gly Val Thr Val Glu Ile Asp Ser Pro Ala Ala
    290                 295                 300

Asp Ala Leu Gly Arg Met Gly Ile Asp Gly Asp Val Asp Asn His Trp
305                 310                 315                 320

Ser Gln Arg Ile Gly Ala Ala Met Leu Leu Gly Val Thr Gln Asp Ala
                325                 330                 335

Ile Gly Tyr Leu Ser Thr Arg Gly Gly Asn Ala Asn Gly Ser Val Val
            340                 345                 350

Phe Gln Ser Thr Gln Gln Gly Asn Asp Met Ala Thr Arg Val Leu
        355                 360                 365

Asp Ser Thr Ile Gly Ile Pro Pro Thr Leu Thr Gln Asn Gln Gly Ala
    370                 375                 380

Glu Phe Thr Ile Val Ile Ala Arg Asp Leu Asp Phe Gly Ser Val Tyr
385                 390                 395                 400

Ala Leu Gln Pro Glu Gly Thr Arg
                405

<210> SEQ ID NO 39
<211> LENGTH: 474
<212> TYPE: PRT
<213> ORGANISM: Sulfitobacter pseudonitzschiae

<400> SEQUENCE: 39

Met Ala Asp Gln Pro Pro Asp Leu Gln Asp Arg Leu Asp Gln Phe
1               5                   10                  15

Ser Gln Arg Gly Lys Ser Lys Arg Arg Gly Asn Ser Leu Gly Val Gly
            20                  25                  30

Ala Leu Ala Ala Ala Leu Ala Leu Gly Gly Ala Gly Val Ala Tyr Phe
        35                  40                  45

Leu Ala Thr Gly Leu Gln Glu Gly Asp Ser Ala Leu Glu Thr Ser Asp
    50                  55                  60

Val Glu Thr Phe Gln Asp Arg Arg Pro Gly Thr Gly Gly Arg Leu Glu
65                  70                  75                  80

Phe Pro Pro Asp Glu Thr Glu Gln Arg Val Asn Asp Ala Leu Ile Ala
                85                  90                  95

Ala Glu Glu Ala Leu Asp Val Pro Ala Ala Pro Ala Pro Glu Ala Ser
            100                 105                 110

Ala Glu Val Leu Ala Glu Ile Ala Lys Leu Arg Glu Ala Leu Ala Ala
        115                 120                 125

Ser Gln Ala Ala Arg Asn Ser Glu Ile Gln Ser Ala Val Ala Asp Leu
```

-continued

```
                130                 135                 140
Arg Glu Ala Phe Asp Glu Gln Lys Ala Ala Leu Glu Ala Thr Leu Ala
145                 150                 155                 160

Ala Lys Glu Thr Glu Leu Ala Asn Leu Gln Arg Gln Thr Glu Thr Arg
                165                 170                 175

Ile Glu Gly Leu Gln Ala Met Leu His Ala Glu Arg Ala Gln Arg Glu
                180                 185                 190

Gly Leu Glu Ala Glu Leu Asp Arg Glu Gly Leu Ile Ala Asp Gln Arg
                195                 200                 205

Leu Leu Glu Glu Arg Gln Arg Gln Glu Glu Gln Arg Gln Arg Glu
        210                 215                 220

Ala Glu Arg Val Ala Glu Glu Leu Leu Thr Ala Gln Ile Lys Ser Pro
225                 230                 235                 240

Ala Val Val Tyr Ala His Gly Pro Arg Gly Ser Thr Ser Gly Ala Ala
                245                 250                 255

Val Ala Asp Pro Ala Ala Gly Leu Gly Gly Pro Val Leu Ser Gly
                260                 265                 270

Asn Glu Gln Phe Leu Gln Thr Ala Arg Pro Leu Glu Val Gln Glu Ala
                275                 280                 285

Ala Arg Leu Thr His Pro Glu Arg Thr Leu Thr Gln Gly Ser Val Ile
                290                 295                 300

Gln Ala Ala Leu Gln Thr Ala Ile Asn Ser Asp Leu Pro Gly Ser Val
305                 310                 315                 320

Val Ala Val Val Ser Glu Pro Val Ser Ala Phe Ser Gly Asp Arg Ile
                325                 330                 335

Leu Ile Pro Arg Gly Ser Arg Leu Phe Gly Gln Tyr Arg Ser Gly Ile
                340                 345                 350

Glu Met His Gln Lys Arg Ile Leu Ile Leu Trp Thr Arg Val Leu Thr
                355                 360                 365

Pro Asp Gly Thr Ser Met Glu Ile Ala Ala Val Gly Gly Asp Gln Leu
                370                 375                 380

Gly Arg Ser Gly Leu Thr Gly Leu Val Asp Thr Lys Phe Ala Glu Arg
385                 390                 395                 400

Phe Gly Gly Ala Ala Leu Ile Ser Val Ile Gly Ala Ala Pro Ala Val
                405                 410                 415

Ala Ala Glu Ser Ala Asn Asn Glu Thr Thr Ser Ile Val Leu Gly Asp
                420                 425                 430

Val Gly Ser Asp Leu Gln Asp Thr Val Gly Ser Val Ile Ala Asp Gln
                435                 440                 445

Val Ser Ile Ala Pro Thr Ile Tyr Val Asp Gln Gly Ala Ser Val Thr
450                 455                 460

Val Leu Val Asp Arg Asp Val Val Ile Tyr
465                 470
```

<210> SEQ ID NO 40
<211> LENGTH: 373
<212> TYPE: PRT
<213> ORGANISM: Erythrobacter litoralis

<400> SEQUENCE: 40

```
Met Arg Leu Pro Pro Lys Lys Gly Asp Thr Thr Ser Gly Ala Asp Gly
1               5                   10                  15

Asp Pro Arg Glu Gln Glu Ser Ala Glu Val Ile Asp Leu Ala Ser Arg
                20                  25                  30
```

```
Ser Ala Phe Pro Gly Ile Ala Asp Arg Lys Ala Lys Thr Asp Gly Leu
         35                  40                  45

Gly Leu Ala Phe Gly Ser Val Leu Val Leu Ala Leu Gly Ala Ala Thr
 50                  55                  60

Phe Trp Ala Met Asn Met Pro Glu Ala Pro Ala Pro Gly Pro Ile Gly
 65                  70                  75                  80

Asn Pro Ala Val Ala Pro Pro Gln Ala Ala Pro Ala Pro Val Glu
                 85                  90                  95

Ala Pro Gln Pro Glu Pro Ala Arg Pro Gln Pro Asp Pro Ala Pro Ala
                100                 105                 110

Pro Ile Leu Ala Arg Asp Pro Gly Ala Asp Ala Ala Ser Ala Ile Asn
                115                 120                 125

Pro Tyr Ala Ser Pro Thr Met Val Tyr Asp Ala Ser Thr Ala Ser Asp
130                 135                 140

Ala Ala Arg Leu Ala Glu Pro Ala Gly Ala Ala Pro Ser Gly Glu Val
145                 150                 155                 160

Met Ala Asn Ala Gly Asp Ile Ala Ala Gly Gly Ser Ala Ala Ala Phe
                165                 170                 175

Ala Ser Arg Ile Gly Gly Val Gly Gly Ala Pro Ala Gln Ala Arg Ala
                180                 185                 190

Met Val Asn Pro Thr Thr Thr Val Thr Gln Gly Thr Met Ile Pro Ala
                195                 200                 205

Val Leu Glu Thr Ala Ile Asn Thr Asp Val Pro Gly Tyr Val Arg Ala
210                 215                 220

Val Val Ser Gln Asp Val Arg Ser Phe Asp Gly Lys Lys Val Leu Ile
225                 230                 235                 240

Pro Arg Ser Ser Arg Leu Ile Gly Gln Tyr Gln Ser Gly Val Gln Gln
                245                 250                 255

Gly Gln Lys Arg Ala Tyr Val Ile Trp Thr Arg Leu Ile Arg Pro Asp
                260                 265                 270

Gly Ala Ser Val Asn Ile Ala Ser Pro Ala Val Ala Phe Asp Gly Thr
                275                 280                 285

Thr Gly Leu Ala Gly Asp Val Asp Ser His Phe Phe Lys Arg Phe Gly
290                 295                 300

Ser Ala Met Leu Leu Ser Val Val Gly Gly Leu Gly Ala Leu Ala Thr
305                 310                 315                 320

Gly Gly Val Gly Gly Val Ile Val Ala Gly Ser Gln Gly Ala Ala
                325                 330                 335

Ser Ser Ala Val Gln Ala Asn Gly Glu Ile Ser Pro Thr Ile Arg Val
                340                 345                 350

Arg Met Gly Glu Pro Ile Arg Val Phe Thr Ala Arg Asp Leu Asp Phe
                355                 360                 365

Ser Thr Val Ser Asn
        370

<210> SEQ ID NO 41
<211> LENGTH: 474
<212> TYPE: PRT
<213> ORGANISM: Thioclava dalianensis

<400> SEQUENCE: 41

Met Ala Asp Gln Asn Pro Pro Asp Leu Gln Asn Arg Leu Asp Gln Phe
1               5                   10                  15

Asn Gln Arg Gly Lys Ser Lys Arg Gly Asn Ser Leu Gly Val Gly
            20                  25                  30
```

```
Ala Leu Ala Ala Ala Leu Ala Leu Gly Gly Ala Gly Val Ala Tyr Phe
        35                  40                  45

Leu Ala Thr Gly Leu Gln Glu Gly Asp Ser Ala Leu Glu Thr Ser Asp
 50                  55                  60

Val Glu Thr Phe Gln Asp Arg Arg Pro Gly Thr Gly Gly Arg Leu Glu
 65                  70                  75                  80

Phe Pro Pro Asp Glu Thr Glu Gln Arg Val Asn Asp Ala Leu Ile Ala
                 85                  90                  95

Val Glu Glu Ala Leu Asp Val Pro Glu Ala Pro Ala Pro Glu Pro Ser
            100                 105                 110

Ala Glu Val Leu Ala Glu Ile Ala Lys Leu Arg Glu Ala Leu Ala Ala
            115                 120                 125

Ser Gln Ala Ala Arg Asn Ser Glu Ile Gln Ser Ala Val Ala Asp Leu
130                 135                 140

Arg Glu Ala Phe Asp Glu Gln Lys Thr Ala Leu Glu Ala Leu Ile Ala
145                 150                 155                 160

Glu Lys Glu Ala Glu Leu Ala Asn Leu Gln Arg Gln Thr Glu Thr Arg
                165                 170                 175

Ile Glu Gly Leu Gln Ala Met Leu Asp Ala Glu Arg Ala Gln Arg Glu
            180                 185                 190

Gly Leu Glu Ala Glu Leu Asp Arg Glu Gly Leu Ile Ala Asp Gln Arg
            195                 200                 205

Leu Leu Glu Glu Arg Arg Arg Gln Glu Glu Gln Arg Gln Arg Glu
210                 215                 220

Ala Glu Arg Val Ala Glu Leu Leu Thr Ala Gln Ile Lys Ser Pro
225                 230                 235                 240

Ala Val Val Tyr Ala Asp Gly Pro Arg Gly Gly Gln Ser Gly Ala Ala
                245                 250                 255

Val Ala Asp Pro Ala Ala Thr Gly Thr Gly Gly Pro Val Leu Ser Gly
            260                 265                 270

Asn Glu Arg Phe Leu Gln Ser Ala Arg Pro Leu Glu Val Gln Glu Ala
            275                 280                 285

Ala Arg Leu Ala Tyr Pro Glu Arg Thr Leu Thr Gln Gly Ser Val Ile
            290                 295                 300

Gln Ala Ala Leu Gln Thr Ala Ile Asn Ser Asp Leu Pro Gly Ser Val
305                 310                 315                 320

Val Ala Val Val Ser Glu Pro Val Pro Ala Phe Ser Gly Asp Arg Ile
                325                 330                 335

Leu Ile Pro Arg Gly Ser Arg Leu Phe Gly Gln Tyr Arg Ser Gly Ile
            340                 345                 350

Glu Met His Gln Lys Arg Ile Leu Ile Leu Trp Thr Arg Val Leu Thr
            355                 360                 365

Pro Asp Gly Thr Ser Met Glu Ile Ala Ala Val Gly Gly Asp Arg Leu
            370                 375                 380

Gly Arg Ser Gly Leu Thr Gly Leu Val Asp Thr Lys Phe Ala Glu Arg
385                 390                 395                 400

Phe Gly Gly Ala Ala Leu Ile Ser Val Ile Gly Ala Ala Pro Ala Val
                405                 410                 415

Ala Ala Glu Ser Ala Asn Asn Glu Thr Thr Ser Ile Val Leu Gly Asp
            420                 425                 430

Val Gly Ser Asp Leu Gln Asp Ala Val Gly Ser Val Ile Ala Asp Gln
            435                 440                 445
```

Val Ser Ile Ala Pro Thr Ile Tyr Val Asp Gln Gly Ala Ser Val Thr
450                 455                 460

Val Leu Val Asp Arg Asp Val Val Ile Tyr
465                 470

<210> SEQ ID NO 42
<211> LENGTH: 438
<212> TYPE: PRT
<213> ORGANISM: Acinetobacter baumannii TYTH-1

<400> SEQUENCE: 42

Met Ser Asn Asp Ile Asp Leu Glu Asn Pro Asn Asp Lys Leu Lys Lys
1               5                   10                  15

Lys Gln Ile Lys Trp Leu Ala Ile Leu Gly Thr Ile Leu Phe Ile Ile
                20                  25                  30

Val Ala Ile Phe Leu Phe Ser Gly Ser Pro Pro Glu Glu Thr Asn Lys
            35                  40                  45

Thr Gln Ala Pro Glu Asn Ala Val Asn Val Glu Lys Pro Gly Asp Ala
50                  55                  60

Glu Glu Gln Asp Lys Trp Arg Gln Thr Ala Ala Ile Asp Gln Glu Ala
65                  70                  75                  80

Gln Lys Lys Gln Ile Asp Asp Leu Thr Gln Thr Val Asn Ser Gln Val
                85                  90                  95

Ala Gln Asn Asp Ala Leu Lys Ser Glu Leu Ser Ile Met Asn Glu Arg
            100                 105                 110

Ile Ser Gln Ile Ala Asn Arg Ser Glu Ser Arg Val Val Ala Gln Pro
        115                 120                 125

Thr Asn Thr Asn Pro Pro Asn Leu Gly Gly Ile Ala Gly Thr Ser Ser
130                 135                 140

Ala Tyr Pro Asn Lys Gln Gly Leu His Gly Gln Ser Ile Leu Ser Asp
145                 150                 155                 160

Pro Asn Gly Thr Gly Ile Asp Pro Gln Thr Gly Glu Arg Ile Pro Leu
                165                 170                 175

Pro Asn Asn Ile Ala Pro Val Lys Thr Phe Gly Ile Ile Asp Met Asn
            180                 185                 190

Lys Ser Ile Asp Glu Gln Gly Asn Thr Thr Ser Thr Val Lys Ser
        195                 200                 205

Gln Arg Pro Glu Lys Thr Thr Phe Ile Pro Asp Gly Ser Phe Val Arg
210                 215                 220

Val Val Met Ile Asn Gly Val Asp Ala Pro Thr Gly Gly Gln Ala Gln
225                 230                 235                 240

Ser Asp Pro Ile Pro Val Val Phe Gln Thr Val Gly Lys Phe Asp Met
                245                 250                 255

Pro Asn Asn Tyr Lys Met Asn Ile Lys Gly Cys Arg Phe Val Gly Ala
            260                 265                 270

Ala Trp Gly Glu Leu Ser Ser Glu Arg Val Lys Ala Thr Ile Gln Ser
        275                 280                 285

Gly Asn Cys Ile Ile Asn Gly Gln Thr Val Pro Ile Gln Ile Lys Gly
290                 295                 300

Gln Val Val Gly Glu Asp Gly Lys Thr Gly Ile Arg Gly Arg Val Val
305                 310                 315                 320

Ser Lys Gln Gly Gln Ile Leu Ala Lys Ala Leu Ala Ser Ala Met
                325                 330                 335

Glu Ala Ile Gly Gly Leu Tyr Gly Ser Thr Val Gly Thr Ala Ser Gln
            340                 345                 350

Ser Ala Leu Gly Thr Val Arg Thr Ile Ser Gly Ser Glu Leu Lys Gln
            355                 360                 365

Ala Ala Val Gly Gly Ala Ile Ser Gly Gly Ala Glu Lys Leu Ser Asp
        370                 375                 380

Phe Tyr Met Gln Arg Ala Asn Asp Leu Phe Pro Val Ile Glu Val Ser
385                 390                 395                 400

Ala Gly Arg Thr Leu Glu Ile Val Val Gln Gln Gly Gly Thr Val Ala
                405                 410                 415

Asn Gln Phe Leu Ile Thr Lys Ser Ala Thr Pro Met Asn Gln Gln Lys
            420                 425                 430

Arg Ile Leu Met Asp Asp
            435

<210> SEQ ID NO 43
<211> LENGTH: 401
<212> TYPE: PRT
<213> ORGANISM: Trabulsiella guamensis ATCC 49490

<400> SEQUENCE: 43

Met Asn Asp Asn Val Lys Ile Ala Glu Pro Ala Glu Asp Asn Val Thr
1               5                   10                  15

Glu Pro Glu Arg Glu Ala Arg Ala Arg Arg Glu Thr Glu Leu Arg Gln
            20                  25                  30

Ala Gln Gln Glu Asp Lys Gly Gln Glu Gln Ile Arg Pro Ala Val Thr
        35                  40                  45

Arg Leu Lys Lys Arg Arg His Gly Arg Ala Thr Ala Leu Phe Ala Leu
    50                  55                  60

Leu Ala Val Ala Leu Ile Val Leu Ala Trp Cys Ser Asn Trp Ile Tyr
65                  70                  75                  80

Arg Ser Phe Ile Arg Gln Pro Pro Glu Thr Arg Gln Gln Ala Glu Thr
                85                  90                  95

Glu Ala Pro Gly Arg Thr Asp Tyr Arg Leu Arg Thr Asp Leu Gly Gln
            100                 105                 110

His Thr Ala Val Gln Pro Glu Asn Glu Pro Gln Thr Arg Arg Gln Glu
        115                 120                 125

Thr Asp Leu Pro Pro Ala Ile Thr Pro Asp Thr Asn Arg Leu Asp Lys
    130                 135                 140

Ala Arg Phe Leu Val Arg Arg Glu Asn Thr Ala Gly Thr Gln Arg Thr
145                 150                 155                 160

Val Arg Thr Arg Gln Asp Glu Met Thr Ala Val Thr Ser Ser Pro Gly
                165                 170                 175

Gly Met Ala Glu Thr Ser Lys Val Ser Leu Pro Asp Thr Ala Gly Thr
            180                 185                 190

Gln Pro Val Arg Arg Ile Pro Tyr Asp Pro Asp Leu Tyr Val Pro Glu
        195                 200                 205

Asn Thr Ala Ile Pro Cys Ser Leu Asp Tyr Arg Phe Val Ser Asp Arg
    210                 215                 220

Ala Gly Lys Ile Arg Cys Thr Val Thr Ser Asp Ile Trp Ser Ala Ser
225                 230                 235                 240

Gly Asn Thr Lys Leu Ile Glu Lys Gly Thr Thr Ala Ser Gly Ile Tyr
                245                 250                 255

Gln Thr Gly Arg Glu Asn Gly Met Gln His Gly Gln Gly Arg Ala Phe
            260                 265                 270

Ile Ile Ile Thr Lys Leu Arg Ser Arg Gln Ser Pro Tyr Leu Asp Ile

```
                275                 280                 285
Pro Leu Val Asp Thr Ser Ala Ala Gly Pro Leu Gly Glu Ala Gly Val
290                 295                 300

Asp Gly Trp Ile Asp Ser His Phe Gly Gln Arg Phe Gly Gly Ala Met
305                 310                 315                 320

Met Val Ser Met Ile Pro Asp Ile Ala Ala Trp Ala Ser Asp Ser Ala
                325                 330                 335

Gly Lys Lys Asp Arg Asn Thr Asp Tyr Thr Glu Asn Ser Arg Gln Ala
                340                 345                 350

Met Ala Glu Met Ala Arg Thr Thr Leu Glu Asn Ser Ile Asn Ile Pro
                355                 360                 365

Pro Thr Leu Tyr Lys Asn Gln Gly Glu Ile Ile Ser Leu Val Thr Gly
370                 375                 380

Gln Asp Ile Asp Phe Ser Ala Ile Tyr Thr Leu Arg Met Lys His Asp
385                 390                 395                 400

Arg

<210> SEQ ID NO 44
<211> LENGTH: 434
<212> TYPE: PRT
<213> ORGANISM: Raoultella planticola ATCC 33531

<400> SEQUENCE: 44

Met Thr Asp Lys Pro Val Pro Asp Lys Pro Glu Lys Thr Thr Ala Glu
1               5                   10                  15

Arg Glu Ala Glu Ala Arg Glu Arg Ala Arg Ala Met Ala Tyr Gln
                20                  25                  30

Glu Pro Glu Gln Arg Thr Pro Gly Gln Pro Glu Val Thr Arg Phe
        35                  40                  45

Arg Lys Ala Ser Gly Arg Arg Thr Leu Thr Val Ser Leu Leu Ser Leu
50                  55                  60

Ala Leu Val Ile Ala Leu Ala Ser Gly Gly Asp Arg Leu Phe Ser Ala
65                  70                  75                  80

Leu Lys Gly Gly Asn Glu Lys Glu Ala Asp Thr Ser Pro Pro Thr Ser
                85                  90                  95

Ala Gly Lys Thr Leu His Glu Arg Gln Asn Leu Gly Met Asp Ser Asn
                100                 105                 110

Pro Phe Gly Leu Phe Gly Pro His Thr Gln Asp Glu Thr Asp Pro Ala
        115                 120                 125

Arg Gln Ala Val Thr Pro Ala Pro Thr Leu Pro Pro Ala Pro Pro Thr
130                 135                 140

Leu Asn Lys Ala Ala Ala Leu Ala Asp Gly Leu Asn Asn Ala Arg Thr
145                 150                 155                 160

Met Pro Gly Asp Asn Ala Arg Thr Ser Pro Gly Glu Met Arg Ser Asn
                165                 170                 175

Ala Glu Thr Ser Asn Ser Pro Ser Ser Thr Thr Tyr Thr Ser Cys
                180                 185                 190

Pro Ser Val Leu Thr Arg Gly Lys Asp Gly Arg Leu Arg Cys Pro Glu
        195                 200                 205

Thr Ala Ser Pro Glu Thr Gly Asn Asn Asp Asn Pro Gly Val Ala Arg
210                 215                 220

Val Thr Gly Val Arg Arg Leu Gly Leu Asp Pro Asp Leu Tyr Ile Pro
225                 230                 235                 240

Val Asp Arg Tyr Ile Pro Cys Ser Met Met Trp Arg Phe Val Ser Asp
```

Val Ala Gly His Ile Ser Cys Leu Val Ser Glu Asp Val Tyr Ser Ala
            245                 250                 255
Ser Asn His Val Thr Leu Ile Pro Ala Gly Thr Val Ala Arg Gly Ile
        260                 265                 270
Tyr Arg Thr Gly Ala Leu Gln His Gly Arg Ser Arg Met Phe Val Leu
    275                 280                 285
Trp Thr Glu Leu Arg Thr Pro Glu Pro Gly Ser Leu Gln Ile Pro Leu
290                 295                 300
Thr Asp Thr Gln Ala Ser Gly Pro Leu Gly Glu Ala Gly Ile Ser Gly
305                 310                 315                 320
Trp Ile Asp Asn His Phe Trp Glu Arg Phe Gly Asn Ala Leu Met Leu
            325                 330                 335
Ser Thr Val Gln Asp Val Ala Ala Ala Ser Asp Ala Ala Pro Gly
        340                 345                 350
Lys Asp Arg Asn Thr Asp Tyr Thr Glu Asn Thr Arg Ala Ala Thr Ala
    355                 360                 365
Glu Met Ala Lys Thr Thr Leu Asp Asn Ser Ile Asn Ile Pro Pro Thr
370                 375                 380
Leu Tyr Leu Asn Gln Gly Asp Val Ile Gly Ile Met Thr Gly Thr Asp
385                 390                 395                 400
Ile Asp Phe Ser Ser Val Trp Gln Leu Arg Leu Lys Arg Trp Tyr
            405                 410                 415
Glu Arg
        420                 425                 430

<210> SEQ ID NO 45
<211> LENGTH: 238
<212> TYPE: PRT
<213> ORGANISM: Afipia felis (Cat scratch disease bacillus)

<400> SEQUENCE: 45

Met Ala Gln Gly Thr Leu Ile Arg Gly Val Leu Glu Thr Ala Val Glu
1               5                   10                  15
Ser Asp Leu Pro Gly Met Val Arg Ala Val Thr Glu Asn Val Trp
            20                  25                  30
Ser Phe Asp Gly Arg Arg Val Leu Ile Pro Ser Gly Ser Arg Leu Ile
        35                  40                  45
Gly Glu Tyr Arg Ser Gly Ile Ala Gln Gly Gln Thr Arg Val Phe Ile
    50                  55                  60
Val Trp Thr Arg Met Leu Arg Ser Asp Gly Val Ser Val Gln Leu Gly
65                  70                  75                  80
Ser Asn Gly Ala Asp Glu Leu Gly Arg Ala Gly Asn Ala Gly Phe Val
            85                  90                  95
Asp Asn His Tyr Leu Glu Arg Phe Gly Ser Ala Ile Val Leu Ser Leu
        100                 105                 110
Val Gly Gly Gly Ala Gln Phe Leu Ser Ala Tyr Gly Gln Asn Thr Asp
    115                 120                 125
Gly Tyr Gly Asn Gly Thr Val Ile Thr Thr Asp Pro Val Thr Gly
130                 135                 140
Val Val Thr Gln Thr Gln Thr Gly Val Asn Gln Asn Gln Leu Ser Leu
145                 150                 155                 160
Gln Ala Arg Gln Ile Ala Ala Gln Asn Ile Ser Gln Thr Leu Thr Asn
            165                 170                 175
Ile Ala Gln Glu Ala Leu Arg Asn Ser Ile Asn Ile Pro Pro Thr Ile

```
                180             185             190
Tyr Leu Asp Gln Gly Thr Arg Ile Ile Val Phe Val Arg Arg Asp Leu
            195                 200                 205

Asp Phe Ser Ala Leu Tyr Pro Asp Pro Val Lys Glu Ala Leu Arg Glu
    210                 215                 220

Leu Lys Arg Glu Arg Ser Gly Ala Lys Pro Asp Gly Leu His
225                 230                 235

<210> SEQ ID NO 46
<211> LENGTH: 474
<212> TYPE: PRT
<213> ORGANISM: Rhodovulum sp. NI22

<400> SEQUENCE: 46

Met Ala Asp Gln Thr Pro Pro Asp Leu Gln Asn Arg Leu Asp Gln Phe
1               5                   10                  15

Ser Gln Arg Gly Lys Ser Lys Arg Arg Gly Asn Ser Leu Gly Val Gly
            20                  25                  30

Ala Leu Ala Ala Ala Leu Ala Leu Gly Gly Ala Gly Val Ala Tyr Phe
        35                  40                  45

Leu Ala Thr Gly Leu Gln Glu Glu Asp Ser Ala Leu Glu Thr Ser Asp
    50                  55                  60

Val Glu Thr Phe Gln Asp Arg Arg Pro Gly Thr Gly Gly Arg Leu Glu
65                  70                  75                  80

Phe Pro Pro Asp Glu Thr Glu Gln Arg Val Asn Asp Ala Leu Ile Ala
                85                  90                  95

Val Glu Glu Ala Leu Asp Val Pro Ala Ala Pro Ala Pro Glu Pro Ser
            100                 105                 110

Ala Glu Val Leu Ala Glu Ile Ala Lys Leu Arg Glu Ala Leu Ala Ala
        115                 120                 125

Ser Gln Ala Ala Arg Asn Ser Glu Ile Gln Ser Ala Val Ala Asp Leu
    130                 135                 140

Arg Glu Ala Phe Asp Glu Gln Lys Ala Ala Leu Glu Ala Leu Ile Ala
145                 150                 155                 160

Glu Lys Glu Ala Glu Leu Ala Asn Leu Gln Arg Gln Thr Glu Thr Arg
                165                 170                 175

Ile Glu Gly Leu Gln Ala Met Leu Asp Ala Glu Arg Ala Gln Arg Glu
            180                 185                 190

Gly Leu Glu Ala Glu Leu Asp Arg Glu Gly Leu Ile Ala Asp Gln Arg
        195                 200                 205

Leu Leu Glu Glu Arg Arg Gln Glu Glu Gln Arg Gln Arg Glu
    210                 215                 220

Ala Glu Arg Val Ala Glu Glu Leu Leu Thr Ala Gln Ile Lys Ser Pro
225                 230                 235                 240

Ala Val Val Tyr Ala Asp Gly Pro Arg Gly Gly Gln Ser Gly Ala Ala
                245                 250                 255

Val Ala Asp Pro Gly Ala Ala Gly Thr Gly Gly Pro Ala Leu Ser Gly
            260                 265                 270

Asn Glu Gln Phe Leu Gln Ser Ala Arg Pro Leu Glu Val Gln Asp Ala
        275                 280                 285

Ala Arg Leu Thr Asn Pro Glu Arg Thr Leu Thr Gln Gly Ser Val Ile
    290                 295                 300

Gln Ala Ala Leu Gln Thr Ala Ile Asn Ser Asp Leu Pro Gly Ser Val
305                 310                 315                 320
```

```
Val Ala Val Val Ser Glu Pro Val Pro Ala Phe Ser Gly Asp Arg Ile
            325                 330                 335

Leu Ile Pro Arg Gly Ser Arg Leu Phe Gly Gln Tyr Arg Ser Gly Ile
            340                 345                 350

Glu Met His Gln Lys Arg Ile Leu Ile Leu Trp Thr Arg Val Leu Thr
            355                 360                 365

Pro Asp Gly Thr Ser Met Glu Val Ala Ala Val Gly Gly Asp Gln Leu
            370                 375                 380

Gly Arg Ser Gly Leu Thr Gly Leu Val Asp Thr Arg Phe Val Glu Arg
385                 390                 395                 400

Phe Gly Gly Ala Ala Leu Ile Ser Val Ile Gly Ala Ala Pro Ala Val
            405                 410                 415

Ala Ala Glu Ser Ala Asn Asn Glu Thr Thr Ser Ile Val Leu Gly Asp
            420                 425                 430

Val Gly Ser Asp Leu Gln Asp Ala Val Gly Ser Val Ile Ala Asp Gln
            435                 440                 445

Val Ser Ile Ala Pro Thr Ile Tyr Val Asp Gln Gly Ala Ser Val Thr
            450                 455                 460

Val Leu Val Asp Arg Asp Val Val Ile Tyr
465                 470
```

<210> SEQ ID NO 47
<211> LENGTH: 404
<212> TYPE: PRT
<213> ORGANISM: Xanthomonas axonopodis pv. Phaseoli

<400> SEQUENCE: 47

```
Met Ser Asp Gln Thr Asn Lys Pro Gln Glu Asp Arg Glu Ala Ala Val
1               5                   10                  15

Arg Glu Trp Glu Lys Gln Ala Asn Ala Ser Leu Val Ala Asp Asp Arg
            20                  25                  30

Lys Lys Lys Met Ser Gly Ile Ala Ile Ala Ala Ile Ala Ala Val Gly
            35                  40                  45

Leu Gly Ala Val Trp Tyr Met Lys His Gly Gly Ser Glu Pro Ala Lys
        50                  55                  60

Pro Val Gly Asn Ser Glu Leu Ser Ile Pro Glu Arg Lys Pro Val Pro
65                  70                  75                  80

Lys Leu Lys Glu Gln Glu Ser Ala Ser Ala Ala Val Thr Ser Thr
            85                  90                  95

Pro Ala Ala Thr Pro Ala Asn Ala Thr Gln Ala Asp Asp Pro Met Lys
            100                 105                 110

Ala Gln Arg Glu Gln Met Glu Met Gln Arg Arg Glu Gln Glu Arg Arg
            115                 120                 125

Met Leu Glu Ala Arg Met Lys Ser Ala Ile Ile Pro Pro Asn Ser Asn
            130                 135                 140

Asn Gln Ala Ala Ala Gln Pro Ala Gly Asp Ser Gly Asp Gln Gly Gln
145                 150                 155                 160

Ser Asn Ala Gly Ile Leu Gly Gly Ala Ser Gly Asp Arg Gly Ala Gln
            165                 170                 175

Asp Pro Asn Ser Arg Phe Ala Arg Ala Val Ser Gly Gly Val Ala
            180                 185                 190

Val Ser Lys Ala Asn Gln Ile Asp Asn Leu Pro Tyr Lys Val Leu Gln
            195                 200                 205

Gly Lys Leu Ile Glu Ala Val Leu Glu Pro Arg Ala Ile Ser Asp Leu
            210                 215                 220
```

```
Pro Gly Met Val Cys Ala Thr Val Gln Arg Asp Val Tyr Gly Ala Gln
225                 230                 235                 240

Asp Arg Asn Lys Leu Ile Pro Trp Gly Ser Arg Val Cys Gly Val Tyr
                245                 250                 255

Ser Ala Glu Val Arg Lys Gly Gln Asp Arg Leu Phe Val Ile Trp Asn
            260                 265                 270

Thr Val Arg Arg Pro Asp Gly Val Gln Val Ala Leu Asp Ser Ala Gly
        275                 280                 285

Ala Asp Gln Leu Gly Thr Ala Gly Met Gly Gly Ile Val Asp Thr His
    290                 295                 300

Phe Ala Gly Ile Phe Gly Thr Ser Ala Leu Leu Ser Ile Ile Gly Ala
305                 310                 315                 320

Gly Ala Ser Asn Ala Gly Val Ser Ser Gly Asp Gln Tyr Asn Ser Ala
                325                 330                 335

Ala Ala Tyr Arg Gln Ser Val Gln Gln Ala Ala Ala Gln Thr Ser Gln
            340                 345                 350

Ser Val Leu Gln Pro Tyr Ile Asn Ile Pro Pro Thr Ile Thr Val Pro
        355                 360                 365

Ala Gly Ser Arg Val Arg Ile Tyr Val Asn Lys Asp Leu Asp Phe Thr
    370                 375                 380

Ala Ile Tyr Lys Asp Glu Ile Asp Ala Ala Lys His Gly Asp Gly Val
385                 390                 395                 400

Thr Phe Ile Gln

<210> SEQ ID NO 48
<211> LENGTH: 374
<212> TYPE: PRT
<213> ORGANISM: Bordetella pertussis B1920

<400> SEQUENCE: 48

Met Leu Asn Arg Pro Ser Ser Pro Asp Gly Gly Glu Ala His Ala Trp
1               5                   10                  15

Pro Pro Asp Pro Glu Ile Pro Val Phe Ala Asn Ala Glu His Ala His
            20                  25                  30

Arg Arg Pro Leu Arg Trp Met Phe Ala Leu Val Ala Val Ala Leu Ser
        35                  40                  45

Cys Leu Leu Ala Thr Gly Ile Trp Arg Ser Arg Ala Ala Pro Pro His
    50                  55                  60

Ala Ala Thr Gln Thr Val Ala Pro Ala Gly Gln Ala Leu Pro Pro Gly
65                  70                  75                  80

Arg Ile Phe Thr Val His Pro Arg Glu Pro Glu Pro Ala Pro Leu Pro
                85                  90                  95

Asp Met Pro Ala Ala Pro Asp Pro Ile Leu Pro Gln Pro Arg Pro Ala
            100                 105                 110

Pro Pro Val Pro Pro Pro Pro Ile Arg Ala Pro Tyr Asp Tyr Asp Glu
        115                 120                 125

Pro Ala Pro Arg Arg Asp Ser Ala Ala Leu Lys Ser Gly Pro Ala Met
    130                 135                 140

Met Val Ala Thr Ala Ala Arg Leu Gly Gln Thr Glu Arg Ala Gly Met
145                 150                 155                 160

Ala Asp Asp Gly Val Ser Ala Asp Ala Ala Thr Leu Ile Gly Arg Asn
                165                 170                 175

Val Ser Arg Ala Thr Arg Ser Gly Gly Arg Asp Tyr Arg Leu Leu Pro
            180                 185                 190
```

```
Gly Thr Phe Ile Asp Cys Ile Leu Gln Thr Arg Ile Val Thr Asn Val
            195                 200                 205

Pro Gly Leu Thr Thr Cys Ile Val Ser Arg Asp Val Tyr Ser Ala Ser
210                 215                 220

Gly Lys Arg Val Leu Val Pro Arg Gly Thr Thr Val Val Gly Glu Tyr
225                 230                 235                 240

Arg Ala Asp Leu Ala Gln Gly Ser Gln Arg Ile Tyr Val Ala Trp Ser
            245                 250                 255

Arg Leu Phe Met Pro Ser Gly Leu Thr Ile Glu Leu Ala Ser Pro Ala
            260                 265                 270

Val Asp Gly Thr Gly Ala Ala Gly Leu Pro Gly Val Val Asp Asp Lys
            275                 280                 285

Phe Ala Gln Arg Phe Gly Gly Ala Leu Leu Ser Val Leu Gly Asp
290                 295                 300

Ala Thr Ser Tyr Met Leu Ala Arg Ala Thr Asp Ala Arg His Gly Val
305                 310                 315                 320

Asn Val Asn Leu Thr Ala Ala Gly Thr Met Asn Ser Leu Ala Ser
                    325                 330                 335

Ala Leu Asn Asn Thr Ile Asn Ile Pro Pro Thr Leu Tyr Lys Asn His
            340                 345                 350

Gly Asp Gln Ile Gly Ile Leu Val Ala Arg Pro Leu Asp Phe Ser Ile
            355                 360                 365

Leu Arg Gly Thr Asn Glu
            370

<210> SEQ ID NO 49
<211> LENGTH: 395
<212> TYPE: PRT
<213> ORGANISM: Collimonas arenae

<400> SEQUENCE: 49

Met Ala Thr Thr Gln Pro Leu Asp Ser Arg Asp Gln Ala Val Asp Ser
1               5                   10                  15

Trp Glu Lys Glu Thr Asn Ala Ser Ile Val Ala Ala Ser Arg Lys Lys
                20                  25                  30

Lys Met Asn Gly Val Ala Ile Gly Val Ile Ala Val Ser Ala Ile Val
            35                  40                  45

Ala Val Tyr Phe Leu Lys Gly Arg Glu Ser Lys Ser Ala Ala Leu Pro
        50                  55                  60

Asp Ala Asn Leu Thr Val Ala Pro Arg Lys Pro Val Pro Gln Leu Lys
65                  70                  75                  80

Glu Gln Ser Ala Ala Val Val Pro Ala Val Thr Pro Thr Ala Thr Pro
                85                  90                  95

Ala Ser Gln Gln Ala Ala Asp Pro Gln Lys Ala Gln Leu Glu Gln Gln
            100                 105                 110

Arg Glu Glu Gln Ala Arg Lys Phe Leu Glu Ala Arg Lys Ser Ala
        115                 120                 125

Ile Glu Pro Ser Gly Val Ser Ala Gln Ala Gly Pro Ser Thr Ala Ala
130                 135                 140

Asp Ala Gln Gly Gln Ala Gly Leu Gly Ala Gly Thr Ala Gly Asp Lys
145                 150                 155                 160

Gly Ala Gln Asp Thr Asn Ser Arg Phe Ala Arg Ser Val Ser Gly Thr
                165                 170                 175

Gly Val Pro Val Ser Leu Ala Tyr Asn Ile Thr Asp Leu Glu Tyr Lys
```

```
                    180             185                 190
Ile Leu Gln Gly Lys Val Leu Asp Gly Ile Val Pro Arg Ser Ile
                195                 200                 205

Ser Asp Leu Pro Gly Thr Ile Cys Ala Thr Ile Gln Ser Asp Val Tyr
210                 215                 220

Ala Glu Arg Gly Arg Leu Lys Leu Ile Pro Trp Gly Ser Arg Met Cys
225                 230                 235                 240

Gly Val Tyr Asn Ser Ser Leu Ala Lys Gly Gln Ser Arg Met Phe Ser
                245                 250                 255

Val Trp Asn Thr Leu Arg Thr Ala Asn Pro Asp Asn Thr Ile Ser Glu
                260                 265                 270

Val Val Leu Asp Ser Ile Gly Ser Asp Gln Leu Gly Thr Ser Gly Ile
                275                 280                 285

Gly Gly Leu Val Asp Thr His Phe Ala Glu Ile Phe Gly Thr Ser Ser
                290                 295                 300

Leu Ile Ser Ile Ile Gly Ala Gly Ala Ser Asn Thr Gly Val Ser Thr
305                 310                 315                 320

Gly Asp Gln Asn Asn Ser Ser Ser Gln Tyr Arg Gln Ser Val Gln Gln
                325                 330                 335

Ala Ala Ala Gln Thr Ser Gln Ser Val Leu Ala Pro Tyr Ile Asn Ile
                340                 345                 350

Pro Pro Thr Ile Thr Ala Pro Ala Gly Thr Arg Ile Arg Ile Phe Val
                355                 360                 365

Asn Arg Asp Leu Asp Phe Ser Lys Ile Tyr Lys Lys Gln Ala Asp Ala
                370                 375                 380

Ala Lys Gln Gln Asp Gly Ala Val Leu Ile Asp
385                 390                 395
```

<210> SEQ ID NO 50
<211> LENGTH: 379
<212> TYPE: PRT
<213> ORGANISM: Salmonella choleraesuis

<400> SEQUENCE: 50

```
Met Lys Asn Lys Asp Asp Glu Lys Asn Asn Asp Ala Gly Asn Arg Gly
1               5                   10                  15

Ile Ile Glu Val Lys Gly Lys Ala Ala Pro Lys Lys Ile Leu Ile Leu
                20                  25                  30

Ile Ile Leu Leu Ile Ala Ala Leu Phe Val Ile Ile Leu Phe Lys
            35                  40                  45

Val Leu Ser Arg Glu Gln Val Gln Gln Thr Pro Leu Glu Lys Ser
        50                  55                  60

Asp Glu Thr Leu Val Thr Asn Thr Asn Gly Val Ser Leu Thr Thr
65                  70                  75                  80

Met Met Lys Asn Ile Glu Glu Lys Glu Lys Ile Asp Ala Ala Asn Arg
                85                  90                  95

Lys Lys Ala Gln Glu Glu Gln Glu Lys Gln Ala Asp Asn Ala Pro
            100                 105                 110

Ser Ala Pro Ala Ser Gln Lys Ala Asp Gln Thr Ala Val Asn Val Ile
                115                 120                 125

Ala Asn Gly Thr Pro Gln Thr Ala Ser Gly Asp Pro Asn Gln Pro Gln
            130                 135                 140

Pro Leu Pro Lys Ser Val Arg Gln Leu Met Gly Asp Thr Met Val Lys
145                 150                 155                 160
```

Ile Asp Asn Gln Glu Pro Gly Glu Lys Asn Gln Glu Arg Asp Asp Leu
            165                 170                 175

Gln Gly Ser Gln Tyr Ala Asp Gly Lys Val Ser Pro Val Leu Asn Arg
        180                 185                 190

Arg Tyr Leu Leu Ser Ala Gly Thr Ala Leu Ser Cys Val Leu Lys Thr
        195                 200                 205

Lys Ile Val Thr Ser Tyr Pro Gly Ile Thr Met Cys Gln Leu Thr Arg
210                 215                 220

Asp Val Trp Ser Asp Asn Gly Glu Val Leu Leu Ala Arg Lys Gly Ala
225                 230                 235                 240

Leu Leu Ile Gly Glu Gln Asn Lys Val Met Thr Gln Gly Val Ala Arg
            245                 250                 255

Val Phe Val Asn Trp Thr Thr Leu Lys Asp Glu Asn Val Asn Val Arg
        260                 265                 270

Ile Gly Ala Leu Gly Thr Asp Ser Leu Gly Ala Ser Gly Leu Pro Ala
        275                 280                 285

Trp Val Asp Asn His Phe Gly Gln Arg Phe Gly Ala Leu Leu Leu
        290                 295                 300

Ser Leu Leu Gly Asp Gly Leu Asp Ile Leu Lys Asn Ser Thr Gln Gln
305                 310                 315                 320

Thr Gly Ser Asn Ser Asn Ile Thr Tyr Glu Asn Thr Ser Asp Ala Thr
            325                 330                 335

Lys Glu Met Ala Lys Thr Thr Leu Asp Asn Thr Ile Asn Ile Pro Pro
        340                 345                 350

Thr Ala Tyr Ile Asn Gln Gly Thr Val Leu Ser Val Ile Val Pro Arg
        355                 360                 365

Asn Ile Asp Phe Ser Ser Val Tyr Glu Leu Gln
        370                 375

<210> SEQ ID NO 51
<211> LENGTH: 405
<212> TYPE: PRT
<213> ORGANISM: bacterium YEK0313

<400> SEQUENCE: 51

Met Ser Glu Asn Pro Pro Arg Asn Glu Glu Val Pro Asp Asp Gly Gln
1               5                   10                  15

Pro Leu Thr Gly Glu Pro Val Gly Pro Ala Pro Met Arg Leu Arg Ala
            20                  25                  30

Glu Pro Pro Arg Val Thr Arg Leu Ser Arg Lys Val Leu Ala Gly Leu
        35                  40                  45

Gly Leu Val Ala Ser Val Gly Leu Gly Gly Ala Leu Ile Tyr Ala Leu
    50                  55                  60

Gln Thr Arg Asp Gly Arg Pro Asn Asp Leu Tyr Ser Thr Glu
65                  70                  75                  80

Asn Arg Ser Thr Ala Asp Gly Leu Ala Gly Leu Pro Arg Asp Tyr Ser
            85                  90                  95

Gly Val Pro Gln Leu Gly Pro Pro Leu Pro Gly Asp Leu Gly Arg Pro
        100                 105                 110

Ile Leu Ser Thr Gln Asp Arg Gly Gln Pro Val Pro Thr Pro Gly Ile
        115                 120                 125

Ala Thr Pro Asn Pro Gly Ile Ser Pro Glu Glu Gln Arg Arg Leu Gln
    130                 135                 140

Glu Ile Glu Thr Ala Arg Thr Ser Arg Leu Phe Ser Gly Ser Glu Ser
145                 150                 155                 160

Arg Gly Ala Pro Ala Ala Gly Gly Val Pro Ala Leu Pro Pro Ala
                165                 170                 175

Pro Asp Leu Thr Ser Leu Gly Leu Ala Pro Pro Ala Thr Pro Ser
            180                 185                 190

Ala Gln Asp Arg Gln Asn Ala Phe Leu Asn Ala Ala Asp Arg Arg
            195                 200                 205

Thr Val Ala Pro Asp Arg Val Val Ala Pro Ala Ser Pro Asn Ile Leu
        210                 215                 220

Gln Ala Gly Ala Val Ile Ser Ala Ala Leu Ile Thr Gly Ile Arg Ser
225                 230                 235                 240

Asp Leu Pro Gly Gln Ile Thr Ala Gln Val Thr Glu Asn Ile Tyr Asp
                245                 250                 255

Ser Pro Thr Gly Arg Ile Leu Leu Val Pro Gln Gly Thr Arg Val Ile
                260                 265                 270

Gly Gln Tyr Asp Asn Asn Val Gln Phe Gly Gln Ser Arg Val Leu Leu
                275                 280                 285

Val Trp Asn Arg Leu Ile Phe Pro Asn Gly Arg Ser Ile Val Leu Glu
                290                 295                 300

Arg Gln Pro Gly Ala Asp Ala Glu Gly Phe Ala Gly Leu Gln Asp Gly
305                 310                 315                 320

Val Asp Tyr His Trp Trp Asp Leu Ala Lys Ala Ala Gly Leu Ser Thr
                325                 330                 335

Leu Leu Ser Val Gly Ala Glu Leu Ala Val Asp Asn Asp Arg Leu
            340                 345                 350

Ile Gln Ala Ile Arg Asn Gly Gly Gln Asp Thr Leu Asn Asp Ala Gly
                355                 360                 365

Gln Gln Ile Val Arg Arg Gln Leu Asn Val Pro Pro Thr Leu Thr Val
            370                 375                 380

Arg Pro Gly Phe Pro Val Arg Val Ile Val Thr Arg Asp Leu Val Leu
385                 390                 395                 400

Glu Pro Tyr Gly Gly
            405

<210> SEQ ID NO 52
<211> LENGTH: 422
<212> TYPE: PRT
<213> ORGANISM: Citrobacter braakii

<400> SEQUENCE: 52

Met Asn Asp Glu Asn Lys Val Pro Val Pro Asp Glu Ala Gln Ala Ser
1               5                   10                  15

Pro Ala His Ala Glu Asp Ile Ala Thr Leu Glu Arg Glu Ala Arg
            20                  25                  30

Ala Lys Arg Glu Ala Glu Leu Leu Asn Ala Gln Asp Asp Glu Glu Lys
        35                  40                  45

Asp Pro Val Gln Pro Ala Val Asn Lys Leu Lys Lys Arg Lys Arg Gly
        50                  55                  60

Lys Ala Thr Ala Phe Leu Ala Ile Val Ala Val Ala Leu Ile Phe Leu
65                  70                  75                  80

Ala Trp Gly Gly Asn Trp Val Tyr Arg Asn Ile Leu Trp Gln Pro Thr
                85                  90                  95

Glu Glu Lys Lys Gln Asp Thr Ala Pro Gln Thr Asn Lys Ser Asp Tyr
            100                 105                 110

Arg Gln Arg Asn Asp Leu Gly Met Ser Thr Asp Thr Ala Glu Glu Glu

```
            115                 120                 125
Pro Glu Gln Gln Asn Asn Gly Gln Ser Ser Thr Ala Gly Thr Gly Gln
        130                 135                 140

Ala Ala Pro Thr Ala Pro Pro Glu Leu Asn Lys Ala Ser Phe Leu Ile
145                 150                 155                 160

Arg Arg Asp Gly Ser Ala Thr Thr Gln Asn Gln Val Lys Thr Arg Gln
            165                 170                 175

Gln Glu Met Thr Leu Arg Ser Ala Thr Thr Thr Gly Gln Gln Asp Ser
        180                 185                 190

Ser Ala Ala Thr Pro Pro Gly Gln Pro Gln Asn Thr Ala Ala Pro Ser
            195                 200                 205

Pro Gly Gln Ser Pro Ala Pro Val Arg Arg Ile Pro Tyr Asn Pro Asp
        210                 215                 220

Leu Tyr Ile Pro Glu Asn Thr Ser Ile Pro Cys Ser Leu Asp Arg Arg
225                 230                 235                 240

Phe Val Ser Asp Arg Ala Gly Lys Leu Arg Cys Thr Ile Thr Thr Asp
            245                 250                 255

Ile Trp Ser Ala Ser Gly Asn Thr Lys Leu Ile Glu Lys Gly Thr Thr
        260                 265                 270

Ala Ser Leu Leu Tyr Arg Ala Ile Ala Glu Glu Gly Met Lys His Gly
            275                 280                 285

Gln Gly Arg Ala Phe Ile Ile Ala Thr Lys Leu Arg Thr Arg Gln Pro
        290                 295                 300

Pro Tyr Leu Asp Ile Pro Leu Val Asp Thr Ser Ala Ala Gly Glu Leu
305                 310                 315                 320

Gly Glu Ala Gly Val Asp Gly Trp Ile Asp Ser His Phe Trp Glu Arg
            325                 330                 335

Phe Gly Gly Ala Leu Met Val Gly Met Ile Pro Asp Ile Gly Ala Trp
        340                 345                 350

Ala Ser Asn Ser Ala Gly Lys Lys Asp Arg Asn Thr Asp Tyr Thr Glu
            355                 360                 365

Asn Ser Arg Gln Ala Met Ala Asp Met Ala Arg Thr Thr Leu Glu Asn
        370                 375                 380

Ser Ile Asn Ile Pro Pro Thr Leu Tyr Lys Asn Gln Gly Glu Ile Ile
385                 390                 395                 400

Asn Leu Ile Thr Gly Glu Asp Ile Asp Phe Ser Asn Ile Tyr Thr Leu
            405                 410                 415

Arg Leu Lys Asn Asp Arg
            420

<210> SEQ ID NO 53
<211> LENGTH: 400
<212> TYPE: PRT
<213> ORGANISM: Mumia flava

<400> SEQUENCE: 53

Met Asn Glu Gln Thr Pro Arg Asn Ala Ile Ala Pro Asp Thr Asp Pro
1               5                   10                  15

Ala Lys Val Thr Asp Thr Ile Asn Gly Asp Leu Ala Ser Pro Pro Thr
            20                  25                  30

Asp Arg Gly Met Pro Glu Leu Gly Gln Ala Gly Gly Arg Pro Arg Val
        35                  40                  45

Trp Trp Leu Ala Pro Leu Leu Ile Val Ala Phe Val Ile Gly Gly Ala
    50                  55                  60
```

Val Trp Thr Ile His Gly Phe Leu Ala Arg His Asp Ala Ala Glu Lys
 65                  70                  75                  80

Ala Lys Arg Asp Thr Val Gln Asp Gln Val Ala Gln Gly Arg Val Phe
                 85                  90                  95

Gly Asp Gly Ala Ala Pro Ala Ser Ala Gly Thr Ala Ser Gly Pro Val
            100                 105                 110

Ala Thr Ser Ala Thr Ala Ser Ala Pro Val Val Ala Ser Ala Arg Pro
        115                 120                 125

Thr Ser Ala His Thr Ala Pro Ala Arg Ser Tyr Tyr Asp Ala Pro Leu
    130                 135                 140

Leu Ser Thr Gly Ser Ser Gly Ser Ala Asn Gly Glu Ala Asp Thr Val
145                 150                 155                 160

Ala Ser Ala Pro Ala Asp Ala Ser Gly Thr Gln Thr Asn Val Ala Met
                165                 170                 175

Val Ser Gly Gly Gln Ser Ser Gln Gly Ser Gly Pro Leu Ala Gln Ala
            180                 185                 190

Leu Thr Pro Thr Val Thr Pro Lys Val Arg Ala Gly Phe Leu Gly Asn
        195                 200                 205

Arg Ser Leu Ile Leu Ala Glu Gly Ala Lys Ile Asp Cys Ala Gly Asp
    210                 215                 220

Thr Ala Phe Asp Ser Thr Gln Ala Gly Ile Ser Thr Cys Thr Val Thr
225                 230                 235                 240

Lys Asn Val Tyr Ser Asp Asp Gly Arg Val Val Leu Ile Glu Arg Gly
                245                 250                 255

Ser Gln Ile Asn Ser Glu Tyr Arg Ser Asn Leu Ala Pro Gly Gln Lys
            260                 265                 270

Arg Val Phe Ile Leu Ser Ala Arg Ile Arg Thr Pro Glu Gly Val Thr
        275                 280                 285

Val Glu Ile Asp Ser Pro Ala Ala Asp Ala Leu Gly Arg Met Gly Ile
    290                 295                 300

Asp Gly Tyr Val Asp Asn His Trp Gly Ala Arg Ile Gly Ala Ala Leu
305                 310                 315                 320

Leu Leu Gly Leu Thr Gln Asp Ala Ile Gly Tyr Leu Ala Thr Arg Gly
                325                 330                 335

Gly Asn Gly Asn Ser Ser Thr Val Tyr Glu Asn Thr Gln Gln Gln Gly
            340                 345                 350

Asn Asp Met Ala Ser Arg Val Leu Asp Ser Thr Ile Asn Ile Pro Pro
        355                 360                 365

Thr Leu Thr Gln Asn Gln Gly Ala Glu Phe Thr Ile Val Val Ala Arg
    370                 375                 380

Asp Leu Asp Phe Ser Pro Val Tyr Ala Leu Gln Pro Glu Gly Thr Arg
385                 390                 395                 400

<210> SEQ ID NO 54
<211> LENGTH: 372
<212> TYPE: PRT
<213> ORGANISM: Kirrobacter mercurialis

<400> SEQUENCE: 54

Met Lys Leu Ala Asn Arg Ile Ser Pro Ser Arg Thr Asn Gly Asp Ala
1               5                   10                  15

Ala Pro Asp Thr Asp Pro Arg Glu Asn Ala Ser Ala Glu Val Ile Asp
            20                  25                  30

Leu Ala Ser Arg Thr Ala Tyr Pro Ala Val Ala Gly Arg Lys Gly Arg
        35                  40                  45

Ser Asp Ala Val Gly Leu Ala Ala Gly Ile Gly Phe Val Ala Leu Leu
 50                  55                  60

Gly Ala Ala Thr Leu Trp Gly Leu Asn Ala Ser Arg Val Pro Asp Ala
 65                  70                  75                  80

Pro Gln Gly Thr Ala Pro Val Val Gln Asn Gly Pro Pro Asn Ala Phe
                 85                  90                  95

Ile Pro Thr Asp Pro Leu Thr Pro Val Pro Val Leu Asn Gly Val Pro
                100                 105                 110

Ala Gly Ala Pro Val Pro Ser Pro Val Phe Ala Ser Pro Pro Gln Thr
            115                 120                 125

Ala Ala Met Pro Met Gly Asn Pro Tyr Ala Ser Pro Thr Val Val Phe
        130                 135                 140

Asp Ala Gly Ala Met Pro Ala Ala Ala Gly Ala Leu Ala Gly Ala
145                 150                 155                 160

Pro Ala Gly Glu Ala Thr Ala Gly Thr Gly Thr Thr Ala Ala Asp Phe
                165                 170                 175

Ala Ser Arg Val Gly Gly Val Gly Gly Pro Ala Val Ala Arg Thr
            180                 185                 190

Asp Val Asp Pro Arg Thr Thr Val Thr Gln Gly Thr Met Ile Pro Ala
        195                 200                 205

Val Leu Glu Thr Ala Ile Asn Thr Asp Val Pro Gly Phe Ala Arg Ala
210                 215                 220

Val Val Ser Gln Asp Val Arg Ser Phe Asp Gly Thr Arg Ile Leu Val
225                 230                 235                 240

Pro Arg Ser Ser Arg Leu Ile Gly Gln Tyr Gln Ser Gly Leu Gln Ala
                245                 250                 255

Gly Gln Arg Arg Ala Tyr Val Ile Trp Thr Arg Leu Ile Arg Pro Asp
            260                 265                 270

Gly Val Ser Val Ala Leu Ala Ser Pro Ala Ser Ala Phe Asp Gly Ser
        275                 280                 285

Gly Gly Leu Pro Gly Arg Val Asp Asn His Phe Phe Gln Arg Phe Gly
    290                 295                 300

Ser Ser Ile Leu Leu Ser Val Ile Gly Gly Leu Thr Ala Val Ala Ser
305                 310                 315                 320

Gly Gly Thr Ser Val Val Leu Gly Gly Gly Gln Asp Ala Ala Ser Thr
                325                 330                 335

Ala Leu Gln Gln Ser Gly Gln Ile Ala Pro Thr Val Arg Val Arg Gln
            340                 345                 350

Gly Glu Pro Ile Arg Val Phe Thr Ala Arg Asp Leu Asp Phe Ser Gln
        355                 360                 365

Ala Pro Arg Leu
    370

<210> SEQ ID NO 55
<211> LENGTH: 441
<212> TYPE: PRT
<213> ORGANISM: Celeribacter indicus

<400> SEQUENCE: 55

Met Thr Glu Gly Thr Glu Asp Leu Ala Ala Arg Leu Ala Ala Leu Glu
 1               5                  10                  15

Gly Ser Thr Gly Lys Ala Lys Ala Asn Lys Arg Pro Ala Pro Leu Ala
             20                  25                  30

Ala Ile Leu Gly Val Val Gly Ile Ala Ala Ala Gly Gly Leu Ala Trp

```
                35                  40                  45
Ala Ala Leu Gln Pro Ser Ala Glu Ala Pro Met Ala Thr Ala Ala Pro
 50                  55                  60
Glu Glu Phe Gln Ser Ser Gly Pro Gly Phe Gly Asp Leu Ala Pro Ile
 65                  70                  75                  80
Ser Thr Pro Glu Pro Ser Gln Ala Pro Pro Ala Asp Thr Gly Pro Ser
                 85                  90                  95
Glu Ser Glu Leu Ala Leu Met Glu Ser Leu Ala Thr Leu Arg Ala Glu
                100                 105                 110
Leu Glu Asp Leu Arg Ala Arg Pro Ala Glu Ala Asp Ser Gly Ala
                115                 120                 125
Glu Gln Ala Ile Ala Asp Leu Thr Ala Gln Ile Ala Thr Leu Gln Glu
130                 135                 140
Ala Ser Ala Glu Ala Gln Arg Ala Leu Glu Arg Gln Leu Thr Glu Arg
145                 150                 155                 160
Asp Arg Glu Leu Asp Gln Leu Arg Met Asp Leu Glu Leu Ala Arg Leu
                165                 170                 175
Ala Pro Pro Glu Pro Thr Ser Leu Gly Pro Ser Glu Glu Leu Arg
                180                 185                 190
Leu Ala Glu Leu Glu Arg Arg Ala Ala Glu Ala Glu Arg Ala
                195                 200                 205
Glu Arg Ile Ala Ser Pro Met Ile Ala Phe Ser Gly Met Gly Ala Gly
                210                 215                 220
Ala Asp Arg Glu Asn Thr Leu Glu Ala Ala Arg Leu Asn Ala Asp Glu
225                 230                 235                 240
Ala Phe Val Arg Ser Gly Ala Gln Pro Ala Gln Val Thr Arg Ala Glu
                245                 250                 255
Val Ile Ala Asn Pro Ser Asn Thr Val Val Gln Gly Thr Met Ile Gln
                260                 265                 270
Ala Val Thr Glu Thr Ala Leu Asp Ser Thr Leu Pro Gly Ala Ile Arg
                275                 280                 285
Ala Ile Val Ser Glu Asp Val His Ser Phe Asp Gly Thr Arg Ile Leu
                290                 295                 300
Ile Pro Arg Gly Ala Arg Leu Ile Gly Arg Tyr Arg Ser Asp Val Ala
305                 310                 315                 320
Leu Ala Gln Ser Arg Val Met Val Ala Trp Asp Arg Ile Ile Leu Pro
                325                 330                 335
Asp Asn Gln Thr Val Gln Ile Ser Ala Phe Gly Gly Asp Glu Leu Gly
                340                 345                 350
Arg Thr Gly Thr Thr Gly Phe Val Asp Thr Arg Phe Ala Gln Arg Phe
                355                 360                 365
Gly Ser Ala Ala Leu Ile Ser Leu Ile Gly Ala Leu Pro Ala Ala Ala
                370                 375                 380
Ala Gly Gln Ile Asp Ser Glu Ala Ala Asp Val Ala Ser Asp Val
385                 390                 395                 400
Gly Thr Asp Leu Arg Asp Ser Thr Gln Ser Val Met Gln Asp Tyr Leu
                405                 410                 415
Ala Ile Arg Pro Val Ile His Val Asp Gln Gly Thr Arg Ile Thr Val
                420                 425                 430
Met Val Asp Arg Asp Leu Glu Ile Phe
                435                 440

<210> SEQ ID NO 56
```

```
<211> LENGTH: 481
<212> TYPE: PRT
<213> ORGANISM: Rickettsia monacensis

<400> SEQUENCE: 56
```

| | | | | | | | | | | | | | | | |
|---|---|---|---|---|---|---|---|---|---|---|---|---|---|---|---|
|Met|Ala|Glu|Glu|Gln|Asn|Asn|Asn|Asn|Thr|Gly|Ser|Leu|Ser|Gly| |
|1| | | |5| | | | |10| | | | |15| |
|Ala|Asp|Phe|Pro|Glu|Val|Gln|Arg|Glu|Leu|Ser|Lys|Val|Ser|Val|Ser|
| | | |20| | | | |25| | | | |30| | |
|Phe|Asn|Lys|Ser|Ile|Val|Ile|Val|Val|Ile|Cys|Gly|Ile|Phe|Ile| |
| | | | |35| | | | |40| | | | |45| |
|Tyr|Ile|Phe|Tyr|Thr|Leu|Phe|Phe|Gly|Thr|Lys|Lys|Glu|Glu|Ile|Pro|
| |50| | | | |55| | | | |60| | | | |
|Glu|Thr|Gln|Ile|Pro|Thr|Asn|Ile|Val|Lys|Pro|Val|Met|Glu|Val|Asp|
|65| | | | |70| | | | |75| | | | |80|
|Tyr|Asn|Ile|Pro|Glu|Ile|Ser|Lys|Leu|Pro|Asp|Pro|Pro|Lys|Leu|Glu|
| | | | |85| | | | |90| | | | |95| |
|Thr|Pro|Thr|Ala|Pro|Pro|Leu|Pro|Pro|Pro|Val|Val|Glu|Val|Pro| |
| | | |100| | | | |105| | | | |110| | |
|Pro|Val|Leu|Pro|Pro|Thr|Thr|Pro|Val|Glu|Glu|Asn|Lys|Asp|Lys|Thr|
| | | | |115| | | | |120| | | | |125| | |
|Pro|Leu|Pro|Pro|Ile|Ser|Leu|Pro|Ser|Thr|Pro|Gly|Thr|Leu|Val|Glu|
| | | |130| | | | |135| | | | |140| | | |
|Ser|Asp|Ala|Lys|Lys|Gln|Arg|Arg|Glu|Ala|Lys|Arg|Lys|Ser|Ala|Ile|
|145| | | | |150| | | | |155| | | | |160|
|Val|Leu|Val|Ser|Gly|Val|Glu|Pro|Lys|Lys|Thr|Pro|Glu|Gln|Ile|Thr|
| | | | |165| | | | |170| | | | |175| | |
|Ala|Glu|Ala|Thr|Phe|Lys|Asp|Arg|Gly|Asp|Met|Ser|Leu|Val|Leu|Gly|
| | | |180| | | | |185| | | | |190| | | |
|Arg|Gly|Lys|Leu|Ile|Asp|Ala|Val|Leu|Glu|Thr|Ala|Ile|Asn|Ser|Asp|
| | | |195| | | | |200| | | | |205| | | |
|Leu|Gly|Gly|Glu|Ile|Arg|Ala|Ile|Ile|Ser|Arg|Asp|Val|Phe|Ser|Glu|
| | | |210| | | | |215| | | | |220| | | |
|Lys|Asp|Lys|Val|Ile|Leu|Ile|Pro|Lys|Gly|Ser|Lys|Ile|Phe|Gly|Lys|
|225| | | | |230| | | | |235| | | | |240|
|Tyr|Ala|Thr|Ser|Thr|Ser|Ser|Asp|Ser|Tyr|Gly|Arg|Val|Ser|Ile|Ile|
| | | | |245| | | | |250| | | | |255| | |
|Trp|Asp|Arg|Ile|Asp|Leu|Thr|Asn|Gly|Tyr|Thr|Ile|Glu|Phe|Asp|Ser|
| | | |260| | | | |265| | | | |270| | | |
|Pro|Ala|Val|Asp|Asn|Leu|Gly|Arg|Leu|Gly|Leu|Gln|Gly|Arg|Val|Asp|
| | | |275| | | | |280| | | | |285| | | |
|Asn|Lys|Tyr|Lys|Glu|Gln|Phe|Ala|Asn|Ala|Val|Leu|Gln|Ser|Gly|Phe|
| | | |290| | | | |295| | | | |300| | | |
|Asn|Ile|Gly|Leu|Ala|Lys|Val|Leu|Asp|Lys|Leu|Val|Pro|Pro|Pro|Ile|
|305| | | | |310| | | | |315| | | | |320|
|Asp|Ser|Gln|Ala|Ala|Thr|Asn|Ser|Ala|Thr|Ala|Thr|Gln|Leu|Leu| |
| | | | |325| | | | |330| | | | |335| |
|Asn|Thr|Ala|Gln|Thr|Ile|Ala|Ser|Asn|Thr|Ala|Met|Asp|Ala|Asn|Thr|
| | | |340| | | | |345| | | | |350| | | |
|Arg|Ile|Val|Thr|Ile|Cys|Thr|Asn|Ile|Leu|Ala|Ala|Ile|Thr|Asp|Lys|
| | | |355| | | | |360| | | | |365| | | |
|Thr|Ser|Thr|Ala|Tyr|Thr|Thr|Met|Gln|Ala|Cys|Thr|Thr|Ala|Gln| |
| | | |370| | | | |375| | | | |380| | | |
|Thr|Ala|Ser|Ser|Ala|Asn|Thr|Ala|Glu|Gln|Arg|Leu|Gln|Thr|Leu|Val|

```
            385                 390                 395                 400
Gln Ala Val Asn Thr Ala Ala Ser Ser Leu Leu Thr Thr Thr Ser Ile
                405                 410                 415
Ala Ser Thr Pro Thr Gln Ala Gln Gln Ala Ser Thr Gln Ala Phe Met
                420                 425                 430
Asp Val Thr Asn Val Val Gln Asn Met Ile Thr Gln Gln Phe Lys
                435                 440                 445
Pro Thr Thr Thr Ile Asn Gln Gly Thr Pro Val Arg Ile Tyr Val Asn
                450                 455                 460
Lys Asp Tyr Lys Phe Pro Lys Ala Val Leu Leu Lys Ser Lys Val Met
465                 470                 475                 480
Lys

<210> SEQ ID NO 57
<211> LENGTH: 343
<212> TYPE: PRT
<213> ORGANISM: Rhizobium fredii (strain HH103) (Sinorhizobium fredii)

<400> SEQUENCE: 57

Met Ser Gly Glu Gly Lys Arg Gln Asp Asn Ala Gln Pro Glu Arg Val
1               5                   10                  15
Val Ile Arg Gln Thr Thr Asn Phe Glu Pro Ala Lys Glu Lys Met Glu
                20                  25                  30
Pro Val Gln Pro Val Pro Glu Val Lys Leu Pro Thr Pro Ile Val Thr
                35                  40                  45
Glu Glu Val Lys Glu Gly Asp Pro Leu Leu Asp Ser Ala Arg Arg Ala
                50                  55                  60
Pro Val Met Ala Tyr Ser Gly Gln Lys Asn Ala Thr Leu His Arg
65              70                  75                  80
Asp Thr Glu Asn Pro Pro Ile Ser Ala Asp Ser Asn Phe Val Pro Phe
                85                  90                  95
Asp Gly Ser Met Met Gly Pro Asn Thr Ala Asn Val Asp Glu Gln Arg
                100                 105                 110
Phe Asn Gly Leu Leu Arg Pro Thr Arg Leu Glu Gly Ser Arg Ala Gly
                115                 120                 125
Thr Leu Gly Asn Arg Asn Phe Ile Val Ala Met Gly Thr Ser Ile Pro
130             135                 140
Cys Val Leu Glu Thr Ala Leu Ala Ser Asp Gln Pro Gly Phe Thr Ser
145             150                 155                 160
Cys Val Ile Asn Arg Asp Val Leu Ser Asp Asn Gly Arg Val Val Leu
                165                 170                 175
Met Glu Lys Gly Thr Gln Val Leu Gly Glu Tyr Arg Gly Gly Leu Gln
                180                 185                 190
Arg Gly Gln Lys Arg Leu Phe Val Leu Trp Asn Arg Ala Lys Thr Pro
                195                 200                 205
Asn Gly Val Ile Val Pro Leu Ala Ser Pro Ala Thr Asp Ala Leu Gly
                210                 215                 220
Arg Ala Gly Val Asp Gly Tyr Val Asp Thr His Trp Trp Glu Arg Phe
225             230                 235                 240
Gly Ser Ala Leu Leu Leu Ser Ile Val Gly Asp Ala Thr Ser Tyr Ala
                245                 250                 255
Asn Ser Arg Leu Gln Asp Ser Asp Val Asp Ala Gln Asn Thr Thr Ser
                260                 265                 270
Ala Gly Gln Gln Ala Ala Ala Ile Ala Val Glu Gln Ser Ile Asn Ile
```

```
            275                 280                 285
Pro Pro Thr Leu Asn Lys His Gln Gly Glu Leu Val Ser Ile Phe Val
    290                 295                 300

Ala Arg Asp Leu Asp Phe Ser Gly Val Tyr Arg Leu Arg Ala Thr Glu
305                 310                 315                 320

Pro Arg Asn Lys Val Leu Asp Arg Ala Val Leu Gly Asp Phe Gly Pro
                325                 330                 335

Arg Ser Thr Leu Val Thr Lys
                340

<210> SEQ ID NO 58
<211> LENGTH: 409
<212> TYPE: PRT
<213> ORGANISM: Chromobacterium piscinae

<400> SEQUENCE: 58

Met Ser Asp Lys Arg Pro Pro Asp Thr Pro Ala Ala Asn Leu Asp Gly
1               5                   10                  15

Val Met Glu Gln Glu Thr Arg Thr Pro Leu Met Thr Glu Ala Gln Arg
            20                  25                  30

Arg Val Ser Gly Met Ala Ile Gly Ala Val Ser Leu Val Ala Leu Gly
        35                  40                  45

Ala Ile Phe Tyr Leu Arg Gln Gly Asp Glu Gly Glu Ser Arg Arg Gln
    50                  55                  60

Gln Thr Glu Val Gly Met Ala Ala Arg Lys Pro Leu Pro Asp Leu Lys
65                  70                  75                  80

Pro Gln Ser Ser Ala Pro Val Asp Glu Glu Arg Pro Ala Gly Ala Gly
                85                  90                  95

Ala Ala Pro Arg Gln Ala Gln Thr Pro Ala Glu Ala Ala Leu Asp Pro
            100                 105                 110

Gln Gln Ala Gln Gln Gln Leu Ala Gln Gln Arg Val Glu Gln Glu
        115                 120                 125

Arg Ala Met Arg Glu Ala Arg Leu Lys Ser Ala Ile Ile Leu Pro Leu
    130                 135                 140

Ser Gln Ser Ser Asp Ser Ala Arg Pro Ala Ala Gly Ser Glu Ser Gly
145                 150                 155                 160

Ser Gln Gly Asn Gly Leu Leu Gly Gly Thr Ala Ala Gly Ser Gly Gly
                165                 170                 175

Glu Arg Gly Ala Gln Asp Ala Asn Ser Arg Phe Ala Arg Ala Val Ser
            180                 185                 190

Gly Asn Gly Val Pro Val Ser Glu Ala Ser Arg Leu Tyr His Leu Gln
        195                 200                 205

Tyr Lys Ile Leu Gln Gly Lys Gln Ile Glu Ala Val Leu Glu Pro Arg
    210                 215                 220

Ala Val Ser Asp Leu Pro Gly Gln Ile Cys Ala Thr Val Gln Arg Asp
225                 230                 235                 240

Val Tyr Gly Ala Gln Gly Arg Ile Lys Leu Ile Pro Trp Gly Ser Arg
                245                 250                 255

Val Cys Gly Val Tyr Ser Ala Glu Leu Arg Lys Gly Gln Asp Arg Leu
            260                 265                 270

Phe Ala Ile Trp Asn Thr Leu Tyr Arg Pro Asp Gly Val Glu Val Thr
        275                 280                 285

Leu Asp Ser Gly Gly Ala Asp Gln Leu Gly Ser Ala Gly Met Gly Gly
    290                 295                 300
```

```
Ile Val Asp Ser His Phe Ala Gln Ile Phe Gly Thr Ser Ala Leu Leu
305                 310                 315                 320

Ser Ile Ile Gly Ala Gly Ala Ala Asn Val Gly Val Asn Ser Asn Asp
            325                 330                 335

Gln Asn Asn Ser Ala Ala Tyr Tyr Arg Gln Gln Val Gln Gln Ala Ala
            340                 345                 350

Ala Gln Thr Ser Gln Gln Val Leu Gln Pro Tyr Leu Ala Ile Gln Pro
            355                 360                 365

Thr Val Thr Val Pro Ala Gly Ser Arg Val Arg Ile Tyr Leu Asn Arg
            370                 375                 380

His Leu Asp Phe Thr Pro Ile Tyr Gln Ala Glu Thr Glu Ala Val Arg
385                 390                 395                 400

Gln Asp Ala Gly Pro Leu His Leu Met
                405

<210> SEQ ID NO 59
<211> LENGTH: 464
<212> TYPE: PRT
<213> ORGANISM: endosymbiont of Acanthamoeba sp. UWC36

<400> SEQUENCE: 59

Met Asn Asp Gly Met Met Met Pro Asp Asp Lys Asn Asn Lys Val Ile
1               5                   10                  15

Glu Val Asp Ala Asn His Thr Glu Ala Ser Gly Ser Glu Ala Glu Pro
            20                  25                  30

Ser Ser Ser Pro Ser Glu Asn Ser Asn Glu Gln Glu Ser Gln Ala Ser
        35                  40                  45

Gln Phe Ser Ile Val Ala Ser Thr Pro Gln His Lys Lys Val Met Ala
50                  55                  60

Ile Gly Ile Val Val Thr Ile Val Val Leu Tyr Tyr Ile Phe Phe
65                  70                  75                  80

Gly Arg Pro Tyr Ser Pro Glu Glu Ile Lys Asp Lys Lys Glu Arg Glu
                85                  90                  95

Ile Ala Ala Gln Lys Glu Glu Leu Leu Lys Thr Ser Ala Pro Val Thr
            100                 105                 110

Lys Pro Ala Glu Ala Thr Val Ser Ile Thr Pro Pro Lys Leu Pro Glu
        115                 120                 125

Pro Pro Pro Leu Thr Asp Pro Thr Pro Glu Pro Pro Pro Pro
130                 135                 140

Thr Pro Leu Ser Pro Ser Ser Pro Leu Phe Asn Gln Pro Asn Asn Ala
145                 150                 155                 160

Pro Ile Ile Thr Asn Ile Val Lys Ser Asn Ser Asp Asp Leu Glu Arg
                165                 170                 175

Val Lys Lys Leu Glu Ala Lys Arg Lys Ala Gly Met Ile Val Val Gly
            180                 185                 190

Gly Gly Gly Ala Phe Ser Thr Thr Asp Lys Lys Gly Ala Ala Asp Glu
        195                 200                 205

Lys Asp Ser Ala Glu Thr Lys Lys Lys Asn Lys Val Asp Phe Leu Gly
210                 215                 220

Phe Gly Asn Gly Ser Leu Asp Gly Val Ser Leu Thr Lys Thr Ser Ser
225                 230                 235                 240

Glu Gln Val Thr Ala Thr Lys Ile Gly Asn Thr Asp Leu Ile Ile Ala
                245                 250                 255

Gln Gly Lys Val Ile Asn Ala Val Leu Glu Thr Ala Ile Asn Thr Asp
            260                 265                 270
```

```
Leu Pro Gly Met Leu Arg Ala Ala Ile Val Arg Asp Val Tyr Ala Glu
            275                 280                 285

Ser Gly Lys Asn Ile Leu Leu Pro Lys Gly Ser Arg Val Val Gly Thr
290                 295                 300

Tyr Asp Ser Glu Ile Lys Asp Gly Gln Thr Arg Val Ser Ile Val Trp
305                 310                 315                 320

Asp Arg Val Ile Arg Pro Asp Gly Ile Asp Leu Ala Ile Ser Ser Pro
                325                 330                 335

Gly Thr Asp Gln Leu Gly Arg Ala Gly Val Glu Gly Lys Leu Asp Asn
                340                 345                 350

Lys Phe Trp Thr Lys Leu Gly Ser Ala Leu Leu Val Ser Tyr Val Ile
                355                 360                 365

Pro Val Leu Ala Asn Lys Phe Thr Asn Val Asn Lys Asn Asp Gln Val
            370                 375                 380

Thr Thr Thr Thr Thr Thr Gly Val Gly Thr Ser Thr Thr Ser Gln
385                 390                 395                 400

Ser Thr Phe Ala Ala Gln Ala Gln Glu Ala Ser Asp Gln Phe Thr
                405                 410                 415

Lys Val Gly Lys Glu Ile Val Glu Lys Thr Phe Ser Thr Lys Pro Thr
            420                 425                 430

Ile Thr Val Asn Gln Gly Ala Tyr Ile Asn Ile Tyr Val Lys Lys Asp
                435                 440                 445

Leu Val Phe Pro Ser Gly Phe Thr Ser Asn Ser Ala Gln Val Leu Lys
            450                 455                 460

<210> SEQ ID NO 60
<211> LENGTH: 400
<212> TYPE: PRT
<213> ORGANISM: Fusobacterium nucleatum subsp. Polymorphum

<400> SEQUENCE: 60

Met Asp Phe Asn Asn Asp Gln Asn Glu Pro Gln Asn Gln Gln Asn Ser
1               5                   10                  15

Asn Met Asn Phe Gln Gln Lys Gly Thr Phe Phe Lys Lys Lys Ile Val
                20                  25                  30

Tyr Gly Phe Phe Ile Phe Val Ile Leu Leu Ile Ile Leu Leu Thr Phe
            35                  40                  45

Arg Lys Glu Ile Phe Ser Ser Glu Asp Thr Asp Gln Asn Asn Lys Lys
        50                  55                  60

Ile Ile Lys Thr Glu Val Ala Lys Glu Asn Glu Ser Pro Asp Leu Asp
65                  70                  75                  80

Asn Val Gln Tyr Gly Glu Glu Asp Met Gln Asp Leu Gly Tyr Gly Glu
                85                  90                  95

Asn Asp Glu Asn Gly Gly Leu Thr Asp Glu Glu Leu Asn Tyr Val Ile
            100                 105                 110

Pro Gly Asp Asp Glu Glu Asn Gln Asp Asn Val Glu Pro Gln Lys Ser
        115                 120                 125

Thr Glu Glu Ile Glu Arg Glu Asn Arg Leu Arg Gln Leu Glu Ser Glu
130                 135                 140

Ala Asp Ala Ala Phe Arg Ser Pro Thr Thr Ile Thr Ile Ala Thr Arg
145                 150                 155                 160

Pro Gln Thr Gln Gln Val Asp Asn Lys Val Leu Leu Ala Gln Asn Gly
                165                 170                 175

Asn Lys Pro Val Glu Asp Tyr Asp Gly Asn Arg Gln Glu Ser Lys Lys
```

-continued

```
                180                 185                 190
Asn Phe Leu Met Asn Glu Gln Ala Gln Lys Phe Tyr Gln Thr Asn Phe
            195                 200                 205
Leu Val Glu Gln Leu Ser Glu Phe Glu Leu Lys Ala Gly Asp Phe Ile
            210                 215                 220
Pro Ala Thr Leu Gln Thr Gly Ile Asn Ser Asp Leu Pro Ser Lys Val
225                 230                 235                 240
Ile Val Ala Val Ser Glu Asn Val Arg Asp Thr Ile Ser Gly Lys
                245                 250                 255
His Ile Leu Ile Pro Gln Gly Thr Arg Val Val Gly Thr Tyr Asp Ser
                260                 265                 270
Ser Val Thr Phe Gly Gln Glu Arg Leu Leu Val Val Trp Gln Arg Leu
                275                 280                 285
Ile Phe Pro Asp Gly Lys Ser Ile Gly Leu Asp Asn Met Gln Gly Val
                290                 295                 300
Asp Leu Ser Gly Lys Ala Gly Ile Thr Gly Glu Ile Asp Asn His Phe
305                 310                 315                 320
Gly Thr Leu Leu Lys Gly Val Val Leu Ser Ser Ile Met Gly Ser Ala
                325                 330                 335
Gly Ala Ile Val Thr Asp Arg Lys Asn Asp Trp Arg Gly Ala Ala Ala
                340                 345                 350
Glu Gly Ala Gly Glu Gln Ile Val Thr Ile Gly Asp Arg Phe Ala Glu
                355                 360                 365
Arg Ala Leu Ser Arg Gln Pro Thr Ile Asn Ile Glu Pro Gly Thr Arg
                370                 375                 380
Leu Asn Ile Met Val His Ser Asp Leu Ile Leu Glu Pro Tyr Gly Glu
385                 390                 395                 400

<210> SEQ ID NO 61
<211> LENGTH: 378
<212> TYPE: PRT
<213> ORGANISM: Acidocella aminolytica 101 = DSM 11237

<400> SEQUENCE: 61

Met Pro Asn Glu Asp Lys Arg Asp Arg Pro Tyr Gly Pro Ile Ser His
1               5                   10                  15
Asp Asn Ala Ala Pro Ser Pro Val Glu Gln Glu Gln Ser Ala Val Ala
            20                  25                  30
Ser Arg Gln Arg Leu Thr Gly Arg Gln Ile Gly Gly Ile Ala Leu Ala
            35                  40                  45
Cys Ala Leu Gly Ala Gly Val Val Leu Val Val Thr Gln Phe Thr Ala
        50                  55                  60
His His Glu Pro Lys Pro Ala Lys Gln Ala Ala Val Thr Gly Gly Thr
65                  70                  75                  80
Glu Gly Arg Pro Phe Val Asn Asn Ala Ser Gly Gly Thr Ala Pro Ala
                85                  90                  95
Ser Lys Pro Ala Ala Leu Pro Leu Pro Ser Lys Gln Asn Thr Gly Phe
            100                 105                 110
His Asn Pro Phe Leu Asn Asn Gln Gln Glu Ser Pro Ala Met Lys Ala
            115                 120                 125
Leu Lys Ala Pro Ile Met Ala Phe Asn Gln Thr Gly Gly Gly Ala Ser
        130                 135                 140
Ala Gln Pro Ala Ser Asn Thr Val Gly Gln Asn Gly Ala Pro Ala Ala
145                 150                 155                 160
```

```
Gly Pro Val Lys Pro Thr Ala Phe Ala Ser Lys Leu Asn Ala Asp Gln
            165                 170                 175

Phe Ser Ala Ala Asp Ala Thr Thr Ile Ala His Pro Asn Phe Thr Ile
            180                 185                 190

Ala Ala Gly Thr Ile Ile Pro Cys Thr Leu Gln Thr Ala Ile Asn Ser
            195                 200                 205

Thr Leu Pro Gly Phe Val Lys Cys Val Leu Pro Gln Pro Val Arg Ser
210                 215                 220

Met Thr Gly Thr Val Thr Leu Leu Asp Lys Gly Thr Gln Val Leu Gly
225                 230                 235                 240

Glu Val Arg Glu Gly Leu Val Gln Gly Gln Asp Arg Leu Phe Ile Leu
            245                 250                 255

Trp Asp Arg Ala Val Thr Pro Gln Asn Val Ala Ile Gln Leu Ala Ser
            260                 265                 270

Pro Ala Ala Asp Pro Leu Gly Arg Ala Gly Val Ser Gly Ala Val Asn
            275                 280                 285

Asn His Phe Leu Glu Arg Phe Gly Ala Ala Ile Met Met Thr Ile Ile
            290                 295                 300

Gly Gly Ser Met Gln Val Ala Ala Asn Ala Ala Gln Asn Ser Ala Gly
305                 310                 315                 320

Asn Thr Tyr Leu Glu Tyr Met Asn Ser Ser Thr Asn Gln Ile Ala Asn
            325                 330                 335

Thr Thr Leu Gln His Thr Ile Asp Ile Pro Pro Thr Leu Thr Lys His
            340                 345                 350

Gln Gly Glu Asn Val Ser Ile Phe Val Ala Arg Asp Leu Asn Phe Ser
            355                 360                 365

Lys Val Tyr Lys Leu Ser Val Val Ser Pro
            370                 375

<210> SEQ ID NO 62
<211> LENGTH: 395
<212> TYPE: PRT
<213> ORGANISM: Anaeromyxobacter sp. PSR-1

<400> SEQUENCE: 62

Met Ala Glu Thr Asp Val Asp Ala Ala Val Glu Leu Glu Lys Arg Glu
1               5                   10                  15

Arg Glu Arg Ala Arg Ala Glu Glu Ala Ala Pro Asp Val Glu Gly Gly
            20                  25                  30

Arg Gly Lys Ala Leu Leu Ala Ser Gly Arg Arg Gln Trp Pro Val Gly
            35                  40                  45

Ala Arg Ile Phe Phe Val Val Thr Gly Leu Val Ala Ala Gly Phe Ala
50                  55                  60

Ser Val Leu Val Leu Lys Ala Arg Ser Ala Arg Lys Ala Ala Glu Ala
65                  70                  75                  80

Arg Ala Arg Glu Ser Pro Ala Ala Thr Asp Arg Val Glu Arg His Val
            85                  90                  95

Pro Pro Leu Val Arg Ala Ala Pro Ala Pro Gln Pro Phe Ala Pro Thr
            100                 105                 110

Pro Ser Pro Ala Ala Ala Gly Ala Gly Asp Ala Ala Pro Val Ala
            115                 120                 125

Ser Pro Glu Ala Glu Leu Leu Gln Arg Arg Leu Ala Arg Gly Phe Gly
            130                 135                 140

Thr Gly Glu Gly Gly Thr Gly Pro Arg Glu Gln Ala Ser Pro Ala Ala
145                 150                 155                 160
```

```
Pro His Ser Leu Val Ala Pro Glu Ser Ala Pro Ala Met Pro Lys Lys
                165                 170                 175

Pro Gly Ala Leu Glu Val Lys Leu Glu Ala Ala Glu Leu Arg Ala Ala
            180                 185                 190

Ala Ala Gly Val Leu Pro Asp Arg Asp His Leu Leu Thr Gln Gly Ala
        195                 200                 205

Met Leu Asp Cys Val Leu Glu Thr Lys Ile Val Ser Thr Val Ala Gly
210                 215                 220

Met Thr Ser Cys His Leu Thr Arg Asp Ile Tyr Ser Thr Ser Gly Arg
225                 230                 235                 240

Val Val Leu Leu Asp Arg Gly Ser Arg Val Val Gly Arg Tyr Gln Gly
                245                 250                 255

Gly Met Gln Gln Gly Asp Thr Arg Ile Phe Val Leu Trp Thr Arg Val
            260                 265                 270

Glu Thr Pro Ala Gly Val Val Glu Leu His Ser Pro Gly Ala Gly
        275                 280                 285

Pro Leu Gly Glu Pro Gly Leu Gly Gly His Val Asp Thr Arg Phe Trp
    290                 295                 300

Asp Arg Phe Gly Ala Ala Ile Leu Leu Ser Val Ile Glu Asp Gly Ala
305                 310                 315                 320

Asp Ala Ala Ala Arg Ala Val Gly Pro Gly Gln Gly Thr Asn Ile
                325                 330                 335

Asn Val Gly Asn Thr Ala Asn Ala Gly Lys Glu Val Ile Ala Arg Ser
            340                 345                 350

Met Glu Pro Thr Ile Asn Ile Pro Val Leu Val Lys Asn Gln Gly
        355                 360                 365

Glu Arg Val Gly Ile Phe Val Ala Arg Asp Leu Asp Phe Arg Ser Val
    370                 375                 380

Tyr Gly Leu Glu Arg Val Ala Arg Thr Gly Arg
385                 390                 395

<210> SEQ ID NO 63
<211> LENGTH: 382
<212> TYPE: PRT
<213> ORGANISM: Aeromonas veronii

<400> SEQUENCE: 63

Met Arg Asn Asp Gly Val Ile Glu Val Lys Gly Lys Ser Gly Ala Gly
1               5                   10                  15

Lys Lys Ile Ile Ile Leu Leu Ala Val Phe Ala Phe Val Phe Val Ala
            20                  25                  30

Leu Ala Val Val Ile Lys Leu Leu Pro Gly Lys Asp Glu Ser Ala Ala
        35                  40                  45

Ser Leu Pro Lys Lys Glu Asn Glu Ser Leu Gln Arg Thr Thr Leu Glu
    50                  55                  60

Glu Arg Gly Leu Leu Gly Lys Ile Lys Glu Ile Glu Asp Ala Lys Lys
65                  70                  75                  80

Arg Glu Glu Ala Glu Lys Ala Ala Glu Lys Arg Arg Leu Asp Glu
                85                  90                  95

Glu Ala Ala Ala Gln Arg Lys Ala Gln Asp Ala Ala Asn Ala Ala
            100                 105                 110

Ala Thr Pro Pro Ser Asn Thr Ser Glu Gln Ile Arg Gln Asn Gln Gly
        115                 120                 125

Gly Gln Met Gln Gln Ala Ser Tyr Ser Ser Gly Asp Asp Lys Asp Arg
```

```
                130                 135                 140
Pro Leu Pro Lys His Leu Arg Val Leu Thr Gly Glu Thr Leu Val Lys
145                 150                 155                 160

Leu Asp Asn Asn Gln Gln Glu His Glu Arg Ala Thr Asp Ser Asp Asp
                165                 170                 175

Tyr Leu Gln Gly Gly Thr Phe Ala Asp Gly Thr Ala Ser Phe Ile Asn
                180                 185                 190

Asn Arg Lys Leu Leu Leu Ser Ala Gly Thr Ser Leu Ser Cys Val Leu
                195                 200                 205

Lys Thr Lys Ile Val Thr Ser Tyr Pro Gly Val Thr Met Cys Gln Leu
            210                 215                 220

Thr Lys Asp Val Tyr Ser Asp Asn Gly Glu Met Val Leu Ala Arg Ala
225                 230                 235                 240

Gly Ser Leu Leu Ile Gly Glu Gln Lys Lys Ala Ile Thr Gln Gly Val
                245                 250                 255

Ala Arg Val Phe Val Thr Trp Thr Asn Ile Lys Asp Gly Asn Val Asn
                260                 265                 270

Val Arg Ile Asp Ala Leu Gly Ala Asp Gly Leu Gly Ala Ser Gly Leu
            275                 280                 285

Pro Ala Trp Val Asp Asn His Phe Trp Glu Arg Phe Gly Gly Ala Met
            290                 295                 300

Leu Leu Ser Phe Ile Asp Asp Gly Leu Ala Ala Ala Ser Thr His Leu
305                 310                 315                 320

Ala Lys Ser Gly Ser Asn Asn Asn Ser Val Ser Phe Asp Asn Thr Ser
                325                 330                 335

Ser Thr Gly Glu Lys Met Ala Glu Ile Ala Leu Glu Asn Ser Ile Asn
                340                 345                 350

Ile Pro Pro Thr Ala Tyr Val Asn Gln Gly Ile Leu Thr Val Ile
            355                 360                 365

Val Pro Arg Asn Ile Asp Phe Ser Ser Val Tyr Glu Thr Arg
        370                 375                 380

<210> SEQ ID NO 64
<211> LENGTH: 480
<212> TYPE: PRT
<213> ORGANISM: Oceanicola batsensis (strain ATCC BAA-863 / DSM 15984 /
      HTCC2597)

<400> SEQUENCE: 64

Met Ala Asp Gln Thr Pro Pro Asp Leu Gln Asp Arg Leu Asp Gln Phe
1               5                   10                  15

Ser Gln Arg Gly Lys Ser Lys Arg Gly Asn Ser Leu Gly Val Gly
            20                  25                  30

Ala Leu Ala Ala Ala Leu Ala Leu Gly Gly Ala Gly Val Ala Tyr Phe
            35                  40                  45

Leu Ala Thr Gly Leu Arg Thr Ser Asp Ser Ala Leu Glu Thr Ser Asp
        50                  55                  60

Val Glu Thr Phe Gln Asp Arg Arg Pro Gly Thr Gly Gly Arg Leu Glu
65                  70                  75                  80

Phe Pro Pro Asp Glu Thr Glu Gln Arg Val Asn Asp Ala Leu Ile Ala
                85                  90                  95

Val Glu Glu Ala Leu Asp Val Pro Ala Ala Pro Ala Pro Glu Pro Ser
            100                 105                 110

Ala Glu Val Leu Ala Glu Ile Ala Lys Leu Arg Glu Ala Leu Ala Ala
            115                 120                 125
```

Ser Gln Ala Ala Arg Asn Ser Glu Ile Gln Ser Ala Val Ala Asp Leu
130                 135                 140

Arg Glu Ala Phe Asp Glu Gln Lys Ala Ala Leu Glu Ala Met Leu Ala
145                 150                 155                 160

Ala Lys Glu Thr Glu Leu Ala Asn Leu Gln Arg Gln Thr Glu Ser Arg
                165                 170                 175

Ile Ala Gly Leu Gln Ala Met Leu Asp Ala Glu Arg Ala Gln Arg Glu
            180                 185                 190

Gly Leu Glu Ser Glu Leu Asp Arg Glu Gly Leu Ile Ala Asp Gln Arg
        195                 200                 205

Leu Leu Glu Glu Arg Arg Gln Glu Glu Gln Arg Gln Arg Glu
210                 215                 220

Ala Glu Arg Val Ala Glu Glu Leu Leu Thr Ala Gln Ile Lys Ser Pro
225                 230                 235                 240

Ala Val Val Tyr Ala Asp Gly Pro Arg Gly Gln Ser Gly Ala Ala
                245                 250                 255

Val Ala Asp Pro Ala Ala Ala Gly Thr Gly Gly Pro Val Leu Ser Gly
            260                 265                 270

Asn Glu Gln Phe Leu Gln Thr Ala Arg Pro Leu Glu Val Gln Glu Ala
        275                 280                 285

Ala Arg Leu Ala Tyr Pro Glu Arg Thr Leu Thr Gln Gly Ser Val Ile
290                 295                 300

Gln Ala Ala Leu Gln Thr Ala Ile Asn Ser Asp Leu Pro Gly Ser Val
305                 310                 315                 320

Val Ala Val Val Ser Glu Pro Val Pro Ala Phe Ser Gly Asp Gln Ile
                325                 330                 335

Leu Ile Pro Arg Gly Ser Arg Leu Phe Gly Gln Tyr Arg Ser Gly Ile
            340                 345                 350

Asp Met His Gln Lys Arg Ile Leu Ile Val Trp Thr Arg Val Leu Thr
        355                 360                 365

Pro Asp Gly Thr Ser Met Glu Ile Ala Ala Val Gly Gly Asp Gln Leu
370                 375                 380

Gly Arg Ser Gly Leu Thr Gly Leu Val Asp Thr Lys Phe Ala Glu Arg
385                 390                 395                 400

Phe Gly Gly Ala Ala Leu Ile Ser Val Ile Gly Ala Ala Pro Ala Val
                405                 410                 415

Val Ala Glu Ser Ala Asn Asn Glu Thr Thr Ser Ile Val Leu Gly Gly
            420                 425                 430

Val Gly Ser Asp Leu Gln Asp Ala Val Gly Ser Val Ile Ala Asp Gln
        435                 440                 445

Val Ser Ile Ala Pro Thr Ile Tyr Val Asp Gln Gly Ala Ser Val Thr
450                 455                 460

Val Leu Val Asp Arg Asp Val Val Ile Tyr Gly Gly Ser Gly Ser Gln
465                 470                 475                 480

<210> SEQ ID NO 65
<211> LENGTH: 392
<212> TYPE: PRT
<213> ORGANISM: Oceanicaulis sp. HTCC2633

<400> SEQUENCE: 65

Met Ser Glu Asp Arg Glu Ser Arg Glu Asp Lys Glu Ile Ala Ala Ser
1               5                   10                  15

Leu Arg Leu Arg Ala Asp Pro Pro Arg Val Met Arg Leu Ser Arg Arg

```
                20                  25                  30
Thr Leu Thr Val Leu Gly Ala Val Gly Gly Leu Gly Leu Gly Thr Ile
             35                  40                  45
Leu Ile Val Ala Leu Gln Asp Arg Lys Pro Val Asp Gly Pro Pro Glu
 50                  55                  60
Leu Tyr Ser Thr Glu Arg Ile Gln Ala Ala Glu Gly Leu Ser Arg Leu
 65                  70                  75                  80
Pro Thr Asp Tyr Thr His Ile Pro Gln Leu Gly Pro Pro Leu Pro Gly
                 85                  90                  95
Glu Leu Gly Arg Pro Ile Leu Ser Ala Gln Gln Arg Gly Gln Pro Val
             100                 105                 110
Pro Ala Val Ala Thr Ala Pro Ala Val Asp Pro Glu Glu Gln Arg Arg
             115                 120                 125
Leu Gln Glu Leu Glu Ala Ala Arg Leu Ser Arg Leu Phe Ala Glu Ala
         130                 135                 140
Lys Thr Ala Ile Gly Glu Gln Pro Gln Ser Ser Pro Val Val Ala Pro
145                 150                 155                 160
Val Leu Ser Gly Thr Gly Ser Phe Phe Pro Ala Ser Ala Thr Asp Thr
                 165                 170                 175
Ala Pro Asp Ala Thr Asp Arg Arg Gln Ala Phe Leu Asp Glu Pro Val
             180                 185                 190
Asp Arg Arg Thr Thr Ala Ala Asp Arg Leu Thr Asp Pro Pro Ser Pro
             195                 200                 205
Tyr Val Val Gln Ala Gly Ala Val Ile Pro Ala Ala Leu Val Thr Gly
         210                 215                 220
Leu Arg Ser Asp Leu Pro Gly Gln Ile Thr Ala Gln Val Thr Ser Asn
225                 230                 235                 240
Val Tyr Asp Ser Pro Thr Gly Arg Phe Leu Leu Ile Pro Gln Gly Ala
                 245                 250                 255
Arg Leu Ile Gly Glu Tyr Asp Ser Arg Val Ala Phe Gly Gln Ser Arg
             260                 265                 270
Val Leu Leu Ala Trp Thr Arg Leu Ile Leu Pro Asn Gly Arg Ser Ile
             275                 280                 285
Val Leu Glu Arg Gln Pro Gly Ala Asp Glu Ala Gly Tyr Ala Gly Leu
         290                 295                 300
Glu Asp Gly Val Asn Asn His Trp Gly Arg Leu Phe Met Ala Ala Gly
305                 310                 315                 320
Leu Ala Thr Val Leu Asn Ile Gly Val Glu Leu Gly Ala Asp Asp Asp
                 325                 330                 335
Asp Asp Ile Ala Arg Ala Ile Arg Glu Gly Thr Gln Asp Thr Ile Gly
             340                 345                 350
Arg Ala Gly Glu Glu Val Val Arg Gln Leu Ser Ile Pro Pro Thr
             355                 360                 365
Leu Thr Ile Arg Pro Gly Phe Pro Val Arg Val Met Val Thr Arg Asp
         370                 375                 380
Leu Ile Leu Glu Pro Tyr Arg Asn
385                 390

<210> SEQ ID NO 66
<211> LENGTH: 475
<212> TYPE: PRT
<213> ORGANISM: Maritimibacter alkaliphilus HTCC2654

<400> SEQUENCE: 66
```

-continued

```
Met Ala Asp Gln Thr Pro Pro Asp Leu Gln Asp Arg Leu Asp Gln Phe
1               5                   10                  15

Ser Gln Arg Gly Lys Ser Lys Arg Arg Gly Asn Ser Leu Gly Val Gly
            20                  25                  30

Ala Leu Ala Ala Leu Ala Leu Gly Gly Ala Gly Val Ala Tyr Phe
        35                  40                  45

Leu Ala Thr Gly Leu Gln Thr Ser Asp Ser Ala Leu Glu Thr Ser Asp
    50                  55                  60

Val Glu Thr Phe Gln Asp Arg Arg Pro Gly Thr Gly Gly Arg Leu Glu
65                  70                  75                  80

Phe Pro Pro Asp Glu Thr Glu Gln Arg Val Asn Asp Ala Leu Ile Ala
                85                  90                  95

Val Glu Glu Ala Leu Asp Val Pro Ala Ala Pro Ala Pro Glu Pro Ser
                100                 105                 110

Ala Glu Val Leu Ala Glu Ile Ala Lys Leu Arg Glu Ala Leu Ala Ala
                115                 120                 125

Ser Gln Ala Thr Arg Asn Ser Glu Ile Gln Ser Ala Val Ser Asp Leu
    130                 135                 140

Arg Glu Ala Phe Asp Glu Gln Lys Ala Thr Leu Glu Ala Thr Leu Ala
145                 150                 155                 160

Glu Lys Glu Thr Glu Leu Ala Asn Leu Gln Arg Gln Thr Glu Thr Arg
                165                 170                 175

Ile Glu Gly Leu Gln Ser Met Leu Asp Ala Glu Arg Ala Gln Arg Glu
                180                 185                 190

Gly Leu Glu Ala Glu Leu Asp Arg Glu Gly Leu Ile Ala Asp Gln Arg
    195                 200                 205

Leu Leu Glu Glu Arg Arg Arg Gln Glu Glu Gln Arg Gln Arg Glu
210                 215                 220

Ala Ala Arg Val Ala Glu Glu Leu Leu Ala Ala Gln Ile Lys Ser Pro
225                 230                 235                 240

Ala Val Val Tyr Ala Asp Gly Pro Arg Gly Ala Ser Gly Ala Ala
                245                 250                 255

Val Ala Glu Pro Thr Ala Ala Ser Gly Ala Gly Gly Pro Ala Leu Ser
                260                 265                 270

Gly Asn Glu Gln Phe Leu Gln Thr Ala Arg Pro Leu Glu Val Gln Glu
    275                 280                 285

Ala Ala Arg Leu Ala Tyr Pro Glu Arg Thr Leu Thr Gln Gly Ser Val
    290                 295                 300

Ile Gln Ala Ala Leu Gln Thr Ala Ile Asn Ser Asp Leu Pro Gly Ser
305                 310                 315                 320

Val Val Ala Val Ser Glu Pro Val Pro Ala Phe Ser Gly Asp Arg
                325                 330                 335

Ile Leu Ile Pro Arg Gly Ser Arg Leu Phe Gly Gln Tyr Arg Ser Gly
                340                 345                 350

Ile Glu Met His Gln Lys Arg Ile Leu Ile Val Trp Thr Arg Val Leu
                355                 360                 365

Thr Pro Asp Gly Thr Ser Ile Glu Ile Ala Ala Val Gly Gly Asp Gln
    370                 375                 380

Leu Gly Arg Ser Gly Leu Thr Gly Leu Val Asp Thr Lys Phe Ala Glu
385                 390                 395                 400

Arg Phe Gly Gly Ala Ala Leu Ile Ser Val Ile Gly Ala Ala Pro Ala
                405                 410                 415

Val Ala Ala Glu Ser Thr Asn Asn Glu Thr Thr Ser Ile Val Leu Gly
```

```
                    420             425             430
Asp Val Gly Ser Asp Leu Gln Asp Ala Val Gly Ser Val Ile Ala Asp
            435                 440                 445

Gln Val Ser Ile Ala Pro Thr Ile Tyr Val Asp Gln Gly Ala Ser Val
            450                 455                 460

Thr Val Leu Val Asp Arg Asp Val Val Ile Tyr
465                 470                 475

<210> SEQ ID NO 67
<211> LENGTH: 476
<212> TYPE: PRT
<213> ORGANISM: Roseobacter sp. MED193

<400> SEQUENCE: 67

Met Ala Asp Glu Asn Thr Pro Asp Leu Arg Asp Arg Leu Ser Thr Phe
1               5                   10                  15

Ser Gln Lys Asn Lys Thr Lys Arg Arg Gly Gly Asn Ile Gly Val Gly
                20                  25                  30

Ala Leu Ala Ile Ala Leu Ala Leu Gly Gly Gly Gly Ala Ala Tyr Leu
            35                  40                  45

Leu Ala Thr Asn Leu Gln Glu Gly Thr Thr Gly Leu Glu Thr Ser Asp
50                  55                  60

Val Glu Thr Phe Gln Asp Gln Arg Thr Gly Asn Gly Gly Arg Leu Glu
65                  70                  75                  80

Phe Pro Pro Asp Glu Ala Glu Gln Val Asn Asp Ala Leu Ile Ala
                85                  90                  95

Val Glu Glu Ala Leu Asp Val Pro Ser Pro Val Pro Ala Ala Glu Pro
                100                 105                 110

Ser Ala Ala Val Leu Glu Glu Ile Ala Lys Leu Arg Glu Ala Leu Ala
            115                 120                 125

Ala Ser Gln Ser Ala Arg Asn Ala Glu Ile Gln Glu Ala Val Ser Asp
130                 135                 140

Leu Arg Glu Ala Phe Gln Val Gln Thr Asp Ala Leu Glu Ala Ser Ile
145                 150                 155                 160

Ala Ala Lys Asp Thr Glu Ile Glu Asn Ala Gln Arg Gln Ser Glu Ala
                165                 170                 175

Arg Leu Ala Gly Leu Gln Ala Met Leu Asp Ala Glu Arg Ala Gln Arg
            180                 185                 190

Glu Gly Leu Glu Ala Glu Met Ala Arg Asp Gly Leu Ile Ala Asp Gln
        195                 200                 205

Arg Leu Leu Glu Glu Arg Gln Arg Gln Glu Glu Gln Arg Gln Arg
    210                 215                 220

Glu Val Glu Gln Ala Ala Gln Glu Leu Leu Asn Ala Gln Ile Val Ser
225                 230                 235                 240

Pro Ser Val Val Tyr Ala Asp Gly Pro Arg Ser Thr Ser Ala Gly Gly
                245                 250                 255

Thr Asn Pro Thr Ala Ala Leu Ala Gly Ala Asp Gly Pro Thr Leu Ser
            260                 265                 270

Glu Asn Glu Gln Tyr Leu Arg Gln Gly Ala Arg Pro Leu Asp Val Gln
        275                 280                 285

Glu Ala Ser Gln Met Ala Phe Pro Glu Arg Thr Leu Ser Gln Gly Ser
    290                 295                 300

Val Ile Gln Ala Ala Leu Gln Thr Ala Ile Asn Ser Asp Leu Pro Gly
305                 310                 315                 320
```

-continued

```
Ser Val Val Ala Val Val Ser Glu Pro Val Pro Ala Phe Ser Gly Asp
            325                 330                 335

Gln Ile Leu Ile Pro Arg Gly Ser Arg Leu Phe Gly Gln Tyr Arg Ser
            340                 345                 350

Gly Ile Glu Leu Asn Gln Lys Arg Ile Leu Ile Leu Trp Thr Arg Val
            355                 360                 365

Leu Thr Pro Asp Gly Thr Ser Ile Glu Ile Ala Ser Val Gly Gly Asp
    370                 375                 380

Gln Leu Gly Arg Ser Gly Leu Thr Gly Ile Val Asp Thr Lys Phe Ala
385                 390                 395                 400

Glu Arg Phe Gly Gly Ala Ala Leu Ile Ser Leu Ile Gly Ala Ala Pro
                405                 410                 415

Ala Val Ala Ala Asn Ser Thr Asp Asn Glu Ile Ala Ser Glu Val Leu
                420                 425                 430

Glu Gly Val Ser Gly Asp Leu Glu Asp Ala Val Gly Ser Val Ile Ala
            435                 440                 445

Glu Gln Val Ser Ile Ser Pro Thr Ile Tyr Ile Asp Gln Gly Ala Ser
        450                 455                 460

Val Thr Val Leu Val Asp Arg Asp Val Val Ile Tyr
465                 470                 475

<210> SEQ ID NO 68
<211> LENGTH: 443
<212> TYPE: PRT
<213> ORGANISM: Orientia tsutsugamushi (strain Boryong) (Rickettsia
      tsutsugamushi)

<400> SEQUENCE: 68

Met Gln Gln Asp Asn Ser Asp Asn Asp Asn Thr Lys Glu Glu Asp Leu
1               5                   10                  15

Glu Leu Asn Asp Lys Leu Lys Ala Glu Ser Ala Val Arg Ser Asn Ser
            20                  25                  30

Lys Leu Ser Glu Leu Ala Ser Ile Ile Arg Arg Lys Pro Val Ile Ala
        35                  40                  45

Leu Thr Phe Ile Ser Ile Thr Ile Met Leu Val Ser Tyr Phe Leu Ser
    50                  55                  60

Glu Ser Gly Lys Thr Lys Glu Ser Ile Thr Phe Thr Glu Asn Arg Glu
65                  70                  75                  80

Ser Arg Glu Ala Ile Ser Gly Val Glu Gln Ala Val Asp Leu Arg Ala
                85                  90                  95

Lys Trp Thr Glu Glu Ile Leu Asn Glu Val Lys Thr Leu Lys Asp Arg
            100                 105                 110

Leu Glu Ser Val Ile Glu Ser Arg Tyr Leu Glu Thr Ala Lys Ile
        115                 120                 125

Asn Asn Phe Asn Gln Lys Leu Glu Ile Leu Glu Asn Gln Pro Lys Gln
130                 135                 140

Ser Leu Tyr Asn Asn Asp Ser Asp Glu Phe Ser Ser Asp Leu Asn Gln
145                 150                 155                 160

His Ile Leu Asn Ser Pro His Asp Asn Lys Thr Glu Gln Ala Pro Val
                165                 170                 175

Gln Ser Phe Val Asn Leu Ser Arg Ala Arg Ser Glu Pro Lys Lys Asn
            180                 185                 190

Val Glu Asn Tyr Val Thr Ser Gly Ser Ser Val Arg Ala Ile Leu Leu
        195                 200                 205

Thr Gly Val Val Val Gly Thr Gly Thr Asn Ser Ser Ser Ser Pro Glu
```

```
    210                 215                 220

Pro Ile Val Leu Gln Leu Leu Asp Thr Ala Ile Leu Tyr Asp Glu Tyr
225                 230                 235                 240

Lys Thr Asp Gln Ile Lys Lys Ala Ile Leu Ile Gly Ser Cys Asn Gly
                245                 250                 255

Glu Met Ser Ser Glu Arg Ala Lys Cys Arg Ile Glu Thr Leu Ser Val
            260                 265                 270

Val Asn Asn Gln Gly Asp Ile Ile Glu Lys Lys Val Glu Gly Trp Leu
        275                 280                 285

Ile Gly Glu Asp Gly Arg Ser Gly Ile Lys Gly Ile Val Val Asp Lys
    290                 295                 300

Ser Ser Lys Val Val Arg Met Ala Ala Leu Asn Gly Val Phe Ser Ser
305                 310                 315                 320

Ile Ala Lys Phe Leu Gln Thr Lys Ala Ile Lys Pro Asp Met Thr Thr
                325                 330                 335

Ala Pro Thr Leu Asn Ile Met Thr Pro Gly Gln Ala Gln Ser Glu Leu
            340                 345                 350

Ser Val Gly Asp Ala Leu Lys Ser Gly Ala Tyr Ser Gly Ala Ser Asn
        355                 360                 365

Ala Phe Asp Lys Leu Ala Asp Phe Ala Ile Lys Arg Ala Asp Ser Met
    370                 375                 380

Ser Pro Val Ile Val Val Ala Ser Gly Arg Val Ile Asp Val Val Phe
385                 390                 395                 400

Lys Lys Gly Phe Asp Leu Cys Glu His Lys Lys Lys Leu Lys Asn Ser
                405                 410                 415

Thr Tyr Val Pro Ser Thr Ser His Glu Lys Val Asn Leu His Asn Lys
            420                 425                 430

Phe Asp Gln Ser Gln Lys Leu Glu Glu His Leu
        435                 440

<210> SEQ ID NO 69
<211> LENGTH: 462
<212> TYPE: PRT
<213> ORGANISM: Yersinia pseudotuberculosis serotype O:1b (strain IP
      31758)

<400> SEQUENCE: 69

Met Ala Asp Glu Asn Asp Ile Gly Glu Thr Ile Pro Pro Glu Asn Glu
1               5                   10                  15

Asp His Phe Ala Pro Asp Tyr Glu Glu Glu Tyr Gln Pro Ser Ala Ala
            20                  25                  30

Glu Ile Gln Arg Thr Thr Lys Glu Arg Arg Arg Ala Glu Lys Ile Arg
        35                  40                  45

Asn Leu Lys Ser Val Phe Gly Ser Gly Val Gly Arg Ile Ser Ile Ile
    50                  55                  60

Cys Val Val Phe Val Val Val Ile Phe Leu Ala Leu Gly Ile Arg Asn
65                  70                  75                  80

Met Arg Ser Pro Gln Pro Leu Gly Thr Ser Thr Thr Val Asp Val Pro
                85                  90                  95

Ala Ala Pro Gln Ile Lys Thr Asp Asn Ser Pro Val Thr Glu Ser Glu
            100                 105                 110

Ala Ala Arg Arg Ser Gln Met Asn Ala Asn Gln Ala Arg Glu Ala Ala
        115                 120                 125

Lys Leu Gly Asp Ser Phe Gln Pro Ser Phe Asp Thr Asn Ile Ile Ala
    130                 135                 140
```

-continued

Asp Gln Lys Ser Lys Pro Asn Tyr Asn Gln Asn Ser Thr Val Ile Pro
145                 150                 155                 160

Asp Ala Ile Asn Phe Asn Arg Asn Gln Ala Ser Ser Asp Thr Gln
            165                 170                 175

Asn Pro Asn Thr Gly Ser Gln Arg Ser Asp Ser Asn Ser Asn Gln Gly
            180                 185                 190

Asn Ser Gln Lys Asn Gln Asp Gly Gln Gln Leu Leu Lys Glu Tyr Thr
            195                 200                 205

Thr Glu Val Asn Lys Arg Asp Lys His Val Glu Asp Met Lys Ser Glu
            210                 215                 220

Ile Ile Lys Gln Phe Ser Gln Val Leu Asp Lys Asp Thr Leu Asn Asn
225                 230                 235                 240

Gln Gly Ser Tyr Ser Thr Val Ile Phe Asn Asp Thr Asn Lys Ser Asn
            245                 250                 255

Asn Asp Arg Lys Pro Glu Glu Ser Val Lys Thr Val Ala Ser Asn Ser
            260                 265                 270

Ser Glu Lys Asn Ala Ala Lys Pro Leu Phe Lys Ala Gly Ser Thr
            275                 280                 285

Leu Tyr Ala Glu Thr Gly Ser Ala Ala Asn Thr Asp Asn Gly Val Asp
            290                 295                 300

Thr Phe Ala Thr Val Arg Gly Gly Lys Trp Asn Gly Ser Val Leu Ile
305                 310                 315                 320

Gly Lys Val Val Gln Thr Asn Asn Ile Leu Phe Gln Tyr Thr Leu
            325                 330                 335

Leu Ala Pro Gln Asp Asn Arg Pro Ser Val Lys Ile Asn Ala Ile Ala
            340                 345                 350

Leu Arg Glu Glu Asp Ala Ser Gln Gly Met Ala Asp Asp Val Asp His
            355                 360                 365

His Ile Leu Met Arg Tyr Gly Ser Leu Gly Ala Ala Ser Leu Leu Ser
            370                 375                 380

Gly Tyr Gly Lys Ser Tyr Glu Asn Ile Gly Thr Thr Thr Asn Asn Gly
385                 390                 395                 400

Ser Thr Thr Thr Gln Thr Thr Asn Thr Pro Ser Asn Lys Gln Ile Ile
            405                 410                 415

Gly Gln Ala Val Gly Glu Leu Gly Ser Asn Phe Ala Asn Glu Ile Lys
            420                 425                 430

Arg Gly Phe Asp Thr Pro Thr Thr Tyr Ser Thr Lys Ala Asn Thr Gly
            435                 440                 445

Phe Ala Leu Leu Phe Met Ser Asp Val Pro Asp Pro Asp Lys
450                 455                 460

<210> SEQ ID NO 70
<211> LENGTH: 417
<212> TYPE: PRT
<213> ORGANISM: Stenotrophomonas maltophilia (strain K279a)

<400> SEQUENCE: 70

Met Ser Gln Gln Asn Thr Pro Glu Asn Asp Pro Asn Pro Ser Pro Tyr
1               5                   10                  15

Gly Gln Gly Pro Ala Ala Gln Glu Pro Ser Ala Asn Pro Tyr Tyr Gly
            20                  25                  30

His Ala Gln Ala Glu Ala Ala Pro Asp Leu Asp Ala Ser Ala Pro Gln
            35                  40                  45

Leu Arg Ser Ala Glu Glu Gln Arg Leu Asn Arg Lys Ala Leu Leu Phe

```
            50                  55                  60
Leu Gly Gly Ile Leu Val Leu Leu Ala Met Gly Phe Leu Leu Leu
65                  70                  75                  80

Arg Lys Gly Lys Glu Asp Ala Glu Ala Lys Ala Pro Pro Gln Val
                85                  90                  95

Ala Arg Ser Ser Thr Pro Asp Leu Pro Ile Ile Ala Pro Ser Ala Ile
                100                 105                 110

Arg Glu Ala Ala Arg Glu Ala Ala Glu Pro Ile Pro Met Leu Pro Pro
                115                 120                 125

Pro Pro Gln Glu Thr Met Gly Pro Thr Phe Ile Pro Arg Ala Glu Pro
            130                 135                 140

Glu Arg Glu Val Glu Arg Gly Pro Ser Leu Leu Asp Arg Arg Ile Ala
145                 150                 155                 160

Gly Ser Gly Gly Ala Gly Val Gly Thr Gly Asp Ala Gly Gly Gln Ala
                165                 170                 175

Ala Ala Gly Asp Asn Asp Pro Tyr Met Gln Ala Thr Leu Ala Ala
                180                 185                 190

Leu Gln Ala Gln Asn Gly Asn Ala Pro Pro Ala Lys Val Arg Arg Gly
            195                 200                 205

Pro Asp Val Glu Asp Val Ser Asn Ala Ser Tyr Ile Arg Ser Pro Asp
210                 215                 220

Ala Leu Leu Val Arg Gly Thr Tyr Leu Arg Cys Val Leu Glu Thr Arg
225                 230                 235                 240

Ile Ile Thr Asp Leu Ala Gly Tyr Thr Ser Cys Leu Leu Thr Glu Pro
                245                 250                 255

Val Tyr Ser Ile Asn Gly Arg Ser Leu Leu Leu Pro Lys Gly Ser Lys
                260                 265                 270

Ile Tyr Gly Ala Tyr Gly Gly Pro Lys Gly Lys Arg Val Glu Val
            275                 280                 285

Ile Trp Asp Arg Ile Thr Thr Pro Asn Gly Ile Asp Val Ala Met Ser
            290                 295                 300

Ser Pro Gly Val Asp Gln Leu Gly Gly Ala Gly His Pro Gly Gln Tyr
305                 310                 315                 320

Ser Ala His Trp Gly Ser Arg Ile Ala Ser Ala Leu Met Ile Ser Leu
                325                 330                 335

Ile Ala Asp Ala Phe Lys Tyr Ala Ala Ala Glu His Gly Pro Glu Ser
                340                 345                 350

Thr Thr Val Ser Ser Asn Gly Phe Ala Val Arg Ser Pro Tyr Glu Ser
                355                 360                 365

Ala Thr Ala Arg Thr Met Glu Arg Leu Ala Asn Glu Ala Leu Thr Ser
            370                 375                 380

Ser Asn Arg Pro Pro Thr Val Thr Ile Asn Gln Gly Thr Ile Val Asn
385                 390                 395                 400

Val Tyr Val Ala Lys Asp Val Asp Phe Thr Asn Val Leu Asn Pro Arg
                405                 410                 415

Arg
```

<210> SEQ ID NO 71
<211> LENGTH: 408
<212> TYPE: PRT
<213> ORGANISM: Phenylobacterium zucineum (strain HLK1)

<400> SEQUENCE: 71

Met Thr Asp Thr Leu Ala Thr Ser Gly Glu Pro Pro Arg Arg Pro Arg

```
 1               5                  10                 15
Leu Pro Asp Glu Leu Ala Ala Arg Tyr Gly Glu Ser Ala Pro Glu Pro
             20                  25                 30
Pro Pro Glu Asp Asn Leu Arg Arg Ala Ala Asn Asp Glu Pro Ala Ser
             35                  40                 45
Glu Arg Gly Ile Ser Pro Val Gly Arg Arg Phe Ala Ala Gly Thr Gln
 50                  55                 60
Gly Lys Val Leu Gly Met Val Gly Met Val Ala Ala Gly Leu Leu
 65                  70                 75                 80
Ile Val Ala Thr Trp Asp Arg Gly Asp Ala Lys Pro Asp Asp Ser Pro
             85                  90                 95
Leu Glu Lys Thr Pro Ala Arg Gln Val Val Asn Tyr Glu Gly Pro Asp
             100                 105                110
Ala Asp Ser Pro Leu Leu Ala Lys Ala Ala His Asp Pro Asn Ala Pro
             115                 120                125
Val Leu Asn Pro Asp Gly Thr Leu Thr Ala Gly Gly Asp Gly Gly Gly
             130                 135                140
Val Pro Pro Met Gln Pro Thr Gln Ala Ala Gly Pro Gly Ala Ala
145                  150                 155                160
Asp Gln Arg Arg Gln Leu Ala Glu Ala Ala Arg Arg Ala Pro Ile Ile
             165                 170                175
Ala Tyr Ser Ala Asn Arg Gly Leu Gly Gly Phe Ser Gly Pro Ala Ala
             180                 185                190
Ala Ala Gly Glu Gly Ala Arg Glu Ala Ser Glu Leu Asp Lys Leu Arg
             195                 200                205
Arg Thr Ala Gly Val Ala Gln Ala Arg Ala Glu Met Leu Pro Asp Arg
             210                 215                220
Asn Phe Leu Ile Thr Ala Gly Ser Ser Ile Pro Cys Val Leu Gln Thr
225                  230                 235                240
Ala Leu Asp Ser Ser Val Pro Gly Tyr Ala Thr Cys Leu Val Pro Arg
             245                 250                255
Asp Val Tyr Ser Asp Asn Gly Arg Val Val Leu Met Glu Lys Gly Thr
             260                 265                270
Lys Val Leu Gly Glu Tyr Arg Gly Ile Arg Gln Gly Gln Lys Arg
             275                 280                285
Leu Phe Val Leu Trp Thr Arg Ala Val Thr Pro Asn Gly Val Ala Val
             290                 295                300
Ser Leu Ala Ser Pro Ala Ala Asp Gly Leu Gly Arg Ala Gly Phe Asp
305                  310                 315                320
Gly Lys Val Asp Thr Phe Phe Trp Glu Arg Phe Gly Gly Ala Leu Leu
             325                 330                335
Leu Ser Ile Ile Asp Asp Ala Ala Asn Ile Ala Ala Gln Ser Ala Gly
             340                 345                350
Arg Gly Arg Phe Asn Thr Thr Met Asp Val Pro Ser Glu Thr Ala Ser
             355                 360                365
Ile Ala Leu Gln Asn Ser Ile Gly Ile Pro Pro Arg Leu Arg Lys Ser
             370                 375                380
Gln Gly Glu Glu Val Ser Ile Phe Val Ala Gln Asp Leu Asn Phe Ala
385                  390                 395                400
Asp Val Tyr Gly Leu Ala Leu Arg
             405

<210> SEQ ID NO 72
```

```
<211> LENGTH: 449
<212> TYPE: PRT
<213> ORGANISM: Oligotropha carboxidovorans (strain ATCC 49405 / DSM
      1227 / OM5)

<400> SEQUENCE: 72
```

| | | | | | | | | | | | | | | |
|---|---|---|---|---|---|---|---|---|---|---|---|---|---|---|
| Met | Pro | Thr | Pro | Asp | Asp | Tyr | Arg | Ser | Phe | Glu | Leu | Glu | Ala | Ala | Ala |
| 1 | | | | 5 | | | | | 10 | | | | | 15 |

| Ala | Thr | Ser | Val | Ala | Arg | Gly | Arg | Thr | Ala | Leu | Gly | Ser | Phe | Leu | Lys |
| | | | 20 | | | | | 25 | | | | | 30 | | |

| Phe | Gly | Val | Pro | Ile | Gly | Ala | Leu | Leu | Val | Ala | Ala | Trp | Met | Ile | Tyr |
| | | | 35 | | | | | 40 | | | | | 45 | | |

| Gly | Thr | Val | Ala | Arg | Arg | Ser | Pro | Thr | Leu | Thr | Thr | Pro | Asp | Lys | Glu |
| | 50 | | | | | 55 | | | | | 60 | | | | |

| Glu | Phe | Arg | Thr | Thr | Gln | Phe | Pro | Ala | Pro | Ser | Leu | Ser | Thr | Pro | Arg |
| 65 | | | | | 70 | | | | | 75 | | | | | 80 |

| Val | Gln | Thr | Asn | Gln | Gly | Thr | Ile | Val | Ile | Pro | Gln | Ala | Pro | Ala | Glu |
| | | | | 85 | | | | | 90 | | | | | 95 | |

| Pro | Ala | Pro | Pro | Pro | Pro | Val | Ala | Pro | Pro | Leu | Ala | Leu | Pro | Ala |
| | | | 100 | | | | | 105 | | | | | 110 | |

| Pro | Pro | Pro | Pro | Glu | Pro | Pro | Leu | Ala | Gly | Ala | Leu | Pro | Asn | Asp | Asp |
| | | | | 115 | | | | | 120 | | | | | 125 | |

| Glu | Ala | Arg | Arg | Leu | Ala | Glu | Leu | Glu | Arg | Gln | Arg | Gln | Glu | Glu | Glu |
| | 130 | | | | | 135 | | | | | 140 | | | | |

| Arg | Arg | Lys | Trp | Glu | Arg | Leu | Arg | Ala | Pro | Gln | Val | Ile | Ala | Asp | Asn |
| 145 | | | | | 150 | | | | | 155 | | | | | 160 |

| Ala | Ala | Ala | Ala | Asn | Thr | Ala | Asn | Pro | Asp | Asp | Gly | Ser | Lys | Ala |
| | | | | 165 | | | | | 170 | | | | | 175 |

| Ala | Ala | Gly | Pro | Glu | Asp | Asp | Pro | Asn | Arg | Arg | Phe | Leu | Ser | Ser | Val |
| | | | 180 | | | | | 185 | | | | | 190 | | |

| Ser | Ala | Ala | Gly | Val | Glu | Val | Ser | Arg | Ala | Ile | Lys | Asn | Asn | Arg | Ile |
| | 195 | | | | | 200 | | | | | 205 | | | | |

| Asp | Ala | Leu | Val | Ala | Gln | Gly | Thr | Met | Ile | Arg | Gly | Val | Leu | Glu | Thr |
| 210 | | | | | 215 | | | | | 220 | | | | | |

| Ala | Val | Gln | Ser | Asp | Leu | Pro | Gly | Met | Val | Arg | Ala | Val | Thr | Glu |
| 225 | | | | | 230 | | | | | 235 | | | | | 240 |

| Asn | Val | Trp | Ser | Phe | Asp | Gly | Arg | Arg | Val | Leu | Ile | Pro | Ala | Gly | Ser |
| | | | | 245 | | | | | 250 | | | | | 255 | |

| Arg | Leu | Val | Gly | Glu | Tyr | Lys | Ser | Gly | Ile | Ala | Gln | Gly | Gln | Thr | Arg |
| | | 260 | | | | | 265 | | | | | 270 | | | |

| Val | Phe | Val | Val | Trp | Thr | Arg | Met | Leu | Arg | Ser | Asp | Gly | Val | Ser | Val |
| | | 275 | | | | | 280 | | | | | 285 | | | |

| Gln | Leu | Gly | Ser | Asn | Gly | Thr | Asp | Asp | Leu | Gly | Arg | Ala | Gly | Asn | Ala |
| | 290 | | | | | 295 | | | | | 300 | | | | |

| Gly | Phe | Val | Asp | Asn | His | Tyr | Leu | Glu | Arg | Phe | Gly | Ser | Ala | Ile | Met |
| 305 | | | | | 310 | | | | | 315 | | | | | 320 |

| Leu | Ser | Val | Val | Gly | Gly | Ala | Ala | Gln | Phe | Leu | Ser | Ala | Tyr | Gly | Gln |
| | | | | 325 | | | | | 330 | | | | | 335 | |

| Asn | Thr | Asn | Thr | Ile | Gly | Asn | Gly | Ser | Ile | Ile | Met | Thr | Thr | Asp | Pro |
| | | | 340 | | | | | 345 | | | | | 350 | | |

| Val | Thr | Gly | Ile | Val | Thr | Gln | Thr | Gln | Thr | Gly | Val | Asn | Gln | Asn | Gln |
| | | 355 | | | | | 360 | | | | | 365 | | | |

| Leu | Ser | Leu | Gln | Ala | Arg | Glu | Ile | Ala | Ala | Gln | Asn | Val | Ser | Gln | Thr |
| | 370 | | | | | 375 | | | | | 380 | | | | |

```
Leu Thr Asn Ile Ala Gln Gln Ala Leu Arg Asn Ser Ile Asn Ile Pro
385                 390                 395                 400

Pro Thr Ile Tyr Leu Asp Gln Gly Thr Arg Ile Ile Val Phe Val Arg
            405                 410                 415

Arg Asp Leu Asp Phe Ser Ala Leu Tyr Pro Asp Pro Val Lys Glu Ala
        420                 425                 430

Leu Arg Glu Leu Lys Arg Glu Arg Ala Gly Ala Lys Ser Asp Gly Leu
    435                 440                 445

His

<210> SEQ ID NO 73
<211> LENGTH: 389
<212> TYPE: PRT
<213> ORGANISM: Agrobacterium radiobacter (strain K84 / ATCC BAA-868)

<400> SEQUENCE: 73

Met Ala Asp Glu Thr Glu Asp Arg Ile Pro Gly Glu Arg Ala Glu Thr
1               5                   10                  15

Asp Val Asn Pro Arg Thr Glu Ala Ser Pro Phe Leu Lys Arg Gly Ala
            20                  25                  30

Val Val Leu Ala Met Val Ala Phe Val Gly Phe Ser Leu Trp Ser Met
        35                  40                  45

Arg Asp Gly Gln Lys Ala Glu Pro Thr Gln Pro Glu His Val Val Ile
50                  55                  60

Arg Gln Thr Ala Asp Phe Glu Pro Ala Lys Glu Val Lys Thr Ala
65                  70                  75                  80

Ala Pro Leu Pro Glu Val Val Leu Pro Thr Pro Ala Pro Lys Glu Gln
            85                  90                  95

Ala Thr Pro Ala Glu Asp Thr Leu Leu Asp Ser Ala Arg Arg Ala Pro
        100                 105                 110

Val Met Ala Tyr Asn Gly Gln Gln Ser Ser Ser Gln Arg Arg Asp Thr
    115                 120                 125

Ala Ala Ala Val Ser Gln Asp Pro Gly Ser Asn Tyr Leu Pro Val Pro
130                 135                 140

Gly Ser Leu Gly Gly Ser Gln Pro Glu Thr Glu Asp Gln Arg Phe Asn
145                 150                 155                 160

Arg Met Leu Thr Pro Thr His Leu Glu Gly Ser Arg Ala Gly Thr Leu
            165                 170                 175

Gly Asn Arg Asp Phe Ile Val Ala Met Gly Thr Ser Ile Pro Cys Val
        180                 185                 190

Leu Glu Thr Ala Leu Ala Ser Asp Gln Pro Gly Phe Ala Ser Cys Val
    195                 200                 205

Ile Asn Arg Asp Val Leu Ser Asp Asn Gly Arg Val Val Leu Met Glu
210                 215                 220

Lys Gly Thr Gln Ile Val Gly Glu Tyr Arg Gly Gly Leu Asn Arg Gly
225                 230                 235                 240

Gln Lys Arg Leu Phe Val Leu Trp Asn Arg Ala Lys Thr Pro Lys Gly
            245                 250                 255

Val Ile Ile Thr Leu Ala Ser Pro Ala Thr Asp Ala Leu Gly Arg Ala
        260                 265                 270

Gly Met Asp Gly Tyr Val Asp Thr His Trp Leu Glu Arg Phe Gly Asn
    275                 280                 285

Ala Ile Leu Leu Ser Ile Val Gly Asp Ala Ser Thr Tyr Ala Gly Ser
290                 295                 300
```

```
Arg Leu Gln Asp Ser Asp Val Gln Ala Gln Asn Thr Thr Ala Gly
305                 310                 315                 320

Gln Gln Ala Ala Ala Thr Ala Val Glu Gln Ser Ile Asn Ile Val Pro
            325                 330                 335

Thr Leu Thr Lys His Gln Gly Glu Leu Val Ser Ile Phe Val Ala Arg
            340                 345                 350

Asp Leu Asp Phe Ser Gly Val Tyr Ser Leu Arg Val Thr Glu Pro Arg
            355                 360                 365

Asn Arg Ile Leu Asp Arg Ala Val Leu Gly Asp Phe Arg Pro Arg Ser
370                 375                 380

Thr Leu Val Thr Lys
385

<210> SEQ ID NO 74
<211> LENGTH: 427
<212> TYPE: PRT
<213> ORGANISM: Pseudomonas fluorescens

<400> SEQUENCE: 74

Met Ala Lys Glu Pro Ile Lys Pro Thr Asp Gln Gln Ala Asp Lys Thr
1               5                   10                  15

Arg Glu Glu Glu Met Ala Glu Trp Asn Glu Ser Gln Ser Asn Ser Met
            20                  25                  30

Leu Lys Ala Gly Ser Gly Gly Lys Arg Ser Gly Val Leu Met Ile Gly
        35                  40                  45

Ala Ala Val Val Ala Cys Gly Phe Val Tyr Trp Leu Lys His Asp Ser
    50                  55                  60

Gly Glu Pro Ala Ala Pro Ala Lys Asn Asp Glu Ile Val Ala Ala Glu
65                  70                  75                  80

Arg Arg Lys Val Gln Asp Pro Thr Pro Lys Arg Glu Ala Ala Lys Val
                85                  90                  95

Lys Pro Val Ser Asn Asp Gly Glu Pro Gly Ala Pro Ala Asp Thr Pro
            100                 105                 110

Arg Ser Thr Ala Glu Arg Gln Thr Asn Gln Glu Gly Leu Ser Glu Ala
        115                 120                 125

Glu Lys Gln Arg Gln Ala Leu Glu Phe Gln Glu Val Ala Arg Lys
    130                 135                 140

Lys Met Leu Ala Ala Arg Gln Arg Ser Ala Ile Phe Ala Thr Ala Lys
145                 150                 155                 160

Asp Asp Gly Phe Ala Gln Gly Arg Asp Asp Gln Asp Pro Ala Gln Pro
                165                 170                 175

Pro Ala Gly Gly Ser Leu Leu Gly Gly Asn Ser Gly Asn Ser Gly Arg
            180                 185                 190

Val Ser Arg Asn Ala Asn Glu Asn Phe Ala Ser Ser Thr Tyr Ser Thr
        195                 200                 205

Gly Val Pro Val Ala Lys Ala Arg Ala Leu Glu Asn Leu Gln Tyr Lys
    210                 215                 220

Val Leu Gln Gly Ala Ala Ile Glu Ala Thr Leu Gln Pro Arg Ala Gln
225                 230                 235                 240

Ser Gln Leu Pro Gly Gln Ile Cys Val Thr Thr Ala Gln Asp Val Tyr
                245                 250                 255

Ala Ala Glu Gly Arg Arg Val Met Ile Pro Trp Gly Ser Ser Val Cys
            260                 265                 270

Gly Ser Tyr Asn Ala Ser Leu Ser Pro Gly Gln Glu Arg Leu Phe Thr
        275                 280                 285
```

```
Val Trp Asn Trp Leu Arg Met Pro Lys Leu Pro Gly Arg Arg Ala Met
    290                 295                 300

Glu Ile Ala Leu Asp Ser Ala Gly Ser Asp Gln Leu Gly Ser Ala Gly
305                 310                 315                 320

Gln Gly Gly Val Val Asp Asn His Trp Ala Gln Ile Phe Gly Val Ala
                325                 330                 335

Ala Ala Val Ser Ile Ile Gly Ala Gly Ala Ser Asn Ser Gly Val Ser
            340                 345                 350

Ser Gly Asp Gln Glu Asn Ser Ala Ser Gln Tyr Arg Thr Glu Val Gln
        355                 360                 365

Gln Ala Ala Ala Glu Ser Ser Gln Thr Ile Leu Ser Arg Tyr Ala Asn
    370                 375                 380

Ile Gln Pro Thr Val Thr Val Pro His Gly Ser Arg Val Val Ile Tyr
385                 390                 395                 400

Leu Gln Arg Asp Leu Asp Phe Thr Glu Gln Phe Ala Glu Glu Ala Lys
                405                 410                 415

Glu Ala Asp Asn Gly Gly Val Lys Phe Ile Asn
            420                 425

<210> SEQ ID NO 75
<211> LENGTH: 413
<212> TYPE: PRT
<213> ORGANISM: Neorickettsia risticii (strain Illinois)

<400> SEQUENCE: 75

Met Gly Phe Phe Phe Ala Tyr Lys Phe Phe Ser Asn Glu Ser Gln Lys
1               5                   10                  15

Glu Asp Thr His Ser Pro Ala Arg Glu Thr Gln Val Glu Glu Arg Val
            20                  25                  30

Val Pro Asp Lys Glu Ile Lys Thr Asp Thr Lys Glu Asp Phe Leu Val
        35                  40                  45

Pro Lys Asp Asp Val Thr Pro Val Leu Leu Pro Pro Lys Met Ser Asp
    50                  55                  60

Leu Pro Lys Leu Pro Ala Ile Pro Val Pro Ala Ile Pro Glu Lys Pro
65                  70                  75                  80

Pro Val Ile Pro Ser Lys Pro Ala Val Gly Pro Ser Leu Pro Ser Phe
                85                  90                  95

Phe Pro Pro Pro Pro Ser Ser Ala Ser Ser Ala Met Asp Pro Pro Gly
            100                 105                 110

Lys Val Ser Ser Gly Val Asn Lys Tyr Asn Arg Ser Thr Pro Met Ile
        115                 120                 125

Ala Phe Gly Gly Gly Gly Val Thr Ser Ser Glu Gly Gln Ser Ser Gly
    130                 135                 140

Ile Ser Ile Ser Asp Pro Ala Ser Leu Leu Asp Pro Ser Lys Leu Gly
145                 150                 155                 160

Glu Leu Arg Arg Ser Leu Gln Gln Arg Asp Thr Thr Ala Pro Glu Asp
                165                 170                 175

Lys Glu Leu Thr Arg Thr Pro Gly Gln Ile Val Ala Gly Tyr Val Gly
            180                 185                 190

Asp Leu Asp Tyr Val Leu Thr Glu Gly Lys Met Leu Asp Ala Val Leu
        195                 200                 205

Glu Thr Ala Val Asn Thr Asp Leu Lys Ala Lys Val Arg Ala Val Val
    210                 215                 220

Ser Arg Asp Val Phe Ser Glu Ser Gly Asn Gln Ile Leu Ile Pro Lys
```

```
                225                 230                 235                 240
        Gly Ser Arg Leu Ile Gly Ser Tyr Ser Thr Asp Ile Ser Phe Thr Gln
                        245                 250                 255

Ser Arg Val Asp Ile Thr Trp Ser Arg Ile Ile Leu Pro Asn Gly Ile
                        260                 265                 270

Asp Ile Asn Leu Gly Gly Phe Asn Gly Val Asp Ser Leu Gly Arg Ala
                        275                 280                 285

Gly Val Arg Gly Thr Val Asn Asn Lys Val Ser Asn Val Met Ser Thr
                        290                 295                 300

Ser Ile Leu Leu Ala Thr Ala Arg Val Ala Ser Gly Met Ile Val Asp
        305                 310                 315                 320

Arg Ile Met Gly Pro Ser Lys Ser Gln Met Ser Ala Pro Lys Lys Arg
                        325                 330                 335

Pro Ser Leu Lys Asp Glu Asn Asp Asp Ser Lys Val Lys Gly Ser
                        340                 345                 350

Pro Gly Ala Ile Ile Ala Val Gln Ala Ile Gln Asp Ala Ser Lys Gln
                        355                 360                 365

Val Thr Asp Tyr Val Lys Arg Thr Ala Asp Val Asn Pro Thr Ile Thr
                        370                 375                 380

Val Asn Gln Gly Thr Arg Leu Lys Val Phe Val Asn Gln Asp Met Val
        385                 390                 395                 400

Phe Pro Arg Ala Ala Phe Gln Glu Tyr Lys Met Leu Asn
                        405                 410

<210> SEQ ID NO 76
<211> LENGTH: 335
<212> TYPE: PRT
<213> ORGANISM: Azospirillum sp. (strain B510)

<400> SEQUENCE: 76

Met Thr Ser Ala Asn Asp Thr Pro Pro Leu Ser Pro Asp Pro Leu
1               5                   10                  15

Ala Arg His Arg Val Val Thr Ser Gly Pro His Val Arg Ile Leu
                20                  25                  30

Leu Val Ala Ala Val Val Ile Gly Leu Gly Leu Ala Ala Tyr Met Leu
                35                  40                  45

Gly Arg Ser Gln Gly Ala Gly Gly Leu Pro Lys Leu Ser Ala Ala Leu
        50                  55                  60

Gly Pro Thr Gln Pro Glu Pro Arg Leu Pro Ser Tyr Glu Asp Met Ala
65                  70                  75                  80

Pro Arg Pro Ala Pro Ala Pro Pro Val Pro Arg Ile Glu Lys Arg
                85                  90                  95

Glu Pro Thr Pro Pro Thr Pro Arg Pro Gln Val Lys Ala Val Pro Lys
                100                 105                 110

Glu Asp Glu Leu Arg Lys Lys Ala Met Asp Ala Gly Val Gly Trp
        115                 120                 125

Ser Arg Lys Glu Glu Gly Ala Thr Val Ala Ser Ala Gln Ala Gly Ala
        130                 135                 140

Ser Asp Phe Ala Pro Ala Gly Ser Asp Cys Leu Val Pro Pro Gly Thr
145                 150                 155                 160

Pro Ile Pro Leu Leu Thr Val Asn Arg Val Val Thr Gly Arg Gly Gly
                165                 170                 175

Ile Val Thr Ala Arg Val Thr Gln Asp Val Trp Asp Ala Gly Phe Ala
                180                 185                 190
```

Cys Leu Ala Val Pro Ala Gly Ser Met Val Thr Leu Glu Val Gly Ser
         195                 200                 205

Gly Val Thr Arg Gly Gln Lys Arg Ile Glu Val Ala Asn Pro Val Ile
    210                 215                 220

Thr Arg Pro Trp Pro Arg Asn Asp Thr Val Arg Val Ala Ala Val Gly
225                 230                 235                 240

Thr Asp Ala Thr Gly Ala Ala Gly Leu Pro Gly Ser Val Glu Val Pro
                245                 250                 255

Trp Leu Gln Thr Gly Leu Leu Ile Ala Ala Ser Thr Ala Val Asp Val
            260                 265                 270

Ala Ser Ala Ala Leu Thr Gly Gly Ser Leu Ile Gly Gly Ile Leu
        275                 280                 285

Gly His Ser Ile Asp Arg Pro Leu Asp Lys Ala Ala Lys Asp Leu Leu
    290                 295                 300

Glu Glu Ala Pro Val Ile Thr Leu Asp Ala Gly Glu Pro Val Leu Leu
305                 310                 315                 320

Leu Leu Arg Gly Gly Leu Arg Ala Asp Asn Phe Gly Arg Asp Asn
                325                 330                 335

<210> SEQ ID NO 77
<211> LENGTH: 413
<212> TYPE: PRT
<213> ORGANISM: Legionella pneumophila serogroup 1 (strain 2300/99
      Alcoy)

<400> SEQUENCE: 77

Met His Lys Asn Asn Asp Tyr Leu Ser Pro Asp Ser Ser Pro Gln Lys
1               5                   10                  15

Leu Gln Thr Thr Gly Val Lys Arg Val Asn Asn Met Pro Leu Phe Ile
            20                  25                  30

Ala Ile Gly Val Leu Thr Val Phe Val Leu Leu Ile Ala Phe Val Ala
        35                  40                  45

Leu Lys Arg Ala Asn Ala Gln Asn Leu Val Thr Glu Pro Ala Lys Leu
    50                  55                  60

Thr Thr Ala Lys Lys Asn Thr Met Ser Leu Ala Tyr Glu Val Ile Gly
65                  70                  75                  80

Asn Arg Lys Pro Glu Thr Asn Gln Pro Val Val Asn Ala Pro Glu Pro
                85                  90                  95

Thr Leu Pro Val Pro Pro Gln Asn Thr His Glu Asn Gln Ser Leu
            100                 105                 110

Asp Ala Gln Ser Val Pro Asp Ala Glu Met Glu Arg Ile Arg Gln Glu
        115                 120                 125

Lys Thr Gln Ala Phe Glu Glu Ala Val Asn Ala Lys Thr Ser Ile Met
    130                 135                 140

Val Asp Asn Ala Arg Leu Asn Ala Arg Glu Ile Thr Asn Ala Ser Thr
145                 150                 155                 160

Ile Asn His Asp Thr Thr Thr Glu Val Asn Val Leu Asn Phe Lys
                165                 170                 175

Glu Gln Leu Asn Lys Leu Gln Ala Arg Gln Asn Ala Arg Pro Met Pro
            180                 185                 190

Gln Thr Leu Gly Gly Glu Gly Glu Ser Arg Trp His Leu Asn Ser
        195                 200                 205

Arg Leu Glu Ser Pro Asn Ser Arg Phe Glu Leu Arg Ala Gly Ser Val
    210                 215                 220

Ile Pro Gly Val Met Val Ser Gly Ile Ser Ser Glu Leu Pro Gly Gln

```
            225                 230                 235                 240

Ile Ile Gly Gln Val Ser Gln Asn Val Tyr Asp Thr Ala Thr Gly Lys
                        245                 250                 255

Tyr Leu Leu Ile Pro Gln Gly Thr Lys Val Ile Gly Leu Tyr Ser Ser
                        260                 265                 270

Asp Val Ser Phe Gly Gln Asp Ser Val Leu Val Ala Trp Gln Arg Leu
                        275                 280                 285

Val Phe Pro Asp Gly Lys Ala Leu Asp Ile Gly Ser Met Pro Gly Ala
                        290                 295                 300

Asp Asn Ala Gly Tyr Ala Gly Phe Arg Asp Gln Val Asp His His Tyr
        305                 310                 315                 320

Ala Arg Ile Tyr Gly Ser Ala Leu Leu Met Ser Gly Ile Val Ala Gly
                        325                 330                 335

Ile Thr Tyr Ser Gln Asn Thr Asn Gln Thr Asn Pro Tyr Gly Tyr Asn
                        340                 345                 350

Gln Pro Thr Ala Gly Ser Val Leu Ser Gln Ala Leu Gly Gln Gln Leu
                        355                 360                 365

Gly Glu Val Thr Ser Gln Met Val Ser Lys Asn Leu Asn Ile Ser Pro
                        370                 375                 380

Thr Ile Asn Ile Arg Pro Gly Tyr Arg Phe Asn Ile Ile Val Ile Lys
        385                 390                 395                 400

Asp Leu Thr Phe Lys Ser Pro Tyr Arg Gln Phe Ala Tyr
                        405                 410

<210> SEQ ID NO 78
<211> LENGTH: 402
<212> TYPE: PRT
<213> ORGANISM: Dickeya dadantii (strain 3937) (Erwinia chrysanthemi
      (strain 3937))

<400> SEQUENCE: 78

Met Thr Asp His Pro Ile Pro Asp Thr Ala Glu Lys Thr Val Ala Glu
        1               5                   10                  15

Arg Glu Ala Glu Ala Arg Glu Arg Ala Arg Ala Arg Glu Ser Gln
                        20                  25                  30

Thr Pro Ala His Asn Thr Pro Pro Gly Gln Pro Asp Val Thr Arg Phe
                        35                  40                  45

Lys Lys Pro Ala Ser Arg Arg Thr Leu Leu Val Ser Leu Leu Ser Leu
                        50                  55                  60

Ala Val Leu Met Leu Leu Ala Trp Ser Gly Asp Arg Phe Phe Gly Ala
        65                  70                  75                  80

Val Lys His Ser Asp Asp Lys Ala Ala Glu Thr Gln Pro Leu Pro Pro
                        85                  90                  95

Thr Gly Ala Ile Pro Pro Ala Arg Lys Asn Leu Gly Met Asp Arg His
                        100                 105                 110

Pro Phe Gly Leu Phe Glu Gln Ser Arg Pro Glu Thr Thr Thr Asp His
                        115                 120                 125

Arg Gln Thr Gln Ala Ala Leu Pro Pro Ala Pro Pro Ala Leu Asn
                        130                 135                 140

Lys Ala Ala Ala Leu Ala Asp Gly Leu Asn Gln Ala Ser Asp Thr Ala
        145                 150                 155                 160

Ser Ala Ser Arg Val Thr Ala Ser Gly Thr Asp Lys Gln Lys Pro Thr
                        165                 170                 175

Thr Ala Pro Ala Pro Glu Ile Lys Asp Thr Ala Pro Gly Val Val Thr
                        180                 185                 190
```

-continued

```
Val Thr His Val Arg Arg Leu Gly Leu Asp Pro Asp Leu Tyr Leu Pro
        195                 200                 205

Val Asp Ser Tyr Ile Pro Cys Ser Met Met Gln Arg Phe Val Ser Asp
210                 215                 220

Val Gly Gly Arg Ile Ser Cys Leu Ile Ser Glu Asp Val Tyr Ser Ala
225                 230                 235                 240

Ser His His Val Lys Leu Ile Pro Ala Gly Thr Ile Ala Arg Gly Ile
                245                 250                 255

Tyr Arg Thr Gly Ala Leu Leu Gln Gly Arg Ser Arg Met Phe Val Ile
                260                 265                 270

Trp Thr Val Leu Arg Thr Pro Glu Pro Gly Ser Leu His Ile Pro Leu
            275                 280                 285

Thr Asp Thr Glu Ala Ser Gly Pro Leu Gly Glu Ala Gly Ile Ser Gly
        290                 295                 300

Arg Ile Asp Thr His Phe Trp Glu Arg Phe Gly Asn Ala Leu Met Leu
305                 310                 315                 320

Ser Thr Val Gln Asp Val Ala Ala Ala Ala Asn Thr Ala Pro Gly
                325                 330                 335

Lys Asp Arg Asn Thr Asp Tyr Thr Glu Asn Thr Arg Ala Ala Ala Ser
                340                 345                 350

Glu Met Ala Lys Thr Ala Leu Glu Asn Ser Ile Asn Ile Pro Pro Thr
                355                 360                 365

Met Tyr Leu Asn Gln Gly Asp Val Ile Gly Ile Met Thr Gly Thr Asp
        370                 375                 380

Ile Asp Phe Ser Ser Val Tyr Gln Leu Arg Leu Lys Thr Arg Trp Tyr
385                 390                 395                 400

Glu Arg

<210> SEQ ID NO 79
<211> LENGTH: 446
<212> TYPE: PRT
<213> ORGANISM: Bilophila wadsworthia 3_1_6

<400> SEQUENCE: 79

Met Gly Trp Lys Leu Trp Gly Lys Pro Glu Lys Glu Leu Glu Gln Pro
1               5                   10                  15

Gln Val Leu Asp Pro Asn Ala Val Pro Ser Gly Ser Gly Lys Arg
            20                  25                  30

Ala Asn Asn Ile Pro Leu Leu Leu Ile Ile Leu Val Val Phe Ile Phe
                35                  40                  45

Leu Ala Ile Val Ala Tyr Val Ala Phe Glu Arg Ser Asn Ser Gln Leu
50                  55                  60

Ser Pro Thr Glu Lys Glu Asn Arg Pro Lys Glu Asn Arg Ser
65                  70                  75                  80

Ala Thr Gln Met Ala Asn Glu Leu Thr Ser Gly Trp Gly Gly Thr Val
                85                  90                  95

Val Ile Pro Thr Glu Pro Ser Pro Ala Thr Asp Glu Glu Lys Ala
            100                 105                 110

His Thr Thr Arg Asp Ala Ala Pro Asn Lys Thr Phe Ala Asp Leu Ser
        115                 120                 125

Leu Val Gln Lys Ser Ala Pro Asp Pro Tyr Leu Leu Glu His Arg Met
    130                 135                 140

Arg Val Gln Glu Leu Lys Ile Gln Ala Leu Glu Ala Ala Arg Thr Ser
145                 150                 155                 160
```

```
Ala Thr Arg Val His Ile Glu Leu Glu Lys Arg Pro Ala Pro Thr Ala
            165                 170                 175

Met Asp Val Asn Ala Arg Ile Ala Ala Thr Arg Gln Arg Leu Ala Asp
            180                 185                 190

Met Ser Asp Pro Ser Ala Ala Tyr Gln Ala Arg Leu Ala Gln Leu Arg
            195                 200                 205

Gly Glu Ser Pro Glu Ser Thr Asp Ala Leu Tyr Glu Pro Thr Arg Ser
            210                 215                 220

Gly Lys Asn Asp Val Arg Gln Phe Thr Gln Lys Asp Ser Trp Asn Leu
225                 230                 235                 240

Asp Ser Gln Val Glu Gly Pro Ala Ser Pro Tyr Met Ile Arg Ala Gly
            245                 250                 255

Phe Val Ile Pro Ala Thr Met Ile Ser Gly Ile Asn Ser Asp Leu Pro
            260                 265                 270

Gly Gln Val Met Ala Gln Val Ser Gln Asn Val Tyr Asp Thr Ala Thr
            275                 280                 285

Gly Lys Tyr Leu Leu Ile Pro Gln Gly Thr Arg Leu Ile Gly Ala Tyr
            290                 295                 300

Ser Ser Asp Val Ala Phe Gly Gln Glu Arg Val Leu Met Ala Trp Gln
305                 310                 315                 320

Arg Leu Ile Phe Pro Asp Gly Lys Ala Leu Asp Ile Arg Ala Met Pro
            325                 330                 335

Gly Ala Asp Ser Ala Gly Tyr Ala Gly Phe Ser Asp Lys Val Asn Ser
            340                 345                 350

His Trp Phe Arg Thr Ile Ser Ser Ala Val Leu Met Ser Gly Val Ile
            355                 360                 365

Ala Ala Val Asp Met Ser Gln Asn Asp Arg Asn Ser Asp Ser Asn Asn
            370                 375                 380

Asp Arg Gln Arg Ala Ser Asp Ser Leu Ser Glu Ala Leu Gly Gln Thr
385                 390                 395                 400

Leu Gly Gln Thr Leu Ser Gln Ile Ile Thr Lys Asn Leu Asn Ile Ser
            405                 410                 415

Pro Thr Leu Glu Ile Arg Pro Gly Tyr Arg Phe Asn Val Met Val Val
            420                 425                 430

Lys Asp Met Ser Leu Pro Gly Ser Tyr Arg Ala Phe Asp Tyr
            435                 440                 445

<210> SEQ ID NO 80
<211> LENGTH: 378
<212> TYPE: PRT
<213> ORGANISM: Acidiphilium multivorum

<400> SEQUENCE: 80

Met Ala Asn Glu Asp Lys Arg Asp Arg Pro Tyr Gly Pro Ile Ser His
1               5                   10                  15

Asp Asn Ala Ala Pro Ser Pro Val Glu Gln Glu Gln Ser Ala Val Ala
            20                  25                  30

Ser Arg Gln Arg Leu Thr Gly Arg Gln Ile Gly Gly Ile Ala Leu Ala
            35                  40                  45

Cys Ala Leu Gly Ala Gly Val Val Leu Val Val Thr Gln Leu Thr Thr
            50                  55                  60

His His Glu Pro Lys Pro Ala Lys Gln Ala Ala Val Thr Gly Gly Thr
65                  70                  75                  80

Glu Gly Arg Pro Phe Val Asn Asn Ala Ser Gly Gly Thr Ala Pro Ala
```

85                  90                  95
Ser Lys Pro Ala Ala Leu Pro Leu Pro Ser Lys Gln Asn Thr Gly Phe
            100                 105                 110

His Asn Pro Phe Leu Asn Asn Gln Gln Glu Ser Pro Ala Met Lys Ala
            115                 120                 125

Leu Lys Ala Pro Ile Met Ala Phe Asn Gln Thr Gly Gly Val Ser
            130                 135                 140

Ala Gln Pro Ala Ser Asn Thr Val Gly Gln Asn Gly Ala Pro Thr Ala
145                 150                 155                 160

Gly Pro Val Lys Pro Thr Ala Phe Ala Ser Lys Leu Asn Ala Asp Gln
                165                 170                 175

Phe Ser Ala Ala Asp Ala Thr Met Ile Ala His Pro Asn Phe Thr Ile
                180                 185                 190

Ala Ala Gly Thr Ile Ile Pro Cys Thr Leu Gln Thr Ala Ile Asn Ser
            195                 200                 205

Thr Leu Pro Gly Phe Val Lys Cys Val Leu Pro Gln Pro Val Arg Ser
210                 215                 220

Met Asn Gly Thr Val Thr Leu Leu Asp Lys Gly Thr Gln Val Leu Gly
225                 230                 235                 240

Glu Val Arg Glu Gly Leu Val Gln Gly Gln Asp Arg Leu Phe Ile Leu
                245                 250                 255

Trp Asp Arg Ala Val Thr Pro Gln Asn Val Ala Ile Gln Leu Ala Ser
            260                 265                 270

Pro Ala Ala Asp Pro Leu Gly Arg Ala Gly Val Ser Gly Ala Val Asn
            275                 280                 285

Asn His Phe Leu Glu Arg Phe Gly Ala Ala Ile Met Met Thr Ile Ile
            290                 295                 300

Gly Gly Ser Met Gln Val Ala Ala Asn Ala Ala Gln Asn Ser Ala Gly
305                 310                 315                 320

Asn Thr Tyr Leu Glu Tyr Met Asn Ser Ser Thr Asn Gln Ile Ala Asn
                325                 330                 335

Thr Thr Leu Gln His Thr Ile Asp Ile Pro Pro Thr Leu Thr Lys His
            340                 345                 350

Gln Gly Glu Asn Val Ser Ile Phe Val Ala Arg Asp Leu Asn Phe Ser
            355                 360                 365

Lys Val Tyr Lys Leu Ser Val Val Ser Pro
            370                 375

<210> SEQ ID NO 81
<211> LENGTH: 375
<212> TYPE: PRT
<213> ORGANISM: Pusillimonas sp. (strain T7-7)

<400> SEQUENCE: 81

Met Thr Glu Lys Glu Gln Asp Gln Ala Gln Ala Ser Gln Glu Gly Asn
1               5                   10                  15

Pro Lys Asp Ala Asn Leu Glu Arg Glu Thr Leu Asn Leu Glu Ala Thr
                20                  25                  30

Gly Arg Ser Ala Pro Arg Gly Ala Arg Ala Phe Leu Trp Leu Thr Ile
            35                  40                  45

Leu Ile Ala Val Ala Val Ala Ala Gly Val Leu Met Lys Val Trp Ser
        50                  55                  60

Arg Glu Pro Ala Ala Lys Ala Asp Ser Gly Leu Glu Ala Asp Gln Ser
65                  70                  75                  80

Gly Ile Thr Asn Arg Leu Lys Ala Pro Lys Val Glu Arg Pro Thr Pro
            85                  90                  95

Pro Pro Thr Leu Pro Pro Ser Ser Glu Pro Thr Val Val Ser Ser
        100                 105                 110

Tyr Asn Val Pro Pro Pro Met Pro Ala Ala Pro Pro Val Asp Glu
            115                 120                 125

Leu Thr Gln Arg Arg Leu Ala Ser Pro Leu Gln Ala Gly Gly Thr Asp
    130                 135                 140

Ala Ser Ala Ala Thr Pro Ser Gln Ser Asn Gly Pro Gln Gly Pro Tyr
145                 150                 155                 160

Ser Asp Ala Gly Pro Leu Ala Asp Lys Leu Arg Pro Leu Glu Leu Ala
                165                 170                 175

Pro Ser Val Ala Gly Gln Leu Gly Asp Arg Asn Phe Leu Leu Thr Gln
            180                 185                 190

Gly Thr Met Ile Asp Cys Thr Leu Gln Thr Lys Leu Val Ser Ala Gln
        195                 200                 205

Ser Gly Leu Leu Thr Cys Leu Ala Thr His Asp Val Met Ser Ala Asn
    210                 215                 220

Gly Lys Val Lys Leu Ile Asp Ala Gly Thr Lys Phe Thr Gly Tyr Gln
225                 230                 235                 240

Ser Gly Gly Ile Gln Gln Gly Gln Ala Arg Ala Phe Val Thr Trp Asn
                245                 250                 255

Arg Leu Glu Thr Pro Thr Gly Val Ile Val Asn Leu Ser Ser Pro Gly
            260                 265                 270

Thr Gly Pro Leu Gly Glu Ala Gly Leu Gly Gly His Ile Asp Asn His
        275                 280                 285

Phe Trp Glu Arg Phe Gly Asn Ala Ile Leu Leu Ser Leu Val Gly Asp
    290                 295                 300

Phe Gly Asn Trp Ala Ser Asn Gln Gln Ser Gly Ser Asn Asn Ile
305                 310                 315                 320

Arg Phe Asp Asn Thr Ala Glu Gly Gly Gln Glu Ala Val Ala Lys Ile
                325                 330                 335

Leu Glu Lys Ser Leu Asp Ile Pro Pro Thr Leu Tyr Lys Asn Gln Gly
            340                 345                 350

Glu Arg Ile Gly Ile Met Val Ala Arg Asp Leu Asp Phe Ser His Val
        355                 360                 365

Tyr Glu Leu Glu Pro Ile His
    370                 375

<210> SEQ ID NO 82
<211> LENGTH: 492
<212> TYPE: PRT
<213> ORGANISM: Midichloria mitochondrii (strain IricVA)

<400> SEQUENCE: 82

Met Glu Lys Val Asn Asp Gln Asp Ser Ser Asn Pro Val Val Glu Thr
1               5                   10                  15

Lys Ser Gln Pro Glu Thr Pro Gly Gly Asn Ser Asn Pro Ser Ser Ser
            20                  25                  30

Gln Gln Pro Val Ser Gly Gly Asn Lys Ile Asp Gly Ile Lys Ala Ala
        35                  40                  45

Lys Asn Asn Met Gln Glu Gln Phe Ser Ser Val Ala Ile Asn Ser Asp
    50                  55                  60

His Lys Lys Leu Val Gly Leu Leu Ser Leu Val Ala Ile Gly Ala Leu
65                  70                  75                  80

```
Val Tyr Phe Leu Phe Phe Ser Gly Thr Pro Thr Pro Asp Lys Gln Lys
                85                  90                  95

Asp Asp Tyr Asn Lys Lys Ile Glu Ala Asn Lys Glu Glu Ile Val Lys
            100                 105                 110

Gln Ser Ile Ser Leu Pro Lys Val Ala Val Asn Asp Asn Thr Asn Val
        115                 120                 125

Val Gln Pro Ala Lys Leu Pro Asp Pro Leu Pro Val Ala Asp Pro Thr
130                 135                 140

Pro Pro Ala Pro Pro Ala Pro Val Pro Val Ala Pro Ala Pro
145                 150                 155                 160

Val Ile Ile Asn Asn Asn Lys Ser Thr Pro Pro Ala Pro Pro Leu Pro
                165                 170                 175

Pro Phe Ile Gln Thr Ala Pro Asn Ser Gly Ala Gly Ser Pro Ser Val
            180                 185                 190

Pro Leu Asn Pro Phe Asp Ser Ser Ala Glu Glu Arg Lys Lys Met Leu
        195                 200                 205

Glu Arg Lys Arg Lys Ala Gly Ile Met Val Thr Gly Ser Gly Lys Gly
    210                 215                 220

Gly Ala Gly Ser Leu Glu Leu Asp Lys Asn Asp Lys Asn Asn Lys Glu
225                 230                 235                 240

Asp Asp Thr Ala Lys Lys Ser Ser Lys Ser Glu Phe Leu Gly Phe Gly
                245                 250                 255

Asn Gly Ser Leu Asp Lys Glu Ser Val Gly Lys Ser Ser Ala Pro Gln
            260                 265                 270

Val Val Ala Thr Lys Val Ser Asp Leu Asn Arg Thr Ile Leu Gln Gly
        275                 280                 285

Lys Ile Ile Asn Ser Val Leu Glu Thr Ala Ile Asn Thr Asp Ile Pro
290                 295                 300

Gly Thr Leu Arg Ala Ile Val Thr Arg Asp Val Tyr Ser Glu Ser Gly
305                 310                 315                 320

Asn Asn Val Leu Ile Pro Lys Gly Ser Arg Leu Val Gly Thr Tyr Glu
                325                 330                 335

Ser Glu Val Lys Pro Gly Gln Thr Arg Val Ser Ile Met Trp Asn Arg
            340                 345                 350

Leu Ile Arg Pro Asp Gly Val Asp Ile Ala Ile Glu Ser Ala Gly Thr
        355                 360                 365

Asp Ala Leu Gly Arg Ala Gly Ala Val Gly Gln Val Asp Ser Lys Phe
    370                 375                 380

Phe Ser Gln Leu Leu Asn Ala Phe Leu Val Ser Tyr Val Ile Pro Leu
385                 390                 395                 400

Gly Ala Gln Gln Leu Ser Gly Ser Gly Asn Asn Gln Ile Ser Thr Ser
                405                 410                 415

Thr Ser Thr Gly Gly Ile Gly Thr Thr Thr Thr Asn Thr Gly Thr Ala
            420                 425                 430

Lys Asp Phe Thr Leu Gln Gln Ala Gln Asp Phe Ser Lys Leu Ala
        435                 440                 445

Ser Asp Thr Val Lys Asn Asn Phe Ser Ser Lys Pro Thr Ile Ser Ile
    450                 455                 460

Asp Gln Gly Thr Val Val Asp Ile Leu Val Gln Lys Asp Leu Ile Phe
465                 470                 475                 480

Pro Thr Ser Ile Ala Gly Ser Arg Thr Val Leu Pro
                485                 490
```

<210> SEQ ID NO 83
<211> LENGTH: 396
<212> TYPE: PRT
<213> ORGANISM: Aliivibrio fischeri (Vibrio fischeri)

<400> SEQUENCE: 83

Met Lys Val Glu His Leu Glu Gly Glu Ala Leu Ser Ile Pro Ser Thr
1               5                   10                  15

Asn Ser Asn Gln Arg Asp Lys Lys His Val Leu Leu Phe Leu Ile Ile
            20                  25                  30

Cys Gly Phe Ile Leu Ser Cys Leu Ile Trp Phe Ile Phe Asn Ser
        35                  40                  45

Ser Asp Lys Glu Ser Val Ser Ala Pro Thr Gln Pro Ser Ile Asn Thr
    50                  55                  60

Ser Thr His Lys Ala Ser Thr Pro Gln Ser Asn Lys Thr Phe Glu Trp
65                  70                  75                  80

Lys Pro Ser Glu Pro Ser Gln Pro Glu Gln Lys Asp Val Glu Asp Thr
                85                  90                  95

Ser Thr Glu Thr Lys Glu Lys Ile Val Asp Thr Pro Val Ala Pro
            100                 105                 110

Val Ser Gln Pro Leu Pro Pro Asn Gly Gln Leu Asn Ser Tyr Thr Pro
        115                 120                 125

Lys Arg Thr Val Ala Gln Ile Asp Lys Ser Lys Ser Ser Met Ser Ser
130                 135                 140

Gly Ser Gln Gly Ser Glu Asn Gly Leu Gln Leu Thr Pro Pro Tyr Pro
145                 150                 155                 160

Thr Tyr Pro Ser Val Pro Thr Thr Gly Thr Pro Ser Ser Phe Phe Asn
                165                 170                 175

Thr Gln Glu Asn Asp Asn Glu Ser Asn Asn Ser Gln Arg Ile Thr Ser
            180                 185                 190

Leu Leu Asn Thr Ser Lys Thr Glu Asn Ser Val Ala Ala Val Leu Tyr
        195                 200                 205

Asn Arg Asp Tyr Leu Leu Ala Lys Gly Ala Tyr Ile Asp Cys Val Leu
210                 215                 220

Asn Thr Ser Met Asn Ser Thr Val Ala Gly Met Thr Lys Cys Thr Leu
225                 230                 235                 240

Thr Arg Asp Ile Tyr Ser Asp Asn Gly Asn Thr Leu Leu Ile Glu Arg
                245                 250                 255

Gly Ser Glu Val Thr Gly Glu Tyr Arg Ala Asn Leu Ser Gln Gly Gln
            260                 265                 270

Ala Arg Leu Phe Val Leu Trp Asp Arg Val Lys Thr Pro His Gly Val
        275                 280                 285

Ile Val Asp Leu Ala Ser Pro Ala Thr Asp Ser Leu Gly Ala Gly Gly
290                 295                 300

Val Asn Gly Tyr Val Asp Thr His Phe Trp Glu Arg Phe Gly Gly Ala
305                 310                 315                 320

Met Met Leu Ser Leu Val Asp Asp Leu Ala Gly Tyr Met Ala Thr Asn
                325                 330                 335

Gly Gly Lys Ser Ile Asn Asn Phe Glu Asn Ser Ser Asn Ala Ala Gln
            340                 345                 350

Asp Met Ala Ala Glu Ala Leu Lys Asn Thr Ile Asn Ile Pro Pro Thr
        355                 360                 365

Phe Tyr Lys Asn Gln Gly Glu Arg Ile Gly Ile Phe Ile Ala Arg Asp
370                 375                 380

```
Ile Asp Phe Ser Lys Val Tyr Arg Leu Lys Val Gln
385                 390                 395
```

<210> SEQ ID NO 84
<211> LENGTH: 321
<212> TYPE: PRT
<213> ORGANISM: Escherichia coli

<400> SEQUENCE: 84

```
Met Ser Ser Gly Asp Glu Lys Pro Ala Ser Asn Ala Val Ser Thr Gly
1               5                   10                  15

Ser Val Lys Arg Ala Thr Gly Leu Ser Asp Val Asp Pro Phe Asn
            20                  25                  30

Thr Arg Ala Glu Pro Ala Lys Thr Glu Glu Arg Lys Glu Ser Ser Asp
                35                  40                  45

Lys Ala Glu Thr Pro Pro Glu Lys Val Gln Gln Asn Phe Ser Arg Ala
    50                  55                  60

Leu Asp Val Ala Tyr Gly Gly Ser Ser Ala Ser Ser Gly Ser Gly
65                  70                  75                  80

Gly Ser Ser Ser Ala Ser Asn Thr Arg Asn Glu Glu Asn Gly Ser
                85                  90                  95

Asp Lys Gln Ala Glu Val Gln Pro Val Asn Ala Gly Gln Pro Ala Gln
                100                 105                 110

Leu Ser Lys Ile Thr Arg Val Pro Tyr Asp Pro Asn Leu Phe Ile Pro
            115                 120                 125

Glu Asn Thr Ala Ile Lys Cys Ser Leu Asp Arg Arg Phe Ile Ser Asp
130                 135                 140

Leu Ala Gly Lys Leu Val Cys Thr Ile Asn Glu Asp Val Tyr Ser Ala
145                 150                 155                 160

Asn Arg Asn Val Lys Leu Ile Glu Lys Gly Thr Ala Ala Tyr Leu Met
                165                 170                 175

Tyr Lys Thr Gly Thr Phe Asn His Gly Gln Gly Ala Val Phe Ile Ala
            180                 185                 190

Ala Thr Lys Leu Arg Thr Arg Lys Glu Pro Phe Ile Asp Ile Pro Leu
        195                 200                 205

Ile Asp Thr Gln Ala Ala Gly Ala Leu Gly Glu Ala Gly Ala Ser Gly
    210                 215                 220

Trp Ile Asp Thr His Phe Ala Asp Arg Phe Met Gly Ala Met Met Val
225                 230                 235                 240

Gly Met Ile Pro Asp Val Ala Gln Ala Ala Ser Gly Ala Ala Lys Ser
                245                 250                 255

Asn Lys Asp Asn Gln Thr Asp Tyr Thr Ala Asn Ser Arg Gln Ala Phe
            260                 265                 270

Ala Asp Ile Ala Arg Glu Ala Phe Ala Asn Ser Val Asn Ile Pro Pro
        275                 280                 285

Thr Leu Tyr Lys Asn Gln Gly Glu Ile Ile Thr Leu Ile Val Gly Gln
    290                 295                 300

Asp Leu Asp Phe Ser Ser Ile Tyr Lys Leu Lys Met Val Gly Ser Arg
305                 310                 315                 320

Arg
```

<210> SEQ ID NO 85
<211> LENGTH: 400
<212> TYPE: PRT
<213> ORGANISM: Helicobacter cetorum (strain ATCC BAA-429 / MIT 00-7128)

<400> SEQUENCE: 85

```
Met Asn Lys Ser Leu Leu Lys Lys Ile Gly Leu Gly Ala Leu Gly Ala
1               5                   10                  15

Ile Thr Leu Met Ala Leu Gly Ile Leu Ala Asn Lys Asn Gln Asn Gln
            20                  25                  30

Asn Asn Gln Glu Glu Ile Phe Gln Val Ser Glu Ser Lys Phe Pro Leu
        35                  40                  45

Ser Asp Tyr Phe Phe Glu Glu Val Lys Glu Glu Pro Lys Glu Lys Ala
    50                  55                  60

Lys Glu Thr Thr Gln Thr Thr Thr Gln Gln Pro Thr Thr Gln Ala Asn
65                  70                  75                  80

Val Ser Thr Asn Pro Ile Val Val Gly Tyr Asn Pro Leu Asn His Ser
                85                  90                  95

Leu Asn Asn Gln Asn Ser Thr Leu Asn His Leu Gln Asn Val Leu Gln
            100                 105                 110

Gln Lys Pro Lys Glu Lys Ser Lys Lys Thr Lys His Thr Lys Glu Gln
        115                 120                 125

Leu Glu Phe Leu Asn Thr Arg Leu Lys Pro Leu Glu Pro Leu Lys Asn
    130                 135                 140

Ala Thr Lys Pro Glu Thr Glu Tyr Gly Val Asp Ser Phe Thr Asn Leu
145                 150                 155                 160

Lys Tyr Lys Asp Val Gly Thr Asn Glu His Lys Leu Leu Arg Thr Ile
                165                 170                 175

Thr Ala Asp Arg Met Ile Pro Ala Phe Leu Ile Thr Pro Ile Ser Ser
            180                 185                 190

Gln Ile Ala Gly Lys Val Thr Ala Gln Val Glu Ser Asp Ile Phe Ala
        195                 200                 205

Asn Met Gly Arg Ala Val Leu Ile Pro Lys Gly Ser Lys Val Ile Gly
    210                 215                 220

Tyr Tyr Asn Asn Asn Asn Gln Ile Gly Glu Tyr Arg Leu Asn Ile Ala
225                 230                 235                 240

Trp Thr Arg Ile Ile Thr Pro Gln Gly Ile Asn Ile Met Leu Thr Asn
                245                 250                 255

Ala Arg Gly Ala Asp Val Lys Gly Tyr Asn Gly Leu Ile Gly Lys Val
            260                 265                 270

Ile Lys Arg Asn Phe Glu Arg Tyr Gly Leu Pro Leu Leu Thr Ser Thr
        275                 280                 285

Leu Ser Asn Gly Leu Leu Ile Gly Leu Thr Ser Ala Leu Ala Asn Arg
    290                 295                 300

Gln Asn Lys Ala Gly Val Gly Asn Pro Phe Phe Gly Asp Tyr Leu Leu
305                 310                 315                 320

Met Gln Leu Thr Arg Asn Thr Gly Met Ser Ile Asn Gln Val Ile Asn
                325                 330                 335

Gln Met Leu Arg Gln Asn Ala Arg Gln Asn Pro Ile Ile Ile Ile Arg
            340                 345                 350

Glu Gly Ser Arg Val Phe Ile Ser Pro Asn Leu Asp Ile Phe Ile Pro
        355                 360                 365

Lys Pro Lys Asp Gly Glu Val Leu Ala Glu Phe Phe Lys Glu Lys Lys
    370                 375                 380

Pro Leu Ile Lys Lys Gln Asn Glu Glu Ile Ser Asn Glu Asp Glu Ile
385                 390                 395                 400
```

<210> SEQ ID NO 86
<211> LENGTH: 422
<212> TYPE: PRT
<213> ORGANISM: Hydrogenophaga sp. PBC

<400> SEQUENCE: 86

```
Met Ser Gln Asp Asp Thr Pro Asp Leu Ala Thr Pro Gln Ala Gly Lys
1               5                   10                  15

Val Ala Pro Glu Ala Val Ala Leu Arg Ala Gln Pro Arg Pro Val Thr
            20                  25                  30

Arg Leu Asn Arg Arg Thr Leu Ala Ile Leu Val Gly Gly Leu Ser Val
        35                  40                  45

Ala Val Leu Gly Ala Thr Ile Trp Ser Leu Gln Pro His Arg Arg Asp
50                  55                  60

Ala Gly Glu Gln Thr Glu Leu Tyr Asn Val Asp Arg Val Ser Lys Ser
65                  70                  75                  80

Glu Gly Leu Asp Gly Leu Pro Ser Asp Tyr Ser Lys Leu Arg Lys Val
                85                  90                  95

Pro Glu Leu Gly Pro Pro Leu Pro Gly Asp Leu Gly Pro Ala Ile Val
            100                 105                 110

Asn Ser Gln Gln Pro Ala Met Ala Ala Tyr Thr Ala Pro Gly His Asp
        115                 120                 125

Pro Asn Asp Ala Leu Arg Lys Glu Ala Glu Ala Ala Ala Ser Ser
130                 135                 140

Val Phe Phe Arg Ser Gly Gln Gly Gln Ala Ala Ala Thr Val Ala
145                 150                 155                 160

Gln Ala Ala Pro Gly Ala Ser Gly Ala Ser Thr Leu Ala Ala Phe Asp
                165                 170                 175

Pro Leu Ala Ala Gly Pro Ala Ser Thr Ala Ala Gln Pro Ala Asp Pro
            180                 185                 190

Thr Ala Val Gln Asn Arg Gln Glu Gln Lys Glu Ala Phe Leu Lys Ala
        195                 200                 205

Gly Ser Thr Glu Thr Arg Asn Ser Gly Asn Leu Ala Leu Pro Ala Ser
210                 215                 220

Pro Tyr Gln Val Met Ala Gly Thr Val Ile Ala Gly Ala Leu Val Thr
225                 230                 235                 240

Gly Ile Lys Ser Asp Leu Pro Gly Asp Val Ile Ala Thr Val Thr Glu
                245                 250                 255

Pro Val Tyr Asp Thr Ala Thr Gly Lys Phe Leu Leu Ile Pro Gln Gly
            260                 265                 270

Ser Arg Ile Leu Gly Arg Tyr Asn Ser Gln Val Ser Tyr Gly Gln Ser
        275                 280                 285

Arg Val Gln Val Val Trp Asn Arg Val Ile Leu Pro Asp Thr Ser Ser
290                 295                 300

Leu Thr Leu Asp Asn Leu Val Gly Thr Asp Pro Ala Gly Tyr Ala Gly
305                 310                 315                 320

Leu Glu Asp Asp Val Asp Trp His Trp Lys Arg Ile Phe Ala Gly Ala
                325                 330                 335

Val Leu Thr Thr Leu Leu Gly Val Gly Ala Glu Leu Ala Ala Pro Glu
            340                 345                 350

Asn Arg Gln Asp Gly Asn Arg Ile Val Ile Ala Gly Arg Asp Ser Ala
        355                 360                 365

Gln Asp Ser Ile Asn Gln Val Gly Gln Glu Ile Thr Arg Arg Asn Met
370                 375                 380
```

```
Asn Ile Gln Pro Thr Leu Thr Ala Arg Pro Gly Leu Pro Val Arg Val
385                 390                 395                 400

Ile Val Ala Arg Asp Leu Val Leu Arg Pro Tyr Gln Pro Met Phe Tyr
                405                 410                 415

Gln Leu Glu Gly Ala Arg
            420

<210> SEQ ID NO 87
<211> LENGTH: 437
<212> TYPE: PRT
<213> ORGANISM: Phaeobacter inhibens

<400> SEQUENCE: 87

Met Ser Glu Thr Ala Glu Leu Lys Lys Arg Leu Glu Ala Leu Glu Gly
1               5                   10                  15

Lys Pro Gln Asn Arg Lys Thr Arg Pro Ser Leu Val Ala Ile Thr Leu
                20                  25                  30

Gly Ile Gly Ala Ile Ala Val Leu Gly Ala Leu Leu Leu Leu Phe Ser
            35                  40                  45

Gly Gly Ser Glu Pro Asp Ser Leu Gln Thr Ala Ser Pro Asp Glu Phe
50                  55                  60

Gln Ala Ala Gly Pro Gly Phe Gly Thr Leu Val Pro Thr Pro Ala Pro
65                  70                  75                  80

Ile Asp Thr Ser Pro Pro Glu Pro Glu Thr Asp Ser Glu Ala Asp
                85                  90                  95

Gly Leu Arg Ala Gln Met Asp Ala Met Arg Ser Glu Leu Glu Ala Leu
            100                 105                 110

Arg Asn Ala Pro Val Pro Glu Ala Pro Ala Val Asp Leu Glu Ala Leu
            115                 120                 125

Asp Thr Leu Gly Ala Glu Ile Asp Ala Leu Arg Ser Glu Ala Ala Ala
    130                 135                 140

Thr Gln Ala Ala Leu Arg Glu Glu Leu Glu Glu Arg Ala Arg Gln Ile
145                 150                 155                 160

Gln Arg Leu Gln Ser Asp Leu Glu Leu Ala Arg Leu Glu Thr Pro Arg
                165                 170                 175

Thr Pro Ala Pro Thr Gly Pro Thr Ala Glu Glu Leu Arg Leu Gln Glu
            180                 185                 190

Leu Glu Arg Arg Gln Ala Glu Leu Glu Glu Leu Gln Ala Arg Ile
            195                 200                 205

Ala Ser Pro Ile Ile Ala Phe Gly Gly Ser Gly Ser Gly Asn Asn Glu
210                 215                 220

Thr Ala Ala Gln Gln Arg Arg Leu Asp Gly Asp Thr Asp Phe Val Arg
225                 230                 235                 240

Asn Gly Ala Glu Pro Ala Glu Val Thr Gln Ala Gln Val Ile Val Asn
                245                 250                 255

Pro Ser Asn Thr Val Val Gln Gly Thr Met Ile Gln Ala Val Leu Glu
            260                 265                 270

Thr Ala Ile Asp Ser Ser Leu Ala Gly Gln Val Arg Ala Met Val Ser
        275                 280                 285

Glu Asp Val His Ala Tyr Asp Gly Ser Arg Val Leu Ile Pro Arg Gly
    290                 295                 300

Ala Arg Leu Ile Gly Arg Tyr Gln Ser Gly Leu Asn Ile Ala Gln Gln
305                 310                 315                 320

Arg Val Thr Ile Ala Trp Asp Arg Ile Ile Leu Pro Ser Asn Gln Thr
                325                 330                 335
```

-continued

Val Glu Ile Ser Ala Phe Gly Gly Asp Glu Leu Gly Arg Ser Gly Thr
                340                 345                 350

Thr Gly Phe Val Asp Ser Arg Phe Gly Thr Arg Phe Gly Ser Ala Ala
            355                 360                 365

Leu Ile Ser Leu Ile Gly Ala Leu Pro Ala Val Ala Val Gln Asn Thr
        370                 375                 380

Glu Asp Glu Ile Ala Ser Asp Val Leu Glu Ile Gly Glu Asp Leu
385                 390                 395                 400

Gln Asp Ser Ala Gln Ser Val Ile Gly Glu Tyr Leu Ser Val Ser Pro
                405                 410                 415

Val Ile Tyr Val Asn Gln Gly Ala Arg Val Thr Val Met Val Asp Arg
            420                 425                 430

Asp Leu Glu Ile Phe
            435

<210> SEQ ID NO 88
<211> LENGTH: 384
<212> TYPE: PRT
<213> ORGANISM: Alcaligenes faecalis subsp. faecalis NCIB 8687

<400> SEQUENCE: 88

Met Thr Thr Asp Thr Tyr Pro Ser Asp Glu Arg Met Val Met Ala
1               5                   10                  15

Thr Ser Pro Ala Gln Ala Met Glu Leu Glu Arg Gly Pro Ala Asp Phe
                20                  25                  30

Gly Asp Thr Arg Lys Ser Ala Pro Arg Gly Ala Arg Ala Phe Leu Trp
            35                  40                  45

Leu Thr Gly Leu Ile Ala Thr Ala Ile Thr Leu Gly Phe Ile Phe His
        50                  55                  60

Arg Tyr Ala Pro Gly Asp Glu Ala Val Ala Ala Ser Asp Leu Asn Thr
65                  70                  75                  80

Thr Thr Ser Gly Ile Thr Asn Arg Leu Glu Ala Pro Gln Leu Arg Arg
                85                  90                  95

Pro Pro Pro Ala Arg Glu Ala Ala Ala Ser Pro Ala Pro Ala Pro Ala
                100                 105                 110

Pro Leu Pro Ile Ile Val Gln Ala Ala Pro Val Thr Ala Pro Ser Ala
            115                 120                 125

Asp Pro Val Thr Glu Arg Arg Leu Ala Ser Pro Leu Gln Ala Asp Gly
        130                 135                 140

Thr Gly Gln Pro Ala Ala Ser Ala Gly Ala Arg Thr Gln Thr Val Ala
145                 150                 155                 160

Thr Pro Met Gln Asp Ala Gly Pro Leu Ala Asp Lys Leu Arg Pro Leu
                165                 170                 175

Glu Leu Ala Pro Ser Val Ala Gly Gln Leu Gly Glu Arg Asn Phe Leu
            180                 185                 190

Ile Thr Gln Gly Thr Met Ile Asp Cys Thr Leu Gln Thr Arg Leu Val
        195                 200                 205

Ser Thr Gln Pro Gly Leu Leu Thr Cys Leu Ala Thr His Asp Val Met
    210                 215                 220

Ser Ala Asn Gly Lys Val Lys Leu Ile Asp Arg Gly Thr Lys Phe Thr
225                 230                 235                 240

Gly Tyr Gln Ser Gly Gly Ile Val Gln Gly Gln Ala Arg Ala Phe Ile
                245                 250                 255

Thr Trp Asn Arg Leu Glu Thr Pro Thr Gly Val Ile Leu Asn Leu Ala

```
                260                 265                 270
Ser Pro Gly Thr Gly Pro Leu Gly Glu Ala Gly Val Asp Gly Asp Val
            275                 280                 285

Asp Asn His Phe Trp Asp Arg Phe Gly Asn Ala Ile Leu Leu Ser Leu
        290                 295                 300

Ile Gly Asp Leu Gly Asn Trp Ala Ser Asn Gln Gly Gln Arg Gly Glu
305                 310                 315                 320

Asn Asn Val Arg Phe Asp Thr Thr Met Asp Gly Gly Gln Glu Val Ile
                325                 330                 335

Thr Ala Ile Leu Glu Arg Ser Leu Asp Ile Pro Pro Thr Leu Tyr Lys
            340                 345                 350

Asn Gln Gly Glu Arg Ile Gly Ile Met Ile Ala Arg Asp Leu Asp Phe
        355                 360                 365

Ser Gln Val Tyr Asp Leu Lys Pro Thr His Leu Ala His Ser Leu Arg
    370                 375                 380

<210> SEQ ID NO 89
<211> LENGTH: 386
<212> TYPE: PRT
<213> ORGANISM: Bartonella alsatica IBS 382

<400> SEQUENCE: 89

Met Asn Asn Glu Met Asp Glu Lys Asn Ile Asn Asp Arg Asp Met Ile
1               5                   10                  15

Lys Asp Phe Gln Gly Asn Lys Gln His Ser Asn Ile Gly Lys Ala Val
            20                  25                  30

Ala Leu Val Ile Leu Phe Gly Val Cys Ile Tyr Leu Ala Tyr Ser Thr
        35                  40                  45

Leu Val Thr Asp Lys Lys Gln Pro Val Glu Leu Pro Lys Glu Gly Ile
    50                  55                  60

Ile Lys Gln Thr Glu Phe Phe Arg Pro Thr Gln Leu Lys Pro Val Ser
65                  70                  75                  80

Phe Glu Gln Thr Gln Lys Asn Ser Val Leu Leu Pro Lys Val Glu Leu
                85                  90                  95

Pro Thr Pro Lys Ile Asn Gln Lys Lys Ser Asn Asp Asp Ser Leu Met
            100                 105                 110

Glu Ala Ala Gln Arg Ala Pro Val Leu Ala Tyr Ala Ser Thr Gln Gln
        115                 120                 125

Asn Lys Met Ser Thr Ala Ile Asn Ala Gly Val Leu Ser Asn Lys Leu
    130                 135                 140

Glu Asn Lys Pro Asp Glu Thr Ala Gln Arg Phe Asn His Leu Leu Lys
145                 150                 155                 160

Pro Thr Thr Leu Glu Gly Ile Arg Ala Ser Thr Leu Gly Asn Arg Asn
                165                 170                 175

Tyr Ile Ile Thr Met Gly Thr Ser Ile Pro Cys Ile Leu Glu Thr Ala
            180                 185                 190

Ile Ser Ser Asp Gln Gln Gly Phe Thr Ser Cys Ile Val Ser Arg Asp
        195                 200                 205

Ile Leu Ser Asp Asn Gly Arg Val Val Leu Asp Lys Gly Thr Gln
    210                 215                 220

Ile Val Gly Glu Tyr Arg Ala Gly Leu Lys Lys Gly Gln Asn Arg Leu
225                 230                 235                 240

Phe Val Leu Trp Asn Arg Ala Lys Thr Pro Asn Gly Ile Ile Ile Thr
                245                 250                 255
```

```
Leu Ala Ser Pro Ala Thr Asp Ala Leu Gly Arg Ser Gly Val Asp Gly
            260                 265                 270

Asp Val Asp Asn His Trp Leu Glu Arg Ile Gly Ser Ala Leu Leu Val
        275                 280                 285

Ser Ile Val Lys Asp Ala Thr Asn Tyr Ala Lys Gly Arg Leu Ser Lys
        290                 295                 300

Gly Pro Glu Lys Asn Asp Thr Glu Thr Leu Ser Ser Gly Pro Asn Ile
305                 310                 315                 320

Ala Asn Ile Leu Val Glu Asn Tyr Ala Asn Ile Pro Pro Thr Leu Thr
                325                 330                 335

Lys Asn Gln Gly Glu Met Val Asn Val Phe Val Ala Arg Asp Leu Asp
            340                 345                 350

Phe Ser Asn Val Tyr Lys Leu Gln Val Ile Glu Ser Lys Lys Gln Ile
            355                 360                 365

Thr Asn Arg Ala Leu Ser Arg Asn Phe Tyr Lys Asn Ser Thr Val Thr
370                 375                 380

Leu Lys
385

<210> SEQ ID NO 90
<211> LENGTH: 410
<212> TYPE: PRT
<213> ORGANISM: Pectobacterium wasabiae CFBP 3304

<400> SEQUENCE: 90

Met Thr Asp Lys Ala Asp Pro Glu Thr Thr Glu Lys Thr Val Thr Glu
1               5                   10                  15

Leu Glu Ala Glu Ala Arg Glu Arg Ala Arg Ser Ala Met Ala Ser Gln
            20                  25                  30

Ala Pro Glu Gln Asn Thr Pro Pro Gly Gln Pro Glu Val Thr Arg Phe
        35                  40                  45

Lys Lys Ala Ser Ser Arg Arg Thr Leu Leu Val Ser Leu Leu Ser Leu
    50                  55                  60

Gly Ala Leu Ile Ala Leu Ala Leu Gly Gly Asp Arg Phe Leu Val Ala
65                  70                  75                  80

Leu Lys Gln Ser Asp Asn Lys Ser Ile Glu Thr Ser Ala Pro Pro Ser
            85                  90                  95

Ala Ser Thr Gly Gln His Glu Arg Lys Asn Leu Gly Met Asp Asn Asn
            100                 105                 110

Pro Phe Gly Leu Phe Gly Gln Asp Lys Gln Glu Thr Ala Thr Asp Asn
        115                 120                 125

Pro Pro Ile Gln Thr Ala Ser Pro Ser Glu Pro Pro Ala Leu Asn Lys
    130                 135                 140

Ala Ala Leu Val Asp Gly Ser Ser Ser Ala Glu Ser Thr Gln
145                 150                 155                 160

Arg Gly Asn Thr Gln Ala Ser Gln Thr Ala Pro Ser Asp Thr Gln Ser
            165                 170                 175

Tyr Gln Asn Lys Gly Thr Pro Glu Thr Thr Ser Gly Thr Glu Ala Asn
            180                 185                 190

Asp Thr Asn Pro Gly Ile Ala Lys Val Thr Ser Val Arg Gln Leu Gly
        195                 200                 205

Leu Asp Pro Asn Leu Tyr Leu Pro Val Asp Arg Tyr Ile Pro Cys Ser
    210                 215                 220

Met Met Arg Arg Phe Val Ser Asp Val Gly Gly Arg Ile Ser Cys Leu
225                 230                 235                 240
```

```
Ile Gly Glu Asp Val Tyr Ser Ala Asn His Tyr Val Lys Leu Leu Pro
                245                 250                 255

Ala Gly Thr Val Ala Arg Gly Ile Tyr Arg Thr Gly Ala Leu Gln His
            260                 265                 270

Gly Arg Ser Arg Met Phe Val Ile Trp Thr Glu Leu Arg Thr Pro Glu
        275                 280                 285

Pro Gly Ser Leu Gln Ile Pro Leu Val Asp Thr Glu Ala Thr Gly Pro
    290                 295                 300

Leu Gly Glu Ala Gly Ile Ser Gly Trp Ile Asp Thr His Phe Trp Glu
305                 310                 315                 320

Arg Phe Gly Asn Ala Leu Met Leu Ser Thr Val Gln Asp Val Ala Ala
                325                 330                 335

Ala Ala Ser Asp Ser Ala Pro Gly Lys Asp Arg Asn Thr Asp Tyr Thr
            340                 345                 350

Glu Asn Thr Arg Ser Ala Ala Ser Glu Met Ala Lys Thr Ala Leu Glu
        355                 360                 365

Asn Ser Ile Asn Ile Pro Pro Thr Met Tyr Leu Asn Gln Gly Asp Leu
    370                 375                 380

Ile Gly Ile Met Thr Gly Thr Asp Ile Asp Phe Ser Val Tyr Gln
385                 390                 395                 400

Leu Arg Leu Lys Lys Arg Trp Tyr Glu Arg
                405                 410

<210> SEQ ID NO 91
<211> LENGTH: 432
<212> TYPE: PRT
<213> ORGANISM: Anaplasma phagocytophilum (Ehrlichia phagocytophila)

<400> SEQUENCE: 91

Met Ala Asp Glu Ile Arg Gly Ser Ser Gly Glu Asn Ile Glu Asp
1               5                   10                  15

Asn Val Asn Val Val Gly Val Ala Lys Ser Lys Lys Leu Phe Val Ile
                20                  25                  30

Ile Val Val Leu Ile Ala Thr Gly Leu Met Tyr Tyr Phe Phe Phe Phe
            35                  40                  45

Asn Lys Glu Ser Ser Glu Asn Glu Glu Asp Thr Gln Ile Pro Arg Val
        50                  55                  60

Ile Glu Glu Lys Glu Val Glu Lys Leu Arg Lys Asp Ala Gly Arg Pro
65                  70                  75                  80

Ala Gln Glu Thr Ala Pro Arg Ile Leu Thr Pro Pro Pro Arg Leu Pro
                85                  90                  95

Glu Leu Pro Pro Leu Val Met Pro Thr Val Pro Asp Ile Pro Val Val
            100                 105                 110

Thr Lys Leu Leu Lys Pro Pro Val Glu Glu Glu Phe Val Glu Glu Tyr
        115                 120                 125

Asn Val Gln Glu Val Pro Ser Pro Met Gly Asn Ile Ala Pro Pro Glu
    130                 135                 140

Arg Glu Glu Ile Ser Leu Pro Leu Pro Tyr Lys Thr Ile Thr Thr Glu
145                 150                 155                 160

Gln Pro Ser Phe Leu Gly Tyr Asp Lys Glu Lys Arg Gly Ala Pro Met
                165                 170                 175

Ile Ala Phe Gly Gly Gly Glu Ala Ala Gly Ser Glu Ser Gly Asp Gly
            180                 185                 190

Ser Val Gly Gly Lys Glu Asp Ala Arg Phe Thr Ala Trp Gln Gly Leu
```

195                 200                 205
Glu Gly Thr Gln Ser Pro Ser Val Arg Ala Thr Arg Val Gly Asp Thr
210                 215                 220

Arg Tyr Ile Ile Leu Gln Gly His Met Ile Asp Ala Val Leu Glu Thr
225                 230                 235                 240

Ala Ile Asn Ser Asp Ile Ser Gly Val Leu Arg Ala Val Val Ser Arg
                245                 250                 255

Asp Val Tyr Ala Ser Ser Gly Asp Ala Val Val Ile Pro Lys Gly Ser
                260                 265                 270

Arg Leu Ile Gly Ser Tyr Phe Phe Asp Ser Ala Gly Asn Asn Val Arg
                275                 280                 285

Val Asp Val Asn Trp Ser Arg Val Ile Leu Pro His Gly Val Asp Ile
290                 295                 300

Gln Ile Ala Ser Ser Gly Thr Asp Glu Leu Gly Arg Asn Gly Ile Ser
305                 310                 315                 320

Gly Val Val Asp Asn Lys Val Gly Ser Ile Leu Thr Ser Thr Ile Phe
                325                 330                 335

Leu Ala Gly Ile Ser Leu Gly Thr Ala Tyr Val Thr Glu Gln Ile Pro
                340                 345                 350

Ser Leu Arg Thr Glu Thr Val Lys Val Glu Thr Pro Ala Asp Gly Lys
                355                 360                 365

Asp Gly Lys Lys Thr Thr Ser Ser Ser Leu Ser Thr Lys Ile Val Ser
370                 375                 380

Asp Ala Ile Lys Asp Phe Ser Glu Ser Met Lys Glu Ile Val Asn Lys
385                 390                 395                 400

Tyr Ser Asn Arg Thr Pro Thr Val Tyr Val Asp Gln Gly Thr Val Met
                405                 410                 415

Lys Val Phe Val Asn Gln Asp Val Val Phe Pro Arg Asp Ala Val Arg
                420                 425                 430

<210> SEQ ID NO 92
<211> LENGTH: 238
<212> TYPE: PRT
<213> ORGANISM: Piscirickettsia salmonis

<400> SEQUENCE: 92

Met Gln Val Ser Gln Lys Glu Arg Lys Met Gln Ser Gln Leu Gln Gly
1               5                   10                  15

Met Val Gly Asp Trp Asp Lys Ala Ser Val Gln Ser Ser Val Val Gly
                20                  25                  30

Gln Leu Pro Ala Gln Ser Thr Thr Ala Gly Gln Gln Gly Gln Asn Ala
                35                  40                  45

Ala Ala Asn Ile Ile Glu Lys Ser Gly Ala Ile Leu Phe Ala Val Leu
                50                  55                  60

Asp Thr Gln Leu Asn Ser Asp Gln Pro Gly Thr Pro Val Met Ala Thr
65                  70                  75                  80

Ile Ile Gln Gly Lys Phe Lys Asp Ala Lys Leu Leu Gly Ser Phe Lys
                85                  90                  95

Arg Glu Asp Asp Lys Leu Val Ile Ser Phe Asp His Met Ser Leu Pro
                100                 105                 110

Ala Leu Asp His Ser Ile Ser Ile Lys Ala Tyr Ala Ile Asn Ala Thr
                115                 120                 125

Thr Ala Gln Asn Ala Leu Ala Ser Asp Val Asp Asn His Tyr Leu Leu
                130                 135                 140

-continued

```
Arg Tyr Gly Gly Leu Phe Ala Ser Ala Phe Leu Gln Gly Phe Gly Glu
145                 150                 155                 160

Tyr Phe Ser Asp Thr Ser Ser Leu Cys Asn Gly Ser Thr Thr Cys
                165                 170                 175

Ile Val Thr Ser Asp Gln Thr Ser Ala Ala Thr Glu Gln Thr Ser Lys
                180                 185                 190

Lys Ala Val Tyr Ser Gly Leu Gly Gln Val Gly Thr Thr Leu Gly Gln
                195                 200                 205

Gln Ala Ala Ser Glu Phe Asn Arg Pro Pro Thr Val Thr Leu Asn Gln
                210                 215                 220

Gly Val Gly Met Gly Ile Leu Phe Met Ser Asp Val Lys Ala
225                 230                 235

<210> SEQ ID NO 93
<211> LENGTH: 422
<212> TYPE: PRT
<213> ORGANISM: Sphingobium japonicum BiD32

<400> SEQUENCE: 93

Met Ala Ala Asn Asp His Asp Asn Ala Pro His Gly Asp Asn Ile Ile
1               5                   10                  15

Ser Gln Gly Glu Thr Val Glu Asn Arg Pro Leu Ala Ser Glu Pro Val
                20                  25                  30

Pro Asp Pro Glu Asp Ile Glu Arg Gln Ser Glu Arg Gln Ala Lys Ile
                35                  40                  45

Ala Ala Leu Pro Asn Arg Ser Ile Asp Pro Lys Lys Ala Val Val Leu
50                  55                  60

Ala Ala Val Ala Cys Gly Ala Ile Val Leu Gly Phe Ser Thr Ile Asp
65                  70                  75                  80

Ala Met Arg Ser Asp Pro Thr Glu Lys Ala Lys Ala Glu Lys Pro
                85                  90                  95

Asp Glu Arg Gln Leu Ala Asn Tyr Asp Pro Lys Ser Ile Ile Ala Pro
                100                 105                 110

Thr Leu Ala Asp Ala Pro Asn Asp Pro Asn Ala Pro Val Pro Met Thr
                115                 120                 125

Glu Val Pro Ala Leu Asp Gly Ser Gln Ala Pro Arg Thr Gly Gly Ala
130                 135                 140

Asn Gly Arg Pro Gln Lys Ser Glu Gly Gln Val Ile Ala Glu Ala Gln
145                 150                 155                 160

Arg Arg Ala Gly Ile Met Ala Tyr Gly Gly Glu Asn Gly Gly Gly Val
                165                 170                 175

Gly Gly Ala Val Ala Ala Ala Thr Gly Leu Pro Met Gly Gly Gly Thr
                180                 185                 190

Gly Ala Gln Gly Ala Gln Leu Ile Gly Ala Ser Ala Asp Gly Asp Gly
                195                 200                 205

Gln Gly Gly Ser Arg Arg Thr Asn Leu Glu Asn Met Arg Gln Thr Ser
                210                 215                 220

Gln Ile Asp Arg Val Ser Gly Arg Asp Ile Gly Asn Arg Asp Met Leu
225                 230                 235                 240

Ile Leu Ala Gly Ser Phe Ile Pro Cys Val Leu Gln Thr Ala Met Asp
                245                 250                 255

Ser Ser Gln Pro Gly Tyr Val Ser Cys Ile Ile Pro Arg Asp Ile Tyr
                260                 265                 270

Ser Asp Asn Gly Arg Val Val Leu Leu Glu Lys Gly Thr Arg Val Leu
                275                 280                 285
```

-continued

```
Gly Glu Tyr Gln Thr Gly Val Gln Arg Gly Lys Tyr Arg Leu Phe Ala
        290                 295                 300

Val Trp Asn Arg Ala Val Thr Pro Arg Gly Val Ala Ile Asp Val Gly
305                 310                 315                 320

Ser Pro Ala Ser Asp Ala Leu Gly Arg Ser Gly Met Ala Gly Gly Val
                325                 330                 335

Lys Asn Phe Phe Trp Glu Arg Phe Gly Ala Ala Leu Leu Phe Ser Ser
                340                 345                 350

Leu Asn Asp Ala Ala Ser Ile Ala Ala Ser Glu Val Ser Asp Ala Asp
                355                 360                 365

Asn Val Thr Arg Val Pro Ser Gln Ala Ser Asp Thr Ile Leu Arg Asp
    370                 375                 380

Thr Met Gln Ile Gln Pro Val Leu Arg Ile Asn Gln Gly Ala Glu Val
385                 390                 395                 400

Gly Ile Met Val Ala Arg Asp Phe Asp Phe Ser Asn Ile Tyr Gly Leu
                405                 410                 415

Arg Leu Arg Arg Gly Gln
            420
```

<210> SEQ ID NO 94
<211> LENGTH: 449
<212> TYPE: PRT
<213> ORGANISM: Fulvimarina pelagi HTCC2506

<400> SEQUENCE: 94

```
Met Ser Glu Val Asp Asp Gln Cys Ser Ala Thr Glu Ser Leu Asp Glu
1               5                   10                  15

Arg Leu Lys Ala Leu Glu Ala Gly Arg Arg Glu Thr Ser Arg Thr Gly
                20                  25                  30

Ser Ala Arg Met Ser Pro Ile Ala Ala Ile Gly Val Thr Ala Ser Leu
            35                  40                  45

Val Ile Val Gly Gly Leu Ala Val Phe Ser Thr Leu Glu Glu Ala Glu
    50                  55                  60

Glu Pro Met Ala Thr Ser Ala Pro Ala Glu Phe Gln Pro Ala Gly Glu
65                  70                  75                  80

Gly Phe Gly Ser Leu Asp Ile Pro Glu Pro Val Ile Gln Ser Glu Pro
                85                  90                  95

Ala Pro Asp Ile Val Glu Thr Glu Ile Pro Thr Val Asp Pro Ala Leu
            100                 105                 110

Met Thr Glu Ile Ala Ser Leu Lys Ser Glu Leu Asp Arg Leu Arg Asn
        115                 120                 125

Ala Pro Lys Pro Val Pro Asp Thr Ser Glu Gln Asp Ala Ala Ile Ala
    130                 135                 140

Asp Leu Val Ala Gln Leu Asp Asn Leu Arg Ala Glu Ser Ala Glu Ala
145                 150                 155                 160

Gln Glu Glu Leu Gln Arg Arg Leu Asp Glu Arg Asp Arg Gln Leu Arg
                165                 170                 175

Arg Leu Ser Ser Glu Leu Glu Met Ala Gln Leu Gln Ser Gly Pro Thr
            180                 185                 190

Gln Thr Gly Pro Ser Glu Glu Asp Ile Arg Leu Ala Glu Leu Glu Arg
        195                 200                 205

Arg Arg Gln Glu Glu Ala Ala Phe Gln Asp Ala Arg Asp Ala Ser Asp
    210                 215                 220

Met Ile Ala Phe Gly Gly Gly Ser Val Gly Ser Glu Ser Tyr Gly Glu
```

```
                225                 230                 235                 240
Asp Gln Arg Leu Ser Arg Asp Ala Ala Phe Val Arg Ser Gly Ala Ala
            245                 250                 255
Asn Ala Lys Val Thr Gln Ala Asp Val Ile Ala Asn Pro Ser His Thr
            260                 265                 270
Val Pro Gln Gly Thr Leu Ile Gln Ala Ser Leu Glu Thr Ala Leu Asp
            275                 280                 285
Ser Ser Leu Pro Gly Asp Ile Arg Ala Ile Val Ser Glu Asn Ile His
    290                 295                 300
Ala Phe Asp Gly Ser Arg Val Leu Ile Pro Arg Gly Ser Arg Leu Val
305                 310                 315                 320
Gly Arg Tyr Gln Ser Asp Ile Asp Leu Ala Gln Glu Arg Val Thr Ile
            325                 330                 335
Gly Trp Asp Arg Ile Ile Leu Pro Ser Asn Gln Ser Val Gln Ile Ser
            340                 345                 350
Ala Tyr Gly Gly Asp Gln Leu Gly Arg Ala Gly Val Thr Gly Asp Val
            355                 360                 365
Asp Lys His Phe Leu Glu Arg Phe Gly Ser Ala Ala Leu Leu Ser Ile
    370                 375                 380
Val Ser Ala Gly Pro Ser Leu Ala Thr Ala Ser Leu Thr Asp Pro Asp
385                 390                 395                 400
Val Ala Asp Thr Val Glu Asp Val Gly Gly Asp Phe Gly Gly Ser Thr
            405                 410                 415
Arg Asp Thr Ile Asp Glu Ser Leu Ser Ile Glu Pro Thr Ile Arg Val
            420                 425                 430
Pro Gln Gly Ser Ala Ile Thr Val Met Val Asp Arg Asp Leu Glu Ile
            435                 440                 445
Phe

<210> SEQ ID NO 95
<211> LENGTH: 422
<212> TYPE: PRT
<213> ORGANISM: Ralstonia metallidurans (strain CH34 / ATCC 43123 / DSM
      2839)

<400> SEQUENCE: 95

Met Ser Gln Asp Asp Thr Pro Asp Leu Ala Ala Pro Ser Ala Gly Lys
1               5                   10                  15
Val Ala Pro Glu Ala Val Ala Leu Arg Ala Gln Pro Arg Pro Val Thr
            20                  25                  30
Arg Leu Asn Arg Arg Thr Leu Ala Ile Leu Val Gly Gly Leu Ser Val
        35                  40                  45
Ala Val Leu Gly Ala Thr Ile Trp Ser Leu Gln Pro His Arg Arg Gly
    50                  55                  60
Ala Gly Glu Gln Thr Glu Leu Tyr Asn Val Asp Arg Val Ser Lys Ser
65                  70                  75                  80
Glu Gly Leu Asp Gly Leu Pro Ala Asp Tyr Ser Lys Leu Pro Pro Lys
                85                  90                  95
Val Pro Glu Leu Gly Pro Pro Leu Pro Gly Asp Leu Gly Pro Ala Ile
            100                 105                 110
Val Asn Ser Gln Gln Pro Ala Val Ala Ala Tyr Ala Ala Pro Gly His
        115                 120                 125
Asp Pro Asn Asp Ala Leu Arg Lys Glu Ala Glu Ala Ala Ala Ala Ser
    130                 135                 140
```

```
Ser Val Phe Phe Arg Ser Gly Gly Gln Ala Ala Thr Val Ala Gln
145                 150                 155                 160

Ala Ala Pro Gly Val Pro Gly Val Ala Ser Thr Leu Ala Ala Phe Asp
            165                 170                 175

Pro Leu Ala Ala Gly Pro Ala Ser Thr Ala Ala Gln Pro Ala Asp Pro
                180                 185                 190

Thr Ala Val Gln Asn Arg Gln Asp Gln Lys Glu Ala Phe Leu Lys Ala
        195                 200                 205

Gly Ser Thr Glu Thr Arg Asn Ser Gly Asn Leu Ala Leu Pro Thr Ser
    210                 215                 220

Pro Tyr Gln Val Met Ala Gly Thr Val Ile Ala Gly Ala Leu Val Thr
225                 230                 235                 240

Gly Ile Lys Ser Asp Leu Pro Gly Asp Val Ile Ala Thr Val Thr Glu
                245                 250                 255

Pro Val Tyr Asp Thr Ala Thr Gly Lys Phe Leu Leu Ile Pro Gln Gly
                260                 265                 270

Ser Arg Ile Leu Gly Lys Tyr Asn Ser Gln Val Ser Tyr Gly Gln Ser
        275                 280                 285

Arg Val Gln Val Val Trp Asn Arg Val Ile Leu Pro Asp Thr Ser Ser
290                 295                 300

Leu Thr Leu Asp Asn Leu Val Gly Thr Asp Pro Ala Gly Tyr Ala Gly
305                 310                 315                 320

Leu Glu Asp Asp Val Asp Trp His Trp Lys Arg Ile Phe Ala Gly Ala
                325                 330                 335

Val Leu Thr Thr Leu Leu Gly Val Gly Ala Glu Leu Ala Ala Pro Glu
                340                 345                 350

Asn Arg Gln Asp Gly Asn Arg Ile Val Ile Ala Gly Arg Asp Ser Ala
        355                 360                 365

Gln Asp Ser Ile Asn Gln Val Gly Gln Glu Ile Thr Arg Arg Asn Met
        370                 375                 380

Asn Ile Gln Pro Thr Leu Thr Ala Arg Pro Gly Leu Pro Val Arg Val
385                 390                 395                 400

Ile Val Ala Arg Asp Leu Val Leu Arg Pro Tyr Gln Pro Met Phe Tyr
                405                 410                 415

Gln Leu Gly Gly Ala Arg
            420

<210> SEQ ID NO 96
<211> LENGTH: 367
<212> TYPE: PRT
<213> ORGANISM: Rhizobium etli (strain CFN 42 / ATCC 51251)

<400> SEQUENCE: 96

Met Ile Gly Asp Asp Gln Gln Pro Ser His Asp Ile Asp Ala Gly Gly
1               5                   10                  15

Ser Leu Val Ser Gly Thr His His Gln Arg Leu Ser Gly Pro Arg Lys
            20                  25                  30

Leu Ile Val Ala Gly Leu Val Leu Val Leu Ser Leu Gly Leu Ile Trp
        35                  40                  45

Leu Gly Gly Arg Gln Lys Lys Ala Asp Ala Asn Pro Pro Ser Pro
    50                  55                  60

Met Ile Ser Thr Asn Thr Gln Pro Phe His Pro Ala Pro Ile Glu Ile
65                  70                  75                  80

Ser Pro Asp Ala Pro Pro Ala Glu Arg Ala Val Gln Leu Pro Ala Pro
                85                  90                  95
```

```
Glu Pro Ala Arg Ser Glu Pro Gln Pro Ala Glu Thr Pro Ile Phe Ala
                100                 105                 110

Tyr Thr Gly Gly Asp Asp Arg Pro Gly His Gly Ala Thr Gly Arg Gln
            115                 120                 125

Asp Asp Lys Asp Glu Glu Arg Thr Pro Pro Asn Gly Glu Val Ser Ala
130                 135                 140

Gly Ser Asp Val Ser Ile Arg Met Lys Pro Thr Glu Leu Gln Pro Ser
145                 150                 155                 160

Lys Ala Thr Leu Leu Pro His Pro Asp Phe Met Ile Thr Gln Gly Thr
                165                 170                 175

Ile Ile Pro Cys Ile Leu Gln Thr Ala Ile Asp Thr Asn Leu Ala Gly
                180                 185                 190

Tyr Val Lys Cys Val Leu Pro Arg Asp Val Arg Gly Thr Thr Asn Asn
            195                 200                 205

Val Val Leu Leu Asp Arg Gly Thr Thr Val Val Gly Glu Ile Gln Arg
210                 215                 220

Gly Leu Gln Gln Gly Asp Ala Arg Val Phe Val Leu Trp Asp Arg Ala
225                 230                 235                 240

Glu Thr Pro Asn His Ala Met Ile Ser Leu Ser Ser Pro Gly Thr Asp
                245                 250                 255

Glu Leu Gly Arg Ser Gly Leu Pro Gly Thr Val Asp Asn His Phe Trp
            260                 265                 270

Gln Arg Phe Gly Gly Ala Met Leu Leu Ser Val Val Gln Gly Ala Phe
        275                 280                 285

Gln Ala Ala Ser Thr Tyr Ala Gly Ser Ser Asp Gly Thr Ser Phe
    290                 295                 300

Asn Ser Ile Gln Asn Asn Gly Glu Gln Thr Ala Asp Thr Ala Leu Lys
305                 310                 315                 320

Ala Thr Ile Asn Ile Pro Pro Thr Leu Arg Lys Asn Gln Gly Asp Thr
                325                 330                 335

Val Ser Ile Phe Val Ala Arg Asp Leu Asp Phe Ser Asp Ile Tyr Gln
                340                 345                 350

Leu Arg Val Thr Gly Gly Ala Thr Arg Tyr Arg Gln His Arg Arg
                355                 360                 365
```

<210> SEQ ID NO 97
<211> LENGTH: 388
<212> TYPE: PRT
<213> ORGANISM: Brucella abortus (strain 2308)

<400> SEQUENCE: 97

```
Met Thr Gln Glu Asn Ile Pro Val Gln Pro Gly Thr Leu Asp Gly Glu
1               5                   10                  15

Arg Gly Leu Pro Thr Val Asn Glu Asn Gly Ser Gly Arg Thr Arg Lys
            20                  25                  30

Val Leu Leu Phe Leu Phe Val Val Gly Phe Ile Val Leu Leu Leu
        35                  40                  45

Leu Leu Val Phe His Met Arg Gly Asn Ala Glu Asn Asn His His Ser
50                  55                  60

Asp Lys Thr Met Val Gln Thr Ser Thr Val Pro Met Arg Thr Phe Lys
65                  70                  75                  80

Leu Pro Pro Pro Pro Pro Ala Pro Pro Glu Pro Pro Ala Pro Pro
                85                  90                  95

Pro Ala Pro Ala Met Pro Ile Ala Glu Pro Ala Ala Ala Ala Leu Ser
```

```
            100                 105                 110
Leu Pro Pro Leu Pro Asp Asp Thr Pro Ala Lys Asp Asp Val Leu Asp
            115                 120                 125

Lys Ser Ala Ser Ala Leu Met Val Val Thr Lys Ser Ser Gly Asp Thr
130                 135                 140

Asn Ala Gln Thr Ala Gly Asp Thr Val Val Gln Thr Thr Asn Ala Arg
145                 150                 155                 160

Ile Gln Ala Leu Leu Asp Ser Gln Lys Asn Thr Lys Gln Asp Ala Gly
            165                 170                 175

Ser Leu Gly Thr Leu Leu His Gly Thr Gln Thr Asp Ala Arg Met Ala
            180                 185                 190

Ser Leu Leu Arg Asn Arg Asp Phe Leu Leu Ala Lys Gly Ser Ile Ile
            195                 200                 205

Asn Cys Ala Leu Gln Thr Arg Leu Asp Ser Thr Val Pro Gly Met Ala
            210                 215                 220

Ala Cys Val Val Thr Arg Asn Met Tyr Ser Asp Asn Gly Lys Val Leu
225                 230                 235                 240

Leu Ile Glu Arg Gly Ser Thr Ile Ser Gly Glu Tyr Asp Ala Asn Val
            245                 250                 255

Lys Gln Gly Met Ala Arg Ile Tyr Val Leu Trp Thr Arg Val Lys Thr
            260                 265                 270

Pro Asn Gly Val Val Ile Asp Leu Asp Ser Pro Gly Ala Asp Pro Leu
            275                 280                 285

Gly Gly Ala Gly Leu Pro Gly Tyr Ile Asp Ser His Phe Trp Lys Arg
            290                 295                 300

Phe Gly Gly Ala Leu Met Leu Ser Thr Ile Glu Thr Leu Gly Arg Tyr
305                 310                 315                 320

Ala Thr Gln Lys Val Gly Gly Gly Ser Asn Gln Ile Asn Leu Asn
            325                 330                 335

Thr Gly Gly Gly Glu Ser Thr Ser Asn Leu Ala Ser Thr Ala Leu Lys
            340                 345                 350

Asp Thr Ile Asn Ile Pro Pro Thr Leu Tyr Lys Asn Gln Gly Glu Glu
            355                 360                 365

Ile Gly Ile Tyr Ile Ala Arg Asp Leu Asp Phe Ser Ser Val Tyr Asp
            370                 375                 380

Val Lys Pro Lys
385

<210> SEQ ID NO 98
<211> LENGTH: 493
<212> TYPE: PRT
<213> ORGANISM: Wolbachia endosymbiont of Armadillidium vulgare

<400> SEQUENCE: 98

Met Asn Lys Glu Arg Arg Asn Asn Ser Glu Asp Glu Ser Glu Ile Glu
1               5                   10                  15

Asn Lys Val Val Thr Val Gly Ser Asn Gln Gly His Arg Ala Leu Met
                20                  25                  30

Ile Met Val Leu Val Leu Leu Ala Gly Gly Val Tyr Tyr Phe Tyr Phe
            35                  40                  45

Ser Pro Ser His Lys Glu Asp Leu Gly Val Val Lys Lys Glu Glu Ile
        50                  55                  60

Lys Gln Asn Val Gln Glu Leu Lys Glu Lys Leu Glu Gln Val Pro Asp
65                  70                  75                  80
```

```
Asn Val Met Val Pro Glu Arg Ile Ile Thr Asp Pro Leu Pro Pro Leu
            85                  90                  95

Pro Pro Leu Pro Thr Pro Gln Ile Ile Pro Glu Val Lys Gln Ile Lys
            100                 105                 110

Lys Glu Glu Val Thr Lys Lys Glu Glu Gln Leu Lys Glu Ile Pro Val
            115                 120                 125

Ser Ser Ile Pro Ile Leu Pro Lys Gln Asn Phe Pro Ser Ser Asn Val
            130                 135                 140

Ile Ser Asn Leu Pro Thr Ser Phe Pro Thr Ile Gly Gly Val Gly Tyr
145                 150                 155                 160

Pro Arg Glu Arg Arg Asn Ala Gln Met Leu Ile Ile Ser Gly Ser Ser
            165                 170                 175

Gly Glu Asn Lys Ala Ala Asp Asp Ile Leu Ser Asp Thr Ser Ala Gln
            180                 185                 190

Ser Ser Lys Ala Thr Arg Val Gly Lys Leu Gly Leu Met Ile Thr Gln
            195                 200                 205

Gly Lys Ile Ile Asp Ala Val Leu Glu Thr Ala Ile Asn Ser Asp Leu
            210                 215                 220

Gln Gly Met Leu Arg Ala Met Val Ser Arg Asp Val Tyr Ala Glu Thr
225                 230                 235                 240

Gly Asp Thr Val Leu Ile Pro Lys Gly Ser Arg Leu Ile Gly Ser Tyr
            245                 250                 255

Ser Phe Asp Ser Asn Val Ala Lys Ser Arg Val Asn Ile Asn Trp Asn
            260                 265                 270

Arg Val Ile Met Pro His Gly Ile Asp Ile Ala Ile Leu Ser Leu Ser
            275                 280                 285

Thr Asp Glu Leu Gly Arg Ala Gly Ile Ala Gly Ile Val Asp Asn Lys
290                 295                 300

Ile Val Ser Ala Leu Phe Ser Ser Val Ala Leu Ala Gly Val Ser Ile
305                 310                 315                 320

Gly Ser Ala Val Ile Gly Gln Lys Ala Ser Asn Leu Ile Asp Thr Leu
            325                 330                 335

Thr Pro Met Asp Ala Val Arg Ser Ile Thr Ala Thr Glu Ile Asp Ile
            340                 345                 350

Ser Ser Leu Lys Asp Ile Ile Gly Lys Lys Ser Met Ser Asn Glu Asp
            355                 360                 365

Glu Glu Asn Ala Lys Asn Asp Lys Trp Lys Leu Gly Leu Gly Ala Ile
            370                 375                 380

Arg Lys Ile Lys Asn Ala Phe Asn Glu Lys Ser Leu Val Glu Thr Phe
385                 390                 395                 400

Lys Gln Val Val Arg Asp Leu Ser Leu Val Ser Ile Asp Ser Ser Lys
            405                 410                 415

Val Asp Glu Ile Thr Leu Glu Asp Ile Lys Gly Leu Leu Arg Lys Gln
            420                 425                 430

Gly Ser Lys Ser Val Tyr Asp Glu Ala Ile Gly Lys Ser Ile Glu Asp
            435                 440                 445

Phe Ser Lys Asp Met Arg Asn Ile Val Ser Arg Tyr Thr Asp Lys Lys
450                 455                 460

Pro Thr Ile Tyr Val Asp Gln Gly Thr Ala Leu Lys Val Phe Val Asn
465                 470                 475                 480

Gln Asp Ile Val Phe Pro Pro Gln Ala Ile Leu Asn Asn
            485                 490
```

```
<210> SEQ ID NO 99
<211> LENGTH: 437
<212> TYPE: PRT
<213> ORGANISM: Neisseria gonorrhoeae

<400> SEQUENCE: 99
```

| | | | | | | | | | | | | | | |
|---|---|---|---|---|---|---|---|---|---|---|---|---|---|---|
| Met | Arg | Val | Lys | Val | Asn | Lys | Phe | Lys | Leu | Ser | Ala | Ala | Arg | Lys | Arg |
| 1 | | | | 5 | | | | | 10 | | | | | 15 | |

| Gln | Leu | Ala | Ile | Ala | Gly | Met | Val | Ala | Gly | Ser | Met | Ala | Ile | Val |
|---|---|---|---|---|---|---|---|---|---|---|---|---|---|---|
| | | | 20 | | | | 25 | | | | 30 | | | |

| Gly | Ser | Ala | Ile | Tyr | Val | Ile | Glu | Gly | Asn | Lys | Lys | Ser | Ala | Glu |
| | | 35 | | | | | 40 | | | | 45 | | | |

| Val | Thr | Gln | Val | Gln | Asn | Lys | Arg | Gln | Ile | Leu | Arg | Thr | Asp | Phe | Thr |
| | 50 | | | | | 55 | | | | | 60 | | | | |

| Ser | Pro | Gln | Ala | Gly | Ile | Thr | Asp | Asn | Ser | Leu | Trp | Met | Asn | Thr | Glu |
| 65 | | | | | 70 | | | | | 75 | | | | | 80 |

| Ser | Ser | Lys | Ile | Glu | Tyr | Ala | Asn | Arg | Lys | Ile | Ser | Glu | Leu | Glu | Thr |
| | | | | 85 | | | | | 90 | | | | | 95 | |

| Met | Val | Gln | Glu | Leu | Lys | Glu | Lys | Glu | Asn | Ser | Ser | Asn | Pro | Asp | Thr |
| | | | 100 | | | | | 105 | | | | | 110 | | |

| Ser | Lys | Gly | Leu | Gly | Pro | Asp | Gly | Leu | Gly | Lys | Pro | Pro | Ala | Ile | Ser |
| | | 115 | | | | | 120 | | | | | 125 | | | |

| Gly | Ile | Gly | Asp | Asn | Gly | Arg | Leu | Pro | Pro | Ala | Pro | Pro | Ala | Gly | Thr |
| | 130 | | | | | 135 | | | | | 140 | | | | |

| Leu | Pro | Asn | Gly | Ala | Pro | Pro | Ala | Asp | Arg | Ser | Ile | Glu | Arg | Lys | Ile |
| 145 | | | | | 150 | | | | | 155 | | | | | 160 |

| Val | Ser | Gly | Ser | Met | Ser | Glu | Ala | Glu | Leu | Gln | Pro | Gly | Thr | Thr | Gly |
| | | | | 165 | | | | | 170 | | | | | 175 | |

| Ser | Val | Asn | Thr | Gly | Asn | Pro | Asn | Glu | Asn | Val | Arg | Val | Ser | Pro | Gln |
| | | | 180 | | | | | 185 | | | | | 190 | | |

| Leu | Lys | Glu | Ala | Glu | Trp | Val | Lys | Ser | Lys | Thr | Pro | Arg | Met | Asn | Ile |
| | | 195 | | | | | 200 | | | | | 205 | | | |

| Glu | Val | Val | Glu | Asp | Gly | Gly | Lys | Val | Val | Ser | Gln | Gly | Lys | Phe |
| | 210 | | | | | 215 | | | | | 220 | | | |

| Arg | Ala | Arg | Asp | Ser | Tyr | Ile | Pro | Ser | Gly | Thr | Phe | Phe | Arg | Ser | Val |
| 225 | | | | | 230 | | | | | 235 | | | | | 240 |

| Leu | Leu | Gly | Gly | Val | Asp | Ala | Pro | Thr | Gly | Gly | Glu | Ala | Gln | Asn | Ala |
| | | | | 245 | | | | | 250 | | | | | 255 | |

| Ser | Pro | His | Pro | Val | Leu | Met | Arg | Val | Thr | Asp | Phe | Ala | Gln | Leu | Pro |
| | | | 260 | | | | | 265 | | | | | 270 | | |

| Asn | Arg | Phe | Lys | Tyr | Asn | Phe | Arg | Glu | Cys | Phe | Val | Thr | Gly | Gln | Ala |
| | | 275 | | | | | 280 | | | | | 285 | | | |

| Tyr | Gly | Asp | Ile | Ser | Ser | Glu | Arg | Ala | Tyr | Ile | Arg | Leu | Gln | Asn | Leu |
| | 290 | | | | | 295 | | | | | 300 | | | | |

| Ser | Cys | Val | Gly | Thr | Asp | Gly | Arg | Ala | Ile | Asp | Met | Pro | Val | Lys | Gly |
| 305 | | | | | 310 | | | | | 315 | | | | | 320 |

| Tyr | Val | Ala | Gly | Glu | Asp | Gly | Lys | Thr | Gly | Val | Arg | Gly | Asn | Leu | Val |
| | | | | 325 | | | | | 330 | | | | | 335 | |

| Thr | Lys | Gln | Gly | Gln | Leu | Leu | Ala | Asn | Ala | Leu | Met | Ser | Gly | Val | Ile |
| | | | 340 | | | | | 345 | | | | | 350 | | |

| Ser | Gly | Met | Gly | Lys | Gly | Val | Ser | Glu | Ala | Phe | Lys | Val | Thr | Asn | Asn |
| | | 355 | | | | | 360 | | | | | 365 | | | |

| Thr | Ala | Phe | Gly | Ser | Thr | Thr | Ser | Ile | Arg | Gly | Ser | Asp | Gln | Tyr | Arg |
| | 370 | | | | | 375 | | | | | 380 | | | | |

```
Ala Gly Ile Ala Ser Gly Ile Gly Gly Ala Ala Asp Arg Leu Ala Glu
385                 390                 395                 400

Tyr Tyr Ile Lys Leu Ala Asp Lys Val Phe Pro Val Val Glu Val Asn
            405                 410                 415

Ala Gly Arg Gln Val Asp Val Val Leu Thr Gln Gly Ile Glu Ile Asp
            420                 425                 430

Thr Gly Glu Thr Lys
            435

<210> SEQ ID NO 100
<211> LENGTH: 392
<212> TYPE: PRT
<213> ORGANISM: Campylobacter coli

<400> SEQUENCE: 100

Met Gln Asp Lys Glu Gln Asp Asn Leu Asp Asn Asp Phe Glu Asn His
1               5                   10                  15

Thr Ser Asp Leu His Glu Gln Lys Asn His Leu Lys Lys Ile Gln Ala
            20                  25                  30

Tyr Ala Ile Phe Ala Val Gly Gly Leu Leu Phe Ile Phe Leu Met Val
            35                  40                  45

Tyr Phe Leu Lys Ser Phe Ser Gly Asn Asn Asn Asp Ile Glu Glu Ala
50                  55                  60

Pro Lys Glu Glu Asn Asn Asp Ile Ala Gln Ser Val Lys Thr Lys Glu
65                  70                  75                  80

Phe Ala Pro Pro Ser Ser Ala Gln Lys Thr Phe Asp Glu Leu Val
            85                  90                  95

Ala Gln Glu Gln Pro Thr Gln Thr Thr Ala Leu Met Leu Glu Ala Glu
            100                 105                 110

Pro Pro Lys Pro Arg Ile Val Lys Gly Ile Gly Val Thr Val Val Ala
            115                 120                 125

Ser Ser Asn Asn Gly Phe Asn Gly Gly Ser Thr Gly Asp Arg Gly Glu
130                 135                 140

Phe Gly Asp Lys Pro Asn Thr Val Phe Glu Phe Gly Gln Asn Gly Ser
145                 150                 155                 160

Gly Ala Leu Gln Asn Ser Asn Asn Phe Gln Ser Gly Gly Glu Phe Thr
                165                 170                 175

Gly Glu Val Phe Thr Pro Thr Ile Ala Lys Val Ser Glu Phe Asp Gln
            180                 185                 190

Asn Leu Leu Leu Pro Lys Gly Thr Tyr Ile Gly Cys Ala Leu Lys Thr
            195                 200                 205

Arg Leu Val Ser Ser Ile Lys Gly Gly Ile Ala Cys Ile Val Ser Asn
210                 215                 220

Asp Val Tyr Ser Ala Asn Gly Asn Thr Leu Leu Ile Glu Lys Gly Ser
225                 230                 235                 240

Thr Ile Thr Gly Thr Phe Asn Ala Gly Gln Leu Asp Asp Gly Met Asp
            245                 250                 255

Arg Leu Phe Val Ile Trp Gln Glu Ile Arg Thr Pro Asn Asn Ile Ile
            260                 265                 270

Ile Pro Val Tyr Ser Gly Ala Thr Asp Glu Leu Gly Ala Ser Gly Met
            275                 280                 285

Gln Gly Trp Val Asp His His Tyr Leu Lys Arg Phe Gly Ser Ala Ile
            290                 295                 300

Leu Leu Ser Met Ile Asp Asp Ser Leu Ala Ile Leu Ala Asp Gln Ile
305                 310                 315                 320
```

```
Thr Gly Lys Asp Asn Lys Asn Asn Tyr Ala Asn Tyr Thr Glu Asn Thr
            325                 330                 335

Arg Asp Ser Ala Lys Glu Ile Ala Asn Thr Ala Leu Glu Lys Met Ile
            340                 345                 350

Asp Ile Lys Pro Thr Leu Tyr Lys Asn His Gly Asp Leu Val Gly Val
        355                 360                 365

Tyr Val Asn Arg Asp Ile Asp Phe Ser Lys Val Tyr Lys Leu Thr Arg
    370                 375                 380

Lys Lys Asn Val Asn Asn Ala Arg
385                 390

<210> SEQ ID NO 101
<211> LENGTH: 447
<212> TYPE: PRT
<213> ORGANISM: Ehrlichia chaffeensis

<400> SEQUENCE: 101

Met Ser Glu Glu Asn Gln Asn Asn Gln Tyr Thr Glu Ile Glu Glu Asn
1               5                   10                  15

Val Asn Val Val Gly Val Asn Lys Gly Lys Lys Phe Ile Thr Ile Gly
            20                  25                  30

Val Met Leu Val Gly Leu Gly Phe Ala Tyr Tyr Tyr Phe Phe Thr Gly
        35                  40                  45

Lys Lys Pro Asp Asp Ser Leu Asn Lys Pro Gln Thr Thr Glu Glu Ala
    50                  55                  60

Asp Ile Glu Lys Leu Leu Lys Glu Ser Val Pro Pro Thr Gln Glu Val
65                  70                  75                  80

Ser Pro Pro Ile Asn Ile Pro Pro Gln Leu Pro Glu Leu Pro Pro Leu
                85                  90                  95

Val Ser Pro Ser Leu Pro Ser Ile Pro Thr Val Glu Lys Pro Lys Val
            100                 105                 110

Leu Glu Ile Pro Lys Ile Pro Lys Ile Lys Pro Lys Gln Pro Val Glu
        115                 120                 125

Ile Lys Pro Lys Pro Gln Pro Gln Pro Glu Pro Leu Pro Lys Ile Pro
    130                 135                 140

Leu Pro Val Gln Asn Lys Ile Asp Ile Ala Ala Pro Ile Ala Pro Ile
145                 150                 155                 160

Thr Thr Gly Tyr Asp Lys Glu Arg Arg Ala Thr Ser Met Leu Ala Val
                165                 170                 175

Ser Gly Gly Gln Asn Val Ala Ser Gly Thr Ser Glu Asn Gly Glu Arg
            180                 185                 190

Glu Ser Asn Ile Asp Thr Thr Ile Asn Lys Met Asn Ser Ile Ile Ser
        195                 200                 205

Leu Gln Thr Thr Ser Ser Pro Asn Val Val Ala Thr Lys Val Ser Asn
    210                 215                 220

Leu Glu Leu Thr Ile Leu Gln Gly Lys Ile Ile Asp Val Val Leu Glu
225                 230                 235                 240

Thr Ala Ile Asn Ser Asp Leu Gln Gly Ala Leu Arg Gly Ile Val Ala
                245                 250                 255

Arg Asp Val Tyr Ala Glu Ala Ser Asn Thr Val Met Ile Pro Lys Gly
            260                 265                 270

Ser Arg Leu Ile Gly Ser Tyr Ser Phe Asp Ala Ser Pro Gly Lys Thr
        275                 280                 285

Arg Val Gln Ile Ser Trp Asn Arg Val Ile Leu Pro His Gly Ile Asp
```

```
            290                 295                 300

Ile Thr Leu Asp Ser Asn Gly Thr Asp Glu Leu Gly Arg Gln Gly Ala
305                 310                 315                 320

Ser Gly Val Val Asp Thr Lys Ile Gly Asn Ile Leu Thr Ser Thr Ile
                325                 330                 335

Leu Leu Ala Gly Val Ser Ile Ala Thr Ser Tyr Ala Thr Ser Lys Ile
                340                 345                 350

Pro Glu Ile Asn Asn Tyr Pro Ile Leu Glu Ser Asp Ser Lys Glu Lys
                355                 360                 365

Lys Asp Lys Glu Lys Asp Asp Thr Gly Asp Lys Ser Lys Ser Thr Lys
                370                 375                 380

Thr Thr Leu Pro Val Lys Ile Leu Ser Gln Ala Val Asp Asp Phe Ser
385                 390                 395                 400

Asn Ser Ile Lys Asp Ile Ile Lys Lys Tyr Ser Asn Asn Asn Pro Thr
                405                 410                 415

Val Tyr Val Asp Gln Gly Thr Leu Leu Lys Val Phe Val Asn Lys Asp
                420                 425                 430

Ile Val Phe Pro Lys Ser Ala Val Arg Gly Ile Asp Ile Val Asn
                435                 440                 445

<210> SEQ ID NO 102
<211> LENGTH: 383
<212> TYPE: PRT
<213> ORGANISM: Caulobacter crescentus (strain ATCC 19089 / CB15)

<400> SEQUENCE: 102

Met Thr Ala Pro Ser Pro Ser Asp Pro Gln Leu Asp Ser Pro Val
1               5                   10                  15

Leu Arg Pro Leu Gly Tyr Gly Pro Thr Ala Val Ser Arg Pro Gln Ser
                20                  25                  30

Pro Trp Gly Leu Ala Leu Gly Ile Val Ala Ile Ile Leu Gly Met
                35                  40                  45

Val Val Tyr Ala Ser Leu Ser Gln Ala Arg Glu Ala Ala Gln Arg Pro
    50                  55                  60

Pro Thr Pro Pro Ala Leu Ala Ala Gly Thr Ala Ser Pro Ser Pro
65                  70                  75                  80

Thr Ala Ser Met Pro Ala Ile Ala Val Ala Asp Ser Gly Ala Met Gln
                85                  90                  95

Gln Gly Leu Pro Ser Pro Glu Gly Leu Pro Glu Gly Pro Leu Thr Pro
                100                 105                 110

Gln Thr Asp Thr Ala Ala Gln Glu Ala Thr Thr Arg Leu Arg Ala Pro
                115                 120                 125

Ala Met Val Val Asp Leu Asp Ser Arg Pro Ala Pro Asp Gly Asp Val
130                 135                 140

Arg Val Ala Ala Thr Ile Gly Ala Glu Pro Ala Pro Thr Arg Ala Ala
145                 150                 155                 160

Pro Arg Pro Leu Ala Asp Asp Ser Lys Ile Ser Ala Glu Glu Arg Phe
                165                 170                 175

Ala Glu Lys Val Ala Gly Ser Asn Ala Asp Ala Ala Arg Ala Thr Arg
                180                 185                 190

Leu Thr Asp Pro Ser Leu Val Ala Pro Gln Gly Thr Val Ile Pro Ala
                195                 200                 205

Ile Leu Glu Thr Ala Ile Asn Ser Asp Leu Pro Gly Phe Val Arg Ala
                210                 215                 220
```

```
Val Val Ser Arg Asp Val Arg Gly Phe Asp Gly Ser Thr Val Leu Ile
225                 230                 235                 240

Pro Arg Gly Ser Lys Leu Ile Gly Gln Tyr Lys Ser Gly Val Ala Ala
            245                 250                 255

Gly Gln Thr Arg Ala Phe Ile Val Trp Ser Arg Val Leu Thr Pro Gln
        260                 265                 270

Gly Val Ser Ile Asp Ile Ala Ser Pro Gly Ala Asp Arg Leu Gly Arg
    275                 280                 285

Gly Gly Leu Asp Gly Glu Thr Asn Thr His Phe Phe Arg Arg Phe Gly
290                 295                 300

Ala Ser Ile Leu Leu Ser Val Leu Asn Ala Gly Leu Asn Ala Ala Ser
305                 310                 315                 320

Asn Asn Gly Asn Gly Gly Asp Asn Thr Ala Ile Ile Ile Gly Ser Pro
            325                 330                 335

Gln Gln Ala Ser Asn Ile Ala Ser Ile Ala Leu Gln Arg Glu Ile Asp
        340                 345                 350

Ile Pro Thr Thr Ile Thr Val Ala Gln Gly Ala Pro Ile Arg Val Phe
    355                 360                 365

Val Ala Arg Asp Leu Asp Phe Ser Gly Val Val Gln Lys Thr Arg
370                 375                 380

<210> SEQ ID NO 103
<211> LENGTH: 369
<212> TYPE: PRT
<213> ORGANISM: Aggregatibacter actinomycetemcomitans

<400> SEQUENCE: 103

Met Asn Asp Asn Lys Thr Ile Gln Pro Thr Asp Lys Thr Glu Thr
1               5                   10                  15

Asp Tyr Gln Pro Glu Val Ser Lys Ile Ala Lys Arg Gly Lys Asn Gln
                20                  25                  30

Asn Leu Phe Ile Phe Leu Ile Ile Ala Leu Leu Ala Val Ala Phe Leu
            35                  40                  45

Gly Tyr Ser Phe Leu Asn Lys Lys Asp Thr Gln Gln Ala Gln Val Lys
    50                  55                  60

Glu Lys Glu Glu Phe Gly Thr Thr Val Arg Ser Lys Thr Phe Thr Ala
65                  70                  75                  80

Pro Pro Ala Glu Ile Pro Ala Ile Leu Asn Pro Glu Pro Gln Pro Ile
                85                  90                  95

Pro Thr Ala Thr Ala Pro Val Glu Asn His Ser Thr Thr Glu Ala Leu
            100                 105                 110

Asp Met Pro Ser Ala Pro Arg Leu Ile Lys Gly Leu Ser Pro Gly Thr
        115                 120                 125

Ile Asp Gly Glu Thr Leu Gln Ala Val Ser Asp Val Gln Asn Thr Asp
    130                 135                 140

Thr Thr Asp Ala Val Ala Asn Gln Pro Glu Pro Ala Lys Gly Asp
145                 150                 155                 160

Met Phe Glu Asp Asn Val Ser Thr Phe Lys Ala Gly Lys Ala His Lys
                165                 170                 175

Leu Ser Val Asn Ala Asn Leu Leu Ala Lys Gly Thr Phe Ile Gln
            180                 185                 190

Cys Ser Leu Arg Thr Lys Leu Val Ser Thr Val Ala Gly Asn Leu Gly
        195                 200                 205

Cys Val Val Ala Asn Asp Val Tyr Ser Ala Asn Gly Thr Val Leu Leu
    210                 215                 220
```

```
Ile Glu Lys Gly Ser Thr Val Phe Gly Glu Phe Arg Asn Gly Gln Ile
225                 230                 235                 240

Gln Gln Gly Glu Glu Arg Leu Phe Val Val Trp Ser Glu Ile Arg Thr
                245                 250                 255

Pro Lys Asn Ile Ile Asn Ile Asn Ser Gly Ala Thr Asp Glu Leu
            260                 265                 270

Gly Gly Thr Gly Ile Pro Gly Tyr Val Asp Asn His Phe Trp Glu Arg
            275                 280                 285

Phe Gly Asn Ala Ile Met Leu Ser Met Ile Thr Asp Ser Thr Ser Ala
            290                 295                 300

Leu Ser Thr Gln Leu Ala Lys Arg Gly Thr Phe Asn Pro Thr Asp Thr
305                 310                 315                 320

Val Gln Ala Gly Ser Glu Ile Ala Gln Ser Ile Leu Glu Lys Thr Ile
                325                 330                 335

Asn Ile Pro Pro Thr Leu Tyr Lys Asn Gln Gly Asp Leu Val Gly Ile
            340                 345                 350

Phe Val Ala Arg Asp Ile Asp Phe Gly Asp Val Tyr Glu Leu Lys Gln
            355                 360                 365

Lys
```

<210> SEQ ID NO 104
<211> LENGTH: 420
<212> TYPE: PRT
<213> ORGANISM: Delftia acidovorans CCUG 15835

<400> SEQUENCE: 104

```
Met Ser Gln Asp Asp Thr Arg Asp Leu Gly Thr Pro Gln Ala Gly Lys
1               5                   10                  15

Val Ala Pro Glu Ala Val Ala Leu Arg Ala Gln Pro Arg Pro Val Thr
                20                  25                  30

Arg Leu Asn Arg Arg Thr Leu Ala Met Leu Thr Gly Gly Leu Ser Val
            35                  40                  45

Ala Val Leu Gly Ala Thr Ile Trp Ser Leu Gln Pro His Arg Arg Gly
50                  55                  60

Ala Gly Glu Gln Thr Glu Leu Tyr Asn Val Asp Arg Val Ser Lys Ser
65                  70                  75                  80

Glu Gly Leu Asp Gly Leu Pro Ser Asp Tyr Ser Lys Leu Arg Lys Val
                85                  90                  95

Pro Glu Leu Gly Pro Pro Leu Pro Gly Asp Leu Gly Pro Ala Ile Val
            100                 105                 110

Lys Ala Gln Gln Pro Val Thr Pro Thr Tyr Ala Pro Gly His Asp
            115                 120                 125

Pro Glu Asp Ala Arg Arg Lys Glu Ala Glu Ala Ala Ala Ser Ser
130                 135                 140

Val Phe Phe His Ser Gly Thr Pro Gly Lys Thr Ala Ala Pro Ala Thr
145                 150                 155                 160

Ala Gln Ala Ala Gly Pro Ala Ser Thr Leu Ala Gly Phe Asp Pro Leu
                165                 170                 175

Ala Ala Gly Pro Ala Ser Thr Ala Ala Gln Pro Ala Asp Pro Thr Ala
            180                 185                 190

Val Gln Asn Arg Gln Asp Gln Lys Glu Ala Phe Leu Lys Gly Gly Ser
            195                 200                 205

Thr Glu Thr Arg Asn Ser Gly Asn Leu Gln Met Pro Ala Ser Pro Tyr
            210                 215                 220
```

```
Gln Met Met Ala Gly Thr Val Ile Ala Gly Ala Leu Val Thr Gly Ile
225                 230                 235                 240

Lys Ser Asp Leu Pro Gly Asp Val Ile Gly Thr Val Thr Glu Pro Val
                245                 250                 255

Tyr Asp Ser Ala Thr Gly Lys Phe Leu Leu Ile Pro Gln Gly Ser Arg
            260                 265                 270

Leu Met Gly Lys Tyr Asn Ser Gln Met Ser Tyr Gly Gln Ser Arg Val
        275                 280                 285

Gln Val Val Trp Asn Arg Ile Ile Leu Pro Asp Thr Ser Ser Leu Lys
    290                 295                 300

Leu Asp Asn Leu Ala Gly Ala Asp Pro Ala Gly Tyr Ser Gly Leu Glu
305                 310                 315                 320

Asp Gly Val Asp Trp His Trp Asp Arg Val Phe Ala Gly Ala Ala Leu
                325                 330                 335

Thr Thr Leu Leu Gly Val Gly Ala Glu Leu Ala Ala Pro Glu Asn Arg
            340                 345                 350

Gln Asn Gly Asn Arg Ile Val Ile Ala Gly Arg Asp Ser Ala Gln Asp
        355                 360                 365

Ser Ile Asn Gln Val Gly Gln Glu Met Thr Arg Arg Asn Met Asn Ile
    370                 375                 380

Gln Pro Thr Leu Thr Glu Arg Pro Gly Leu Pro Val Arg Ile Ile Val
385                 390                 395                 400

Asn Arg Asp Leu Val Leu Arg Pro Tyr Gln Pro Met Phe Phe Gln Arg
                405                 410                 415

Gly Ala Met Arg
            420

<210> SEQ ID NO 105
<211> LENGTH: 406
<212> TYPE: PRT
<213> ORGANISM: Paracoccus aminophilus JCM 7686

<400> SEQUENCE: 105

Met Ser Gly Ala Pro Asp Asp Leu Ser Ala Arg Leu Lys Ala Ile Glu
1               5                   10                  15

Ala Ser Thr Gly Lys Arg Lys Val Pro Ala Arg Pro Ser Leu Phe Ala
            20                  25                  30

Ala Leu Leu Gly Ser Ala Ala Ile Leu Val Ile Gly Gly Leu Gly Trp
        35                  40                  45

Leu Leu Leu Gln Pro Lys Pro Glu Pro Ser Leu Pro Thr Ala Ala Ala
    50                  55                  60

Glu Glu Phe Gln Ser Ala Gly Ser Gly Phe Gly Glu Phe Pro Val Thr
65                  70                  75                  80

Pro Val Ser Glu Pro Ala Pro Ala Pro Thr Pro Val Pro Glu Gly Pro
                85                  90                  95

Ser Ala Ala Glu Leu Glu Leu Arg Glu Thr Leu Gly Arg Leu Gln Ala
            100                 105                 110

Glu Leu Ala Glu Met Arg Ala Arg Pro Val Glu Thr Gly Asp Pro Ala
        115                 120                 125

Ala Gln Ala Ala Ile Ala Asp Leu Thr Ala Gln Leu Ala Ala Leu Asp
    130                 135                 140

Ala Ser Asn Ala Glu Ala Arg Ser Ala Leu Glu Arg Gln Leu Val Glu
145                 150                 155                 160

Arg Asp Arg Glu Leu Glu Arg Ile Arg Met Asp Leu Glu Ile Ala Arg
```

```
            165                 170                 175
Leu Gly Ala Pro Gly Asn Gly Glu Glu Asp Ala Arg Leu Ala Glu Leu
            180                 185                 190

Glu Arg Arg Arg Ala Ala Glu Ala Ala Ala Arg Glu Ala Arg Ile Thr
            195                 200                 205

Ser Pro Met Leu Ala Trp Ser Gly Val Gly Gly Val Asn Gly Glu
            210                 215                 220

Thr Glu Val Glu Ala Ala Arg Leu Ser Ala Asp Glu Ala Phe Val Arg
225                 230                 235                 240

Gly Gly Ala Ala Ala Pro Met Thr Arg Ala Glu Ile Ile Val Asn
            245                 250                 255

Pro Gly His Thr Val Val Gln Gly Thr Met Ile Gln Ala Val Leu Glu
            260                 265                 270

Thr Ala Met Asp Ser Thr Leu Pro Gly Val Ile Arg Ala Val Val Ser
            275                 280                 285

Glu Asp Val His Ser Phe Asp Gly Thr Arg Ile Leu Ile Pro Arg Gly
            290                 295                 300

Ala Gln Leu Ile Gly Arg Tyr Arg Ser Glu Val Ser Leu Ala Gln Ser
305                 310                 315                 320

Arg Val Met Val Gly Trp Asp Arg Ile Ile Leu Pro Asp Asn Gln Thr
            325                 330                 335

Val Gln Ile Ser Ala Phe Gly Asp Glu Leu Gly Arg Ser Gly Val
            340                 345                 350

Thr Gly Asp Val Asp Ser Ala Leu Ala Pro Ala Leu Ala Arg Arg His
            355                 360                 365

Ser Phe Pro Ser Ser Ala Arg Ser Arg Gln Arg Pro Pro Arg Ala Leu
            370                 375                 380

Thr Thr Thr Arg Pro Arg Met Arg Pro Ala Met Trp Arg Arg Thr Cys
385                 390                 395                 400

Ala Met Pro Ala Ala Ala
            405

<210> SEQ ID NO 106
<211> LENGTH: 464
<212> TYPE: PRT
<213> ORGANISM: Litoreibacter arenae DSM 19593

<400> SEQUENCE: 106

Met Ser Asp Lys Pro Asn Gln Pro Asp Met Ser Glu Arg Leu Ala Arg
1               5                   10                  15

Leu Glu Ala Ser Ala Ser Gly Ser Pro Arg Thr Thr Arg Arg Ser
            20                  25                  30

Pro Leu Met Ala Leu Leu Val Val Ala Leu Val Gly Leu Gly Gly Thr
            35                  40                  45

Val Leu Tyr Leu Leu Asn Gln Pro Glu Glu Val Ala Leu Pro Thr
50                  55                  60

Ala Thr Pro Asp Glu Phe Gln Pro Glu Gly Asp Gly Phe Gly Thr Ile
65                  70                  75                  80

Glu Pro Phe Val Pro Ala Pro Pro Glu Pro Glu Val Val Ala Val
            85                  90                  95

Pro Ala Pro Ala Pro Glu Pro Asn Ala Glu Leu Leu Ala Gln Ile Ala
            100                 105                 110

Ala Leu Gln Ala Gln Ile Glu Glu Leu Arg Asn Ala Pro Asp Pro Val
            115                 120                 125
```

```
Val Glu Glu Asp Thr Ala Ala Ala Glu Ala Ile Asn Ala Leu Thr Ala
130                 135                 140

Gln Leu Ala Glu Leu Gln Lys Ala Ser Glu Ala Ala Gln Gln Gln Phe
145                 150                 155                 160

Ala Asp Glu Leu Glu Ala Arg Asp Arg Ala Leu Gln Gln Leu Arg Met
                165                 170                 175

Asp Leu Asp Leu Ala Arg Leu Glu Ala Gln Gln Pro Ala Pro Ala Pro
            180                 185                 190

Ser Gly Pro Thr Glu Glu Glu Leu Arg Arg Leu Glu Glu Arg Leu
        195                 200                 205

Arg Arg Glu Glu Glu Ala Arg Arg Leu Ala Glu Leu Gln Arg Arg Ser
    210                 215                 220

Glu Glu Glu Arg Ala Phe Gln Glu Arg Arg Ile Leu Ser Pro Val Thr
225                 230                 235                 240

Ala Phe Gly Gly Ala Thr Gly Gly Thr Asp Gly Thr Gln Leu Ala Glu
                245                 250                 255

Arg Thr Phe Gly Glu Val Thr Asp Phe Val Leu Asn Arg Ala Phe Pro
                260                 265                 270

Ser Pro Val Thr Arg Ser Glu Val Ile Ala Asn Pro Ala Asn Thr Val
            275                 280                 285

Ile Gln Gly Thr Val Ile Gln Ala Ala Leu Glu Asn Ala Ile Thr Ser
290                 295                 300

Glu Leu Ala Gly Gln Val Arg Ala Ile Thr Ser Glu Asn Val Tyr Ser
305                 310                 315                 320

Tyr Asp Gly Thr Arg Leu Leu Ile Pro Ala Gly Ser Arg Leu Ile Gly
                325                 330                 335

Arg Tyr Arg Ser Gly Ala Asp Ile Ala Gln Arg Arg Leu Thr Ile Ala
            340                 345                 350

Trp Asp Arg Ile Ile Leu Pro Asn Asp Gln Thr Ile Gln Ile Ser Ala
        355                 360                 365

Phe Gly Ala Asp Glu Leu Gly Arg Ser Gly Thr Thr Gly Phe Val Asp
    370                 375                 380

Thr Arg Phe Ala Glu Arg Phe Gly Ser Ala Ala Leu Ile Ser Leu Ile
385                 390                 395                 400

Ser Ala Ala Pro Thr Val Ala Ala Asn Glu Thr Glu Asp Glu Leu Ser
                405                 410                 415

Glu Asp Val Leu Lys Asn Ile Gly Asp Asp Leu Ala Asp Ala Thr Asp
                420                 425                 430

Ser Val Ile Gly Glu Tyr Leu Ser Ile Gly Pro Val Ile Tyr Val Asn
            435                 440                 445

Gln Gly Ala Arg Ile Thr Val Met Val Asp Arg Asp Leu Glu Ile Phe
        450                 455                 460

<210> SEQ ID NO 107
<211> LENGTH: 238
<212> TYPE: PRT
<213> ORGANISM: Novosphingobium lindaniclasticum LE124

<400> SEQUENCE: 107

Gly Ala Ala Pro Ala Pro Glu Asn Pro Phe Ala Asn Pro Thr Val
1               5                   10                  15

Val Phe Asp Ala Gly Gly Asn Ala Val Thr Ile Pro Ala Val Gly Pro
                20                  25                  30

Ala Gly Glu Ala Lys Gly Gly Asn Pro Asn Asp Asp Phe Ala Ala Arg
            35                  40                  45
```

```
Ile Gly Gly Thr Gly Ser Thr Ala Ala Ala Arg Thr Phe Asp Pro
        50                  55                  60

Ala Thr Thr Val Thr Gln Gly Thr Leu Ile Pro Ala Val Leu Glu Thr
 65                  70                  75                  80

Ala Ile Asp Thr Asp Val Pro Gly Tyr Val Arg Ala Ile Val Ser Ala
                85                  90                  95

Asp Val Arg Ser Phe Asp Gly Lys Arg Thr Leu Val Pro Arg Ser Ser
                100                 105                 110

Arg Leu Ile Gly Gln Tyr Lys Ser Gly Leu Thr Ala Gly Gln Lys Arg
            115                 120                 125

Ala Tyr Val Ile Trp Ser Arg Leu Ile Arg Pro Asp Gly Val Ser Val
    130                 135                 140

Asn Leu Gly Ser Pro Ala Ile Ala Phe Gly Gly Glu Thr Gly Leu Pro
145                 150                 155                 160

Gly Lys Val Asn Ser His Phe Phe Glu Arg Phe Gly Ser Ala Met Leu
                165                 170                 175

Leu Ser Val Val Gly Gly Leu Ser Thr Leu Ala Thr Ser Gly Ser Ser
                180                 185                 190

Val Val Ile Gly Gly Gln Ser Ala Ala Ala Ala Val Gln Gln
            195                 200                 205

Ser Gly Thr Val Gly Pro Thr Ile Arg Val Arg Gln Gly Glu Pro Ile
    210                 215                 220

Arg Val Phe Thr Ala Lys Asp Leu Asp Phe Ser Gln Val Gln
225                 230                 235

<210> SEQ ID NO 108
<211> LENGTH: 278
<212> TYPE: PRT
<213> ORGANISM: Photorhabdus temperata subsp. temperata M1021

<400> SEQUENCE: 108

Met Gln Pro Asn Pro Ala Tyr Leu Arg Lys Leu Thr Gly Gly Val Phe
  1               5                  10                  15

Val Gln Glu Thr Gly Gly Ser Ser Ser Pro Ala Ser Thr Asn Ala Asp
                20                  25                  30

Val Asp Pro Asp Glu Gln Arg Ile Arg Ser Tyr Glu Asp Ala Ala Leu
            35                  40                  45

Val Thr Pro Asp Val Asn Ser Asn Ala Thr Leu Ser Ala Pro Ala Asp
    50                  55                  60

Asn Thr Arg Gly Ser Leu Ser Asn Leu Lys Gly Ser Asn Tyr Val Pro
 65                  70                  75                  80

Thr Thr Ala Tyr Leu Ser Pro Asp Arg Lys Phe Leu Leu Lys Arg Lys
                85                  90                  95

Ser Asn Val Arg Cys Ala Leu Tyr Thr Ala Val Lys Thr Asp His Pro
                100                 105                 110

Gly Phe Val Lys Cys Ile Leu Thr Gln Pro Leu Tyr Ser Ser Asp Gly
            115                 120                 125

Ser Val Ile Ile Ala Glu Ala Gly Ala Glu Leu Asp Gly Glu Gln Lys
    130                 135                 140

Val Glu Ile Arg Pro Gly Gln Thr Ser Val Phe Thr Thr Trp Thr Glu
145                 150                 155                 160

Leu Glu Thr Thr Ala Gly Val Arg Ala Asn Leu Asn Ala Leu Gly Thr
                165                 170                 175

Gly Ala Met Gly Glu Ser Gly Thr Glu Ala Tyr Val Asp Asn His Thr
```

```
                180                 185                 190
Gly Gln Arg Tyr Ser Gly Ala Val Met Leu Ser Phe Ile Gln Asp Val
            195                 200                 205

Phe Ala Ser Ala Ala Asn Ala Thr Lys Arg Asn Asn Thr Thr Tyr Ser
        210                 215                 220

Phe Asp Asn Ser Glu Ser Asn Ala Glu Asn Met Ala Ser Lys Ala Leu
225                 230                 235                 240

Glu His Asn Ile Asn Ile Pro Pro Thr Gly Tyr Val Leu Pro Gly Thr
                245                 250                 255

Val Ile Asn Val Ile Val Ala His Asp Val Asp Phe Ser Ser Val Phe
            260                 265                 270

Lys Thr Arg Pro Gly Arg
        275

<210> SEQ ID NO 109
<211> LENGTH: 445
<212> TYPE: PRT
<213> ORGANISM: Variovorax paradoxus B4

<400> SEQUENCE: 109

Met Thr Trp Met Ser Glu Pro Arg Arg Ala Ser Arg Thr Asp Pro Gln
1               5                   10                  15

Glu Pro Gly Asp Ala Pro Glu Ile Asp Pro Asp Thr Gly Glu Ile Leu
            20                  25                  30

Ser Gly Gln Arg Ala Ala Pro Gly Asp Gly Thr Phe Arg Thr Ala
        35                  40                  45

Glu Glu Arg Pro Thr Ile Gln Gly Glu Arg Ala Ile Pro Ser Val Asn
    50                  55                  60

Arg Glu Arg Ser Ile Gln Ser Arg Ile Ser Gly Phe Leu Ala Leu Thr
65                  70                  75                  80

Ala Ile Met Leu Leu Gly Ala Gly Phe Leu Phe Trp Tyr Tyr Asn Thr
                85                  90                  95

Gln Tyr Ala Lys Thr Gln Glu Ala Glu Glu Ala Ala Arg Lys Thr Ala
            100                 105                 110

Ala Ala Arg Ala Gly Gly Glu Met Lys Val Pro Pro Leu Gly Arg Ile
        115                 120                 125

Asp Pro Pro Arg Ala Ala Pro Glu Ala Ala Thr Ala Ala Pro Pro
130                 135                 140

Ser Pro Pro Ser Pro Ser Ala Asn Gly Ala Asn Thr Gly Pro Pro Gln
145                 150                 155                 160

Lys Thr Pro Glu Gln Ile Ala Leu Glu Arg Gln Leu Gly Ala Pro Val
                165                 170                 175

Leu Arg Arg Ala Gln Ala Ala Gln Ala His Ser Ala Thr Thr Pro His
            180                 185                 190

Ala Phe Ala Asp Pro Ala Met Leu Ser Ala Gly Gly Val Pro Ser Met
        195                 200                 205

Ala Gln Leu Ile Gly Ala Leu Gln Pro Pro His Ala Gly Ser Ala Ala
    210                 215                 220

Pro Gly Gly Gly Gln Leu Ala Ala Ser Leu Arg Pro Thr Pro Thr Pro
225                 230                 235                 240

Ala Val Val Ala Gln Thr Leu Pro Thr Arg Arg Met Leu Leu Pro Lys
                245                 250                 255

Gly Ala Phe Ile Asp Cys Thr Leu Glu Thr Ala Ile Asp Ser Thr Tyr
            260                 265                 270
```

```
Glu Gly Met Ala Thr Cys Ile Gly Ala Ser Asp Val Tyr Gly Ala Asp
            275                 280                 285

Gly Lys Val Val Leu Leu Glu Arg Gly Thr Lys Tyr Val Gly Glu Gln
        290                 295                 300

Arg Gly Thr Pro Arg Gln Gly Gln Gly Arg Val Phe Ile Val Trp Asn
305                 310                 315                 320

Glu Ala Arg Thr Pro Thr Gly Val Val Gln Leu Ala Ser Pro Gly
                325                 330                 335

Thr Asp Glu Leu Gly Arg Ser Gly Leu Pro Gly Phe Val Asp Thr His
            340                 345                 350

Phe Trp Asp Arg Phe Gly Ala Ala Val Leu Ile Ser Val Ile Asp Gly
            355                 360                 365

Thr Met Gln Thr Ile Ala Ala His Gln Gln Ser Gly Thr Ser Val Gly
            370                 375                 380

Ser Gly Gly Gly Val Val Leu Ala Pro Gln Gly Ser Arg Asp Val Ile
385                 390                 395                 400

Thr Glu Val Leu Arg Ser Thr Val Ser Ile Pro Pro Thr Val Ile Lys
                405                 410                 415

Asn Gln Gly Glu Arg Ile Gln Ile Leu Val Ala Arg Asp Val Asp Phe
                420                 425                 430

Arg Ser Val Tyr Ala Leu Arg Thr Glu Pro Ala Ile Pro
            435                 440                 445

<210> SEQ ID NO 110
<211> LENGTH: 353
<212> TYPE: PRT
<213> ORGANISM: Bradyrhizobium sp. DFCI-1

<400> SEQUENCE: 110

Met Ile Arg Phe Gly Leu Leu Gly Cys Gly Arg Ile Ala Lys Arg His
1               5                   10                  15

Ser Asp Leu Leu Gly Gly Asn His Ile Ala Gly Ala Ser Leu Val Ala
            20                  25                  30

Val Cys Asp Pro Ile Arg Ala Arg Ala Asp Ala Val Ala Gly Lys Phe
        35                  40                  45

Ala Val Pro Ala His Tyr Asp Met Asp Glu Phe Leu Ala Arg Lys Asp
    50                  55                  60

Ile Asp Ala Val Ala Val Leu Thr Pro Ser Gly Leu His Pro Ala His
65                  70                  75                  80

Val Ile Ala Cys Ala Lys Ala Gly Lys His Val Val Glu Lys Pro
                85                  90                  95

Met Ala Leu Arg Leu Gln Asp Ala Asp Asp Met Ile Arg Ala Cys Asp
            100                 105                 110

Glu Ala Gly Val Lys Met Phe Ile Val Lys Gln Asn Arg Phe Asn Val
            115                 120                 125

Pro Val Val Lys Ala Arg Glu Ala Leu Asp Ala Gly Arg Phe Gly Lys
        130                 135                 140

Leu Ile Leu Gly Thr Val Arg Val Arg Trp Cys Arg Asp Gln Ala Tyr
145                 150                 155                 160

Tyr Asp Gln Asp Asp Trp Arg Gly Thr Trp Ala Tyr Gly Gly Val
                165                 170                 175

Leu Thr Asn Gln Ala Ser His His Val Asp Met Leu Glu Trp Phe Phe
            180                 185                 190

Gly Asp Val Val Ser Val His Ala Arg Ala Thr Thr Ala Leu Ala Asn
            195                 200                 205
```

```
Ile Glu Thr Glu Asp Thr Ala Val Ala Thr Leu Lys Phe Arg Asn Gly
    210                 215                 220

Ala Leu Gly Ile Ile Glu Ala Thr Thr Ala Ala Arg Pro Thr Asp Leu
225                 230                 235                 240

Glu Gly Ser Leu Ser Ile Leu Gly Glu Lys Gly Thr Val Glu Ile Ser
                245                 250                 255

Gly Phe Ala Val Asn Gln Ile Arg His Trp Arg Phe Val Asp Glu Leu
                260                 265                 270

Pro Ser Asp Lys Asp Val Val Glu Lys Phe Ser Val Asn Pro Pro Asn
                275                 280                 285

Val Tyr Gly Phe Gly His Gln Ala Tyr His His Val Val Asp Cys
                290                 295                 300

Leu Glu Asn Gln Arg Ala Ala Leu Val Asp Gly Leu Glu Gly Arg Lys
305                 310                 315                 320

Ser Leu Glu Leu Ile Ser Ala Leu Tyr Glu Ser Ile Glu Thr Gly Glu
                325                 330                 335

Glu Val Ala Leu Arg Phe Thr Pro Arg Leu Ser Arg Leu Gly Val Val
                340                 345                 350

Ser

<210> SEQ ID NO 111
<211> LENGTH: 409
<212> TYPE: PRT
<213> ORGANISM: Advenella kashmirensis W13003

<400> SEQUENCE: 111

Met Asn Gln Glu Asp Lys Asp Arg Gln Phe Ser Ala Glu Gly Gly Ser
1               5                   10                  15

Asp Glu Tyr Glu Ser Asn Arg Ile Ala Pro Asp Gly Gln Glu His
                20                  25                  30

Glu Thr Leu Gln Lys Lys Val Gly Asp Asp Glu Val Glu Arg Gly Ile
            35                  40                  45

Pro Gln Asn Leu Ser Ser Arg Lys Lys Thr Asn Val Gly Lys Val Phe
50                  55                  60

Val Phe Gly Gly Ile Val Leu Ala Val Ser Leu Ile Val Ile Thr Ala
65                  70                  75                  80

Met Gly Leu Ser Gly Arg Asp Asp Ser Ser Glu Glu Ala Ala Pro Lys
                85                  90                  95

Glu Val Asp Met Val Lys Asn Ser Arg Pro Lys Asn Phe Ala Leu Glu
                100                 105                 110

Gln Ala Glu Leu Thr Pro Pro Ala Pro Glu Pro Pro Val Val Ile
            115                 120                 125

Pro Pro Ala Glu Lys Pro Thr Ala Asp Pro Ala Ala Thr Lys Thr Gln
130                 135                 140

Thr Ala Gly Val Asn Gln Gly Lys Glu Gln Pro Pro Val Asp Arg Arg
145                 150                 155                 160

Leu Thr Gly Pro Val Thr Ile Asp Ala Asn Ala Gly Gln Ser Ala Asp
                165                 170                 175

Gly Lys Ser Lys Gln Pro Val Ser Arg Thr Glu Ser Ser Ala Gly
                180                 185                 190

Gly Phe Val Ser Lys Leu Arg Pro Thr Thr Glu Pro Thr Ile Ala
            195                 200                 205

Gln Arg Arg Ala Asp Leu Thr Tyr Leu Leu Lys Lys Gly Thr Asn Ile
                210                 215                 220
```

Ala Cys Thr Leu Asn Thr Lys Ile Val Thr Gln Pro Gly Ile Thr
225                 230                 235                 240

Arg Cys Met Val Ser Lys Asp Val Tyr Ser Ala Asn Gly Arg Val Leu
            245                 250                 255

Leu Ile Glu Arg Gly Ser Glu Val Val Gly Glu Gln Thr Ala Ala Leu
        260                 265                 270

Val Gln Gly Gln Ala Arg Val Tyr Val Leu Trp Ser Met Ile Glu Thr
    275                 280                 285

Pro Ala Gly Val Ser Val Thr Val Asn Ser Ala Ser Ala Asp Ser Leu
290                 295                 300

Gly Ala Ser Gly Gln Glu Ala Gln Val Asp Thr His Phe Trp Lys Arg
305                 310                 315                 320

Phe Gly Gly Ala Ile Met Leu Ser Leu Ile Lys Asp Gly Ile Arg Met
                325                 330                 335

Ala Asp Ser Ser Asn Arg Asn Gln Gly Gly Val Thr Phe Asp Ser Ser
            340                 345                 350

Ser Asp Ser Ala Glu Asp Met Ala Thr Glu Ala Leu Lys Asn Thr Ile
        355                 360                 365

Asn Ile Pro Pro Thr Gly Tyr Val Asn Gln Gly Thr Leu Val Asn Val
    370                 375                 380

Met Val Ala Arg Asp Val Asp Phe Arg Ser Val Tyr Glu Leu Val Gln
385                 390                 395                 400

Pro Tyr Phe Tyr Ser Ser Ser Thr Lys
                405

<210> SEQ ID NO 112
<211> LENGTH: 379
<212> TYPE: PRT
<213> ORGANISM: Mesorhizobium sp. L103C105A0

<400> SEQUENCE: 112

Met Asn Glu Thr Gly Pro Gln Ser Gly His Asp Val His Ala Ser Gly
1               5                   10                  15

Ser Met Val Ser Glu Pro Ala Arg Arg His Val Ser Gly Leu Gln Lys
            20                  25                  30

Leu Ala Val Ala Ala Leu Val Leu Ile Ser Ser Leu Ser Leu Ile Trp
        35                  40                  45

Leu Gly Gly Arg Pro Ser Thr Gln Asp Glu Pro Thr Gln Pro Lys Pro
    50                  55                  60

Pro Ile Val Ala Asp Ala Glu Pro Phe Arg Pro Val Pro Ile Glu Ile
65                  70                  75                  80

Ala Pro Glu Ala Pro Ala Pro Val Gln Ala Gln Ala Gly Asp Ser
                85                  90                  95

Ala Pro Ser Thr Pro Pro Thr Pro Ala Asp Pro Pro Glu Glu
            100                 105                 110

Thr Pro Ile Phe Ala Tyr Ser Gly Ser Gly Gln Met Pro Asn Asp Gly
        115                 120                 125

Gln Arg Ser Glu Asp Asn His Arg Asp Ala Pro Ala Thr Ser His Glu
    130                 135                 140

Ile Ser Asp Ala Gly Asp Leu Thr Gly Arg Leu Lys Pro Asp Ile Gln
145                 150                 155                 160

Glu Pro Ser Arg Ala Thr Leu Leu Pro His Pro Asp Leu Val Ile Thr
                165                 170                 175

Gln Gly Thr Ile Ile Pro Cys Ile Leu Gln Thr Ala Val Asp Thr Asn

```
                    180                 185                 190
Leu Pro Gly Tyr Val Lys Cys Val Leu Pro Lys Asp Val Arg Gly Ala
            195                 200                 205

Thr Asn Asn Val Val Leu Leu Asp Arg Gly Thr Thr Val Ile Gly Glu
        210                 215                 220

Ile Gln Arg Gly Leu Gln Gln Gly Asp Ala Arg Val Phe Val Leu Trp
225                 230                 235                 240

Thr Arg Ile Glu Thr Pro Asp His Ala Leu Val Ser Leu Ala Ser Pro
                245                 250                 255

Gly Ala Asp Glu Leu Gly Arg Ser Gly Met Pro Gly Thr Val Asp Asn
            260                 265                 270

His Phe Trp Gln Arg Phe Gly Gly Ala Met Leu Met Ser Val Ile Gln
        275                 280                 285

Gly Ala Phe Gln Ala Ala Gly Gln Tyr Ala Gly Ser Ser Gly Gly Gly
            290                 295                 300

Ser Gly Ile Asn Ser Phe Gln Ser Asn Ala Gly Gln Ala Val Asp Thr
305                 310                 315                 320

Thr Leu Arg Ala Thr Ile Asn Val Pro Pro Thr Leu Lys Lys Asn Gln
                325                 330                 335

Gly Asp Ala Val Ser Ile Phe Val Ala Arg Asp Leu Asp Phe Ser Asp
            340                 345                 350

Val Tyr Asp Leu Arg Pro Ile Ala Val Ala Pro Ala Pro Gln His Arg
        355                 360                 365

Gln Arg Arg Arg Asp Asn Asn Ala Thr Gly Gly
    370                 375

<210> SEQ ID NO 113
<211> LENGTH: 474
<212> TYPE: PRT
<213> ORGANISM: Roseivivax halodurans JCM 10272

<400> SEQUENCE: 113

Met Ala Glu Asp Pro Asp Leu Gln Lys Arg Leu Glu Thr Phe Ser Ala
1               5                   10                  15

Ser Arg Gln Arg Arg Pro Gly Arg Gly Ile Asn Ile Thr Leu Leu Ala
            20                  25                  30

Leu Met Leu Gly Leu Gly Gly Ala Gly Ile Ala Tyr Val Leu Ala Val
        35                  40                  45

Asp Trp Gln Glu Ala Arg Asp Ala Leu Arg Thr Ser Asp Val Glu Pro
    50                  55                  60

Phe Gln Asp Asp Arg Pro Glu Thr Gly Gly Gly Leu Glu Phe Pro Glu
65                  70                  75                  80

Glu Glu Ala Gly Gly Arg Ile Glu Asp Ala Leu Ile Ala Ile Glu Asp
                85                  90                  95

Ala Leu Val Pro Pro Ala Ala Pro Glu Pro Ala Val Pro Ser Ala
            100                 105                 110

Glu Ile Leu Ala Glu Leu Gln Arg Leu Arg Asp Ala Leu Ala Ala Ser
        115                 120                 125

Gln Ala Glu Arg Asn Ala Gln Ile Gln Ser Ala Val Gly Glu Leu Arg
    130                 135                 140

Ala Ala Phe Gly Asp Gln Thr Arg Ser Leu Glu Ala Ala Val Ala Glu
145                 150                 155                 160

Arg Asp Glu Arg Ile Ser Arg Leu Glu Arg Glu Asn Glu Thr Arg Leu
                165                 170                 175
```

Asn Ser Leu Glu Ala Met Leu Glu Ala Arg Ala Gln Arg Glu Ala
            180                 185                 190
Leu Glu Ala Glu Arg Ala Asp Asp Ala Leu Ile Arg Asp Leu Glu Leu
        195                 200                 205
Leu Glu Glu Arg Arg Gln Glu Ala Glu Gln Arg Leu Glu Ala
210                 215                 220
Glu Arg Gln Ala Thr Glu Leu Leu Ser Ala Gln Ile Arg Ser Pro Ala
225                 230                 235                 240
Val Val Tyr Ser Ala Gly Ser Thr Gly Ser Ala Asp Val Ala Ser
            245                 250                 255
Gly Ala Glu Gly Ala Arg Ala Ser Pro Ser Leu Pro Leu Glu Ala Asp
        260                 265                 270
Glu Ala Tyr Leu Arg Arg Gly Ala Arg Ala Leu Glu Ile Asp Glu Ala
            275                 280                 285
Thr Arg Met Glu Thr Pro Glu Arg Thr Leu Ala Gln Gly Thr Val Ile
290                 295                 300
Gln Ala Ala Leu Gln Thr Ala Ile Asn Ser Asp Leu Pro Gly Asn Val
305                 310                 315                 320
Val Ala Val Ala Glu Pro Val Tyr Gly Phe Ala Gly Asp Arg Val
            325                 330                 335
Leu Val Pro Lys Gly Ala Arg Leu Phe Gly Gln Tyr Arg Ser Gly Ile
        340                 345                 350
Asp Val Asn Gln Lys Arg Ile Leu Val Leu Trp Thr Arg Ile Leu Thr
355                 360                 365
Pro Glu Gly Ile Ser Met Glu Ile Ala Ala Val Gly Gly Asp Pro Leu
370                 375                 380
Gly Arg Ser Gly Leu Thr Gly Leu Val Asp Thr Lys Phe Asp Glu Arg
385                 390                 395                 400
Phe Gly Gly Ala Ala Leu Ile Ser Ile Ile Gly Ala Ala Pro Ala Val
            405                 410                 415
Ala Ala Asn Ser Ala Glu Asp Glu Ile Thr Gly Asp Val Leu Ala Glu
        420                 425                 430
Ile Gly Ser Gly Leu Glu Glu Ala Thr Gly Ser Val Ile Ala Asp Gln
        435                 440                 445
Val Ser Ile Ser Pro Thr Ile Tyr Val Asp Gln Gly Ala Met Val Thr
450                 455                 460
Val Leu Val Asp Arg Asp Ile Val Ile Phe
465                 470

<210> SEQ ID NO 114
<211> LENGTH: 29
<212> TYPE: DNA
<213> ORGANISM: Artificial sequence
<220> FEATURE:
<223> OTHER INFORMATION: PCR primer

<400> SEQUENCE: 114
caccatgagc acaaatattg gcgtaccag                                29

<210> SEQ ID NO 115
<211> LENGTH: 35
<212> TYPE: DNA
<213> ORGANISM: Artificial sequence
<220> FEATURE:
<223> OTHER INFORMATION: PCR primer

<400> SEQUENCE: 115
actaagagcc tgattcacaa cttctacact cctgc    35

<210> SEQ ID NO 116
<211> LENGTH: 34
<212> TYPE: DNA
<213> ORGANISM: Artificial Sequence
<220> FEATURE:
<223> OTHER INFORMATION: PCR primer

<400> SEQUENCE: 116
caccatggct gatgatcaca ttaagaccttt gaac    34

<210> SEQ ID NO 117
<211> LENGTH: 25
<212> TYPE: DNA
<213> ORGANISM: Artificial sequence
<220> FEATURE:
<223> OTHER INFORMATION: PCR primer

<400> SEQUENCE: 117
tttccggcgt ctttcagcac ccttc    25

<210> SEQ ID NO 118
<211> LENGTH: 30
<212> TYPE: DNA
<213> ORGANISM: Artificial sequence
<220> FEATURE:
<223> OTHER INFORMATION: PCR primer

<400> SEQUENCE: 118
caccatggct gacgaaataa ggggttctag    30

<210> SEQ ID NO 119
<211> LENGTH: 28
<212> TYPE: DNA
<213> ORGANISM: Artificial sequence
<220> FEATURE:
<223> OTHER INFORMATION: PCR primer

<400> SEQUENCE: 119
cctcaccgca tcacgaggaa atactacg    28

<210> SEQ ID NO 120
<211> LENGTH: 20
<212> TYPE: DNA
<213> ORGANISM: Artificial sequence
<220> FEATURE:
<223> OTHER INFORMATION: PCR primer

<400> SEQUENCE: 120
agatgctgac tggggatgag    20

<210> SEQ ID NO 121
<211> LENGTH: 20
<212> TYPE: DNA
<213> ORGANISM: Artificial sequence
<220> FEATURE:
<223> OTHER INFORMATION: PCR primer

<400> SEQUENCE: 121
tcggcatcaa ccaagtacaa    20

<210> SEQ ID NO 122
<211> LENGTH: 24
<212> TYPE: DNA
<213> ORGANISM: Artificial sequence

```
<220> FEATURE:
<223> OTHER INFORMATION: PCR probe
<220> FEATURE:
<221> NAME/KEY: modified_base
<222> LOCATION: (1)..(1)
<223> OTHER INFORMATION: Hexachloro-fluorescein (HEX)
<220> FEATURE:
<221> NAME/KEY: modified_base
<222> LOCATION: (24)..(24)
<223> OTHER INFORMATION: Tetramethylrhodamine TAMRA

<400> SEQUENCE: 122
cgtaggtgag tctgatagtg aagg                                          24

<210> SEQ ID NO 123
<211> LENGTH: 224
<212> TYPE: PRT
<213> ORGANISM: Anaplasma marginale

<400> SEQUENCE: 123

Asp Gly Thr Ser Ser Pro Ser Val Lys Ala Thr Arg Val Gly Asp Pro
1               5                   10                  15

Gly Tyr Val Ile Leu Gln Gly His Met Ile Asp Ala Val Leu Glu Thr
            20                  25                  30

Ala Ile Asn Ser Asp Ile Pro Gly Val Leu Arg Ala Ile Val Ser Arg
        35                  40                  45

Asp Val Tyr Ala Glu Ala Gly Asn Met Val Met Ile Pro Lys Gly Ser
    50                  55                  60

Arg Leu Ile Gly Ser Tyr Phe Phe Asp Ala Ser Gly Asn Asn Thr Arg
65                  70                  75                  80

Val Thr Val Ser Trp Ser Arg Val Ile Leu Pro His Gly Ile Asp Ile
                85                  90                  95

Gln Ile Asn Ser Ala Gly Thr Asp Glu Leu Gly Arg Asn Gly Ser Ala
            100                 105                 110

Gly Phe Ile Asp Thr Lys Met Gly Asn Val Leu Thr Ser Thr Ile Leu
        115                 120                 125

Leu Ala Gly Val Ser Met Gly Thr Ala Phe Val Thr Ser Lys Ile Pro
    130                 135                 140

Ala Leu Gln Ser Glu Ile Lys Asp Thr Thr Glu Lys Gly Glu Lys
145                 150                 155                 160

Lys Lys Glu Glu Lys Ser Ser Thr Leu Pro Val Lys Ile Val Ser Asp
                165                 170                 175

Ala Val Lys Asp Phe Ser Glu Ser Met Lys Ala Leu Ile Lys Lys Tyr
            180                 185                 190

Val Asp Thr Ser Lys Pro Thr Ile Tyr Val Asp Gln Gly Thr Val Met
        195                 200                 205

Lys Val Phe Val Asn Gln Asp Ile Val Phe Pro Arg Glu Ala Val Arg
    210                 215                 220

<210> SEQ ID NO 124
<211> LENGTH: 224
<212> TYPE: PRT
<213> ORGANISM: Anaplasma phagocytophilum

<400> SEQUENCE: 124

Glu Gly Thr Gln Ser Pro Ser Val Arg Ala Thr Arg Val Gly Asp Thr
1               5                   10                  15

Arg Tyr Ile Ile Leu Gln Gly His Met Ile Asp Ala Val Leu Glu Thr
            20                  25                  30
```

Ala Ile Asn Ser Asp Ile Ser Gly Val Leu Arg Ala Val Ser Arg
            35                  40                  45

Asp Val Tyr Ala Ser Ser Gly Asp Ala Val Ile Pro Lys Gly Ser
50                  55                  60

Arg Leu Ile Gly Ser Tyr Phe Phe Asp Ser Ala Gly Asn Asn Val Arg
65                  70                  75                  80

Val Asp Val Asn Trp Ser Arg Val Ile Leu Pro His Gly Val Asp Ile
                85                  90                  95

Gln Ile Ala Ser Ser Gly Thr Asp Glu Leu Gly Arg Asn Gly Ile Ser
            100                 105                 110

Gly Val Val Asp Asn Lys Val Gly Ser Ile Leu Thr Ser Thr Ile Phe
        115                 120                 125

Leu Ala Gly Ile Ser Leu Gly Thr Ala Tyr Val Thr Glu Gln Ile Pro
    130                 135                 140

Ser Leu Arg Thr Glu Thr Val Lys Val Glu Thr Pro Ala Asp Gly Lys
145                 150                 155                 160

Asp Gly Lys Lys Thr Thr Ser Ser Ser Leu Ser Thr Lys Ile Val Ser
                165                 170                 175

Asp Ala Ile Lys Asp Phe Ser Asp Ser Met Lys Glu Ile Val Asn Lys
            180                 185                 190

Tyr Ser Asn Arg Thr Pro Thr Val Tyr Val Asp Gln Gly Thr Val Met
        195                 200                 205

Lys Val Phe Val Asn Gln Asp Val Val Phe Pro Arg Asp Ala Val Arg
    210                 215                 220

<210> SEQ ID NO 125
<211> LENGTH: 233
<212> TYPE: PRT
<213> ORGANISM: Ehrlichia chaffeensis

<400> SEQUENCE: 125

Gln Thr Thr Ser Ser Pro Asn Val Val Ala Thr Lys Val Ser Asn Leu
1               5                   10                  15

Glu Leu Thr Ile Leu Gln Gly Lys Ile Ile Asp Val Val Leu Glu Thr
            20                  25                  30

Ala Ile Asn Ser Asp Leu Gln Gln Gly Ala Leu Arg Gly Ile Val Ala
        35                  40                  45

Arg Asp Val Tyr Ala Glu Ala Ser Asn Thr Val Met Ile Pro Lys Gly
    50                  55                  60

Ser Arg Leu Ile Gly Ser Tyr Ser Phe Asp Ala Ser Pro Gly Lys Thr
65                  70                  75                  80

Arg Val Gln Ile Ser Trp Asn Arg Val Ile Leu Pro His Gly Ile Asp
                85                  90                  95

Ile Thr Leu Asp Ser Asn Gly Thr Asp Glu Leu Gly Arg Gln Gly Ala
            100                 105                 110

Ser Gly Val Val Asp Thr Lys Ile Gly Asn Ile Leu Thr Ser Thr Ile
        115                 120                 125

Leu Leu Ala Gly Val Ser Ile Ala Thr Ser Tyr Ala Thr Ser Lys Ile
    130                 135                 140

Pro Glu Ile Asn Asn Tyr Pro Ile Leu Glu Ser Asp Ser Lys Glu Lys
145                 150                 155                 160

Lys Asp Lys Glu Lys Asp Asp Thr Gly Asp Lys Ser Lys Ser Thr Lys
                165                 170                 175

Thr Thr Leu Pro Val Lys Ile Leu Ser Gln Ala Val Asp Phe Ser
            180                 185                 190

```
Asn Ser Ile Lys Asp Ile Ile Lys Lys Tyr Ser Asn Asn Pro Thr
        195                 200                 205

Val Tyr Val Asp Gln Gly Thr Leu Leu Lys Val Phe Val Asn Lys Asp
    210                 215                 220

Ile Val Phe Pro Lys Ser Ala Val Arg
225                 230

<210> SEQ ID NO 126
<211> LENGTH: 230
<212> TYPE: PRT
<213> ORGANISM: Ehrlichia ruminantium

<400> SEQUENCE: 126

Thr Ser Ser Pro Asn Val Val Ala Thr Lys Ile Asn Asn Leu Glu Leu
1               5                   10                  15

Thr Ile Leu Gln Gly Lys Ile Ile Asp Val Val Leu Glu Thr Ala Ile
            20                  25                  30

Asn Ser Asp Leu Gln Gly Thr Leu Arg Gly Ile Val Ala Arg Asp Val
        35                  40                  45

Tyr Ser Glu Ala Gly Asn Val Val Met Ile Pro Lys Gly Ser Arg Leu
    50                  55                  60

Ile Gly Asn Tyr Ser Phe Asn Ala Ser Pro Gly Lys Thr Arg Val Gln
65                  70                  75                  80

Ile Ser Trp Asn Arg Val Ile Leu Pro His Gly Val Asp Ile Ala Leu
                85                  90                  95

Asp Ser Thr Gly Thr Asp Glu Leu Gly Arg Gln Gly Ala Ser Gly Val
            100                 105                 110

Val Asp Thr Lys Val Gly Ser Ile Leu Thr Ser Thr Ile Leu Leu Ala
        115                 120                 125

Gly Val Ser Ile Ala Thr Ser Tyr Val Thr Ser Lys Ile Pro Glu Ile
    130                 135                 140

Asn Asp His Pro Ile Ile Glu Ser Lys Ser Asp Asp Lys Asp Lys Asp
145                 150                 155                 160

Lys Asp Lys Asp Lys Asp Lys Asp Lys Thr Lys Thr Thr Leu
                165                 170                 175

Pro Val Lys Ile Leu Ser Lys Ala Val Asp Asp Phe Ser Gln Ser Ile
            180                 185                 190

Lys Asp Ile Ile Gln Lys Tyr Thr Asn Asn Pro Thr Val Tyr Val
        195                 200                 205

Asp Gln Gly Thr Leu Leu Lys Val Phe Val Asn Lys Asp Ile Val Phe
    210                 215                 220

Pro Lys Glu Ala Val Arg
225                 230

<210> SEQ ID NO 127
<211> LENGTH: 310
<212> TYPE: PRT
<213> ORGANISM: Rickettsia typhi

<400> SEQUENCE: 127

Pro Glu Gln Ile Thr Glu Ala Val Thr Phe Lys Asp Arg Gly Asp Met
1               5                   10                  15

Phe Leu Leu Leu Gly Arg Gly Lys Leu Ile Asp Ala Val Leu Glu Thr
            20                  25                  30

Gly Ile Asn Ser Asp Leu Gly Gly Glu Ile Arg Ala Ile Ser Arg
        35                  40                  45
```

```
Asp Val Phe Ser Glu Lys Gly Lys Val Ile Leu Ile Pro Lys Gly Ser
 50                  55                  60

Lys Ile Phe Gly Lys Tyr Ala Thr Ser Thr Ser Asp Ser Tyr Gly
 65                  70                  75                  80

Arg Val Ser Ile Ile Trp Asp Arg Val Asp Leu Thr Asn Gly Tyr Thr
                 85                  90                  95

Ile Glu Phe Asp Ser Pro Ala Val Asp Asn Leu Gly Arg Pro Gly Leu
            100                 105                 110

Gln Gly Arg Val Asp Asn Lys Tyr Lys Glu Gln Phe Ala Asn Ala Val
        115                 120                 125

Leu Gln Ser Gly Phe Asn Ile Gly Leu Ala Lys Ile Leu Asp Lys Leu
    130                 135                 140

Val Pro Pro Ile Asp Ser Gln Ala Ala Thr Asn Ser Ala Thr
145                 150                 155                 160

Ala Thr Gln Ile Leu Asn Ile Ala Gln Thr Ile Ser Ser Asn Thr Ala
                165                 170                 175

Ile Asp Val Asn Thr Arg Ile Val Thr Ile Cys Thr Asn Ile Leu Ala
            180                 185                 190

Ala Ile Thr Asp Lys Thr Ser Ile Ala Tyr Thr Thr Met Thr Gln Ala
        195                 200                 205

Cys Ala Thr Ala Gln Asn Ala Ser Ser Ala Asn Thr Ser Glu Gln Arg
    210                 215                 220

Leu Gln Thr Leu Val Gln Ala Val Asn Thr Ala Ala Ser Asn Leu Leu
225                 230                 235                 240

Thr Thr Thr Ser Ile Ala Ser Thr Pro Thr Gln Ala Gln Ala Ser
                245                 250                 255

Thr Gln Ala Phe Thr Asp Val Thr Asn Val Val Gln Asn Met Ile Thr
            260                 265                 270

Gln Gln His Phe Lys Pro Thr Thr Thr Val Asn Gln Gly Thr Pro Ile
        275                 280                 285

Arg Ile Tyr Val Asn Lys Asp Tyr Lys Phe Pro Arg Thr Val Leu Leu
    290                 295                 300

Lys Ser Lys Val Met Lys
305                 310

<210> SEQ ID NO 128
<211> LENGTH: 310
<212> TYPE: PRT
<213> ORGANISM: Rickettsia prowazekii

<400> SEQUENCE: 128

Pro Glu Gln Met Thr Glu Ala Val Thr Phe Lys Asp Arg Gly Asp Met
 1                   5                  10                  15

Phe Leu Leu Leu Gly Arg Gly Lys Leu Ile Asp Ala Val Leu Glu Thr
                20                  25                  30

Gly Ile Asn Ser Asp Leu Gly Gly Glu Ile Arg Ala Ile Ile Ser Arg
            35                  40                  45

Asp Val Phe Ser Glu Lys Gly Lys Val Ile Leu Ile Pro Lys Gly Ser
 50                  55                  60

Lys Ile Phe Gly Lys Tyr Ala Thr Ser Thr Ser Asp Ser Tyr Gly
 65                  70                  75                  80

Arg Val Ser Ile Ile Trp Asp Arg Val Asp Leu Thr Asn Gly Tyr Thr
                 85                  90                  95

Ile Glu Phe Asp Ser Pro Ala Val Asp Asn Leu Gly Arg Pro Gly Leu
```

```
              100                 105                 110
Gln Gly Arg Val Asp Asn Lys Tyr Lys Glu Gln Phe Ala Asn Ala Val
        115                 120                 125

Leu Gln Ser Gly Phe Asn Ile Gly Leu Ala Lys Ile Leu Asp Lys Leu
130                 135                 140

Val Pro Pro Ile Asp Ser Gln Ala Ala Thr Asn Ser Ala Thr
145                 150                 155                 160

Ala Thr Gln Ile Leu Asn Val Ala Gln Thr Ile Ser Ser Asn Thr Ala
                165                 170                 175

Met Asp Val Asn Thr Arg Ile Val Thr Ile Cys Thr Asn Ile Leu Ala
                180                 185                 190

Ala Ile Thr Asp Lys Thr Ser Ile Ala Tyr Ala Thr Met Thr Gln Ala
                195                 200                 205

Cys Thr Thr Ala Gln Asn Ala Ser Ser Ala His Thr Ser Glu Gln Arg
        210                 215                 220

Leu Gln Thr Leu Ile Gln Ala Val Asn Thr Ala Ala Ser Asn Leu Leu
225                 230                 235                 240

Thr Thr Thr Ser Ile Ala Ser Thr Pro Thr Gln Ala Gln Gln Ala Ser
                245                 250                 255

Thr Gln Ala Phe Thr Asp Val Thr Asn Val Val Gln Asn Met Ile Thr
                260                 265                 270

Gln Gln His Phe Lys Pro Thr Thr Val Asn Gln Gly Thr Pro Ile
        275                 280                 285

Arg Ile Tyr Val Asn Lys Asp Tyr Lys Phe Pro Lys Thr Val Leu Leu
        290                 295                 300

Lys Ser Lys Val Met Lys
305                 310

<210> SEQ ID NO 129
<211> LENGTH: 309
<212> TYPE: PRT
<213> ORGANISM: Rickettsia conorii

<400> SEQUENCE: 129

Pro Glu Gln Ile Thr Ala Glu Thr Thr Phe Lys Asp Arg Gly Asp Met
1               5                   10                  15

Ser Leu Val Leu Gly Arg Gly Lys Leu Ile Asp Ala Val Leu Glu Thr
                20                  25                  30

Ala Ile Asn Ser Asp Leu Gly Gly Glu Ile Arg Ala Ile Ile Ser Arg
            35                  40                  45

Asp Val Phe Ser Glu Lys Asp Lys Val Ile Leu Ile Pro Lys Gly Ser
        50                  55                  60

Lys Ile Phe Gly Lys Tyr Ala Thr Ser Thr Ser Ser Asp Ser Tyr Gly
65                  70                  75                  80

Arg Val Ser Ile Ile Trp Asp Arg Ile Asp Leu Thr Ser Gly Tyr Thr
                85                  90                  95

Ile Glu Phe Asp Ser Pro Ala Val Asp Asn Leu Gly Arg Pro Gly Leu
                100                 105                 110

Gln Gly Arg Val Asp Asn Lys Tyr Lys Glu Gln Phe Ala Asn Ala Val
        115                 120                 125

Leu Gln Ser Gly Phe Asn Ile Gly Leu Ala Lys Val Leu Asp Lys Leu
130                 135                 140

Val Pro Pro Ile Ala Ser Gln Ala Ala Ala Thr Asn Ser Ala Thr
145                 150                 155                 160
```

```
Ala Lys Gln Leu Leu Asn Ile Ala Gln Thr Ile Ala Ser Asn Thr Ala
            165                 170                 175

Met Asp Ala Asn Thr Arg Ile Val Thr Ile Cys Thr Asn Ile Leu Ala
        180                 185                 190

Ala Ile Thr Asp Lys Thr Ser Thr Ala Tyr Thr Thr Met Thr Gln Ala
            195                 200                 205

Cys Thr Thr Ala Gln Thr Ala Ser Ser Ala Asn Thr Ala Glu Gln Arg
    210                 215                 220

Leu Gln Thr Leu Val Gln Ala Val Asn Thr Ala Ala Ser Ser Leu Leu
225                 230                 235                 240

Thr Thr Thr Ser Ile Ala Ser Thr Pro Thr Gln Ala Gln Gln Ala Ser
                245                 250                 255

Thr Gln Ala Phe Thr Asp Val Thr Asn Val Val Lys Asn Met Ile Thr
            260                 265                 270

Gln Gln Gln Phe Lys Pro Thr Thr Thr Val Asn Gln Gly Thr Pro Val
        275                 280                 285

Arg Ile Tyr Val Asn Lys Asp Tyr Lys Phe Pro Lys Ala Val Leu Leu
    290                 295                 300

Lys Ser Lys Val Met
305
```

<210> SEQ ID NO 130
<211> LENGTH: 310
<212> TYPE: PRT
<213> ORGANISM: Rickettsia rickettsii

<400> SEQUENCE: 130

```
Pro Glu Gln Ile Thr Ala Glu Thr Thr Phe Lys Asp Arg Gly Asp Met
1               5                   10                  15

Ser Leu Val Leu Gly Arg Gly Lys Leu Ile Asp Ala Val Leu Glu Thr
            20                  25                  30

Ala Ile Asn Ser Glu Leu Gly Gly Glu Ile Arg Ala Ile Ile Ser Arg
        35                  40                  45

Asp Val Phe Ser Glu Lys Asp Lys Val Ile Leu Ile Pro Lys Gly Ser
    50                  55                  60

Lys Ile Phe Gly Lys Tyr Ala Thr Ser Thr Ser Asn Ser Tyr Gly
65                  70                  75                  80

Arg Val Ser Ile Ile Trp Asp Arg Ile Asp Leu Thr Ser Gly Tyr Thr
                85                  90                  95

Ile Glu Phe Asp Ser Pro Ala Val Asp Asn Leu Gly Arg Pro Gly Leu
            100                 105                 110

Gln Gly Arg Val Asp Asn Lys Tyr Lys Glu Gln Phe Ala Asn Ala Val
        115                 120                 125

Leu Gln Ser Gly Phe Asn Ile Gly Leu Ala Lys Val Leu Asp Lys Leu
    130                 135                 140

Val Pro Pro Pro Ile Ala Ser Gln Ala Ala Thr Asn Ser Ala Thr
145                 150                 155                 160

Ala Lys Gln Leu Leu Asn Thr Ala Gln Thr Ile Ala Ser Asn Thr Ala
                165                 170                 175

Met Asp Ala Asn Thr Arg Ile Val Thr Ile Cys Thr Asn Ile Leu Ala
            180                 185                 190

Ala Ile Thr Asp Lys Thr Ser Thr Ala Tyr Thr Thr Met Thr Gln Ala
        195                 200                 205

Cys Thr Thr Ala Gln Thr Ala Ser Ser Ala Asn Thr Ala Glu Gln Arg
    210                 215                 220
```

```
Leu Gln Thr Leu Val Gln Ala Val Asn Thr Ala Ala Ser Ser Leu Leu
225                 230                 235                 240

Thr Thr Thr Ser Ile Ala Ser Thr Pro Thr Gln Ala Gln Gln Ala Ser
                245                 250                 255

Thr Gln Ala Phe Thr Asp Val Thr His Val Val Lys Asn Met Ile Thr
            260                 265                 270

Gln Glu Gln Phe Lys Pro Thr Thr Thr Val Asn Gln Gly Thr Pro Val
        275                 280                 285

Arg Ile Tyr Val Asn Lys Asp Tyr Lys Phe Pro Lys Ala Val Leu Leu
    290                 295                 300

Lys Ser Lys Val Met Lys
305                 310

<210> SEQ ID NO 131
<211> LENGTH: 302
<212> TYPE: PRT
<213> ORGANISM: Orienta tsutsugamushi

<400> SEQUENCE: 131

Glu Glu Met Glu Gln Ile Arg Asn Phe Thr Asp Ala Gly Glu Leu Arg
1               5                   10                  15

Tyr Leu Leu Gly Arg Gly Thr Val Ile Asp Ala Val Ile Ile Ser Ala
            20                  25                  30

Val Asn Ser Asp Phe Ile Gly Glu Ile Val Ala Met Val Ser Arg Asp
        35                  40                  45

Val Tyr Ser Gln Glu Gly Lys Thr Ile Leu Ile Pro Arg Gly Ser Lys
    50                  55                  60

Ile Phe Gly Tyr Pro Ser Val Leu Asp Asn Ala Ala Tyr Gly Arg Met
65                  70                  75                  80

Met Ile Thr Trp Ser Glu Val Gln Ile Ala Gly Ser Gln Tyr Lys Leu
                85                  90                  95

Asn Leu Ser Ala Pro Thr Ile Asp Arg Leu Gly Lys Ile Gly Val Ala
            100                 105                 110

Gly Lys Val Asn Asn Lys Asn Leu Ala Arg Ile Met His Ala Val Leu
        115                 120                 125

Val Ser Ala Val Asn Ile Gly Ala Ala Phe Thr Leu Asp Lys Val Val
    130                 135                 140

Ala Leu Gln Gln Gln Met Ala Asn Thr Thr Ser Gly Leu Thr Gly Thr
145                 150                 155                 160

Leu Ile Lys Asn Ala Met Asn Ile Asn Asn Asp Ser Val Lys Ser Asp
                165                 170                 175

Ser Gln Lys Ile Thr Glu Ile Cys Gly Met Ser Arg Ser Leu Ile Thr
            180                 185                 190

Asp Lys Ser Ser Ser Val Tyr Thr Thr Ile Asn Lys Lys Cys Met Glu
        195                 200                 205

Ile Glu Thr Ser Ile Ile Ala Asn Val Asp Asp Lys Gln Lys Leu Ser
    210                 215                 220

Ser Leu Ile Asn Thr Ile Ile Asn Ile Ser Asn Ser Thr Ala Asn Asn
225                 230                 235                 240

Ser Asn Ser Asn Thr Gln Lys Ala Thr Asp Thr Ala Leu Asn Asp Val
                245                 250                 255

Val Asn Ala Ile Lys Lys Ile Ile Pro Ser Gln Glu Phe Asn Arg Thr
            260                 265                 270

Ile Thr Leu Asn Gln Gly Gln Asn Ile Lys Ile Tyr Val Asn Lys Asp
```

```
                275                 280                 285
Tyr Leu Phe Pro Thr Lys Ala Val Ser Gly Ile Lys Val Leu
    290                 295                 300

<210> SEQ ID NO 132
<211> LENGTH: 227
<212> TYPE: PRT
<213> ORGANISM: Escherichia coli
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (153)..(153)
<223> OTHER INFORMATION: Xaa can be any naturally occurring amino acid
<220> FEATURE:
<221> NAME/KEY: misc_feature
<222> LOCATION: (194)..(194)
<223> OTHER INFORMATION: Xaa can be any naturally occurring amino acid

<400> SEQUENCE: 132

Ser Asn Ser Pro Gly Ala Gln Pro Gln Asp Asn Glu Thr Ser Glu Gly
1               5                   10                  15

Ser Ser Ala Leu Ala Lys Asn Leu Thr Pro Ala Arg Leu Lys Ala Ser
            20                  25                  30

Arg Ala Gly Val Xaa Ala Asn Pro Ser Leu Thr Val Pro Lys Gly Lys
        35                  40                  45

Xaa Ile Pro Cys Gly Thr Gly Thr Glu Leu Asp Thr Thr Val Pro Gly
    50                  55                  60

Gln Val Ser Cys Arg Val Ser Gln Asp Val Tyr Ser Ala Asp Gly Leu
65                  70                  75                  80

Val Arg Leu Ile Asp Lys Gly Ser Trp Val Asp Gly Gln Ile Thr Gly
                85                  90                  95

Gly Ile Lys Asp Gly Gln Ala Arg Val Phe Val Leu Trp Glu Arg Ile
            100                 105                 110

Arg Asn Asp Gln Asp Gly Thr Ile Val Asn Ile Asp Ser Ala Gly Thr
        115                 120                 125

Asn Ser Leu Gly Ser Ala Gly Ile Pro Gly Asn Val Asp Ala His Xaa
    130                 135                 140

Trp Glu Arg Leu Arg Gly Ala Ile Xaa Ile Ser Leu Phe Ser Asp Thr
145                 150                 155                 160

Leu Thr Ala Leu Val Asn Gln Thr Gln Ser Asn Ile Gln Tyr Asn
                165                 170                 175

Ser Thr Glu Asn Ser Gly Gly Gln Leu Ala Ser Glu Ala Leu Arg Ser
            180                 185                 190

Tyr Xaa Ser Ile Pro Pro Thr Leu Tyr Asp Gln Gln Gly Asp Ala Val
        195                 200                 205

Ser Ile Phe Val Ala Arg Asp Leu Asp Phe Ser Gly Val Tyr Thr Leu
    210                 215                 220

Ala Asp Asn
225
```